US007655397B2

(12) United States Patent
Khan et al.

(10) Patent No.: US 7,655,397 B2
(45) Date of Patent: Feb. 2, 2010

(54) SELECTIONS OF GENES AND METHODS OF USING THE SAME FOR DIAGNOSIS AND FOR TARGETING THE THERAPY OF SELECT CANCERS

(75) Inventors: Javed Khan, Derwood, MD (US); Markus Ringnér, Lund (SE); Carsten Peterson, Lund (SE); Paul Meltzer, Rockville, MD (US)

(73) Assignee: The United States of America as represented by the Department of Health and Human Services, Washington, DC (US)

( * ) Notice: Subject to any disclaimer, the term of this patent is extended or adjusted under 35 U.S.C. 154(b) by 0 days.

(21) Appl. No.: 10/159,563

(22) Filed: May 31, 2002

(65) Prior Publication Data

US 2004/0009154 A1    Jan. 15, 2004

Related U.S. Application Data

(63) Continuation-in-part of application No. 10/133,937, filed on Apr. 25, 2002.

(51) Int. Cl.
*C12Q 1/68* (2006.01)
*C12P 19/34* (2006.01)
*C07H 21/02* (2006.01)
*C07H 21/04* (2006.01)

(52) U.S. Cl. .................. 435/6; 435/91.1; 435/91.2; 435/91.21; 435/91.5; 435/91.51; 536/23.5

(58) Field of Classification Search .................. 435/6, 435/287.2, 283; 536/23.1, 24.3
See application file for complete search history.

(56) References Cited

U.S. PATENT DOCUMENTS

| 6,794,137 B2 | 9/2004 | Blumenberg |
| 7,062,384 B2 | 6/2006 | Rocke et al. |
| 7,229,774 B2 | 6/2007 | Chinnaiyan et al. |
| 7,341,552 B2 | 3/2008 | Zhang et al. |
| 7,370,021 B2 | 5/2008 | Reeve et al. |
| 7,384,736 B2 | 6/2008 | Hakonarson |
| 7,402,388 B2 | 7/2008 | Gillis et al. |
| 7,402,399 B2 | 7/2008 | Mukherjeei et al. |
| 2003/0207278 A1 | 11/2003 | Khan et al. |

OTHER PUBLICATIONS

GeneCard for IGF2 via URL: <genecards.org/cgi-bin/carddisp.pl?gene=IGF2&snp=93#snp>.*
GeneCard for CCND1 available via URL: <genecards.org/cgi-bin/carddisp.pl?gene=Ccnd1&snp=97#snp>.*
ECgene Summary for CCND1 available via URL: <genome.ewha.ac.kr/cgi-bin/ECquery.cgi?organism=human&query=CCND1>.*
ECgene Summary for IGF2 available via URL: <genome.ewha.ac.kr/cgi-bin/ECquery.cgi?organism=human&query=IGF2>.*
Wang et al. Human Genetics. 2006. 120: 297-300.*
Li et al. Human Pathology. 2008. 39: 1792-1801.*
Khan, J. et al, "Classification and diagnostic prediction of cancers using gene expression profiling and artificial neural networks", *Nature Medicine*, vol. 7, No. 6., pp. 673-679 (Jun. 2001).
Peterson, C. et al., "JETNET 3.0—A versatile artificial neural network package", *Computer Physics Communications*, vol. 81, pp. 185-220 (1994).
Tusher, V. et al., "Significance analysis of microarrays applied to the ionizing radiation response", *PNAS*, vol. 98, No. 9, pp. 5116-5121 (Apr. 24, 2001).
Van Gelder, R. et al., "Amplified RNA synthesized from limited quantities of heterogeneous cDNA", *Proc. Natl. Acad. Sci. USA*, vol. 87, No. 5, pp. 1663-1667 (Mar. 1990).
Golub, T. et al.. "Molecular Classification of Cancer, Class Discovery and Class Prediction by Gene Expression Monitoring", *Science*, 286:531-537 (1999).
Gruvberger, S. et al., "Estrogen Receptor Status in Breast Cancer is Associated with Remarkably Distinct Gene Expression Patterns", *Cancer Research*, 61:5979-5984 (2001).
Kwon, S. et al., "DNA Microarray Data Analysis for Cancer Classification Based on Stepwise Discriminant Analysis and Boyesian Decision Theory", *Genome Informatics*, 12:252-254 (2001).
Cover page of Nature Medicine, vol. 7, No. 6, Jun. 2001 (received Jun. 15, 2001).
NHGRI Protocol, http://www.nhgri.hih.gov/DIR/LGG/SK/HTML/protocol.html, 27 pages (Apr. 25, 2002).
Furey et al., *Bioinformatics*, 16(10):906-914 (2000).
Herrero et al., *Bioinformatics*, 17(2):126-136 (2001).
Muller et al., *IEEE Transactions on Neural Networks*, 12(2):181-201 (2001).
Raychaudhuri et al., *Trends in Biotechnology*, 19(5):189-193 (2001).
GenBank Accession No. NM_000612, dated Oct. 31, 2000.
Blast Alignment between GenBank Accession No. NM_000612 and SEQ ID No. 72, dated Aug. 16, 2007.
Agilent Technology Webpage, dated Aug. 16, 2007.
Image Consortium Record printed Aug. 15, 2007.
GenBank Accession No. N54901, dated Jan. 28, 1997.
GenBank Sequence Revision History page printed Aug. 15, 2007.
GenCard Database Record IGF2 printed Aug. 15, 2007.
Sperduti et al., *IEEE Transactions on Neural Networks*, 8:714-735 (1997).
Ancoca et al., "On the statistical assessment of classifiers using DNA microarray data", *BMC Bioinformatics*, 7:387 (2006).
Chen et al., "Diagnosis of the Small Round Blue Cell Tumors Using Multiplex Polymerase Chain Reaction", *Journal of Molecular Diagnostics*, 9(1):80-88 (2007).
Kim et al., "ECgene: genome annotation for alternative splicing", *Nucleic Acids Research*, 33:D75-D79 (2005).
Mateos et al., "Supervised Neural Networks for Clustering Conditions in DNA Array Data after Reducing Noise by Clustering Gene Expression Profiles", *Microarray data analysis II*, Kluwer Academic Publ., pp. 91-103 (2002).
U.S. Appl. No. 10/133,937 Office Action dated Jun. 10, 2008.

* cited by examiner

*Primary Examiner*—Carla Myers
(74) *Attorney, Agent, or Firm*—Merchant & Gould P.C.

(57) ABSTRACT

A method of diagnosing a disease that includes obtaining experimental data on gene selections. The gene selection functions to characterize a cancer when the expression of that gene selection is compared to the identical selection from a noncancerous cell or a different type of cancer cell. The invention also includes a method of targeting at least one product of a gene that includes administration of a therapeutic agent. The invention also includes the use of a gene selection for diagnosing a cancer.

10 Claims, 9 Drawing Sheets

SELECTIONS OF GENES AND METHODS OF USING THE SAME FOR DIAGNOSIS AND FOR TARGETING THE THERAPY OF SELECT CANCERS

This application is a continuation in part of a U.S. patent application Ser. No. 10/133,937 entitled "METHODS FOR ANALYZING HIGH DIMENSIONAL DATA FOR CLASSIFYING, DIAGNOSING, PROGNOSTICATING, AND/OR PREDICTING DISEASES AND OTHER BIOLOGICAL STATES", filed on Apr. 25, 2002.

FIELD OF THE INVENTION

The invention relates generally to selections of genes expressed in a cancer cell that function to characterize a cancer, and methods of using the same for diagnosis and for targeting the therapy of select cancers. The invention also relates generally to the use of supervised pattern recognition methods to classify and diagnose disease. More specifically, the invention relates to the use of supervised pattern recognition methods, such as artificial neural networks for the classification, diagnosis, prognosis and prediction of disease using high dimensional data, such as gene expression profiling data.

BACKGROUND OF THE INVENTION

Disease is generally diagnosed based on a myriad of factors, both objective and subjective, including but not limited to symptoms, laboratory test values, demographic factors and environmental factors. Diagnosis relies on a clinician such as a physician or a veterinarian being able to identify and evaluate the relevant factors. Often this task can be difficult, and becomes exceedingly more so as the number of factors to be considered increases.

An example of a disease whose diagnosis is difficult is tumors. Tumors are currently diagnosed on the basis of clinical presentation, routine histology, immunohistochemistry and electron microscopy. However the histological appearance may not reveal the genetic aberrations or underlying biologic processes that contribute to the malignancy. Monitoring global gene expression levels using DNA microarrays would provide an additional tool for elucidating tumor biology as well as the potential for molecular diagnostic classification of cancers. Several studies have demonstrated that gene expression profiling using DNA microarrays is able to classify tumors with a high accuracy, and discover new cancer classes.

A specific type of tumors which could benefit is the small, round blue cell tumors (SRBCTs) of childhood as a model. SRBCTs include, neuroblastoma (NB), rhabdomyosarcoma (RMS), Burkitt's lymphoma (also called Burkitt's) (BL) and the Ewing family of tumors (EWS), are so named because of their similar appearance on routine histology. However, accurate diagnosis of SRBCTs is essential because the treatment options, responses to therapy, and prognoses vary widely depending on the diagnosis. As their name implies, these cancers are difficult to distinguish by light microscopy, and currently no single test can precisely distinguish these cancers.

In clinical practice, several techniques are used for diagnosis, including immunohistochemistry, cytogenetics, interphase fluorescence in situ hybridization and reverse transcription (RT)-PCR. Immunohistochemistry allows the detection of protein expression, but it can only examine one protein at a time. Molecular techniques such as RT-PCR are used increasingly for diagnostic confirmation following the discovery of tumor-specific translocations such as EWS-FLI1; t(11;22)(q24;q12) in EWS, and the PAX3-FKHR; t(2;13)(q35;q14) in alveolar rhabdomyosarcoma (ARMS). However, molecular markers do not always provide a definitive diagnosis, as on occasion there is failure to detect the classical translocations, due to either technical difficulties or the presence of variant translocations.

An example of a diagnostic method replete with such problems is the diagnostic method for Ewing sarcoma. Ewing sarcoma is diagnosed by immunohistochemical evidence of MIC2 expression and lack of expression of the leukocyte common antigen CD45 (excluding lymphoma), muscle-specific actin or myogenin (excluding RMS). However, reliance on detection of MIC2 alone can lead to incorrect diagnosis as MIC2 expression occurs occasionally in other tumor types including RMS and BL.

One objective factor that can, in certain circumstances, be entirely predictive of a diseased state is the genetic makeup of the individual. Genetic makeup of an individual cell can also be considered in terms of the level of expression of the genes of that individual cell through gene expression data.

DNA microarray technology is a recently developed high throughput technology for monitoring gene expression at the transcription level. Its use is akin to performing tens of thousands of northern blots simultaneously, and has the potential for parallel integration of the expression levels of an entire genome. A DNA microarray consists of DNA probes immobilized on a solid support such as a glass microscope slide. The DNA probes can be double stranded cDNA or short (25mers) or long (50-70mers) oligonucleotides of known sequences. An ideal DNA microarray should be able to interrogate all of the genes expressed in an organism.

In DNA microarrays using cDNA, the probes are PCR amplified from plasmid cDNA clones that have been purified and robotically printed onto coated glass slides. DNA microarrays using oligonucleotide have an advantage over cDNA microarrays because physical clones are not necessary. The oligonucleotides can either be previously synthesized and printed on glass slides, or can be synthesized directly on the surface of silicon or glass slides. Several print-ready oligonucleotide (60-70 mers) sets are commercially available for human, mouse and other organisms (http://www.cgen.com, http://www.operon.com).

Another technique for fabricating oligonucleotides microarrays chemically synthesizes the oligonucleotides (25 mers) on a silicon surface using photolithography techniques. (Affymetrix Inc., Santa Clara, Calif.). Originally such arrays were designed to detect single-nucleotide mutations, but now have applications for gene expression profiling studies. Yet another technique delivers single nucleic acids, which ultimately form longer oligonucleotides (60 mers), by ink-jet onto glass surfaces.

One method of utilizing gene expression data from microarrays is given by Tusher et al., PNAS 98(9) p. 5116-21, April, 2001. The method of Tusher et al. is a statistical method titled Significance Analysis of Microarrays ("SAM"). The general approach in SAM is based on commonly used statistical tests, t-tests specifically, to find genes that discriminate between two classes in a gene-by-gene fashion. SAM uses replication of experiments to assign a significance to the discriminating genes in terms of a false discover rate. SAM therefore offers a method of choosing particular genes from a set of gene expression data, but does not offer a diagnosis based on those genes.

DNA microarrays would be an invaluable tool for disease diagnosis. Gene-expression profiling using DNA microarrays permits a simultaneous analysis of multiple markers, and can be used for example to categorize cancers into subgroups. The only limitation associated with the use of DNA microarrays is the vast amount of data generated thereby. A method that would allow for the easy and automated use of DNA microarray data in disease diagnosis is therefore desirable. Despite the many statistical techniques to analyze gene-expression data, none so far has been rigorously tested for their ability to accurately distinguish diseases belonging to several diagnostic categories. Such methods have also not been used to extract the genes or features that are the most important for the classification performance. Such genes would also generally be those that are of use to biologists and physicians as offering avenues to research in investigating cures.

However, these other methods have not been used to extract the genes or features that are most important for the classification performance and which also will be of interest to cancer biologists.

Therefore, there remains a need for a method of using gene expression data to diagnose, predict, or prognosticate about a disease condition.

SUMMARY OF THE INVENTION

In accordance with one embodiment of the invention, there is provided a selection of genes, expressed in a cancer cell, that functions to characterize the cancer when the expression of a gene selection from the cancer cell is compared to the expression of an identical selection of genes from a noncancerous cell or an identical selection of genes from a different type of cancer cell.

Another embodiment of the invention includes a method of targeting a product of at least one of the genes in table 5 (below) that includes administering a therapeutic agent. Another embodiment of the invention includes a method of targeting a product of at least one of the genes in tables 2, 6, 7, 8, or 9 (below) that includes administering a therapeutic agent having an effect on said gene product. Yet another embodiment of the invention includes a method of targeting a product of at least one of the genes in table 10 (below) that includes administering a therapeutic agent having an effect on said gene product.

Another embodiment of the invention includes a method of using a selection of genes expressed in a cell having a particular type of cancer, wherein the gene selection functions to characterize the particular type of cancer when the expression of the gene selection from the cell is compared to the expression of an identical selection of genes from a cell without that particular type of cancer for diagnosing the particular type of cancer. Devices for carrying out the above methods of the invention are also included within the scope of the invention.

Another embodiment of the invention provides a method of diagnosing, predicting, and/or prognosticating about a disease including obtaining experimental data, wherein the experimental data includes high dimensional data, filtering noise from the data, reducing the dimensionality of the data by using one or more methods of analysis, training a supervised pattern recognition and/or classification method, ranking individual data from the overall data based on the relevance of the individual data to the diagnosis, prediction, prognosis or classification, choosing multiple individual data members, wherein the choice is based on the relative ranking of the individual data, and using the chosen data to determine if an unknown set of experimental data indicates a particular diseased condition, prognosis, prediction, or classification.

The invention offers a method of diagnostic classification of cancers from their gene-expression signatures and also identifies the genes that contributed to this classification. One embodiment of the method diagnoses SRBCTs of childhood, which occasionally present diagnostic difficulties.

The invention also offers a method of diagnosing, predicting, and/or prognosticating about SRBCTs including obtaining gene expression data, filtering noise from the gene expression data, reducing the dimensionality of the data by using principal component analysis (PCA), training an ANN, ranking the individual genes from the gene expression data, choosing multiple genes from the gene expression data, wherein the choice is based on the relative ranking of the individual genes and using the chosen genes to determine if an unknown set of gene expression data indicates a particular diseased condition, prognosis, and/or a prediction.

Methods of the invention can be utilized in a number of different applications. For example, diagnostic chips can be fabricated based on the identification of the diagnostic genes. Such chips would be very useful in clinical settings, as it would allow clinicians to diagnose cancers from a relatively small set of genes instead of purchasing entire gene sets.

Methods of the invention can also be used to define which patients with the same types of cancers are likely to respond to treatment. This would allow a physician to intensify treatment for those with a more negative prognosis based on their gene expression profiles as detected utilizing a method of the invention.

Methods of the invention can also be used for identifying pharmaceutical targets. Pharmaceutical companies can utilize methods of the invention to determine which genes to target in efforts to target specific diseases.

Methods of the invention can also be utilized as a research tool for analyzing all types of gene expression data including cDNA and oligonucleotide microarray data.

Methods of the invention can also be utilized to identify and rank, by importance, the genes that contribute to a diagnosis. A minimal set of genes that can correctly classify and identify diagnostic categories can also be determined using methods of the invention.

Methods of the invention identify the most significant genes, by calculating the sensitivity of the classification to a change in the expression level of each gene. A list of genes, ranked by their significance to the classification, is produced thereby. In an embodiment of the invention utilized for classifying SRBCTs the most important 96 genes reduced the misclassifications to zero. This allows for cost effective fabrication of SRBCT subarrays for diagnostic use. When a method of the invention used the 96 genes on 25 unknown samples, all 20 samples of SRBCTs and 5 non-SRBCTs were correctly classified.

One embodiment of the invention calibrates ANN models on the expression profiles of 63 SRBCTs of 4 diagnostic categories. Preferred embodiments of the invention utilize linear (that is no hidden layers) ANN models because of the high performance achieved. Methods of the invention may utilize other linear methods as well, and methods of the invention can easily accommodate nonlinear features of expression data if required. Hidden layers will be utilized for non linear data. Preferably, both tumor samples and cell line samples are used in order to compensate for heterogeneity within unknown samples (which contain both malignant and stromal cells) based on possible artifacts due to growth of cell lines in tissue culture.

Data from such samples is complementary, because tumor tissue, though complex, provides a gene-expression pattern representative of tumor growth in vivo, while cell lines contain a uniform malignant population without stromal contamination. Despite using only neuroblastoma (NB) cell lines for calibrating the ANN models, all four NB tumors among the test samples were correctly diagnosed with high confidence. This not only demonstrates the high similarity of NB cell lines to the tumors of origin, but also validates the use of cell lines for ANN calibration. One embodiment of a method of the invention accurately classified all 63 training SRBCTs and showed no evidence of over-training, thereby demonstrating the robustness of this method.

DETAILED DESCRIPTION OF THE PREFERRED EMBODIMENTS

The invention is a method of classifying, diagnosing, prognosticating about, and predicting disease conditions or other biological states using supervised pattern recognition methods to analyze high dimensional data.

Figure 1:
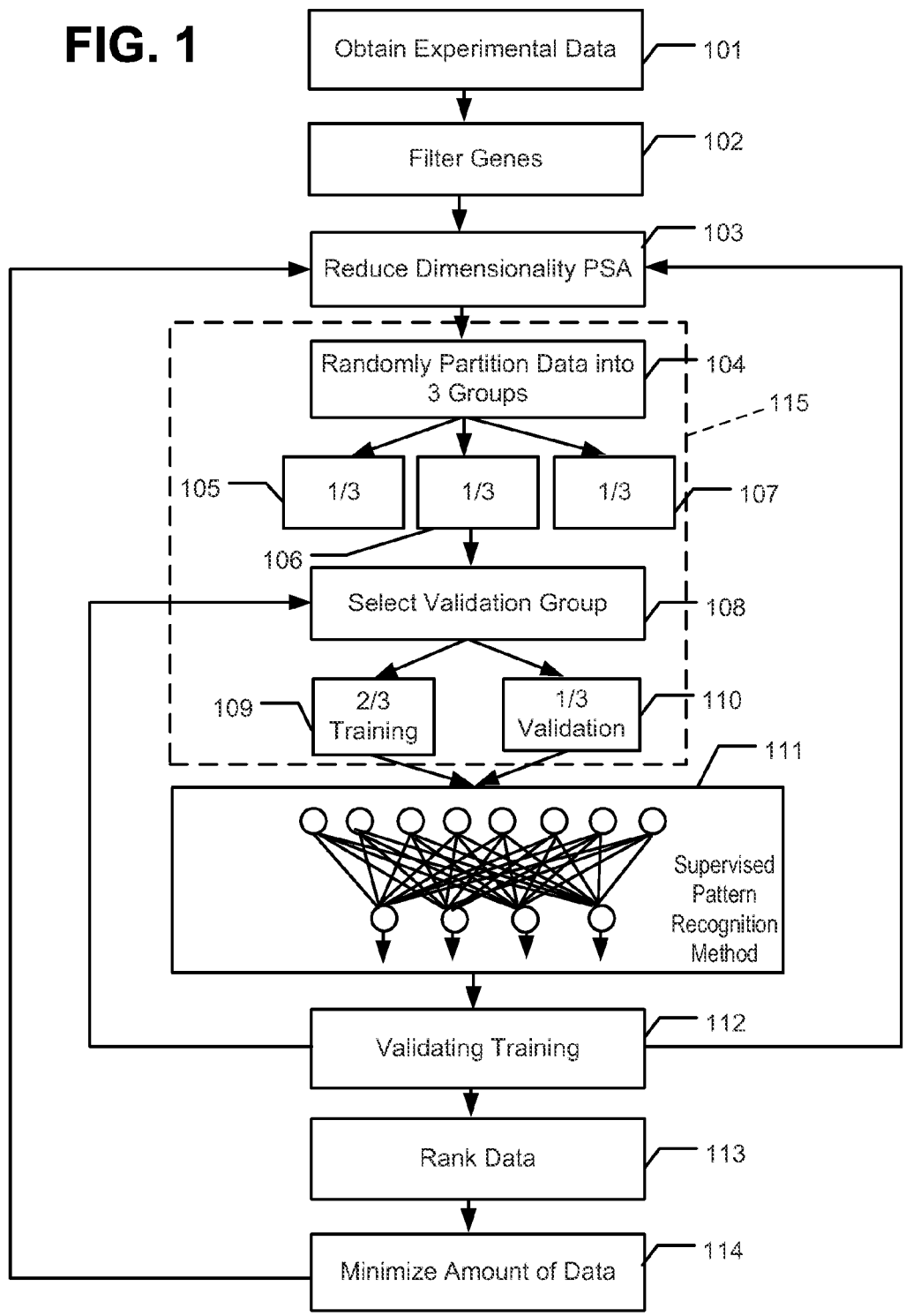
FIG. 1 illustrates a process flow for a method to classify and diagnose diseases using artificial neural networks according to one embodiment of the invention.

One embodiment of the invention is illustrated in FIG. 1. This process flow describes an embodiment of the method that includes obtaining experimental data 101, filtering the data 102, reducing the dimensionality of the data 103, setting up a validation method 115, training a supervised pattern recognition method 111, validating the outcome of the supervised pattern recognition method 112, and once the supervised pattern recognition method is validated, ranking the data based on the outcome of the supervised pattern recognition method 113. Further detail and more specific embodiments of methods of the invention are described below.

Any diagnostic categories can be diagnosed using the technology described here. It includes distinguishing patients with multiple sclerosis, rheumatoid arthritis, and other inflammatory or autoimmune diseases. It may also diagnose other systemic diseases based on gene expression profiles of white cells, including infections with particular organisms, cancer, or myocardial infarctions.

Obtaining Experimental Data

The first step in methods of the invention is to obtain experimental data. Experimental data utilized in methods of the invention is high dimensional data. High dimensional data is data that has at least hundreds of individual pieces of information associated with one sample. An example of high dimensional data useful in methods of the invention is gene expression data. Gene expression data is high dimensional data because each sample or person has a large number of gene expression levels. Generally speaking, gene expression data generally has thousands of gene expression levels for each sample. Other examples of high dimensional data useful in the invention include but are not limited to protein arrays and protein chips, cell array based expression analysis, analysis of patterns of single nucleotide polymorphisms in disease conditions, and comparative genomic hybridization on methaphase, BAC genomic, cDNA and oligonucleotide arrays.

Preferably, the gene expression data is obtained through use of DNA microarray technology. DNA microarrays are preferred as a source of data because they generally offer a more complete picture of the interactions of a large number of genes with a limited number, or even one experiment. An example of a general description of how gene expression data can be obtained by using cDNA microarray technology is given below.

DNA microarrays, although a relatively new technology, have already been saddled with a number of different names, biochip, DNA chip, gene chip, genome chip, cDNA microarray, and gene array. The use of any of these terms herein refers generally to DNA microarrays. The underlying principle of DNA microarrays is base pairing or hybridization i.e., A-T and G-C for DNA, and A-U and G-C for RNA.

DNA microarrays provide a medium for matching known and unknown DNA samples based on the base pairings given above. DNA microarrays can either be fabricated by high-speed robotics or can be fabricated in a laboratory setting. They are generally patterned on glass, but can also be fabricated on nylon substrates. Microarrays generally have sample spot sizes of less than 200 μm diameter, and generally contain thousands of DNA spots on one microarray.

One method of fabricating cDNA microarrays begins by first producing gene-specific DNA by polymerase chain reaction (PCR) amplification of purified template plasmid DNAs from cloned expressed sequence tags (ESTs). The PCR product is then purified, resuspended and printed onto a substrate. DNA microarrays are also commercially available from a number of sources, including but not limited to Affymetric, Inc. (Santa Clara, Calif.), Agilent Technologies (Palo Alto, Calif.), and Research Genetics (Huntsville, Ala.).

One general procedure for a cDNA microarray experiment begins by preparing DNA samples and arraying them (either with an arraying robot, or by hand), to form a DNA microarray. Next, the RNA samples are extracted from the cells of interest, purified, reverse transcribed into cDNA and differentially fluorescently labeled to create probes. Then, the fluorescently labeled cDNA probes are hybridized to the cDNA microarray. If a probe contains a cDNA whose sequence is complementary to the DNA on a given spot, the cDNA probe will hybridize to that spot. After the cDNA probes are hybridized to the array, and any loose probe has been washed away, the microarray is imaged to determine how much of each probe is hybridized to each spot. This indicates how much of each gene from the microarray is expressed in the two samples. If the amount of starting material is small, for example from needle biopsies, the RNA can first be subject to amplification by modified Eberwine methods as described by Gelder et al. (Amplified RNA synthesized from limited quantities of heterogeneous cDNA. Proc Natl Acad Sci USA 1990 March; 87(5):1663-7). The experimental high dimensional data, preferably obtained from gene expression experiments, preferably performed using cDNA microarrays, is then further analyzed by a method of the invention.

Filtering the Data

The next step in a method of the invention is filtering the data 102 to remove individual pieces of data that are deemed undesirable. This filtering step functions to eliminate weak and/or problematic data from further use in the method. Accomplishment of the step of filtering depends greatly on the type of high dimensional data utilized. Any method known to those of ordinary skill in the art can be used to eliminate data determined to be undesirable.

One basis for carrying out this filtering, if a DNA microarray is being utilized for obtaining the high dimensional data, is the intensity of the fluorescence from the individual microarray spots. This basis of omitting data is based on failure or error in the imaging of the specific spots. A preferred method of performing initial data filtering on cDNA microarray data to remove those spots where imaging was a problem is to utilize the intensity of the various spots and utilize only those spots that have an intensity over a certain threshold value. Other methods of filtering DNA microarray data include but are not limited to eliminating spots in which the number of pixels represented is less than a threshold defined by the user, eliminating spots in which the standard deviation of the signal on the spots is too large, as defined by the user, eliminating spots in which the background intensity of a single spot is too high, or any combination thereof. In addition quality values based on intensity, can be assigned to each spot, standard deviation of intensity, background and/or size of each spot, then a spot could be eliminated if its quality value falls below a threshold as defined by the user.

Reducing the Dimensionality of the Data

The next step in methods of the invention is reducing the dimensionality of the data 103. The number of samples needed to calibrate a classifier with good predictive ability, depends critically on the number of features used in the design of the classifier. In the case of high-dimensional data, such as microarray data, where the number of samples is much smaller than the number of individual pieces of data there exists a large risk of over-fitting. There are two different solutions to this problem. First, the calibration process can be carefully monitored using a cross-validation scheme to avoid over-fitting (see below). Second, the dimension of the data can be reduced, either by using a dimensional reduction algorithm or by selecting a smaller set of data for input to the supervised pattern recognition method. Dimensionality reduction allows the number of parameters representing each sample to be reduced. This allows for the design of a classifier that has less risk of over-fitting, thereby increasing its predictive ability. Examples of methods of reducing the dimensionality of the data include but are not limited to principal component analysis (PCA), weighted gene analysis, t-test, rank based Wilcoxon or Mann-Whitney tests, signal-to-noise statistic, Fisher's discriminant analysis, or ANOVA tests.

In a preferred embodiment of the invention, PCA is used to reduce the dimensionality of the data.

In the case of PCA on gene expression data, reduction of the dimensionality is achieved by rotating gene expression space, such that the variance of the expression is dominated by as few linear combinations of genes as possible. Even though the formal dimension of the problem is given by the number of individual data points, the effective dimension is just one less than the number of samples. Hence the eigenvalue problem underlying PCA can be solved without diagonalizing 2308×2308 matrices by using singular value decomposition. Thus each sample is represented by 88 numbers, which are the results of projections of the data using the PCA eigenvectors.

A potential risk when using PCA on relatively few samples is that components might be singled out due to strong noise in the data. It could be argued that the outputs (labels) should be included in the dimensional reduction, using e.g. the Partial Least Squares (PLS) algorithm, in order to promote components with strong relevance for the output. However, based on explorations with similar data sets, this is not optimal; bias is introduced and implicitly "over-trains" from the outset by including the outputs in the procedure.

Setting up a Validation Method for the Supervised Pattern Recognition Method

Once the data has been filtered 102 and its dimensionality reduced 103, a validation method is set up for monitoring and validating the training of the supervised pattern recognition method 115. Any method commonly used by those of skill in the art for validating the training of a supervised pattern recognition method can be used.

In one embodiment, the first step in setting us a validation method is to randomly divide the data into three groups of data, 105, 106, and 107. Then, one of those groups is chosen as a validation group 108. The first two of the groups 105 and 106 are combined into a training group 109, which is used to train the supervised pattern recognition method 111 and the third group 107 is used to validate the performance of the supervised pattern recognition method 111, once trained, and is called a validation group 110.

In this specific preferred embodiment, the 3-fold cross validation procedure (steps 104 through 110) is performed on all of the samples. A data group having 63 samples is given as an example. The 63 known (labeled) samples are randomly shuffled 104 and split into 3 equally sized groups (105, 106, and 107). The supervised pattern recognition method 111 is then calibrated as discussed below using the training group 109. The third group, a validation group 110, is reserved for testing predictions. Comparisons with the known answers refer to the results from the validation group 110 (i.e. when using a model, the samples used for training the model are never used in predictions). This procedure is repeated 3 times, each time with a different group used for validation. The random shuffling 104 is done about 100 to 10000 times. For each shuffling, one supervised pattern recognition method 111 model is generated. Thus, in total each sample belongs to a validation group 110, 1250 times and 3750 supervised pattern recognition methods 111 have been calibrated.

Training the Supervised Pattern Recognition Method

The supervised pattern recognition method 111 is then trained. The specific method of training the supervised pattern recognition method 111 is dependent on the specific form that the supervised pattern recognition method 111 takes. The choice of the supervised pattern recognition method 111 and the training thereof is well within one of skill in the art, having read this specification.

One example of a supervised pattern recognition method is an artificial neural network (ANN). ANNs are computer-based algorithms that are modeled on the structure and behavior of neurons in the human brain and can be trained to recognize and categorize complex patterns. Pattern recognition is achieved by adjusting parameters of the ANN by a process of error minimization through learning from experience. They can be calibrated using any type of input data, such as gene-expression levels generated by cDNA microarrays, and the output can be grouped into any given number of categories. ANNs have been recently applied to clinical problems such as diagnosing myocardial infarcts and arrhythmias from electrocardiograms and interpreting radiographs and magnetic resonance images. However, ANNs have not been used to decipher gene-expression signatures of SRBCTs or for diagnostic classification.

In embodiments where an artificial neural network (ANN) is employed as the supervised pattern recognition method 111, calibration is preferably performed using JETNET (C. Peterson, T. Roegnvaldsson and L. Loennblad, "JETNET 3.0—A versatile artificial neural network package," *Computer Physics Communications* 81, 185-220 (1994)). Preferably, the software is used with a learning rate η=0.7, momentum coefficient p=0.3 and the learning rate is decreased with a factor 0.99 after each iteration. Initial weight values are chosen randomly from [−r,r], where r=0.1/max$_i$ F$_i$ and the "fanin" F$_i$ is the number of nodes connecting to node i. The calibration is performed using a training set and it is monitored both for the training set and a validation set, which is not subject to calibration (see below). The weight values are updated after every 10 samples and the calibration is terminated after 100 passes (epochs) through the entire training set. In one embodiment of a method of the invention, the resulting parameters for the completed training of a supervised pattern recognition method 111 defines a "model".

In preferred embodiments, due to the limited amount of calibration data and the fact that four output nodes are needed (Ewing's sarcoma (EWS), Burkitt's lymphoma (BL), neuroblastoma (NB) and rhabdomyo sarcoma (RMS)), linear perceptrons (LP) with 10 input nodes representing the PCA components described above are utilized. In other words, the supervised pattern recognition method 111 generally contains 44 parameters including four threshold units. Since 10 components could be used without risking "over-training" the optimization of the number of components to a smaller number is generally not necessary.

The possibility of using all the PCA components as inputs followed by a subsequent pruning of weights to avoid "over-fitting" is also one alternative. This resulted in the dominant 4-8 PCA components (depending on the composition of the training set 107) being the surviving inputs. Generally, the less dominant PCA components contain variance not related to separating the four cancers, but rather to, for example, experimental conditions (noise) or variance related to sub-groupings within a cancer type.

Verifying the Outcome of the Supervised Pattern Recognition Method

Once the supervised pattern recognition method 111 is trained, the next step is to determine whether the validation of the supervised pattern recognition method 111 is successful 112. This step determines whether the supervised pattern recognition method 111 adequately predicted the results for the validation data set 110 using any number of performance measurements and error measurements.

Any method known to those of ordinary skill in the art can be utilized to evaluate the performance of the training of the supervised pattern recognition method 111. Generally speaking, the performance is evaluated by comparison with some predetermined level of correct predictions that the user has determined is acceptable.

If the performance of the supervised pattern recognition method 111 is sufficiently poor, and a measure of error is greater than an allowable threshold, the processing may return to module 103 where the dimensionality of the data is reduced in a different manner and the entire training and validation process is repeated.

Ranking the Data

Once module 112 determines that the network 111 has been adequately trained, the processing proceeds to rank the output of the supervised pattern recognition method 113.

The outcome of the supervised pattern recognition method 111 can be looked at either independently or in a compiled form. Each supervised pattern recognition method 111 gives a number between 0 (not this disease type) and 1 (this disease type) as an output for each disease type. If the predictions are viewed independently, the maximal output is forced to 1 while the other outputs are forced to 0. Then it is determined how many of the predictions are correct. If the predictions are viewed in a compiled form, all of the predicted outputs are considered in their numerical form, after which all of the numbers are averaged and the resulting average is forced to 0 or 1.

In one embodiment of the method, the predictions, as compiled, are used to classify samples. For validation samples the compilation is based on 1250 models, while for additional unknown samples all 3750 models are used in the compilation.

In one embodiment, each sample is classified as belonging to the disease type corresponding to the largest average in the compilation. In addition, it is desirable to be able to reject the second largest vote as well as test samples that do not belong to any of the disease types. In order to reject those samples that do not belong, a distance d, from a sample to the ideal vote for each disease type is defined as $$d_c = \frac{1}{2} \sum_{i=1}^{4} (o_i - \delta_{i,c})^2 \tag{1}$$

where c is a disease type, $o_i$ is the average from the compilation for disease type i, and $\sigma_{i,c}$ is unity if i corresponds to disease type c and zero otherwise. The distance is normalized such that the distance between two ideal samples belonging to different disease categories is unity. Based on the validation group, an empirical probability distribution of its distances is generated for each disease type.

The empirical probability distributions are preferably built using each supervised pattern recognition method 111 independently (not the average from the compilation). Thus, the number of entries in each distribution is given by 1250 multiplied by the number of samples belonging to the disease type. For a given test sample, the possible classifications based on these probability distributions can be rejected. This means that for each disease category a cutoff distance from an ideal sample is defined, within which, based on the validation samples, a sample of this category is expected to be. The distance given by the 95th percentile of the probability distribution is preferably chosen as a cutoff, which means that if a sample is outside of this cutoff distance it cannot be confidently diagnosed. It should be noted that the classification as well as the extraction of important genes (see below) converges using less than 100 supervised pattern recognition method 111 models. 3750 supervised pattern recognition method 111 models are preferred is because sufficient statistics exist for these empirical probability distributions.

For each disease category the sensitivity and specificity of the diagnosis may be calculated (see Table 1 below). Table 1 gives sensitivity, specificity and ROC curve areas for both validation and test samples. Both the sensitivity and the specificity are very high for all categories. It should be noted, that they generally depend on the kind of samples that are used as test samples.

TABLE 1

| Category | Sensitivity | Specificity | ROC curve area |
|---|---|---|---|
| EWS | 93% | 100% | 1.0 |
| BL | 100% | 100% | 1.0 |
| NB | 100% | 100% | 1.0 |
| RMS | 96% | 100% | 1.0 |

For example, in the case of SRBCT classification, using normal muscle samples as tests makes it harder to separate out RMS samples. If only samples from the four categories were used as blind distance cutoffs, it could easily have been designed such that both the sensitivity and the specificity would have been 100% for all diseases. However, it is preferred that the method is tested using a variety of blind tests. If it is desirable to improve rejection of for example normal muscle samples, one could incorporate them as a fifth category in the training process. However, using more samples of all four categories in the training is initially probably the best way to improve the diagnostic separation.

The Receiver Operator Characteristic (ROC) curve area is identical to another more intuitive and easily computed measure of discrimination: the probability that in a randomly chosen pair of samples, one belonging to and one not belonging to the disease category, the one belonging to the category is the one with the closest distance to the ideal for that particular category. Since the ROC curve areas are unity for all disease categories (see Table 1), it is possible to define cutoff distances such that both the sensitivity and the specificity are 100% for all diseases. However, based on the training and validation groups it is difficult to motivate such cutoff distances.

The next step in a method in accordance with the invention is to actually rank the data. This step can in principle be done in two ways; (1) model-independent and (2) model-dependent analysis respectively. Due to the relative small number of samples, the model-dependent analysis is preferred when using ANN models.

The sensitivity (S) of the outputs (o) with respect to any of the 2308 input variables $(x_k)$ is defined as:

$$S_k = \frac{1}{N_s} \frac{1}{N_o} \sum_{s=1}^{N_s} \sum_{i=1}^{N_o} \left| \frac{\delta o_i}{\delta x_k} \right| \quad (2)$$

where $N_s$ is the number of samples (63 or 88) and $N_o$ is the number of outputs (4). The procedure for computing $S_k$ involves a committee of 3750 models. In addition we have defined a sensitivity for each output i ($S_i$), which is analogous to Eq. (2) but without the sum over outputs. Furthermore, a sensitivity can be defined for each sample (or subsets of samples) individually, by only using that sample(s) in the sum over samples in Eq. (2). For all these sensitivities the sign of the sensitivity has also been defined. The sign signals whether the largest contribution to the sensitivity stems from positive or negative terms. A positive sign implies that increasing the expression rate of the gene increases the possibility that the sample belongs to this cancer type, while a negative sign means that decreasing the expression rate of the gene increases the same possibility. In other words, the sign does not tell whether a gene is up- or down-regulated but if it is more or less expressed in this cancer type as compared to the others. This means the genes are ranked not only according to their importance for the total classification, but also according to their importance for the different disease categories separately. The genes are preferably given a total rank as well as a separate rank for each disease category. Based on these ranks each gene is classified according to which disease category it is highly expressed in.

In one embodiment, once ranked, a relevant set of data can be selected module 114 by minimizing the amount of data to be used to classify and identify a particular disease. In one embodiment, a pre-determined amount of data having the highest ranking are selected. Of course, other selection methods may be employed without deviating from the spirit and scope of the present invention as recited in the attached claims.

Implementation of Methods of the Invention

Figure 2:
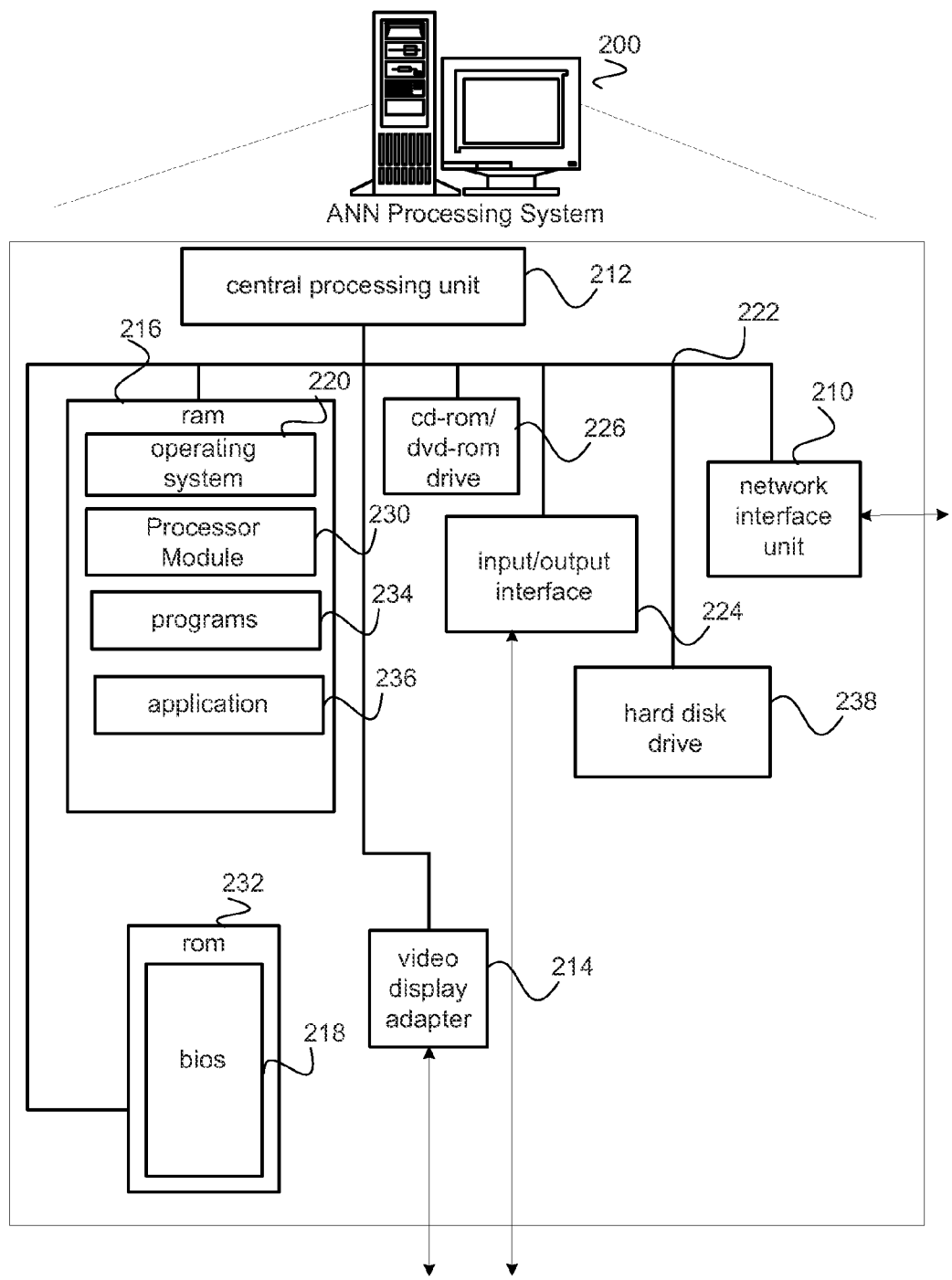
FIG. 2 illustrates a general purpose computing system utilized as part of an artificial neural network according to another embodiment of the invention.

In embodiments of the method in which the supervised pattern recognition method 111 is an artificial neural network, a general purpose computing system as depicted in FIG. 2 can be utilized. An exemplary ANN processing system 200 provides an artificial neural network that also receives experimental data to train the artificial neural network, to verify the output of an artificial neural network, and to identify relevant genes using the neural network.

Those of ordinary skill in the art will appreciate that the ANN processing system 200 may include many more components than those shown in FIG. 2. However, the components shown are sufficient to disclose an illustrative embodiment for practicing the present invention. As shown in FIG. 2, the ANN processing system 200 is connected to a WAN/LAN, or other communications network, via network interface unit 210. Those of ordinary skill in the art will appreciate that network interface unit 210 includes the necessary circuitry for connecting the ANN processing system 200 to a WAN/LAN, and is constructed for use with various communication protocols including the TCP/IP protocol. Typically, network interface unit 210 is a card contained within the ANN processing system 200.

The ANN processing system 200 also includes processing unit 212, video display adapter 214, and a mass memory, all connected via bus 222. The mass memory generally includes RAM 216, ROM 232, and one or more permanent mass storage devices, such as hard disk drive 228, a tape drive, CD-ROM/DVD-ROM drive 226, and/or a floppy disk drive. The mass memory stores operating system 220 for controlling the operation of ANN processing system 200. It will be appreciated that this component may comprise a general purpose server operating system as is known to those of ordinary skill in the art, such as UNIX, LINUX, MAC OS®, or Microsoft WINDOWS NT®. Basic input/output system ("BIOS") 218 is also provided for controlling the low-level operation of ANN processing system 200.

The mass memory as described above illustrates another type of computer-readable media, namely computer storage media. Computer storage media may include volatile and nonvolatile, removable and non-removable media implemented in any method or technology for storage of information, such as computer readable instructions, data structures, program modules or other data. Examples of computer storage media include RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which can be used to store the desired information and which can be accessed by a computing device.

The mass memory also stores program code and data for providing an ANN processing and network development. More specifically, the mass memory stores applications including ANN processing module 230, programs 234, and other applications 236. ANN processing module 230 includes computer executable instructions which, when executed by ANN processing system 200, performs the logic described above.

The ANN processing system 200 also comprises input/output interface 224 for communicating with external devices, such as a mouse, keyboard, scanner, or other input devices not shown in FIG. 2. Likewise, ANN processing system 200 may further comprise additional mass storage facilities such as CD-ROM/DVD-ROM drive 226 and hard disk drive 228. Hard disk drive 228 is utilized by ANN processing system 200 to store, among other things, application programs, databases, and program data used by ANN processing module 230. For example, customer databases, product databases, image databases, and relational databases may be stored. The operation and implementation of these databases is well known to those skilled in the art.

Figure 3:
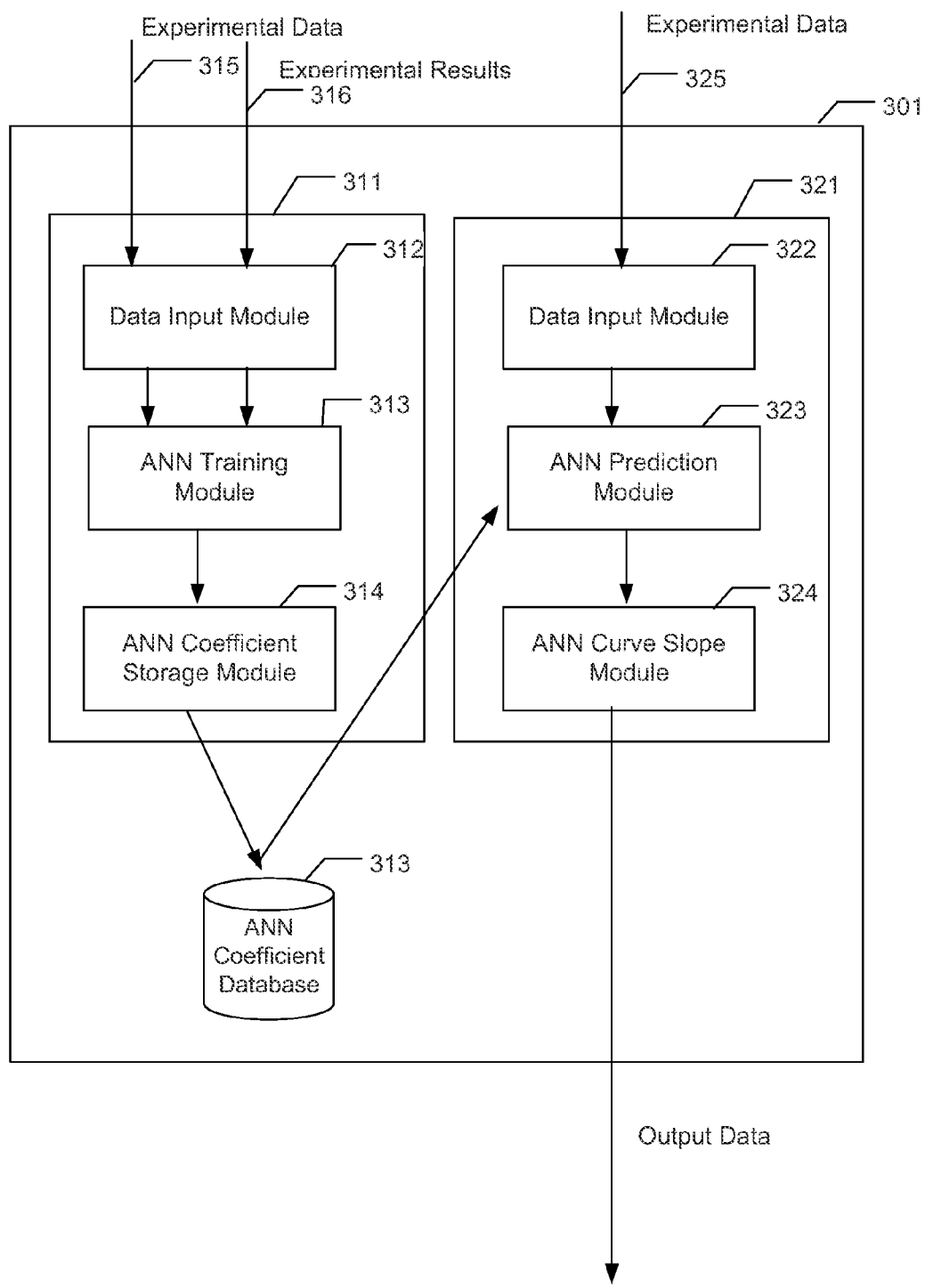
FIG. 3 illustrates a set of processing modules making up an embodiment of an artificial neural network according to the invention.

A set of processing modules making up an embodiment of an artificial neural network according to the invention is illustrated in FIG. 3. The artificial neural network disclosed herein corresponds to a generic neural network of no particular topology for the network of nodes contained therein. The neural network typically utilizes a form of competitive learning for the operation of the nodes within the network. Within competitive learning networks, a large number of data vectors are distributed in a highly dimensional space. These data vectors represent known values for experimental data that typically reflect a probability distribution of the input experimental data. From this probability distribution representation, predictions for unknown values for similar input data may be determined.

In all of these competitive learning networks, the networks are typically presented a set of input data that possesses a corresponding set of results data. From these data values, the network of nodes "learns" a relationship between the input data and its corresponding results data. In this process, the probability distribution relationship is estimated using the multi-dimensional network of nodes. This relationship is represented within a set of artificial neural network coefficients for a particular topology of nodes.

One skilled in the art will recognize that competitive learning networks include a nearly infinite number of network topologies that may be used to represent a particular probability distribution relationship without deviating from the spirit and scope of the present invention as recited within the attached claims. In addition, artificial neural networks may utilize various well-known algorithm architectures, including hard-competitive learning (i.e. "winner-take-all" learning), soft competitive learning without a fixed network dimensionality, and soft competitive learning with a fixed network dimensionality, to specify an artificial neural network according to the invention as recited within the attached claims. Each of these algorithm architectures represents the same probability distribution relationship; however each of the various algorithm architectures better optimize corresponding processing parameters, which are often mutually exclusive with each other. These parameters include error minimization or the minimization of an expected quantization error, entropy maximization for the reference vectors used within a network, and topology-preserving or feature mapping architectures that attempt to map high-dimensional inputs signals onto lower-dimensional structures in a manner that attempts to preserve similar relationships found within the original data within the post-mapping data. As such, any of these types of algorithm architectures may be used to construct an artificial neural network without deviating from the spirit and scope of the present invention as recited within the attached claims.

Now referring to FIG. 3, an artificial neural network processing system 301 comprises a learning module 311, a prediction module 321, and a database of network node coefficients 313. The learning module 311 is used with a set of experimental data 315 that possesses a corresponding set of experimental results 316 to generate a set of network node coefficients that represent a probability distribution relationship for the experimental data 315-experimental result 316 data set for a particular neural network topology and algorithm architecture. The learning module 311 includes a data learning input module 312 that receives the experimental data 315-experimental result 316 data set generated using the process described above. The learning module 311 also includes an ANN training module 313 that processes the experimental data 315-experimental result 316 data set to generate the coefficients used to specify the probability distribution relationship and an ANN coefficient storage module 314 for storing the coefficients that have been previous generated within the database 313 for later use.

The data processing within the learning module 311 may proceed in a batch processing fashion in which all of the vectors within the experimental data 315 -experimental result 316 data set are processed at a single time. In such a process, the experimental data 315-experimental result 316 data set is received by the input module 312, processed by the training module 313, and the generated coefficients are placed within the database 313 by the storage module 314. Alternatively, the experimental data 315-experimental result 316 data set may be processed as a sequence of smaller data sets in which the experimental data 315-experimental result 316 data set data values are generated at different times. In such a process, the training module 313 uses the previously stored coefficients retrieved by the storage module along with a new small data set provided by the input module 312 to generate an updated set of coefficients. These updated coefficients may be once again stored within the database 313 for use at a later time.

Once an artificial neural network 301 has been trained, the prediction module 321 may be used to predict, or classify, a particular test data value 325. The prediction module 321 includes a data prediction input module 322, an ANN prediction module 323, and an ANN curve slope module 324. The data prediction input module 322 receives the input test data generated as described above for use in the prediction module. The ANN prediction module 323 receives and utilizes the network coefficient values for the neural network from the ANN coefficient database 313 to predict the possible result for the probability distribution relationship specified within the neural network. This output value is used by the ANN curve slope module 324 to determine all possible values for a given gene, in the manner discussed above, to determine a curve slope value. This slope value is then output for later use in ranking and classifying the individual genes used to determine the presence, or lack there of, for a disease.

The embodiments described herein are implemented as logical operations performed by a computer. The logical operations of these various embodiments of the present invention are implemented (1) as a sequence of computer implemented steps or program modules running on a computing system and/or (2) as interconnected machine modules or hardware logic within the computing system. The implementation is a matter of choice dependent on the performance requirements of the computing system implementing the invention. Accordingly, the logical operations making up the embodiments of the invention described herein can be variously referred to as operations, steps, or modules.

While the above embodiments of the invention describe the use of an artificial neural network to identify relevant genes associated with diseases and use the identified genes to classify and identify diseases, one skilled in the are will recognize that the use of the processing system discussed above are merely example embodiments of the invention. As long as experimental data is used to self-train a processing system using competitive learning processing, the present invention to would be useable in other data processing systems. It is to be understood that other embodiments may be utilized and operational changes may be made without departing from the scope of the present invention as recited in the attached claims.

Devices and Methods for Detecting, Monitoring and Treating SRBCTs

The genes given in table 2, 2b, or 5 below can be used to make up a selection of genes for detection of any one of the four SRBCT types of cancers: neuroblastoma (NB), rhabdoymosarcoma (RMS), Burkitt's lymphoma (BL), or the Ewing family of Tumors (EWS). The gene selection can be used to distinguish a SRBCT type cancer cell from a non-cancerous cell, from a cell of a different type of SRBCT cancer, or from a cell of any other different type of cancer. The cancer type of a gene indicates which cancer that it is differentially expressed in.

TABLE 2

| Image Id. | Gene symbol | ES Rank | Sign | RMS Rank | Sign | NB Rank | Sign | BL Rank | Sign | Cancer Type |
|---|---|---|---|---|---|---|---|---|---|---|
| 812105 | AF1Q | 670 | − | 934 | − | 2 | + | 51 | − | NB |
| 383188 | RCV1 | 478 | − | 808 | + | 13 | + | 42 | − | NB |
| 82225 | SFRP1 | 160 | − | 264 | − | 17 | + | 85 | − | NB |
| 878280 | CRMP1 | 602 | − | 1255 | + | 12 | + | 45 | − | NB |
| 135688 | CATA2 | 354 | + | 155 | − | 37 | + | 88 | − | NB |
| 308231 | EST | 524 | − | 1015 | + | 10 | + | 117 | − | NB |
| 486110 | PFN2 | 1554 | + | 1500 | + | 31 | + | 31 | − | NB |
| 377048 | EST | 733 | − | 560 | + | 23 | + | 102 | − | NB |
| 784257 | KIF3C | 577 | + | 1099 | − | 64 | + | 44 | − | NB |
| 395708 | DPYSL4 | 1269 | + | 591 | + | 28 | + | 91 | − | NB |
| 292522 | EST | 221 | − | 667 | + | 32 | + | 189 | − | NB |
| 813266 | FHL1 | 1045 | + | 1610 | − | 91 | + | 46 | − | NB |
| 244618 | EST | 22 | − | 3 | + | 273 | − | 86 | − | RMS |
| 298062 | TNNT2 | 43 | − | 4 | + | 95 | − | 475 | − | RMS |
| 324494 | HSPB2 | 1605 | − | 13 | + | 7 | − | 420 | − | RMS |
| 122159 | COL3A1 | 791 | + | 29 | + | 1062 | − | 16 | − | RMS |
| 788107 | AMPHL | 74 | + | 14 | + | 817 | + | 108 | − | RMS |
| 377671 | ITGA7 | 1044 | + | 24 | + | 66 | − | 135 | − | RMS |
| 784224 | FGFR4 | 36 | − | 5 | + | 431 | − | 604 | + | RMS |
| 293500 | EST | 262 | − | 9 | + | 1084 | − | 138 | − | RMS |
| 42558 | GATM | 379 | − | 12 | + | 25 | − | 1020 | − | RMS |
| 246377 | EST | 719 | − | 36 | + | 641 | + | 75 | − | RMS |
| 809901 | COL15A1 | 1516 | − | 23 | + | 35 | − | 385 | − | RMS |
| 769959 | COL4A2 | 1575 | + | 66 | + | 1786 | − | 26 | − | RMS |
| 755750 | NME2 | 1840 | + | 26 | + | 591 | − | 82 | − | RMS |
| 770394 | FCGRT | 3 | + | 186 | + | 79 | − | 18 | − | EWS |
| 866702 | PTPN13 | 2 | + | 74 | − | 230 | − | 62 | − | EWS |
| 357031 | TNFAIP6 | 5 | + | 119 | − | 103 | − | 60 | − | EWS |
| 377461 | CAV1 | 6 | + | 91 | − | 90 | − | 101 | − | EWS |
| 52076 | NOE1 | 7 | + | 33 | − | 1673 | + | 37 | − | EWS |
| 1473131 | TLE2 | 10 | + | 1884 | − | 16 | − | 217 | − | EWS |
| 208718 | ANXA1 | 12 | + | 827 | − | 1202 | − | 33 | − | EWS |
| 80338 | SELENBP1 | 20 | + | 1316 | + | 42 | − | 151 | − | EWS |
| 377731 | GSTM5 | 13 | + | 310 | − | 34 | − | 381 | − | EWS |
| 814260 | FVT1 | 9 | + | 61 | − | 330 | − | 335 | − | EWS |
| 364934 | DAPK1 | 42 | + | 1481 | + | 707 | − | 40 | − | EWS |
| 755599 | IFI7 | 16 | + | 177 | − | 30 | − | 918 | − | EWS |
| 291756 | TUBB5 | 17 | + | 31 | − | 1325 | + | 245 | − | EWS |
| 308497 | EST | 27 | + | 1971 | − | 43 | − | 231 | − | EWS |
| 609663 | PRKAR2B | 198 | − | 55 | − | 550 | + | 29 | + | BL |
| 868304 | ACTA2 | 1286 | − | 151 | − | 122 | − | 71 | + | BL |

TABLE 2b

| Rank | Image Id. | Gene | EWS Rank | Sign | RMS Rank | Sign | NB Rank | Sign | BL Rank | Sign | Cancer Type |
|---|---|---|---|---|---|---|---|---|---|---|---|
| 1 | 296448 | IGF2 | 8 | − | 1 | + | 918 | − | 19 | − | RMS |
| 2 | 207274 | IGF2 | 19 | − | 2 | + | 1152 | − | 11 | − | RMS |
| 3 | 841641 | CCNID1 | 11 | + | 38 | − | 118 | + | 6 | − | EWS/NB |
| 4 | 365826 | GAS1 | 25 | + | 69 | + | 22 | − | 9 | − | EWS/RMS |

TABLE 2b-continued

| | | | EWS | | RMS | | NB | | BL | | |
|---|---|---|---|---|---|---|---|---|---|---|---|
| Rank | Image Id. | Gene | Rank | Sign | Rank | Sign | Rank | Sign | Rank | Sign | Cancer Type |
| 5 | 486787 | CNN3 | 130 | − | 39 | + | 14 | + | 17 | − | RMS/NB |
| 6 | 770394 | FCGRT | 3 | + | 186 | − | 79 | − | 18 | − | EWS |
| 7 | 244618 | EST | 22 | − | 3 | + | 273 | − | 86 | − | RMS SEQ ID NO:77 |
| 8 | 233721 | IGFBP2 | 148 | + | 43 | + | 598 | + | 1 | − | Not BL |
| 9 | 43733 | GYG2 | 4 | + | 261 | − | 99 | − | 21 | − | EWS |
| 10 | 295985 | EST | 1 | − | 51 | + | 9 | + | 522 | + | Not EWS SEQ ID NO:26 |
| 11 | 629896 | MAP1B | 360 | − | 893 | + | 1 | + | 23 | − | NB |
| 12 | 840942 | HLA-DPB1 | 1161 | + | 383 | − | 6 | − | 12 | + | BL |
| 13 | 80109 | HLA-DQA1 | 226 | − | 1589 | − | 20 | − | 3 | + | BL |
| 14 | 41591 | MN1 | 257 | + | 18 | + | 4 | − | 169 | − | EWS/RMS |
| 15 | 866702 | PTPN13 | 2 | + | 74 | − | 230 | − | 62 | − | EWS |
| 16 | 357031 | TNFAIP6 | 5 | + | 119 | − | 103 | − | 60 | − | EWS |
| 17 | 782503 | EST | 26 | + | 219 | − | 104 | + | 14 | − | EWS/NB SEQ ID NO:7 |
| 18 | 377461 | CAV1 | 6 | + | 91 | − | 90 | − | 101 | − | EWS |
| 19 | 52076 | NOE1 | 7 | + | 33 | − | 1673 | + | 37 | − | EWS |
| 20 | 811000 | LGALS3BP | 24 | + | 246 | + | 257 | + | 13 | − | EWS/NB |
| 21 | 308163 | EST | 49 | + | 88 | + | 191 | − | 22 | − | RMS/EWS SEQ ID NO:57 |
| 22 | 812105 | AF1Q | 670 | − | 934 | − | 2 | + | 51 | − | NB |
| 23 | 183337 | HLA/DMA | 317 | − | 1574 | − | 24 | − | 8 | + | BL |
| 24 | 714453 | IL4R | 208 | − | 20 | + | 8 | − | 238 | + | RMS/BL |
| 25 | 298062 | TNNT2 | 43 | − | 4 | + | 95 | − | 475 | − | RMS |
| 26 | 39093 | MNPEP | 46 | + | 224 | + | 21 | − | 103 | − | EWS/RMS |
| 27 | 212542 | EST | 62 | + | 993 | + | 1086 | + | 2 | − | Not BL SEQ ID NO:53 |
| 28 | 204545 | EST | 471 | + | 49 | + | 1455 | + | 5 | − | Not BL SEQ ID NO:58 |
| 29 | 383188 | RCV1 | 478 | + | 808 | + | 13 | + | 42 | − | NB |
| 30 | 82225 | SFRP1 | 160 | − | 264 | + | 17 | + | 85 | − | NB |
| 31 | 44563 | GAP43 | 693 | − | 191 | − | 3 | + | 166 | − | NB |
| 32 | 289645 | APLP1 | 41 | + | 102 | − | 107 | + | 61 | − | EWS/NB |
| 33 | 324494 | HSPB2 | 1605 | − | 13 | + | 7 | − | 420 | − | RMS |
| 34 | 563673 | ATQ1 | 35 | + | 1527 | − | 523 | + | 7 | − | Not BL |
| 35 | 1473131 | TLE2 | 10 | + | 1884 | − | 16 | − | 217 | − | EWS |
| 36 | 1416782 | CKB | 134 | + | 416 | + | 851 | + | 4 | − | Not BL |
| 37 | 417226 | MYC | 63 | + | 222 | − | 29 | − | 110 | + | EWS/BL |
| 38 | 878280 | CRMP1 | 602 | − | 1522 | + | 12 | + | 45 | − | NB |
| 39 | 812965 | MYC | 23 | + | 296 | − | 11 | − | 308 | + | EWS/BL |
| 40 | 122159 | COL3A1 | 791 | + | 29 | + | 1062 | − | 16 | − | RMS |
| 41 | 609663 | PRKAR2B | 198 | − | 55 | + | 550 | + | 29 | + | BL |
| 42 | 461425 | MYL4 | 98 | + | 7 | + | 80 | − | 419 | − | RMS |
| 43 | 1469292 | PIM2 | 1007 | + | 242 | − | 53 | − | 36 | + | BL |
| 44 | 809910 | 1-8U | 52 | + | 168 | + | 159 | − | 56 | − | RMS/EWS |
| 45 | 824602 | IFI16 | 336 | + | 149 | − | 33 | − | 89 | + | EWS/BL |
| 46 | 245330 | IGF2 | 65 | − | 6 | + | 147 | − | 434 | − | RMS |
| 47 | 135688 | GATA2 | 354 | + | 155 | − | 37 | + | 88 | − | NB |
| 48 | 1409509 | TNNT1 | 141 | − | 8 | + | 153 | − | 313 | − | RMS |
| 49 | 788107 | AMPHL | 74 | − | 14 | + | 817 | + | 108 | − | RMS |
| 50 | 784593 | EST | 224 | − | 299 | + | 39 | + | 68 | − | RMS/NB SEQ ID NO:41 |
| 51 | 756556 | C1NH | 90 | + | 238 | + | 284 | − | 38 | − | RMS/EWS |
| 52 | 208718 | ANXA1 | 12 | + | 827 | − | 1202 | − | 33 | − | EWS |
| 53 | 308231 | EST | 524 | − | 1015 | + | 10 | + | 117 | − | NB SEQ ID NO:39 |
| 54 | 486110 | PFN2 | 1554 | + | 1500 | + | 31 | + | 31 | − | NB |
| 55 | 21652 | CTNNA1 | 104 | + | 117 | + | 2245 | − | 15 | − | Not BL |
| 56 | 377671 | ITGA7 | 1044 | + | 24 | + | 66 | − | 135 | − | RMS |
| 57 | 745343 | REG1A | 166 | + | 93 | − | 40 | − | 153 | + | EWS/BL |
| 58 | 241412 | ELF1 | 882 | − | 1473 | − | 60 | − | 27 | + | BL |
| 59 | 504791 | GSTA4 | 276 | + | 2003 | + | 108 | + | 24 | − | Not BL |
| 60 | 841620 | DPYSL2 | 51 | + | 100 | − | 366 | + | 70 | − | EWS/NB |
| 61 | 859359 | PIG3 | 58 | − | 28 | + | 288 | + | 152 | − | RMS/NB |
| 62 | 45542 | IGFBP5 | 991 | + | 89 | + | 1661 | − | 10 | − | RMS |
| 63 | 80338 | SELENBP1 | 20 | + | 1316 | + | 42 | − | 151 | − | EWS |
| 64 | 45291 | DRPLA | 532 | + | 81 | + | 872 | − | 28 | − | Not BL |
| 65 | 323371 | APP | 1689 | − | 90 | + | 594 | − | 65 | − | Not BL |
| 66 | 897788 | PTPRF | 59 | + | 1358 | − | 734 | − | 20 | − | Not BL |
| 67 | 377731 | GSTM5 | 13 | + | 310 | − | 34 | − | 381 | − | EWS |
| 68 | 784224 | FGFR4 | 36 | − | 5 | + | 431 | − | 604 | − | RMS |
| 69 | 293500 | EST | 262 | − | 9 | + | 1084 | − | 138 | − | RMS SEQ ID NO:80 |
| 70 | 767183 | HCLS1 | 1481 | − | 1424 | − | 50 | − | 32 | + | BL |
| 71 | 297392 | MT1L | 1361 | − | 483 | − | 113 | − | 30 | + | BL |
| 72 | 325182 | CDH2 | 590 | − | 919 | − | 5 | + | 260 | − | NB |
| 73 | 1435862 | MIC2 | 14 | + | 518 | − | 371 | − | 97 | − | EWS |
| 74 | 377048 | EST | 733 | − | 560 | + | 23 | + | 102 | − | NB SEQ ID NO:40 |
| 75 | 814260 | FVT1 | 9 | + | 61 | − | 330 | − | 335 | − | EWS |
| 76 | 784257 | KIF3C | 577 | + | 1099 | − | 64 | + | 44 | − | NB |
| 77 | 42558 | GATM | 379 | − | 12 | + | 25 | − | 1020 | − | RMS |
| 78 | 814526 | HSRNASEB | 164 | − | 198 | + | 98 | − | 105 | + | RMS/BL |
| 79 | 839736 | CRYAB | 516 | + | 67 | + | 51 | − | 183 | − | EWS/RMS |

TABLE 2b-continued

| | | | EWS | | RMS | | NB | | BL | | |
|---|---|---|---|---|---|---|---|---|---|---|---|
| Rank | Image Id. | Gene | Rank | Sign | Rank | Sign | Rank | Sign | Rank | Sign | Cancer Type |
| 80 | 395708 | DPYSL4 | 1269 | + | 591 | − | 28 | + | 91 | − | NB |
| 81 | 416959 | NFIB | 1420 | − | 86 | + | 160 | + | 72 | − | RMS/NB |
| 82 | 364934 | DAPK1 | 42 | + | 1481 | + | 707 | − | 40 | − | EWS |
| 83 | 868304 | ACTA2 | 1286 | − | 151 | − | 122 | − | 71 | + | BL |
| 84 | 755599 | IFI17 | 16 | + | 177 | − | 30 | − | 918 | − | EWS |
| 85 | 246377 | EST | 719 | − | 36 | + | 641 | + | 75 | − | RMS SEQ ID NO:51 |
| 86 | 291756 | TUBB5 | 17 | + | 31 | − | 1325 | + | 245 | − | EWS |
| 87 | 809901 | COL15A1 | 1516 | − | 23 | + | 35 | − | 385 | − | RMS |
| 88 | 769959 | COL4A2 | 1575 | + | 66 | + | 1786 | − | 26 | − | RMS |
| 89 | 796258 | SGCA | 30 | − | 10 | + | 521 | − | 758 | − | RMS |
| 90 | 854899 | DUSP6 | 774 | + | 150 | + | 838 | + | 39 | − | Not BL |
| 91 | 755750 | NME2 | 1840 | + | 26 | + | 591 | − | 82 | − | RMS |
| 92 | 292522 | EST | 221 | − | 667 | + | 32 | + | 189 | − | NB SEQ ID NO:36 |
| 93 | 308497 | EST | 27 | + | 1971 | − | 43 | − | 231 | − | EWS SEQ ID NO:24 |
| 94 | 813266 | FHL1 | 1045 | + | 1610 | − | 91 | + | 46 | − | NB |
| 95 | 200814 | MME | 639 | − | 1081 | + | 78 | − | 66 | + | BL |
| 96 | 768370 | TIMP3 | 547 | + | 1132 | + | 606 | + | 25 | − | Not BL |

One embodiment of the invention offers a selection of genes that are expressed in a cancer cell. Such selections of genes function to characterize the cancer when the gene selection from the cancer cell is compared to the expression of an identical selection of genes from a noncancerous cell, or a different type of cancer cell. As used herein, the phrase "function to characterize" can mean to identify, to be indicative of, to be highly and/or differentially expressed in. The cancer to be identified can be neuroblastoma, rhabdomyosarcoma, Burkitt's, Ewing family of tumors, or combinations thereof. In one embodiment, at least one of the genes is chosen from table 5. In another embodiment, at least one of the genes is chosen from table 2, or 2b. In yet another embodiment, at least one of the genes is chosen from at least one of tables 6, 7, 8, or 9. In a further embodiment, there are at least 9 genes chosen from table 5, preferentially selected from the top ranked genes. In an even further embodiment, there are at least 9 genes chosen from at least one of tables 2, 2b, 6, 7, 8, or 9, preferentially selected from the top ranked genes.

As used herein, "Image ID" or "Clone ID" refer to particular genes that are given in various tables. In some embodiments of the invention, gene selections include one or more genes with a given Image ID. In one embodiment, the cancer to be identified is neuroblastoma, and the gene selection includes at least one of the genes with the following Image Id: 812105 (SEQ. ID. NO. 32), 383188 (SEQ. ID. NO. 38), 82225 (SEQ. ID. NO. 42), 878280 (SEQ. ID. NO. 33), 135688 (SEQ. ID. NO. 44), 308231 (SEQ. ID. NO. 39), 486110 (SEQ. ID. NO. 45), 377048 (SEQ. ID. NO. 40), 784257 (SEQ. ID. NO. 34), 395708 (SEQ. ID. NO. 30), 292522 (SEQ. ID. NO. 36), or 813266 (SEQ. ID. NO. 47). In another embodiment, the cancer to be identified is rhabdomyosarcoma and the gene selection includes at least one of the genes with the following Image Id: 244618 (SEQ. ID. NO. 77), 298062 (SEQ. ID. NO. 74), 324494 (SEQ. ID. NO. 62), 122159 (SEQ. ID. NO. 66), 788107 (SEQ. ID. NO. 52), 377671 (SEQ. ID. NO. 68), 784224 (SEQ. ID. NO. 71), 293500 (SEQ. ID. NO. 80), 42558 (SEQ. ID. NO. 79), 246377 (SEQ. ID. NO. 51), 809901 (SEQ. ID. NO. 67), 769959 (SEQ. ID. NO. 69), or 755750 (SEQ. ID. NO. 49). In yet another embodiment, the cancer to be identified is Burkitt's, and the gene selection includes at least one of the genes with the following ImageID: 609663 (SEQ. ID. NO. 95), or 868304 (SEQ. ID. NO. 86). In a further embodiment, the cancer to be identified is a Ewing family of tumors cancer, and the gene selection includes at least one of the genes with the following Image Id: 770394 (SEQ. ID. NO. 20), 866702 (SEQ. ID. NO. 16), 357031 (SEQ. ID. NO. 18), 377461 (SEQ. ID. NO. 19), 52076 (SEQ. ID. NO. 13), 1473131 (SEQ. ID. NO. 15), 208718 (SEQ. ID. NO. 2), 80338 (SEQ. ID. NO. 14), 377731 (SEQ. ID. NO. 23), 814260 (SEQ. ID. NO. 17), 364934 (SEQ. ID. NO. 12), 755599 (SEQ. ID. NO. 25), 291756 (SEQ. ID. NO. 1), 308497 (SEQ. ID. NO. 24), or combinations thereof.

Another embodiment of the invention includes a selection of least one product of a selection of genes. As used herein, the term "product of a gene" or "gene product" can include entities that are naturally produced by the cancer cell. Examples of gene products include, but are not limited to, DNA, mRNA, and proteins. Gene products can be utilized in methods of the invention for diagnosing a cancer or as a target for therapeutic treatment.

The invention includes gene selections that can include one or more genes chosen from Table 2, 2b or 5. Table 2 lists 41 genes that are specifically expressed in one of the four types of SRBCTs that have not been previously reported to relate to cancer, and which could be used, in any combination, to make up a selection of genes in accordance with the invention. Table 2b shows the 96 top ranked genes, including the 41 genes of Table 2. Alternatively, Table 5 lists the top 200 ranked genes that also include those of Table 2b.

One embodiment of the invention includes a method of targeting a product of at least one of the genes in table 5 that includes administering a therapeutic agent having a therapeutic effect on said gene product. Another embodiment includes a method of therapeutic treatment of a cancer by using a selection of genes or their products that are expressed in a cancer cell, wherein the genes and/or their products function to characterize the cancer when the gene selection from the cancer cell is compared to the expression of an identical selection of genes from a noncancerous cell, or a different type of cancer cell. Another embodiment includes a method of targeting a product of at least one of the genes in table 2. Yet another embodiment includes a method of targeting a product of at least one of the genes of in table 6, 7, 8 or 9. A therapeutic agent is a biological or chemical entity that are based on some aspect of a gene. Examples of therapeutic agents include, but are not limited to, vaccines, antibodies, oligonucleotide DNA antisense, RNAi, chemical molecules, proteins, inhibitors, antagonists, or combinations thereof. Having a therapeutic effect on a gene product can include, but is not limited to, inhibition of some activity or process of a cell, cessation of some activity or process of a cell, an increase in some activity or process of a cell, interference with some process or activity of a cell, modification of the expression of at least one gene, modification of the expression of at least one gene product, modification of the function of at least one gene, and modification of the function of at least one gene product.

Administration of a therapeutic agent can include delivery of the therapeutic agent to the cell, to the vicinity of the cell, to the vicinity of a tumor, to a patient that has a tumor, or any combination thereof. In one embodiment of the invention, a method of targeting the product of at least one gene is undertaken in order to have an effect on a cancer cell or tumor. To have an effect on a cancer cell means to alter the course of progression, development, or metastasis of a cancer cell. Cancer cells that can be affected by methods of the invention include, but are not limited to, neuroblastoma, rhabdomyosarcoma, Burkitt's, and the Ewing family of tumors. Methods of having an effect on these various types of cancers can be accomplished by having an effect on a product of at least one gene of tables 6, 7, 8, and 9 respectively.

Another embodiment of the invention includes a method of targeting the product of at least one gene of table 10 that includes administering a therapeutic agent having a therapeutic effect on said gene product. A therapeutic agent is a biological or chemical entity that are based on some aspect of a gene. Examples of therapeutic agents include, but are not limited to, vaccines, antibodies, oligonucleotide DNA antisense, RNAi, chemical molecules, proteins, inhibitors, antagonists, or combinations thereof. Having a therapeutic effect on a gene product can include, but is not limited to, inhibition of some activity or process of a cell, cessation of some activity or process of a cell, an increase in some activity or process of a cell, and interference with some process or activity of a cell.

Administration of a therapeutic agent can include delivery of the therapeutic agent to the cell, to the vicinity of the cell, to the vicinity of a tumor, to a patient that has a tumor, or any combination thereof. In one embodiment of the invention, a method of targeting the product of at least one gene is undertaken in order to have an effect on a cancer cell or tumor. To have an effect on a cancer cell means to alter the course of progression, development, or metastasis of a cancer cell. Cancer cells that can be affected by methods of the invention include, but are not limited to, neuroblastoma, rhabdomyosarcoma, Burkitt's, and the Ewing family of tumors. Methods of having an effect on these various types of cancers can be accomplished by having an effect on a product of at least one gene of tables 6, 7, 8, and 9 respectively.

Another embodiment of the invention includes methods of using a selection of genes that function to characterize the cancer when the gene selection from a cancer cell is compared to the expression of an identical selection of genes from a noncancerous cell or an identical selection of genes from a different type of cancer cell expressed in a cell for diagnosing a cancer. As used herein, diagnosing can include detection, prognosis and prediction, classification, and or monitoring.

One embodiment of the invention includes such a method for diagnosis that includes use of a gene selection that includes at least one gene in Table 5. Another embodiment includes such a method for diagnosis that includes use of a gene selection that includes at least one gene from Table 2. The cancer to be diagnosed can include neuroblastoma, rhabdomyosarcoma, Burkitt's, Ewing family of tumors, or combinations thereof.

As used herein, "Image ID" or "Clone ID" refer to particular genes that are given in the various tables. In some embodiments of the invention, methods for diagnosing include use of a gene selection that includes one or more genes with a given Image ID. In one embodiment, the cancer to be diagnosed is neuroblastoma, and the gene selection includes at least one of the genes with the following Image Id: 812105 (SEQ. ID. NO. 32), 383188 (SEQ. ID. NO. 38), 82225 (SEQ. ID. NO. 42), 878280 (SEQ. ID. NO. 33), 135688 (SEQ. ID. NO. 44), 308231 (SEQ. ID. NO. 39), 486110 (SEQ. ID. NO. 45), 377048 (SEQ. ID. NO. 40), 784257 (SEQ. ID. NO. 34), 395708 (SEQ. ID. NO. 30), 292522 (SEQ. ID. NO. 36), or 813266 (SEQ. ID. NO. 47). In another embodiment, the cancer to be diagnosed is rhabdomyosarcoma and the gene selection includes at least one of the genes with the following Image Id: 244618 (SEQ. ID. NO. 77), 298062 (SEQ. ID. NO. 74), 324494 (SEQ. ID. NO. 62), 122159 (SEQ. ID. NO. 66), 788107 (SEQ. ID. NO. 52), 377671 (SEQ. ID. NO. 68), 784224 (SEQ. ID. NO. 71), 293500 (SEQ. ID. NO. 80), 42558 (SEQ. ID. NO. 79), 246377 (SEQ. ID. NO. 51), 809901 (SEQ. ID. NO. 67), 769959 (SEQ. ID. NO. 69), or 755750 (SEQ. ID. NO. 49). In yet another embodiment, the cancer to be diagnosed is Burkitt's, and the gene selection includes at least one of the genes with the following ImageID: 609663 (SEQ. ID. NO. 95), or 868304 (SEQ. ID. NO. 86). In a further embodiment, the cancer to be diagnosed is a Ewing family of tumors cancer, and the gene selection includes at least one of the genes with the following Image Id: 770394 (SEQ. ID. NO. 20), 866702 (SEQ. ID. NO. 16), 357031 (SEQ. ID. NO. 18), 377461 (SEQ. ID. NO. 19), 52076 (SEQ. ID. NO. 13), 1473131 (SEQ. ID. NO. 15), 208718 (SEQ. ID. NO. 2), 80338 (SEQ. ID. NO. 14), 377731 (SEQ. ID. NO. 23), 814260 (SEQ. ID. NO. 17), 364934 (SEQ. ID. NO. 12), 755599 (SEQ. ID. NO. 25), 291756 (SEQ. ID. NO. 1), 308497 (SEQ. ID. NO. 24), or combinations thereof. Another embodiment of the invention includes use of a product of at least one of those genes for diagnosis of a cancer.

Another embodiment of the invention includes devices for use in a method of diagnosis. Examples of such devices can include protein arrays, cell arrays, a device to detect single polymorphisms in disease conditions, devices containing metaphase BAC genomes, cDNA arrays, and oligonucleotide arrays.

WORKING EXAMPLES

The following examples provide a nonlimiting illustration of various embodiments of the invention.

Example 1

Preparation of Microarrays

Preparation of Glass cDNA Microarrays, Probe Labeling, Hybridization and Image acquisition were performed according to the protocol given below, which is a standard NHGRI protocol (nhgri/nih/gov/DIR/LCG/ISK/HTML/protocol)

Gene-specific DNA was produced by PCR amplification of purified template plasmid DNAs from cloned ESTs. The PCR product was purified by ethanol precipitation, thoroughly resuspended in 3×SSC, and printed onto a poly-L-lysine coated slide.

The materials, reagents, and solutions used include: 96 well alkaline lysis miniprep kit (Edge BioSystems, Gaithersburg, Md.); LB Broth (Biofluids, Rockville, Md.); Superbroth (Biofluids, Rockville, Md.); dATP, dCTP, dGTP, dTTP, 100 mM each #27-2035-$O_2$, store frozen, −20° C. (Pharmacia, Peapack, N.J.); PCR primer AEK M13F (5'-GTTG-TAAAACGACGGCCAGTG-3') (SEQ. ID. NO. 97) and AEK M13R (5'-CACACAGGAAACAGCTATG-3') (SEQ. ID. NO. 98) at 1 mM concentration, store frozen, −20° C.; 10×PCR Buffer, # N808-0189, and Ampli-Taq DNA polymerase, # N808-4015 store frozen, −20° C. (Perkin Elmer, Norwalk, Conn.); Carbenicillin (Gibco-BRL, Rockville, Md.); Ethanol (200 Proof USP Ethyl Alcohol); 1M Tris-HCl (pH 8); 0.5M NaEDTA (pH 8); T Low E; Buffer; 20×SSC; Glycerol (enzyme grade); Sodium Acetate (tri-hydrate); Boric Acid; Sodium Hydroxide (1M); Glacial Acetic Acid; Succinic anhydride, #23969-0 and 1-methyl-2-pyrrolidinone, # 32863-4 (Aldrich Chemical Co., St. Louis, Mo.); Diethyl Pyrocarbonate (DEPC) treated $H_2O$; Master set of clone-purified, sequence verified human ESTs (e.g. gf211 release, Research Genetics, Huntsville, Ala.); 96 pin inoculating block (#VP 4088, V&P Scientific, Inc, San Diego, Calif.); Airpore Tape Sheets, (# 19571, QIAGEN Inc., Valencia, Calif.); Sterile 96-well plate seals, (e.g. # SEAL-THN-STR (Elkay Products, Inc., Shrewsbury, Mass.); 96-well U-Bottom Microtiter Plates, #3799 and 96-well V-Bottom Microtiter Plates, #3894 (Corning Inc., Corning, N.Y.); Thin wall PCR plate and Cylcleseal PCR plate sealer (e.g. #1038-50-0 and #1044-39-4, Robbins Scientific Corp. Sunnyvale, Calif.); household one-gallon sealable storage bags (e.g. Glad Lock); heat sealable storage bags and heat sealer; 0.2 mm Sterile Filtration unit; Diamond scribe for writing on slides; Pyrex baking dish (~24×34×5 cm); UV transparent plastic wrap (e.g. Glad Cling Wrap); 30 slide rack (stainless steel) #113 and 30 slide glass tank, #122 (Shandon Lipshaw, Pittsburgh, Pa.); 1 L glass tank; 1 L glass beaker; 1 L graduated; cylinder; Stir bar; Slide Box (plastic with no paper or cork liners), (e.g. #60-6306-$O_2$, PGC Scientific, Gaithersburg, Md.); PCR heat cycler (e.g. DNA Engine Tetrad, MJ Research, Waltham, Mass.); Centrifuge with a horizontal ("swinging bucket") rotor with a depth capacity of 6.2 cm for spinning microtiter plates and filtration plates (e.g. Sorvall Super T 21, Sorvall Inc., Newtown, Conn.); 37° C. Shaker incubator with holders for deep-well plates; 37° C. Waterbath; 65° C. Incubator; Vortex mixer; Immunowash microtiter plate washer, #1575 (BioRad, Hercules, Calif.); pH Meter; Platform Shaker; UV Stratalinker 2400, (Stratagene La Jolla, Calif.); Stirrer/Hotplate; Robotic slide printer; −80° C. Freezer; −20° C. Freezer; 45% (w/v) Sterile Glycerol; 450 grams enzyme grade glycerol per liter 9 Autoclave and store at room temperature); T low E Buffer; 1M Tris-HCl (pH 8.0) 10 mL; 0.5 M EDTA (pH 8.0) 0.2 mL; DEPC treated $H_2O$ 990 mL (Autoclave and store at room temperature); Carbenicillin stock solution (1 gram of carbenicillin in 10 mls of sterile water, Sterile filter with a 0.2 micron filter, Store frozen at −20° C.); LB with 100 µg/ml carbenicillin (Add 1 ml of carbenicillin stock solution to 1 liter of LB, Make fresh); 3M Sodium Acetate pH=6.0 (408.24 grams sodium acetate (trihydrate) per liter, 3M acetic acid (172.4 ml per liter), Titrate the pH of the 3M sodium acetate solution to pH 6.0 with the 3M acetic acid solution, Filter sterilize using a 0.2 micron filter, Store at room temperature); Ethanol/acetate mix (Ethanol (100%) 950 ml, Sodium acetate pH=6.0, 50 ml); 1000 ml 3×SSC; DEPC $H_2O$ 42.5 ml; 20×SSC 7.5 ml; 50 ml 70% Ethanol; Ethanol (100%) 350 ml; DEPC $H_2O$ 150 ml; 500 ml.

The first step was to grow the EST clones. The cDNA clones were obtained from Research Genetics (Huntsville, Ala.) and were their standard microarray set, which consisted of 3789 sequence-verified known genes and 2778 sequence-verified ESTs.

The sealed master plates were incubated over night at 37° C. Most suppliers provide low density bacterial cultures. Replicating directly from these dilute stocks frequently results in non-growth in the secondary culture. If making the template from a plate that had previously been cultured to high density before freezing, this initial growth step should not be used, as it will reduce the viability of the cultures.

A set of standard 96 well round (U) bottom plates were then prepared by labeling all plates and placing 100 µl of LB broth containing 100 µg/ml carbenicillin in each well. These plates were used as working copies. To preserve the master set of plates, it was useful to make replicate copies of the master plate to serve as working copies when the master plate was first replicated. The EST clones were then checked to insure that they were in a vector conferring ampicillin resistance, as is common with human IMAGE clones.

The master plates were spun briefly (about two minutes) at 1000 rpm in a horizontal microtiter plate rotor to remove condensation and droplets from the seals before opening. Bacterial culture fluid on the sealers can easily be transferred from one well to others, cross-contaminating the stocks.

Then a container was partially filled with 100% alcohol. The 96 pin-replicating tool was dipped in the alcohol, removed and then the pins were flamed.

The inoculation block was allowed to cool briefly, then the replicating tool was dipped in the master plate and then into the daughter plate. This was repeated as necessary for each plate inoculated. It is useful to color the plate corner near the A-1 well of all master and daughter plates with a marker pen before beginning the replication process in order to reduce mistakes in the relative orientation of the plates. The suggested plates have a notch at this corner as well.

The inoculated LB plates, with the lids on, were placed into a one gallon sealable bag containing a moistened paper towel and grow overnight at 37° C. Many 37° C. incubators tend to dry out microtiter plate cultures. Placing the plates in a highly humidified bag avoids this problem.

Next, deep well plates were filled with 1 ml of Superbroth (100 µg/ml carbenicillin) per well. These plates served as the source of culture for template preparation. Using the replicating tool, the deep well plates were then inoculated directly from the freshly grown LB plates. Next, the openings of the deep well plates were covered with Qiagen Airpore Tape Sheets and the plastic lids were placed over the sheet. The plates were then placed in a 37° C. shaker incubator at 200 RPM for twenty-four hours. 50 l of 45% (w/v) sterile glycerol was added to each well of any working plates that are to be frozen (−80° C.) and subsequently used as culture sources.

After the EXT clones were grown, the plasmid templates have to be isolated. First, the lysis buffer (Edge Biosystems Kit) was warmed to 37° C. to dissolve the SDS. Then the RNAse solution was added to the resuspension buffer (Edge Biosystems Kit), 1 ml/100 ml, and stored at 4° C. The receiving plates were prepared from the Edge Biosystems Kit by adding 350 µl of ethyl alcohol to each well of the receiving plates. The filter plate was then placed on top and secured with tape. The bacterial cultures in the deep well plates were centrifuged at 1500×g for seven minutes in a centrifuge equipped with a horizontal rotor for 96-well plates. They were then briefly inverted and excess media was tapped out on a clean paper towel. The pellets will loosen and may be lost when pouring off excess media if this step is delayed.

The pellet was then resuspended in 100 µl of Resuspension Buffer, and Vortexed until the entire pellet was re-suspended. This step is critical. Poor resuspension of the cells results in clumps of cells that do not lyse in subsequent steps. This reduces the yield and decreases the purity of the product. 100 µl of Lysis Buffer was then added and the solution was mixed gently by rocking the plates from side to side, to avoid shearing the bacterial chromosomal DNA. 100 µl of Precipitation buffer was added to each well and briefly mixed. Then, 100 µl of Neutralization buffer was added to each well and Vortexed.

The contents of the deep wells were then transferred to the waiting filter plates/receiving plate stacks using the wide bore pipette tips provided in the kits. The stacked plates were then centrifuged at 1500×g for twelve minutes in a centrifuge equipped with a horizontal rotor for 96-well plates. The stacked plates were then removed from the centrifuge. The filter plates were removed and discarded. The alcohol and filtrate were decanted from the receiver plate and the excess alcohol was touched off on clean paper towels. 500 µl of 70% ethanol was added to each well and immediately decanted and excess alcohol was touched off with a clean paper towel. Then, the plates were placed in a clean drawer without their lids, covered with a clean paper towel and allowed to dry overnight.

The next day, the DNA was resuspended in 200 µl of T Low E Buffer. The top was sealed with plate sealer and rehydrated at 4° C. for at least two days before using. They were stored at −20° C. in the interim.

After the plasmid templates have been isolated, the EST inserts were amplified. For each 96 well plate to be amplified, a PCR reaction mixture was prepared containing the following ingredients: 1000 µl of 10×PCR Buffer, 20 µL of dATP (100 mM), 20 µL of dGTP (100 mM), 20 µL of dCTP (100 mM), 20 µL of dTTP (100 mM), 5 µL of AEK M13F primer (1 mM), 5 µL of AEK M13R primer (1 mM), 100 µL of Ampli-Taq polymerase (5 U/µl), and 8800 mL of $H_2O$. The 96-well PCR plates were then labeled and 100 µl of the PCR reaction mixture from above was aliquotted to each well. The plates were then gently tapped to insure that no air bubbles were trapped at the bottom of the wells. 1 µl of purified EST plasmid template from above was then added to each well. The donor and recipient plates were then marked at the corner, near the A1 well to facilitate correct orientation during transfer of the template. It was important to make sure that the pipette tips were all submerged in the PCR reaction mix when delivering the template. Missing the liquid was easier when multi-channel pipettes were used.

The following thermal cycle series was then performed: 1 initial cycle of heating to 96° C. and holding for 30 sec, 25 cycles of denaturing at 94° C. for 30 sec, reannealing at 55° C. for 30 sec, and extending at 72° C. for 150 sec, one final cycle of holding at 72° C. for 5 minutes, then cooling to ambient temperature. After the above cycle, the plates were held at 4° C. while quality controls were performed.

The quality control was done by agarose gel electrophoresis of the ESTs. If this was the first time the template for these ESTs was being amplified, 2 µl of each PCR product was analyzed on a 2% agarose gel. If amplified products from this template had been previously tested, then one row of wells from each plate amplified was analyzed. Gel imaging allowed a rough quantitation of product while giving an excellent characterization of the product. Band size, as well as the number of bands observed in the PCR products, contributed to an understanding of the final results of the hybridization. The use of gel well formats suitable for loading from 96 well plates and programmable pipetters made this form of analysis feasible on a large scale.

The materials, reagents and solutions for the quality control check included: Electrophoresis apparatus with capacity for four 50 well combs, (e.g. #D3, Owl Scientific, Woburn, Mass.); 50× Tris-Acetate Electrophoresis BufferM; Agarose; Dye Solution (Xylene Cyanol/Bromophenol Blue) (e.g. #351-081-030, Quality Biological Inc., Gaithersburg Md.); Glycerol (enzyme grade); Ethidium Bromide solution (10 mg/ml); 100 base-pair ladder size standard; Programmable, 12-channel pipetter (e.g. #2019, Matrix Technologies, Lowell, Mass.); Disposable microtiter mixing trays (e.g. Falcon #353911, Becton Dickinson, Franklin Lake, N.J.); Electrophoresis power supply; 1×TAE Buffer; 50×TAE Buffer 40 ml; Ethidium Bromide (10 mg/ml) 0.1 ml and Water 960 ml; 1000 ml; Loading Buffer; Glycerol (enzyme grade) 4.0 ml, DEPC Water 0.9 ml, and Dye Solution* 0.1 ml for a total of 5.0 ml (*This solution is 0.25% (w/v) Xylene Cyanol and 0.25% (w/v) Bromophenol Blue); 100 bp Size Standards; DNA ladder (1 mg/ml) 50 µL, 1 M Tris-HCl (pH 8.0) 5 µl, 0.5 M EDTA (pH 8.0) 5 µl, and Loading Buffer 440 µl for a total of 500 µl The electrophoresis was carried out with a 2% agarose gel (1×TAE) with four combs (50 tooth) that was submerged in an electrophoresis apparatus with sufficient 1×TAE buffer to just cover the surface of the gel. A reservoir of Loading Buffer was prepared, using 12 wells of a microtiter plate. Then a pipetter was programmed to sequentially carry out the following steps: fill with 2 µl, fill with 1 µL, fill with 2 µl, mix a volume of 5 µl five times, expel 5 µl. Twelve (12) disposable tips were then placed on the pipetter. 2 µl of PCR product from wells A1-A12 of the PCR plate were loaded, followed by 1 µl of air, then 2 µl of Loading Buffer from the reservoir. The tips were then placed in clean wells of a disposable mixing tray and the pipette was allowed to mix the sample and loading dye. The pipette tip was then placed in a 50 well row so that the tip containing the PCR product from well A1 is in the second well of the row, and the other tips are in every other succeeding well.

The process was repeated (changing tips each time), to load PCR plate row B starting in the 3rd well, interleaved with the A row, the C row starting at well 26, and the D row at well 27, interleaved with the C row. Then 5 µl of 100 bp Size Standards were placed in wells 1 and 50. This process was repeated, to load samples from rows E, F, G, and H in the second, 50 well row of gel wells, to load samples from two 96 well PCR plates per gel, or single row samples from 16 PCR plates. To reduce diffusion and mixing, a voltage was applied to the gel for a minute between loading each well strip. This caused the DNA to enter the gel, and reduced band spreading and sample loss.

A voltage was then applied to the gel and it was run until the bromophenol blue (faster band) had nearly migrated to the next set of wells. For a gel that is 14 cm in the running dimension, and 3 cm between each row of wells, 200 volts were applied for 15 minutes. Digital photos of the gel were taken and the images stored for future reference. The gels should show bands of fairly uniform brightness distributed in size between 600 to 2000 base-pairs. Further computer analysis of such images can be carried out with image analysis packages to provide a list of the number and size of bands. Ideally this information can be made available during analysis of the data from hybridizations involving these PCR products.

After the quality control checks are run on the plates, the next step involves purifying the PCR products. 96 well V-bottom plates were filled with 200 µl per well of ethanol/acetate mix. The ethanol acetate solution used for precipitation is less acidic (pH 6) than is typically used. In this instance, more acidic solutions produce precipitates which are harder to resuspend without improving yield.

100 µl per well of PCR product was transferred into V-bottom plates and mixed by pipetting a volume of 75 µl per well four times. The plates were then placed in a −80° C. freezer for one hour or stored overnight at −20° C. The plates were stored at −20° C. if they were to be left for more than one hour, because aggressive precipitation produces precipitates which are hard to resuspend. The plates were then thawed to reduce brittleness and melt any ice, which may have formed in the wells.

The plates were loaded into a centrifuge with a horizontal microtiter plate rotor and spun at 2600×g for 40 minutes at 4° C. Next, the supernatant from each well was aspirated using the Immunowash plate washer. Settings for the depth of aspiration by the plate washer needed to be adjusted to suit the microtiter plates used. It is advisable to leave approximately 10-20 ml in the bottom of the well to avoid disturbing the pellet.

200 µl of 70% ethanol was delivered to each well in the plate using the Immunowash plate washer, and the plates were centrifuged at 2600×g for 40 minutes. The supernatant was aspirated from each well using the Immunowash plate washer, and the plates were dried overnight in a closed drawer. They should not be dried in a speed-vac because desiccated PCR products are hard to resuspend.

After the PCR products were purified, they were then resuspended by adding 40 µl of 3×SSC per well. The plates were then sealed with a foil sealer, taking care to achieve a tight seal over each well. The plates were then placed in heat sealable bags with paper towels moistened with 3×SSC and the bag was sealed with a heat sealer. The high external humidity within the sealed bag helped to keep the volumes in the individual wells from varying. The bags were then placed in a 65° C. incubator for 2 hours. The heat in the incubator was then turned off, and the plates were allowed to cool gradually in the incubator to avoid condensation on the sealers. The plates were stored at −20° C.

The yield of the PCR suspension was then checked by fluorometric determination of DNA concentration. 1 µl of resuspended PCR product from one row of wells from each plate on a 2% agarose gel was analyzed as previously described. Adequate precipitation and resuspension produced very intense bands, with no material failing to leave the loading well, and no smear of material from the band towards the loading well.

While it would be ideal to be able to exactingly quantify each EST PCR product and spot each DNA species at equivalent concentrations, it is impractical for most labs to do so when thousands of ESTs must be prepared. Fortunately, it is possible to use a strategy where excess DNA is spotted, so that the exact quantities used do not produce much variation in the observed results. When using this strategy, it is necessary to track the average productivity of the PCR reactions. Fluorometry provides a simple way to obtain an approximate concentration of the double-stranded PCR product in the PCR reaction mix.

Next, the double stranded DNA was quantified. The materials, reagents, and solutions necessary include: reference double-stranded DNA (0.5 mg/ml) (e.g. #15612-013 Gibco/BRL, Bethesda, Md.), 96 well plates for fluorescent detection (e.g. #7105, Dynex, Chantilly, Va.), Fluorometer (e.g. #LS50B, Perkin Elmer, Norwalk, Conn.), FluoReporter Blue dsDNA Quantitation Kit (#F-2962, Molecular Probes, Eugene, Oreg.), TE, 12 channel multi-pipetters, Computer equipped with Microsoft Excel software, Ds-DNA Standards: 50 µg/ml, 100 µg/ml, 250 µg/ml, 500 µg/ml, µl TE 90, 80, 50, 0 µl dsDNA (0.5 mg/ml) 10, 20, 50, 100, (It is good practice to check both the integrity (agarose gel) and the concentration (absorbance) of the standard before use); Fluor Buffer (Hoechst 33258 solution (contains the dye at an unspecified concentration in a 1:4 mixture of DMSO:$H_2O$) (from kit) 25 µl, TNE Buffer (TNE Buffer is 10 mM Tris-HCl (pH 7.4), 2 M NaCl, 1 mM EDTA) (from kit) 10 ml.

The double stranded DNA was quantified as follows. 96 well plates were labeled for fluorescence assay. 200 µl of Fluor Buffer was added to each well. 1 µl of PCR product from each well in a row of a PCR plate was added to a row of the fluorometry plate. Samples were added to rows A through G of the fluorometry plate. In the final row of the fluorometry plate 1 µl of each of the series of ds-DNA standards 0 µg/ml (TE only), 50, 100, 250 and 500 µg/ml ds-DNA were added. This series was repeated twice in the final row.

The fluorometer was set for excitation at 346 nm and emission at 460 nm, and adjusted as necessary to read the plate. If the fluorometer used did not support automated analysis, the data table was exported to Excel. The response for the standards was tested to see that it was linear and reproducible from the range of 0 to 500 µg/ml of ds-DNA.

Next, the concentration of ds-DNA in the PCR reactions was calculated using the following equation, after subtracting the average 0 µg/ml value from all other sample and control values:

[ds-DNA(µg/ml)]=((PCR sample value)/(average 100 µg/ml value))*100

Constantly tracking the yields of the PCRs makes it possible to rapidly detect many ways in which PCR can fail or perform poorly. This assay can also be applied after precipitation and resuspension of the PCR products to monitor overall recovery of product. 1 µl of amplified products from one row of wells from each amplified plate by fluorometry was analyzed.

Slides were then coated with poly-L-lysine to have a surface that is both hydrophobic and positively charged. The hydrophobic character of the surface minimizes spreading of the printed spots, and the charge appears to help position the DNA on the surface in a way that makes cross-linking more efficient.

Materials, reagents, and solutions for coating the slides includes: Gold Seal Microscope Slides (#3011, Becton Dickinson, Franklin Lake, N.J.), Ethanol (100%), Poly-L-lysine (#P8920, Sigma, St. Louis, Mo.), 50 Slide Stainless Steel Rack, #900401, and 50 Slide Glass Tank, #900401, (Wheaton Science Products, Millville, N.J.), Sodium Hydroxide, Stir Plate, Stir Bar, Platform Shaker, 30 Slide Rack, #196, plastic, and 30 slide Box, #195, plastic, (Shandon Lipshaw, Pittsburgh, Pa.), Sodium Chloride, Potassium Chloride, Sodium Phosphate Dibasic Heptahydrate, Potassium Phosphate Monobasic, Autoclave, 0.2 mm Filter: Nalgene, Centrifuge: Sorvall Super 20, Slide Box (plastic with no paper or cork liners), (e.g. #60-6306-02, PGC Scientific, Gaithersburg, Md.), 1 L Glass Beaker; 1 L Graduated Cylinder, 1M Sodium Borate (pH 8.0) (Dissolve 61.83 g of Boric acid in 900 ml of DEPC $H_2O$. Adjust the pH to 8.0 with 1N NaOH. Bring volume up to one liter. Sterilize with a 0.2 micron filter and store at room temperature), Cleaning Solution ($H_2O$ 400 ml, Ethanol 600 ml, NaOH 100 g—Dissolve NaOH in $H_2O$. Add ethanol and stir until the solution clears. If the solution does not clear, add $H_2O$ until it does), and Poly-L-lysine Solution (poly-L-lysine (0.1% w/v) 35 ml PBS 35 ml $H_2O$ 280 ml 350 ml)

First, the slides are placed into 50 slide racks and the racks are placed in glass tanks with 500 ml of cleaning solution. Gold Seal Slides are highly recommended, as they have been found to have consistently low levels of autofluorescence. It was important to wear powder free gloves when handling the slides to avoid contamination.

The tanks are placed on platform shakers for two hours at 60 rpm. After being shook, the cleaning solution was poured out, and the slides were then washed in $H_2O$ for three minutes.

This wash was repeated four times. The slides were then transferred to 30 slide plastic racks and placed into small plastic boxes for coating. The slides were then submerged in 200 ml poly-L-lysine solution per box. The slide boxes were then placed on platform shaker for one hour at 60 rpm. The slides were rinsed three times with $H_2O$, and submerged in $H_2O$ for one minute, and then centrifuged for two minutes at 400×g and the slide boxes used for coating were dried.

The slides were then placed back into the slide box used for coating and allowed to stand overnight before transferring to a new slide box for storage. This allowed the coating to dry before it was handled. The slides were allowed to age for two weeks on the bench, in a new slide box, before they were printing on. The coating dried slowly, becoming more hydrophobic with time.

Slide boxes used for long term storage should be plastic and free of cork lining. The glue used to affix the cork will leach out over time and give slides stored in these types of boxes a greasy film that has a high degree of autofluorescence. All glassware and racks used for slide cleaning and coating should be cleaned with highly purified $H_2O$ only, and detergent should not be used.

Once the slides were coated, they were printed. The variety of printers and pens for transferring PCR products from titer plates to slides precludes highly detailed descriptions of the process. The following steps provide a general description of the processing.

The print pens were pre-cleaned according to the manufacturer's specification. The printer slide deck was then loaded with poly-L-lysine coated slides from above. The plates containing the purified EST PCR products were thawed and centrifuged briefly, (about two minutes) at 1000 rpm in a horizontal microtiter plate rotor to remove condensation and droplets from the seals before being opening. 5 to 10 μl of the purified EST PCR products were transferred to a plate that served as the source of solution for the printer. Printing with quill-type pens usually requires that the volume of fluid in the print source was sufficiently low, so that when the pen was lowered to the bottom of the well, it was submerged in the solution to a depth of less than a millimeter. This keeps the pen from carrying a large amount of fluid on the outside of the pen shaft and producing variable, large spots on the first few slides printed.

A repetitive test print was run on the first slide. In this operation, the pens were loaded with the DNA solution, and then the pens serially deposited this solution on the first slide in the spotting pattern specified for the print. This test was run to check the size and shape of the specified spotting pattern, as well as its placement on the slide. It also served to verify that the pens were loading and spotting, and that a single loading produced as many spots as were required to deliver material to every slide in the printer.

If one or more of the pens was not performing at the desired level, it was re-cleaned or substituted with another pen and tested again. If all pens were performing, the full print was carried out.

At the end of the print, the slides were removed from the printer, labeled with the print identifier and the slide number by writing on the edge of the slide with a diamond scribe and placed in a dust free slide box to age for one week. It was useful to etch a line, which outlined the printed area of the slide, onto the first slide. This served as a guide to locate the area after the slides have been processed, and the salt spots were then washed off.

The slides were placed, printed side face up, in a casserole dish and covered with cling wrap. The slides were then exposed to a 450 mJ dose of ultraviolet irradiation in the Stratalinker. Slides should have been and were aged at ambient temperature in a closed slide box for one week prior to blocking. The slides were then transferred to a 30 slide stainless steel rack and the rack was placed into a small glass tank. 6.0 g succinic anhydride was dissolved in 325 ml 1-methyl-2-pyrrolidinone in a glass beaker by stirring with a stir bar. Nitrile gloves were worn and the work was carried out in a chemical fume hood while handling 1-methyl-2-pyrrolidinone (a teratogen).

25 ml 1M sodium borate buffer (pH 8.0) was added to the beaker. The solution was allowed to mix for a few seconds, then rapidly poured into a glass tank with slides. Succinic anhydride hydrolyzed quite rapidly once the aqueous buffer solution was added. To obtain quantitative passivation of the poly-L-lysine coating, it was critical that the reactive solution be brought in contact with the slides as quickly as possible. The glass tank was placed on a platform shaker in a fume hood for 20 minutes. Small particulates resulting from precipitation of reaction products may be visible in the fluid.

While the slides were incubating on the shaker a boiling $H_2O$ bath was prepared to denature the DNA on the slides. After the slides were incubated for 20 minutes, they were transferred into the boiling $H_2O$ bath. The heating element was immediately turned off after the slides were submerged in the bath. The slides were allowed to stand in the $H_2O$ bath for 2 minutes. The slides were then transferred into a glass tank filled with 100% ethanol and incubated for 4 minutes. The slides were removed and centrifuged at 400 rpm for 3 minutes in a horizontal microtiter plate rotor to dry the slides. The slides were then transferred to a clean, dust free slide box and allowed to stand overnight before being used for collection of gene expression data.

Example 2

Cell Culture and Tumor Samples

The source and other information for the cell lines and tumor samples used herein are described in Table 3 below for both the training set and the test samples.

TABLE 3

Supplement Table: Known Molecular Characteristics of Samples.

| Sample Label | Histological Diagnosis | Molecular Markers | Source Label | Source |
|---|---|---|---|---|
| EWS-C1 | EWS-C | EWS-FLI1, 10–6 | A4573 | NCI |
| EWS-C2 | EWS-C | EWS-FLI1, type I | TC71 | NCI |
| EWS-C3 | EWS-C | EWS-FLI1, type I | TC106 | NCI |
| EWS-C4 | EWS-C | EWS-FLI1, type I | 5838 | NCI |
| EWS-C6 | EWS-C | EWS-FLI1, type I | A673 | NCI |
| EWS-C7 | EWS-C | EWS-FLI1, type I | ES-CL1 | MSKCC |

TABLE 3-continued

Supplement Table: Known Molecular Characteristics of Samples.

| Sample Label | Histological Diagnosis | Molecular Markers | Source Label | Source |
|---|---|---|---|---|
| EWS-C8 | EWS-C | EWS-FLI1, type I | TC32 | NCI |
| EWS-C9 | EWS-C | EWS-FLI1, type II | SK-ES-1 | ATCC |
| EWS-C10 | EWS-C | EWS-FLI1, type II | SK-N-MC | ATCC |
| EWS-C11 | EWS-C | EWS-FLI1, type II | RDES | ATCC |
| EWS-T1 | EWS-T | EWS-FLI1, type I | ES20 | MSKCC |
| EWS-T2 | EWS-T | EWS-FLI1, type II | ES13 | MSKCC |
| EWS-T3 | EWS-T | EWS-FLI1, type I | ES16 | MSKCC |
| EWS-T4 | EWS-T | EWS-FLI1, type I | ES17 | MSKCC |
| EWS-T6 | EWS-T | EWS-FLI1, 7–8 | ES22 | MSKCC |
| EWS-T7 | EWS-T | EWS-ERG, 7–9 | ES25 | MSKCC |
| EWS-T9 | EWS-T | EWS-FLI1, type I | 9602P006 | CHTN |
| EWS-T11 | EWS-T | EWS-FLI1, type I | 9703P152 | CHTN |
| EWS-T12 | EWS-T | EWS-FLI1, type I | 9704P218 | CHTN |
| EWS-T13 | EWS-T | EWS-FLI1, type I | ES23 | MSKCC |
| EWS-T14 | EWS-T | EWS-FLI1, type I | 9605P074 | CHTN |
| EWS-T15 | EWS-T | EWS-FLI1, type I | 9609P027 | CHTN |
| EWS-T19 | EWS-T | EWS-FLI1, type I | SARC75 | CHTN |
| RMS-C2 | ERMS-C | — | RD | ATCC |
| RMS-C3 | ARMS-C | ND | RH4 | NCI |
| RMS-C4 | ARMS-C | PAX3-FKHR | RH3 | NCI |
| RMS-C5 | ARMS-C | PAX3-FKHR | RH5 | NCI |
| RMS-C6 | ARMS-C | PAX3-FKHR | RH28 | NCI |
| RMS-C7 | ARMS-C | ND | RH30 | NCI |
| RMS-C8 | ERMS-C | — | CTR | ATCC |
| RMS-C9 | ARMS-C | PAX3-FKHR | RH4 | NCI |
| RMS-C10 | ARMS-C | PAX3-FKHR | RMS13 | NCI |
| RMS-C11 | ERMS-C | — | TE671 | ATCC |
| RMS-T1 | ARMS-T | PAX3-FKHR | RMS3 | MSKCC |
| RMS-T2 | ARMS-T | PAX3-FKHR | RMS6 | MSKCC |
| RMS-T3 | ERMS-T | — | RMS2 | MSKCC |
| RMS-T4 | ERMS-T | no PAX-FKHR | RMS5 | MSKCC |
| RMS-T5 | ARMS-T | PAX3-FKHR | RMS10 | MSKCC |
| RMS-T6 | RMS-T | ND | RT1 | CHTN |
| RMS-T7 | ERMS-T | — | RT4 | CHTN |
| RMS.T8 | RMS-T | ND | RT5 | CHTN |
| RMS.T10 | RMS-T | ND | RT2 | CHTN |
| RMS.T11 | ERMS-T | — | RHAB2 | CHTN |
| NB-C1 | NB-C | MYCN amp | KCNR | NCI |
| NB-C2 | NB-C | — | GICAN | NCI |
| NB-C3 | NB-C | — | SK-N-AS | ATCC |
| NB-C4 | NB-C | MYCN amp | LAN5 | NCI |
| NB-C5 | NB-C | MYCN amp | SK-N-BE2 | ATCC |
| NB-C6 | NB-C | MYCN amp | SK-N-DZ | ATCC |
| NB-C7 | NB-C | — | GICAN | NCI |
| NB-C8 | NB-C | — | NGP | NCI |
| NB-C9 | NB-C | — | SH-SY5Y | ATCC |
| NB-C10 | NB-C | MYCN amp | SK-N-FI | ATCC |
| NB-C11 | NB-C | Single copy MYCN | SK-N-SH | ATCC |
| NB-C12 | NB-C, | MYCN amp | CHP-134B | NCI |
| BL-C1 | BL-C | — | RAMOS (RAI) | ATCC |
| BL-C2 | BL-C | — | ST486 | ATCC |
| BL-C3 | BL-C | — | CA46 | ATCC |
| BL-C4 | BL-C | — | ST486 | ATCC |
| BL-C5 | BL-C | — | RAJI | ATCC |
| BL-C6 | BL-C | — | MC116 | ATCC |
| BL-C7 | BL-C | — | DAUDI | ATCC |
| BL-C8 | BL-C | — | SULTAN | ATCC |
| Teat1 | NB-C | MYCN amp | IMR32 | ATCC |
| Teat2 | EWS-C | ND | CHOP1 | NCI |
| Test3 | Osteosarcoma-C | — | OsA-CI | ATCC |
| Test4 | ARMS-T | — | ARMD1 | CHTN |
| Test5 | Sarcoma | — | A204 | ATCC |
| Test 6 | EWS-T | EWS-FLI1, type I | 9608P053 | CHTN |
| Test7 | BL-C | — | EB1 | ATCC |
| Test8 | NB-C | — | SMSSAN | NCI |
| Test9 | Sk. Muscle | — | SkM1 | CHTN |
| Test10 | ERMS-T | — | ERDM1 | CHTN |
| Test11 | Prostate Ca-C | — | PC3 | ATCC |
| Test12 | EWS-T | — | SARC67 | CHTN |
| Test13 | Sk. Muscle | — | SkM2 | CHTN |
| Test 14 | NB-T | Single copy MYCN | NB3 | DZNSG |
| Test 15 | BL-C | — | EB2 | ATCC |
| Test 16 | NB-T | Single copy MYCN | NB1 | DZNSG |
| Test 17 | ARMS-T | — | ARMD2 | CHTN |
| Test 18 | BL-C | — | GA10 | ATCC |

TABLE 3-continued

Supplement Table: Known Molecular Characteristics of Samples.

| Sample Label | Histological Diagnosis | Molecular Markers | Source Label | Source |
| --- | --- | --- | --- | --- |
| Test 19 | EWS-T | ND | ET3 | CHTN |
| Test 20 | EWS-T | EWS-FLI1, type I | 9903P1339 | CHTN |
| Test 21 | EWS-T | EWS-FLI1, type II | ES23 | MSKCC |
| Test 22 | ERMS-T | — | ERMD2 | CHTN |
| Test 23 | NB-T | Single copy MYCN | NB2 | DZNSG |
| Test 24 | ERMS-T | no PAX-FKHR | RMS4 | MSKCC |
| Test 25 | NB-T | Single copy MYCN | NB4 | DZNSG |

Supplement Table: Known molecular characteristics of samples. Table labels and abbreviations are described in Table 1 in the manuscript.
EWS and ARMS samples with noted translocations were verified by RT-PCR.
ND; not determined.
Amp.: amplification.

All the original histological diagnoses were made at tertiary hospitals, which have reference diagnostic laboratories with extensive experience in the diagnosis of pediatric cancers. Approximately 20% of all samples in each category were randomly selected, blinded and set aside for testing. To augment this test set, we added 4 neuroblastoma tumors and 5 non-SRBCT samples (also blinded to the authors performing the analysis). The EWSs had a spectrum of the expected translocations, and the RMSs were a mixture of both ARMS containing the PAX3-FKHR translocation and embryonal rhabdomyosarcoma (ERMS). The NBs contained both MYCN amplified and single copy samples. The BLs were cell lines derived from BL. Table 3 gives details of these samples as well.

This protocol details the methods used to extract RNA from cells, purify the RNA by a combination of phase extraction and chromatography, and prepare a labeled cDNA copy of the message fraction of the purified RNA. The protocol also describes the process of making fluorescent cDNA representations of the message pools within the isolated total RNA pools. This is accomplished by using the pure total RNA as a substrate for reverse transcription in the presence of nucleotides derivatized with either a Cy3 or a Cy5 fluorescent tag.

The materials, reagents, and solutions needed include: Trizol Reagent (#15596-018, Life Technologies, Rockville, Md.); RNeasy Maxi Kit (# 75162, Qiagen, Valencia, Calif.); Chloroform; Ethanol (200 Proof USP Ethyl Alcohol); DPBS (Dulbecco's phosphate buffered saline); 3M sodium acetate (pH 5.2); dATP, dCTP, dGTP, dTTP, 100 mM each, store frozen, −20° C. (#27-2035-O$_2$, Pharmacia, Peapack, N.J.); pd(T)12-18 resuspend at 1 mg/ml, and store frozen −20° C. (#27-7858, Amersham Pharmaca Biotech); Anchored oligo primer (anchored; 5'-TTT TTT TTT TTT TTT TTT TTV N-3') (SEQ. ID. NO. 99); resuspend at 2 mg/ml, store frozen −20° C. (e.g. # 3597-006, Genosys); CyTM3-dUTP, 1 mM, and CyTM5-dUTP, 1 mM, store −20° C., light sensitive; RNasinâ Rnase inhibitor, store −20° C. (#N211A, Promega); SUPERSCRIPT™ II Rnase H' Reverse Transcriptase Kit, store −20° C., (#18064-014, Life Technologies, Rockville, Md.); C0t-1 DNA, 1 mg/ml, store frozen −20° C. (#15279-011, Life Technologies, Rockville, Md.); 0.5M EDTA(pH 8.0); 1 N NaOH; 1M TRIS-HCL; (pH7.5); TE pH 7.4; DEPC water 50× Tris Acetate Buffer; 15 ml round bottom; polypropylene centrifuge tubes; 50 ml conical polypropylene centrifuge tubes; 1.5 ml; Eppendorf tubes; 0.2 ml thin wall PCR tube; MicroCon 100 (Amicon Cat No. 42412); High speed centrifuge for 15 ml tubes; Clinical centrifuge with horizontal rotor for 50 ml conical tubes; Tissue homogenizer (e.g. Polytron PT1200 with Polytron-Aggregate-Dispergier-und-Mischtechnik 147a Ch6014 #027-30-520-0, Brinkmann Instruments Inc., Westbury, N.Y.); RPE Buffer (Add 4 volumes of ethanol per volume of RPE concentrate supplied in Quiagen Kit0; RW1 Buffer (Supplied in Qiagen Kit) 75% EtOH (Ethanol (100%) 375 ml, and DEPC H2O 125 ml for a total of 500 ml); 10× low T dNTP Mix (25 µL dGTP (100 mM), 25 µL dATP (100 mM), 25 µL dCTP (100 mM), 10 µL dTTP (100 mM), and 415 µL DEPC H$_2$O for a total of 500 µL); 5× First Strand Buffer (Provided with Superscript II); TAE Buffer (50× Tris Acetate Electrophoresis Buffer 20 ml, and DEPC H2O 980 mL for a total of 1000 ml)

If the cells that were used were harvested from tissue culture, the cell pellet was washed twice in DPBS. If the cells that were used were from tissue culture, 1 ml of Trizol was added per 2×10$^7$ cells and mixed by shaking. If tissue was being used, 100 mg of frozen tissue was added directly to 4 ml of Trizol, and dissociate by homogenization with a rotating blade tissue homogenizer.

Whatever the source, 2/10 volume of chloroform was added to the cells and shook for 15 seconds, and then allowed to stand for 3 minutes, followed by centrifugation at 12,000×g for 15 minutes at 4° C. The supernatant was taken off and added to a polypropylene tube, while recording the volume of the supernatant.

Then 0.53 volumes of ethanol were slowly added to the supernatant while vortexing, this produced a final ethanol concentration of 35%. The ethanol was added drop by drop and allowed to mix completely with the supernatant before more ethanol is added. If a high local concentration of ethanol is produced, the RNA in that vicinity will precipitate.

The supernatant from an extraction of 2×10$^7$ to 1×08 cells was added to an RNeasy maxi column, which is seated in a 50 ml centrifuge tube. The tube was then centrifuged at 2880×g in a clinical centrifuge with a horizontal rotor at room temperature for 5 minutes. The flow-through was then poured back onto the top of the column and centrifuged again. This step is necessary because a significant amount of RNA is not captured by the column matrix in the first pass of the RNA containing solution through the column.

The flow-through was discarded and 15 ml of RW1 buffer was added to the column, followed by centrifugation at 2880×g for 5 minutes. The flow-through was discarded again and then 10 ml of RPE buffer was added, followed again by centrifugation at 2880×g for 5 minutes. Once again, the flow through was discarded and another 10 ml of RPE buffer was added, and the column was centrifuged at 2880×g for 10 minutes.

Next, the column was placed in a fresh 50 ml tube and add 1 ml of DEPC treated water from the kit was added to the column, and the column was allowed to stand for 1 minute. The column was then centrifuged at 2880×g for 5 minutes, and another 1 ml of water was added to the column. The column was allowed to stand for 1 minute, followed by centrifugation at 2880×g for 10 minutes.

Then, 400 µl portions of the column eluate was aliquotted to 1.5 ml Eppendorf tubes, to which 1/10 volume of 3M sodium acetate (pH 5.2) was added, along with 1 ml of ethanol. The tubes were then allowed to stand for 15 minutes, after which they were centrifuged at 12000×g at 4 C for 15 minutes. The pellet was then washed two times in 75% EtOH and stored at −80° C.

The RNA was resuspended at approximately 1 mg/ml in DEPC $H_2O$. It was then concentrated to greater than 7 mg/ml by centrifugation on a MicroCon 100 filter unit, centrifuged at 500×g, checking as necessary to determine the rate of concentration. This step removes many residual, small to medium sized, molecules that inhibit the reverse transcription reaction in the presence of fluorescently derivatized nucleotides. The concentration of RNA in the concentrated sample was then determined by spectrophotometry, and the sample was stored at −80° C.

If an anchored oligo dT primer was used, the primer was annealed to the RNA in the following 17 µl reaction (a 0.2 ml thin wall PCR tube was used so that incubations could be carried out in a PCR cycler):

| Component | addition for Cy5 labeling | addition for Cy3 labeling |
| --- | --- | --- |
| Total RNA (>7 mg/ml) | 150–200 µg | 50–80 µg |
| Anchored primer (2 µg/µl) | 1 µl | 1 µl |
| DEPC H2O | to 17 µl | to 17 µl |

If an oligo dT(12-18) primer was used, the primer was annealed to the RNA in the following 17 µl reaction:

| Component | addition for Cy5 labeling | addition for Cy3 labeling |
| --- | --- | --- |
| Total RNA (>7 mg/ml) | 150–200 µg | 50–80 µg |
| dT(12–18) primer (1 µg/µl) | 1 µl | 1 µl |
| DEPC H2O | to 17 µl | to 17 µl |

The incorporation rate for Cy5-dUTP is less than that of Cy3-dUTP, so more RNA is labeled to achieve more equivalent signal from each species.

It was then heated to 65° C. for 10 minutes and cooled on ice for 2 minutes. Then, 23 µl (8 µl of 5× first strand buffer, 4 µl of 10× low T dNTPs mix, 4 µl of Cy5 or Cy3 dUTP (1 mM), 4 µl of 0.1 M DTT, 1 µl of Rnasin (30 u/µl), and 2 pt of Superscript II (200 u/µl)) of reaction mixture containing either Cy5-dUTP or Cy3-dUTP nucleotides was added, mixed well by pipetting and a brief centrifuge spin was used to concentrate it in the bottom of the tube. Superscript polymerase is very sensitive to denaturation at air/liquid interfaces, so we were careful to suppress foaming in all handling of this reaction.

It was then incubated at 42° C. for 30 min., after which 2 µl Superscript II was added, making sure the enzyme was well mixed in the reaction volume and incubated at 42° C. for 30-60 min. Then, 5 µl of 0.5M EDTA was added, making sure the reaction was stopped with EDTA before adding NaOH (the next step), since nucleic acids precipitate in alkaline magnesium solutions.

Then, 10 µl 1N NaOH was added and it was incubated at 65° C. for 60 minutes to hydrolyze residual RNA, after which it was cooled to room temperature. The purity of the sodium hydroxide solution used in this step is crucial. Slight contamination or long storage in a glass vessel can produce a solution that will degrade the Cy5 dye molecule, turning the solution yellow. Some researchers achieve better results by reducing the time of hydrolysis to 30 minutes.

It was then neutralized by adding 25 µl of 1M Tris-HCl (pH 7.5). Then, the labeled cDNA was desalted by adding the neutralized reaction, 400 µl of TE pH 7.5 and 20 µg of human C0t-1 DNA to a MicroCon 100 cartridge. It was then pipetted to mix, and spun for 10 minutes at 500×g. 200 µl TE pH 7.5 was added, and the solution was then concentrated to about 20-30 µl (approximately 8-10 min at 500×g). Alternatively, a smaller pore MicroCon 30 was used to speed the concentration step. In this case, the first wash was centrifuged for approximately 4.5 minutes at 16,000×g and the second (200 µl wash) for about 2.5 minutes at 16,000×g.

It was then recovered by inverting the concentrator over a clean collection tube and spinning for 3 min at 500×g. In some cases, the cy5 labeled cDNA formed a gelatinous blue precipitate that was recovered in the concentrated volume. The presence of this material signaled the presence of contaminants. The more extreme the contamination, the greater the fraction of cDNA which will be captured in this gel. Even if heat solubilized, this material tends to produce uniform, non-specific binding to the DNA targets. When concentrating by centrifugal filtration, the times required to achieve the desired final volume were variable. Overly long spins can remove nearly all the water from the solution being filtered. When fluor-tagged nucleic acids are concentrated onto the filter in this fashion, they are very hard to remove, so it is necessary to approach the desired volume by conservative approximations of the required spin times. If control of volumes proves difficult, the final concentration can be achieved by evaporating liquid in the speed-vac. Vacuum evaporation, if not to dryness, does not degrade the performance of the labeled cDNA.

Next, a 2-3 µl aliquot of the Cy5 labeled cDNA was taken for analysis, leaving 18-28 µl for hybridization. This probe was run on a 2% agarose gel (6 cm wide×8.5 cm long, 2 mm wide teeth) in Tris Acetate Electrophoresis Buffer (TAE). For maximal sensitivity when running samples on a gel for fluor analysis, a loading buffer with minimal dye was used and no ethidium bromide was added to the gel or running buffer.

The gel was then scanned on a Molecular Dynamics Storm fluorescence scanner (setting: red fluorescence, 200 micron resolution, 1000 volts on PMT). Successful labeling produces a dense smear of probe from 400 bp to >1000 bp, with little pile-up of low molecular weight transcripts. Weak labeling and significant levels of low molecular weight material indicates a poor labeling. A fraction of the observed low molecular weight material is unincorporated fluor nucleotide.

Next, the fluorescent cDNA had to be hybridized to the microarray. The volume of hybridization solution required was first determined. The rule of thumb is to use 0.033 μl for each mm 2 of slide surface area covered by the cover slip used to cover the array. An array covered by a 24 mm by 50 mm cover slip required 40 μl of hybridization solution. The volume of the hybridization solution is critical. When too little solution is used, it is difficult to seat the cover slip without introducing air bubbles over some portion of the arrayed ESTs, and the cover slip will not sit at a uniform distance from the slide. If the cover slip is bowed toward the slide in the center, there will be less labeled cDNA in that area and hybridization will be non-uniform. When too much volume is applied, the cover slip will move easily during handling, leading to misplacement relative to the arrayed ESTs, and non-hybridization in some areas of the array.

For a 40 μl hybridization, the Cy3 and Cy5 labeled cDNAs were pooled into a single 0.2 ml thin wall PCR tube and the volume was adjusted to 30 μl by either adding DEPC $H_2O$, or removing water in a SpeedVac. If a vacuum device was used to remove water, high heat or heat lamps were not used to accelerate evaporation because the fluorescent dyes could be degraded.

For a 40 μl hybridization the following components were combined:

|  | High Sample Blocking | High Array Blocking |
|---|---|---|
| Cy5 + Cy3 probe | 30 μl | 28 μl |
| Poly d(A) (8 mg/ml) | 1 μl | 2 μl |
| Yeast tRNA (4 mg/ml) | 1 μl | 2 μl |
| Human C0t-1 DNA (10 mg/ml) | 1 μl | 0 μl |
| 20x SSC | 6 μl | 6 μl |
| 50x Denhardt's blocking solution | 1 μl (optional) | 2 μl |
| Total volume | 40 ul | 40 ul |

Arrays and samples can vary somewhat, making it necessary to vary the composition of the hybridization cocktail. In cases where there is residual hybridization to control repeat DNA samples on the array, more C0t-1 DNA was used, as in the High Sample Blocking formulation. When there is diffuse background or a general haze on all of the array elements, more of the non-specific blocker components was used, as in the High Array Blocking formulation.

The components were mixed well by pipetting, heated at 98° C. for 2 minutes in a PCR cycler, cooled quickly to 25° C. and 0.6 ul of 10% SDS was added. It was then centrifuged for 5 min at 14,000×g. The fluor labeled cDNAs have a tendency to form small, very fluorescent, aggregates which result in bright, punctuate background on the array slide. Hard centrifugation will pellet these aggregates, allowing you to avoid introducing them to the array.

The labeled cDNA was applied to a 24 mm×50 mm glass cover slip and then touched with the inverted microarray. Applying the hybridization mix to the array and cover slipping it is an operation which requires some dexterity to get the positioning of the cover slip and the exclusion of air bubbles just right. It was helpful to practice this operation with buffer and plain slides before attempting actual samples. The hybridization solution was added to the cover slip first, since some aggregates of fluor remain in the solution and will bind to the first surface they touch.

The slide was then placed in a microarray hybridization chamber, 5 μl of 3×SSC was added to the reservoir, if the chamber provided one, or at the scribed end of the slide and the chamber was sealed. The chamber was submerged in a 65° C. water bath and the slide was allowed to hybridize for 16-20 hours. There are a wide variety of commercial hybridization chambers. It was worthwhile to prepare a mock hybridization with a blank slide, load it in the chamber and incubate it to test for leaks, or drying of the hybridization fluid, either of which cause severe fluorescent noise on the array.

Next, the unbound fluorescent cDNA was washed off. The hybridization chamber was removed from the water bath, cooled and carefully dried off. The chamber was unsealed and the slide was removed. As there may be negative pressure in the chamber after cooling, it is necessary to remove water from around the seals so that it was not pulled into the chamber and onto the slide when the seals are loosened.

The slide was placed, with the cover slip still affixed, into a Coplin jar filled with 0.5×SSC/0.01% SDS wash buffer. The cover slip was allowed to fall from the slide and then removed from the jar with a forceps. The slide was allowed to wash for 2-5 minutes. The slide was transferred to a fresh Coplin jar filled with 0.06×SSC, and allowed to wash for 2-5 minutes. The sequence of washes may need to be adjusted to allow for more aggressive noise removal, depending on the source of the sample RNA. Useful variations are to add a first wash which is 0.5×SSC/0.1% SDS or to repeat the normal first wash twice.

The slide was then transferred to a slide rack and centrifuged at low rpm (700-1000) for 3 minutes in a clinical centrifuge equipped with a horizontal rotor for microtiter plates. If the slide is simply air dried, it frequently acquires a fluorescent haze. Centrifuging off the liquids results in a lower fluorescent background. As the rate of drying can be quite rapid, it is suggested that the slide be placed in the centrifuge immediately upon removal from the Coplin jar.

Image analysis was performed using DeArray software (Chen, Y., Dougherty, E. R. and Bittner, M. L. Ratio-based decisions and the quantitative analysis of cDNA microarray images, Biomedical Optics 2, 364-374 (1997).

Example 3

Data Analysis

To calibrate ANN models to recognize cancers in each of the four SRBCT categories, gene-expression data from cDNA microarrays as obtained via Examples 1 and 2 above were used. The 63 training samples included both tumor biopsy material (13 EWS and 10 RMS) and cell lines (10 EWS, 10 RMS, 12 NB and 8 Burkitt lymphomas (BL; a subset of BL). For two samples, ST486 (BL-C2 and C4) and GICAN (NB-C2 and C7), we performed two independent microarray experiments to test the reproducibility of the experiments and these were subsequently treated as separate samples.

Genes were filtered based on the intensity of the fluorescence gathered from the cDNA microarray. This type of filtering was designed to remove spots for which image analysis failed. Genes were filtered by requiring that a gene have a red intensity greater than 20 across all experiments. The number of genes that passed this filter was 2308. Each slide was normalized across all experiments. Therefore the expression level was based on a relative (or normalized) red intensity (RRI) for each gene, RRI=mean intensity of that spot/mean intensity of filtered genes. The natural logarithm (In) of RRI was used as a measure of the expression levels.

Principal component analysis (PCA) further reduced the dimensionality. To allow for a supervised regression model with no over-training (when we have low number of parameters as compared to the number of samples), the dimensionality of the samples was reduced by PCA using centralized in (RRI) values as input. Thus each sample was represented by 88 numbers, which are the results of projection of the gene expressions using PCA eigenvectors. We used the 10 dominant PCA components for subsequent analysis. These 10 dominant components contained 63% of the variance in the data matrix. The remaining PCA components contained variance unrelated to separating the four cancers.

Figure 5:
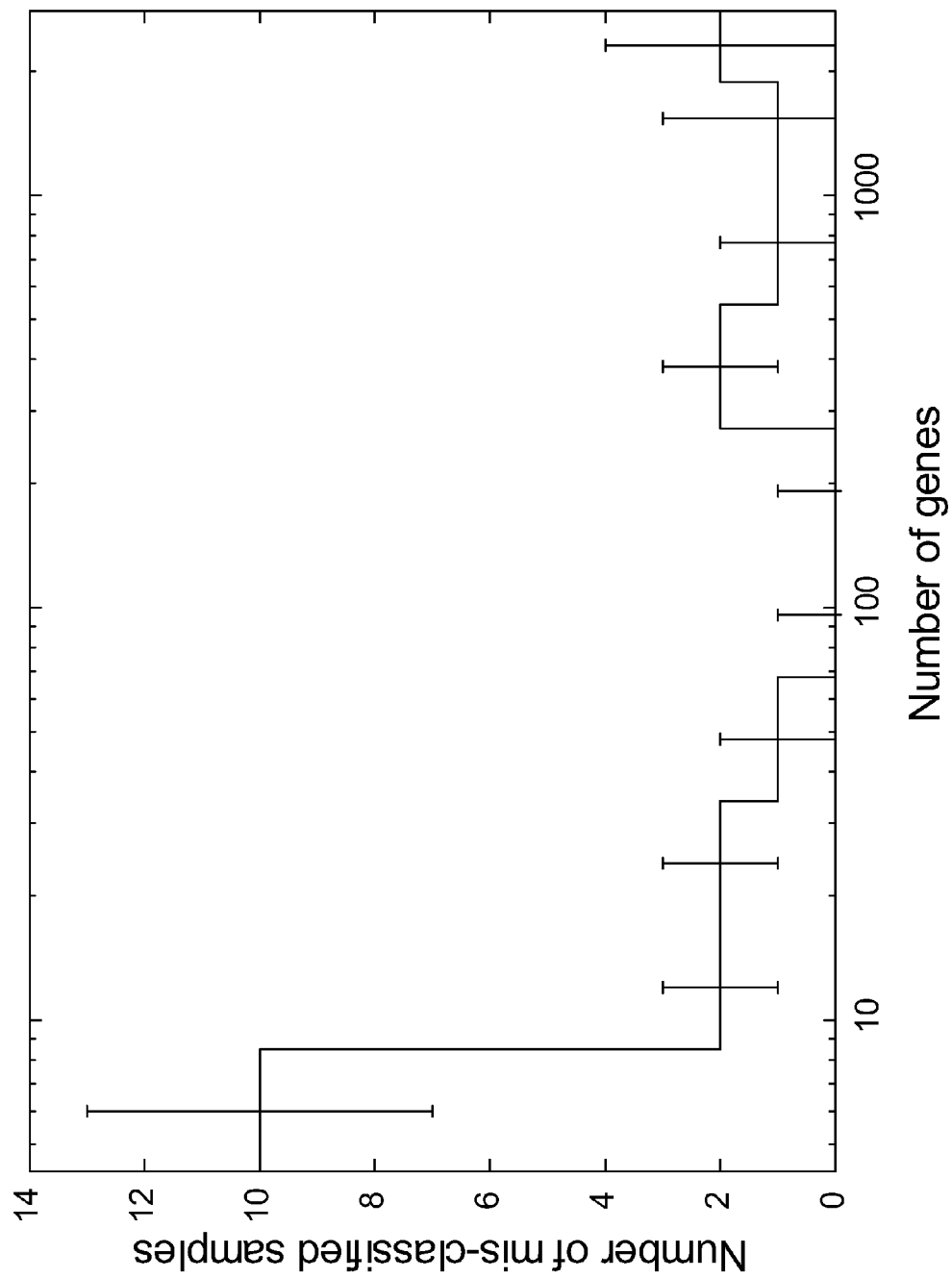
FIG. 5 represents a plot of the average number of misclassified samples for all 3750 models plotted against an increasing number of used genes.

We classified the training samples in the 4 categories using a 3-fold cross validation procedure: the 63 training (labeled) samples were randomly shuffled and split into 3 equally sized groups. Each linear ANN model was then calibrated with the 10 PCA input variables (normalized to centralized z-scores) using 2 of the groups, with the third group reserved for testing predictions (validation). This procedure was repeated 3 times, each time with a different group used for validation. The random shuffling was redone 1250 times and for each shuffling we analyzed 3 ANN models. Thus, in total, each sample belonged to a validation set 1250 times, and 3750 ANN models were calibrated. The three-fold cross-validation procedure produced at total of 3750 ANN models, and the training and validation was successful, see FIG. 5.

Figure 4:
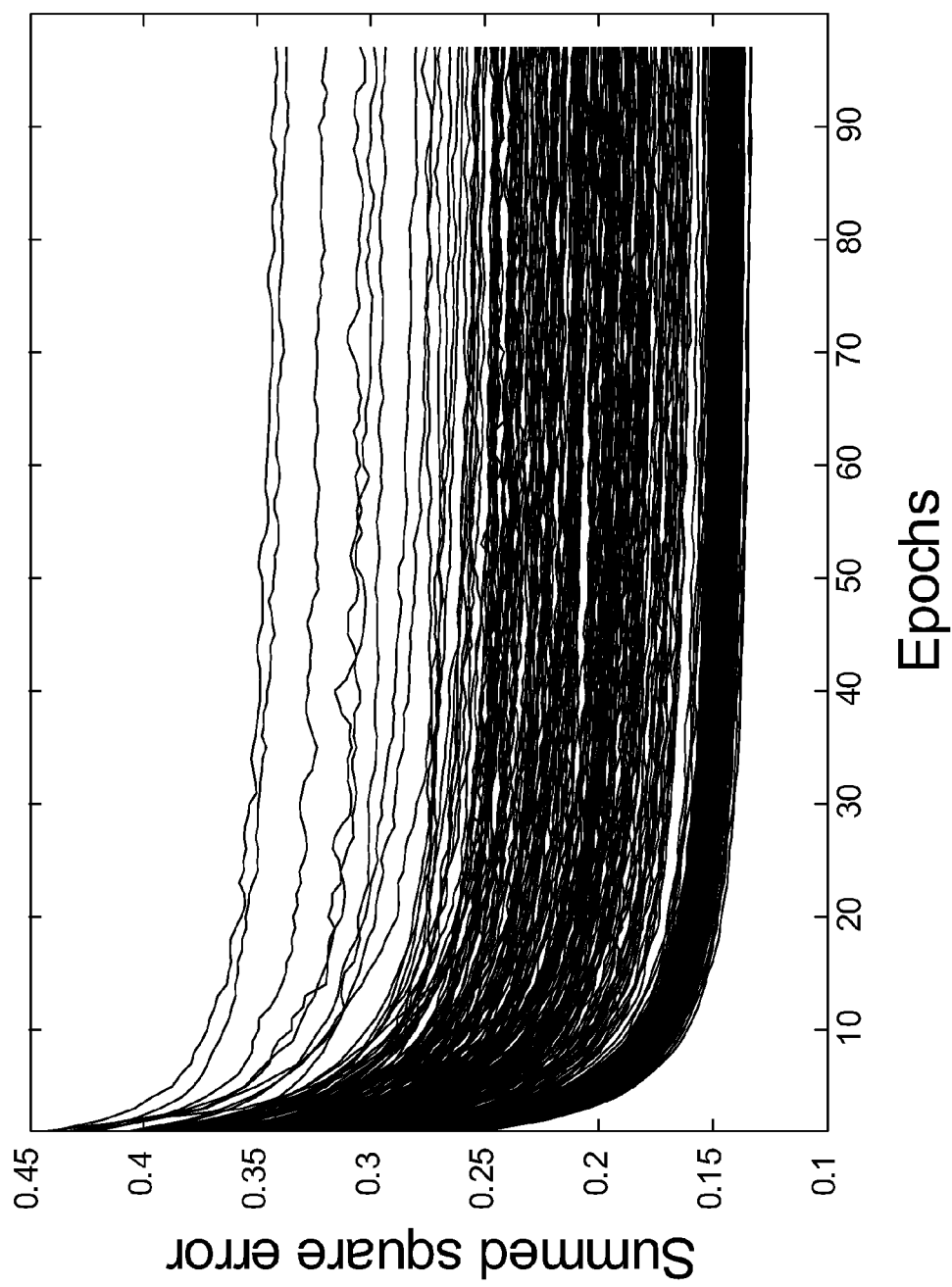
FIG. 4 represents a plot of the average classification error per sample (using a summed square error function) plotted during the training iterations (epochs) for both the training and validation samples.

In addition, there was no sign of 'over-training' of the models, as would be shown by a rise in the summed square error for the validation set with increasing training iterations or 'epochs', see FIG. 4.

For each diagnostic category (EWS, RMS, NB or BL), each ANN model gave an output between 0 (not this category) and 1 (this category). The 1250 outputs for each validation sample were used as a committee as follows. We calculated the average of all the predicted outputs (a committee vote) and then a sample was classified as a particular cancer if it received the highest committee vote for that cancer. In clinical settings, it is important to be able to reject a diagnostic classification including samples not belonging to any of the four diagnoses. Therefore, to be able to reject classification we did as follows. A squared Euclidean distance was computed for each cancer type, between the committee vote for a sample and the 'ideal' output for that cancer type; normalized such that it is unity between cancer types as described above. Using the 1250 ANN models for each validation sample we constructed for each cancer type an empirical probability distribution for the distances. Using these distributions, samples are only diagnosed as a specific cancer if they lie within the 95th percentile. All 3750 models were used to classify the additional 25 test samples.

Using these ANN models, all of the 63 training samples were correctly assigned/classified to their respective categories, having received the highest committee vote (average output) for that category.

Diagnostic results for the 63 training samples can be seen in Table 4 below.

TABLE 4

Training sample characteristics

| Sample Label | Source Label | Histological Diagnosis | ANN EWS | Committee RMS | NB | Vote BL | Source |
|---|---|---|---|---|---|---|---|
| EWS-C1 | A4573 | EWS-C | | 0.02 | 0.27 | 0.04 | NCI |
| EWS-C2 | TC71 | EWS-C | | 0.03 | 0.16 | 0.08 | NCI |
| EWS-C3 | TC106 | EWS-C | | 0.04 | 0.10 | 0.08 | NCI |
| EWS-C4 | 5838 | EWS-C | | 0.09 | 0.08 | 0.04 | NCI |
| EWS-C6 | A673 | EWS-C | | 0.11 | 0.03 | 0.05 | NCI |
| EWS-C7 | ES-CL1 | EWS-C | | 0.06 | 0.08 | 0.04 | MSKCC |
| EWS-C8 | TC32 | EWS-C | | 0.05 | 0.04 | 0.04 | NCI |
| EWS-C9 | SK-ES-1 | EWS-C | | 0.10 | 0.03 | 0.05 | ATCC |
| EWS-C10 | SK-N-MC | EWS-C | | 0.22 | 0.03 | 0.07 | ATCC |
| EWS-C11 | RDES | EWS-C | | 0.05 | 0.03 | 0.07 | ATCC |
| EWS-T1 | ES20 | EWS-T | | 0.04 | 0.03 | 0.06 | MSKCC |
| EWS-T2 | ES13 | EWS-T | | 0.08 | 0.06 | 0.04 | MSKCC |
| EWS-T3 | ES16 | EWS-T | | 0.10 | 0.05 | 0.03 | MSKCC |
| EWS-T4 | ES17 | EWS-T | | 0.14 | 0.11 | 0.02 | MSKCC |
| EWS-T6 | ES22 | EWS-T | | 0.12 | 0.04 | 0.04 | MSKCC |
| EWS-T7 | ES25 | EWS-T | | 0.04 | 0.03 | 0.04 | MSKCC |
| EWS-T9 | 9602P006 | EWS-T | | 0.13 | 0.03 | 0.03 | CHTN |
| EWS-T11 | 9703P152 | EWS-T | | 0.03 | 0.06 | 0.03 | CHTN |
| EWS-T12 | 97049218 | EWS-T | | 0.02 | 0.03 | 0.03 | CHTN |
| EWS-T13 | ES23 | EWS-T | | 0.28 | 0.16 | 0.04 | MSKCC |

TABLE 4-continued

Training sample characteristics

| | | | | | | | |
|---|---|---|---|---|---|---|---|
| EWS-T14 | 9605P074 | EWS-T | 0.99 | 0.02 | 0.04 | 0.05 | CHTN |
| EWS-T15 | 9609P027 | EWS-T | 0.99 | 0.03 | 0.06 | 0.03 | CHTN |
| EWS-T19 | SARC75 | EWS-T | 0.93 | 0.06 | 0.09 | 0.04 | CHTN |
| RMS-C2 | RD | ERMS-C | 0.06 | 0.81 | 0.11 | 0.03 | ATCC |
| RMS-C3 | RH4 | ARMS-C | 0.04 | 0.84 | 0.05 | 0.03 | NCI |
| RMS-C4 | RH3 | ARMS-C | 0.00 | 0.88 | 0.11 | 0.05 | NCI |
| RMS-C5 | RH5 | ARMS-C | 0.01 | 0.91 | 0.09 | 0.04 | NCI |
| RMS-C6 | RH28 | ARMS-C | 0.00 | 0.87 | 0.07 | 0.07 | NCI |
| RMS-C7 | RH30 | ARMS-C | 0.01 | 0.88 | 0.09 | 0.03 | NCI |
| RMS-C8 | CTR | ERMS-C | 0.03 | 0.86 | 0.07 | 0.03 | ATCC |
| RMS-C9 | RH4 | ARMS-C | 0.05 | 0.86 | 0.03 | 0.05 | NCI |
| RMS-C10 | RMS13 | ARMS-C | 0.01 | 0.90 | 0.14 | 0.03 | NCI |
| RMS-C11 | TE671 | ERMS-C | 0.07 | 0.77 | 0.08 | 0.03 | ATCC |
| RMS-T1 | RMS3 | ARMS-T | 0.02 | 0.93 | 0.03 | 0.06 | MSKCC |
| RMS-T2 | RMS6 | ARMS-T | 0.06 | 0.86 | 0.03 | 0.04 | MSKCC |
| RMS-T3 | RMS2 | ERMS-T | 0.08 | 0.80 | 0.07 | 0.02 | MSKCC |
| RMS-T4 | RMS5 | ERMS-T | 0.07 | 0.93 | 0.03 | 0.03 | MSKCC |
| RMS-T5 | RMS10 | ARMS-T | 0.05 | 0.84 | 0.08 | 0.03 | MSKCC |
| RMS-T6 | RT1 | RMS-T | 0.04 | 0.93 | 0.05 | 0.03 | CHTN |
| RMS-T7 | RT4 | ERMS-T | 0.10 | 0.75 | 0.05 | 0.05 | CHTN |
| RMS-T8 | RT5 | RMS-T | 0.06 | 0.90 | 0.05 | 0.02 | CHTN |
| RMS-T10 | RT2 | RMS-T | 0.02 | 0.92 | 0.06 | 0.03 | CHTN |
| RMS-T11 | RHA82 | ERMS-T | 0.03 | 0.76 | 0.06 | 0.03 | CHTN |
| NB-C1 | KCNR | NB-C | 0.00 | 0.08 | 0.93 | 0.03 | NCI |
| NB-C2 | GICAN | NB-C | 0.03 | 0.10 | 0.70 | 0.08 | NCI |
| NB-C3 | SK-N-AS | NB-C | 0.01 | 0.26 | 0.64 | 0.04 | ATCC |
| NB-C4 | LAN5 | NB-C | 0.02 | 0.03 | 0.85 | 0.06 | NCI |
| NB-C5 | SK-N-BE2 | NB-C | 0.02 | 0.02 | 0.92 | 0.06 | ATCC |
| NB-C6 | SK-NDZ | NB-C | 0.02 | 0.02 | 0.89 | 0.09 | ATCC |
| NB-C7 | GICAN | NB-C | 0.07 | 0.05 | 0.80 | 0.08 | NCI |
| NB-C8 | NGP | NB-C | 0.00 | 0.06 | 0.96 | 0.04 | NCI |
| NB-C9 | SH-SY5Y | NB-C | 0.06 | 0.04 | 0.85 | 0.04 | ATCC |
| NB-C10 | SK-N-Fl | NB-C | 0.00 | 0.12 | 0.91 | 0.03 | ATCC |
| NB-C11 | SK-N-SH | NB-C | 0.06 | 0.01 | 0.95 | 0.05 | ATCC |
| NB-C12 | CHP-134B | NB-C | 0.02 | 0.24 | 0.41 | 0.06 | NCI |
| BL-C1 | RAMOS(RA1) | BL-C | 0.03 | 0.06 | 0.08 | 0.90 | ATCC |
| BL-C2 | ST486 | BL-C | 0.04 | 0.12 | 0.04 | 0.82 | ATCC |
| BL-C3 | CA46 | BL-C | 0.07 | 0.09 | 0.02 | 0.80 | ATCC |
| BL-C4 | ST486 | BL-C | 0.04 | 0.06 | 0.08 | 0.80 | ATCC |
| BL-C5 | RAJI | BL-C | 0.10 | 0.04 | 0.04 | 0.87 | ATCC |
| BL-C6 | MC116 | BL-C | 0.10 | 0.02 | 0.09 | 0.87 | ATCC |
| BL-C7 | DAUDI | BL-C | 0.09 | 0.04 | 0.02 | 0.93 | ATCC |
| BL-C8 | SULTAN | BL-C | 0.20 | 0.03 | 0.03 | 0.80 | ATCC |

Source label refers to the original name of the sample as labeled by the source. Histological diagnosis is defined as cancer type suffixed with —T for a tumor sample and —C for a cell line.
Highlighted in gray is the ANN classification of the samples.
NCI: National Cancer Institute, National Institutes of Health, ATCC: American Type Culture Collection, MSKCC: Memorial Sloan-Kettering Cancer Center, CHTN: Cooperative Human Tissue Network.

Example 4

Optimization of Genes Utilized for Classification

The contribution of each gene to the classification by the ANN models was determined by measuring the sensitivity of the classification to a change in the expression level of each gene, using the 3750 previously calibrated models.

The sensitivity to the different genes was determined by the absolute value of the partial derivative of the output with respect to the gene expressions, averaged over samples and ANN models. A large sensitivity implied that changing the expression influences the output significantly.

In this way the genes were ranked according to their significance for the classification. The top 200 ranked genes are seen below in Table 5. The weight of each gene is the sensitivity measurement as calculated by Equation (2), page 19 above

TABLE 5

| Rank | Unique Image_Id | Name of Gene | Unigene number | Weight |
|---|---|---|---|---|
| 1 | 296448 | "insulin-like growth factor 2 (somatomedin A)" | Hs.251664 | 1.00 + −0.03 |
| 2 | 207274 | "insulin-like growth factor 2 (somatomedin A)" | Hs.251664 | 0.97 + −0.03 |
| 3 | 295985 | "*Homo sapiens* cDNA FLJ20653 fis, clone KAT01739" | Hs.180059 | 0.87 + −0.02 |
| 4 | 41591 | "meningioma (disrupted in balanced translocation) 1" | Hs.268515 | 0.86 + −0.02 |
| 5 | 365826 | "growth arrest-specific 1" | Hs.65029 | 0.86 + −0.02 |
| 6 | 714453 | "interleukin 4 receptor" | Hs.75545 | 0.85 + −0.02 |
| 7 | 812965 | "v-myc avian myelocytomatosis viral oncogene homolog" | Hs.79070 | 0.81 + −0.02 |
| 8 | 486787 | "calponin 3, acidic" | Hs.194662 | 0.81 + −0.02 |
| 9 | 244618 | "ESTs" | Hs.15463 | 0.80 + −0.02 |
| 10 | 417226 | "v-myc avian myelocytomatosis viral oncogene homolog" | Hs.79070 | 0.80 + −0.02 |
| 11 | 840942 | "major histocompatibility complex, class II, DP beta 1" | Hs.814 | 0.79 + −0.02 |
| 12 | 770394 | "Fc fragment of IgG, receptor, transporter, alpha" | Hs.160741 | 0.78 + −0.02 |
| 13 | 812105 | "ALL1-fused gene from chromosome 1q" | Hs.75823 | 0.76 + −0.02 |
| 14 | 357031 | "tumor necrosis factor, alpha-induced protein 6" | Hs.29352 | 0.75 + −0.02 |
| 15 | 629896 | "microtubule-associated protein 1B" | Hs.103042 | 0.74 + −0.02 |
| 16 | 308163 | "ESTs" | Hs.84520 | 0.73 + −0.02 |
| 17 | 43733 | "glycogenin 2" | Hs.58589 | 0.72 + −0.02 |
| 18 | 489631 | "chondroitin sulfate proteoglycan 2 (versican)" | Hs.81800 | 0.71 + −0.02 |
| 19 | 866702 | "protein tyrosine phosphatase, non-receptor type 13 (APO-1/CD95 (Fas)-associated phosphatase)" | Hs.211595 | 0.71 + −0.02 |
| 20 | 377461 | "caveolin 1, caveolae protein, 22 kD" | Hs.281621 | 0.70 + −0.02 |
| 21 | 324494 | "heat shock 27 kD protein 2" | Hs.78846 | 0.69 + −0.02 |
| 22 | 80109 | "major histocompatibility complex, class II, DQ alpha 1" | Hs.198253 | 0.69 + −0.02 |
| 23 | 39093 | "methionine aminopeptidase; eIF-2-associated p67" | Hs.78935 | 0.69 + −0.01 |
| 24 | 82225 | "secreted frizzled-related protein 1" | Hs.7306 | 0.67 + −0.01 |
| 25 | 308231 | "*Homo sapiens* cDNA FLJ20153 fis, clone COL08656, highly similar to AJ001381 *Homo sapiens* incomplete cDNA for a mutated allele" | Hs.109805 | 0.67 + −0.02 |
| 26 | 211758 | "ribosomal protein S23" | Hs.3463 | 0.67 + −0.01 |
| 27 | 1E+06 | "troponin T1, skeletal, slow" | Hs.73980 | 0.66 + −0.02 |
| 28 | 878280 | "collapsin response mediator protein 1" | Hs.155392 | 0.65 + −0.02 |
| 29 | 383188 | "recoverin" | Hs.80539 | 0.64 + −0.01 |
| 30 | 795877 | "serum-inducible kinase" | Hs.3838 | 0.64 + −0.01 |
| 31 | 784593 | "ESTs" | Hs.6838 | 0.63 + −0.01 |
| 32 | 135688 | "GATA-binding protein 2" | Hs.760 | 0.62 + −0.01 |
| 33 | 325182 | "cadherin 2, N-cadherin (neuronal)" | Hs.161 | 0.62 + −0.01 |
| 34 | 461425 | "myosin, light polypeptide 4, alkali; atrial, embryonic" | Hs.154156 | 0.61 + −0.01 |
| 35 | 1E+06 | "transducin-like enhancer of split 2, homolog of Drosophila E(sp1)" | Hs.173063 | 0.61 + −0.02 |
| 36 | 298062 | "troponin T2, cardiac" | Hs.89749 | 0.61 + −0.02 |
| 37 | 841641 | "cyclin D1 (PRAD1: parathyroid adenomatosis 1)" | Hs.82932 | 0.61 + −0.01 |
| 38 | 745343 | "regenerating islet-derived 1 alpha (pancreatic stone protein, pancreatic thread protein)" | Hs.1032 | 0.60 + −0.01 |
| 39 | 755599 | "interferon induced transmembrane protein 1 (9–27)" | Hs.146360 | 0.59 + −0.02 |
| 40 | 809901 | "collagen, type XV, alpha 1" | Hs.83164 | 0.59 + −0.01 |
| 41 | 859359 | "quinone oxidoreductase homolog" | Hs.50649 | 0.59 + −0.01 |
| 42 | 784224 | "fibroblast growth factor receptor 4" | Hs.165950 | 0.59 + −0.02 |
| 43 | 42558 | "glycine amidinotransferase (L-arginine: glycine amidinotransferase)" | Hs.75335 | 0.58 + −0.01 |
| 44 | 183337 | "major histocompatibility complex, class II, DM alpha" | Hs.77522 | 0.58 + −0.01 |
| 45 | 289645 | "amyloid beta (A4) precursor-like protein 1" | Hs.74565 | 0.58 + −0.01 |
| 46 | 377048 | "*Homo sapiens* cDNA FLJ20153 fis, clone COL08656, highly similar to AJ001381 *Homo sapiens* incomplete cDNA for a mutated allele" | Hs.109805 | 0.57 + −0.01 |

TABLE 5-continued

| Rank | Unique Image_Id | Name of Gene | Unigene number | Weight |
|---|---|---|---|---|
| 47 | 122159 | "collagen, type III, alpha 1 (Ehlers-Danlos syndrome type IV, autosomal dominant)" | Hs.119571 | 0.57 + −0.01 |
| 48 | 245330 | "insulin-like growth factor 2 (somatomedin A)" | Hs.251664 | 0.57 + −0.01 |
| 49 | 814260 | "follicular lymphoma variant translocation 1" | Hs.74050 | 0.57 + −0.01 |
| 50 | 824602 | "interferon, gamma-inducible protein 16" | Hs.155530 | 0.57 + −0.01 |
| 51 | 44563 | "growth associated protein 43" | Hs.79000 | 0.56 + −0.01 |
| 52 | 767495 | "GLI-Kruppel family member GLI3 (Greig cephalopolysyndactyly syndrome)" | Hs.72916 | 0.56 + −0.01 |
| 53 | 769716 | "neurofibromin 2 (bilateral acoustic neuroma)" | Hs.902 | 0.55 + −0.01 |
| 54 | 486110 | "profilin 2" | Hs.91747 | 0.55 + −0.01 |
| 55 | 1E+06 | "pim-2 oncogene" | Hs.80205 | 0.55 + −0.01 |
| 56 | 756556 | "complement component 1 inhibitor (angioedema, hereditary)" | Hs.151242 | 0.54 + −0.01 |
| 57 | 377731 | "glutathione S-transferase M5" | Hs.75652 | 0.54 + −0.01 |
| 58 | 52076 | "olfactomedin related ER localized protein" | Hs.74376 | 0.54 + −0.02 |
| 59 | 810057 | "cold shock domain protein A" | Hs.1139 | 0.54 + −0.01 |
| 60 | 233721 | "insulin-like growth factor binding protein 2 (36 kD)" | Hs.162 | 0.54 + −0.01 |
| 61 | 293500 | "ESTs" | Hs.49714 | 0.54 + −0.01 |
| 62 | 75254 | "cysteine and glycine-rich protein 2 (LIM domain only, smooth muscle)" | Hs.10526 | 0.54 + −0.01 |
| 63 | 377468 | "sprouty (Drosophila) homolog 1 (antagonist of FGF signaling)" | Hs.88044 | 0.53 + −0.01 |
| 64 | 809910 | "interferon induced transmembrane protein 3 (1-8U)" | Hs.182241 | 0.53 + −0.01 |
| 65 | 395708 | "dihydropyrimidinase-like 4" | Hs.100058 | 0.53 + −0.01 |
| 66 | 416959 | "nuclear factor I/B" | Hs.33287 | 0.53 + −0.01 |
| 67 | 1E+06 | "antigen identified by monoclonal antibodies 12E7, F21 and O13" | Hs.177543 | 0.52 + −0.01 |
| 68 | 609663 | "protein kinase, cAMP-dependent, regulatory, type II, beta" | Hs.77439 | 0.51 + −0.01 |
| 69 | 212640 | "Rho GTPase activating protein 4" | Hs.3109 | 0.51 + −0.01 |
| 70 | 130057 | "ESTs" | Hs.23057 | 0.51 + −0.01 |
| 71 | 563673 | "antiquitin 1" | Hs.74294 | 0.51 + −0.01 |
| 72 | 770059 | "heparan sulfate proteoglycan 2 (perlecan)" | Hs.211573 | 0.51 + −0.01 |
| 73 | 782503 | "*Homo sapiens* clone 23716 mRNA sequence" | Hs.12214 | 0.50 + −0.01 |
| 74 | 292522 | "ESTs" | Hs.38022 | 0.50 + −0.01 |
| 75 | 365515 | "fibroblast growth factor 7 (keratinocyte growth factor)" | Hs.164568 | 0.50 + −0.01 |
| 76 | 1E+06 | "cysteine-rich protein 1 (intestinal)" | Hs.17409 | 0.50 + −0.01 |
| 77 | 767183 | "hematopoietic cell-specific Lyn substrate 1" | Hs.14601 | 0.50 + −0.01 |
| 78 | 811000 | "lectin, galactoside-binding, soluble, 3 binding protein (galectin 6 binding protein)" | Hs.79339 | 0.50 + −0.01 |
| 79 | 308497 | "KIAA0467 protein" | Hs.11147 | 0.49 + −0.01 |
| 80 | 80338 | "selenium binding protein 1" | Hs.7833 | 0.49 + −0.01 |
| 81 | 200814 | "membrane metallo-endopeptidase (neutral endopeptidase, enkephalinase, CALLA, CD10)" | Hs.1298 | 0.49 + −0.01 |
| 82 | 898219 | "mesoderm specific transcript (mouse) homolog" | Hs.79284 | 0.49 + −0.01 |
| 83 | 796258 | "sarcoglycan, alpha (50 kD dystrophin-associated glycoprotein)" | Hs.99931 | 0.49 + −0.01 |
| 84 | 377671 | "integrin, alpha 7" | Hs.74369 | 0.48 + −0.01 |
| 85 | 839736 | "crystallin, alpha B" | Hs.1940 | 0.48 + −0.01 |
| 86 | 208718 | "annexin A1" | Hs.78225 | 0.48 + −0.01 |
| 87 | 32299 | "inositol(myo)-1(or 4)-monophosphatase 2" | Hs.5753 | 0.48 + −0.01 |
| 88 | 246377 | "EST" | Hs.102670 | 0.48 + −0.01 |
| 89 | 413633 | "EST" | — | 0.48 + −0.01 |
| 90 | 140806 | "peptidylglycine alpha-amidating monooxygenase" | Hs.83920 | 0.47 + −0.01 |
| 91 | 294496 | "ESTs" | Hs.23037 | 0.47 + −0.01 |
| 92 | 755750 | "non-metastatic cells 2, protein (NM23B) expressed in" | Hs.275163 | 0.47 + −0.01 |

TABLE 5-continued

| Rank | Unique Image_Id | Name of Gene | Unigene number | Weight |
|---|---|---|---|---|
| 93 | 811108 | "thyroid hormone receptor interactor 6" | Hs.119498 | 0.47 + −0.01 |
| 94 | 246035 | "ESTs" | Hs.78026 | 0.47 + −0.01 |
| 95 | 796904 | "pleomorphic adenoma gene-like 1" | Hs.75825 | 0.47 + −0.01 |
| 96 | 788107 | "bridging integrator 1" | Hs.193163 | 0.47 + −0.01 |
| 97 | 714106 | "plasminogen activator, urokinase" | Hs.77274 | 0.47 + −0.01 |
| 98 | 842918 | "FERM, RhoGEF (ARHGEF) and pleckstrin domain protein 1 (chondrocyte-derived)" | Hs.183738 | 0.47 + −0.01 |
| 99 | 788472 | "nucleobindin 1" | Hs.172609 | 0.47 + −0.01 |
| 100 | 52096 | "platelet-derived growth factor receptor, alpha polypeptide" | Hs.74615 | 0.46 + −0.01 |
| 101 | 823886 | "Smooth muscle myosin heavy chain isoform SMemb [human, umbilical cord, fetal aorta, mRNA Partial, 971 nt]" | Hs.2094 | 0.46 + −0.01 |
| 102 | 782193 | "thioredoxin" | Hs.76136 | 0.46 + −0.01 |
| 103 | 214990 | "gelsolin (amyloidosis, Finnish type)" | Hs.80562 | 0.46 + −0.01 |
| 104 | 144932 | "deleted in oral cancer (mouse, homolog) 1" | Hs.3436 | 0.46 + −0.01 |
| 105 | 782811 | "high-mobility group (nonhistone chromosomal) protein isoforms I and Y" | Hs.139800 | 0.46 + −0.01 |
| 106 | 813698 | "sprouty (Drosophila) homolog 2" | Hs.18676 | 0.45 + −0.01 |
| 107 | 212542 | "*Homo sapiens* mRNA; cDNA DKFZp586J2118 (from clone DKFZp586J2118)" | Hs.21851 | 0.45 + −0.01 |
| 108 | 204545 | "ESTs" | Hs.8966 | 0.45 + −0.01 |
| 109 | 341588 | "CGI-119 protein" | Hs.25615 | 0.45 + −0.01 |
| 110 | 297392 | "metallothionein 1L" | Hs.94360 | 0.45 + −0.01 |
| 111 | 813841 | "plasminogen activator, tissue" | Hs.274404 | 0.45 + −0.01 |
| 112 | 491692 | "collagen, type IV, alpha 1" | Hs.119129 | 0.44 + −0.01 |
| 113 | 142134 | "hypothetical protein FLJ20185" | Hs.272972 | 0.44 + −0.01 |
| 114 | 214572 | "ESTs" | Hs.280460 | 0.44 + −0.01 |
| 115 | 878182 | "alpha-2-macroglobulin" | Hs.74561 | 0.44 + −0.01 |
| 116 | 360047 | "SWI/SNF related, matrix associated, actin dependent regulator of chromatin, subfamily d, member 3" | Hs.77069 | 0.44 + −0.01 |
| 117 | 878652 | "procollagen C-endopeptidase enhancer" | Hs.202097 | 0.44 + −0.01 |
| 118 | 450152 | "Meis (mouse) homolog 3" | Hs.117313 | 0.44 + −0.01 |
| 119 | 45542 | "Human insulin-like growth factor binding protein 5 (IGFBP5) mRNA" | Hs.103391 | 0.44 + −0.01 |
| 120 | 742132 | "interferon-stimulated protein, 15 kDa" | Hs.833 | 0.44 + −0.01 |
| 121 | 82903 | "TAP binding protein (tapasin)" | Hs.179600 | 0.44 + −0.01 |
| 122 | 773215 | "runt-related transcription factor 1 (acute myeloid leukemia 1; aml1 oncogene)" | Hs.129914 | 0.44 + −0.01 |
| 123 | 789253 | "presenilin 2 (Alzheimer disease 4)" | Hs.25363 | 0.44 + −0.01 |
| 124 | 814526 | "seb4D" | Hs.236361 | 0.44 + −0.01 |
| 125 | 435953 | "inositol 1,4,5-triphosphate receptor, type 3" | Hs.77515 | 0.44 + −0.01 |
| 126 | 245860 | "*Homo sapiens* mRNA; cDNA DKFZp564H1916 (from clone DKFZp564H1916)" | Hs.181104 Hs.181104 | 0.44 + −0.01 0.44 + −0.01 |
| 127 | 159455 | "similar to vaccinia virus HindIII K4L ORF" | Hs.74573 | 0.44 + −0.01 |
| 128 | 220096 | "—" | — | 0.44 + −0.01 |
| 129 | 45291 | "dentatorubral-pallidoluysian atrophy (atrophin-1)" | Hs.169488 | 0.43 + −0.01 |
| 130 | 241412 | "E74-like factor 1 (ets domain transcription factor)" | Hs.154365 | 0.43 + −0.01 |
| 131 | 1E+06 | "matrix metalloproteinase 2 (gelatinase A, 72 kD gelatinase, 72 kD type IV collagenase)" | Hs.111301 | 0.43 + −0.01 |
| 132 | 250654 | "secreted protein, acidic, cysteine-rich (osteonectin)" | Hs.111779 | 0.43 + −0.01 |
| 133 | 343867 | "allograft inflammatory factor 1" | Hs.76364 | 0.43 + −0.01 |
| 134 | 234237 | "Pirin" | Hs.279663 | 0.42 + −0.01 |
| 135 | 713922 | "glutathione S-transferase M1" | Hs.278633 | 0.42 + −0.01 |
| 136 | 823928 | "glutathione S-transferase theta 2" | Hs.1581 | 0.42 + −0.01 |
| 137 | 810504 | "proteolipid protein 2 (colonic epithelium-enriched)" | Hs.77422 | 0.42 + −0.01 |
| 138 | 788511 | "ribosomal protein S6 kinase, 90 kD, polypeptide 1" | Hs.149957 | 0.41 + −0.01 |
| 139 | 471266 | "DiGeorge syndrome critical region gene 6" | Hs.153910 | 0.41 + −0.01 |
| 140 | 299737 | "*Homo sapiens* clone 24411 mRNA sequence" | Hs.20952 | 0.41 + −0.01 |

TABLE 5-continued

| Rank | Unique Image_Id | Name of Gene | Unigene number | Weight |
|---|---|---|---|---|
| 141 | 740554 | "Homo sapiens mRNA; cDNA DKFZp434I0812 (from clone DKFZp434I0812); partial cds" | Hs.263671 | 0.41 + −0.01 |
| 142 | 754600 | "nuclear factor I/X (CCAAT-binding transcription factor)" | Hs.35841 | 0.41 + −0.01 |
| 143 | 151261 | "ESTs" | Hs.237971 | 0.41 + −0.01 |
| 144 | 815239 | "Rho guanine nucleotide exchange factor (GEF) 1" | Hs.252280 | 0.41 + −0.01 |
| 145 | 624360 | "proteasome (prosome, macropain) subunit, beta type, 8 (large multifunctional protease 7)" | Hs.180062 | 0.41 + −0.01 |
| 146 | 213136 | "BTG family, member 2" | Hs.75462 | 0.41 + −0.01 |
| 147 | 21652 | "catenin (cadherin-associated protein), alpha 1 (102 kD)" | Hs.178452 | 0.41 + −0.01 |
| 148 | 813266 | "four and a half LIM domains 1" | Hs.239069 | 0.41 + −0.01 |
| 149 | 236282 | "Wiskott-Aldrich syndrome (ecezema-thrombocytopenia)" | Hs.2157 | 0.41 + −0.01 |
| 150 | 755228 | "dynamin 1" | Hs.166161 | 0.41 + −0.01 |
| 151 | 161993 | "CCAAT/enhancer binding protein (C/EBP), beta" | Hs.99029 | 0.41 + −0.01 |
| 152 | 358433 | "retinoid X receptor, gamma" | Hs.26550 | 0.41 + −0.01 |
| 153 | 841620 | "dihydropyrimidinase-like 2" | Hs.173381 | 0.41 + −0.01 |
| 154 | 293859 | "Putative prostate cancer tumor suppressor" | Hs.71119 | 0.41 + −0.01 |
| 155 | 190887 | "myeloid differentiation primary response gene (88)" | Hs.82116 | 0.41 + −0.01 |
| 156 | 362483 | "spectrin, beta, non-erythrocytic 1" | Hs.107164 | 0.41 + −0.01 |
| 157 | 139376 | "hypothetical protein" | Hs.91973 | 0.40 + −0.01 |
| 158 | 786084 | "chromobox homolog 1 (Drosophila HP1 beta)" | Hs.77254 | 0.40 + −0.01 |
| 159 | 193182 | "transfoming, acidic coiled-coil containing protein 1" | Hs.173159 | 0.40 + −0.01 |
| 160 | 768246 | "glucose-6-phosphate dehydrogenase" | Hs.80206 | 0.40 + −0.01 |
| 161 | 774502 | "protein tyrosine phosphatase, non-receptor type 12" | Hs.62 | 0.40 + −0.01 |
| 162 | 868304 | "actin, alpha 2, smooth muscle, aorta" | Hs.195851 | 0.40 + −0.01 |
| 163 | 379708 | "chromodomain helicase DNA binding protein 3" | Hs.25601 | 0.40 + −0.01 |
| 164 | 504791 | "glutathione S-transferase A4" | Hs.169907 | 0.40 + −0.01 |
| 165 | 755506 | "annexin A4" | Hs.77840 | 0.40 + −0.01 |
| 166 | 1E+06 | "homeo box B7" | Hs.819 | 0.40 + −0.01 |
| 167 | 824704 | "mannose phosphate isomerase" | Hs.75694 | 0.40 + −0.01 |
| 168 | 770014 | "T cell receptor alpha locus" | Hs.74647 | 0.40 + −0.01 |
| 169 | 22040 | "matrix metalloproteinase 9 (gelatinase B, 92 kD gelatinase, 92 kD type IV collagenase)" | Hs.151738 | 0.40 + −0.01 |
| 170 | 66714 | "peanut (Drosophila)-like 2" | Hs.155524 | 0.40 + −0.01 |
| 171 | 172783 | "hypothetical protein FLJ10390" | Hs.133475 | 0.40 + −0.01 |
| 172 | 2734345 | "v-yes-1 Yamaguchi sarcoma viral oncogene homolog 1" | Hs.194148 | 0.40 + −0.01 |
| 173 | 323371 | "amyloid beta (A4) precursor protein (protease nexin-II, Alzheimer disease)" | Hs.177486 | 0.39 + −0.01 |
| 174 | 344134 | "immunoglobulin lambda-like polypeptide 3" | Hs.170116 | 0.39 + −0.01 |
| 175 | 291756 | "tubulin, beta, 5" | Hs.108014 | 0.39 + −0.01 |
| 176 | 47475 | "p53 inducible protein" | Hs.258503 | 0.39 + −0.01 |
| 177 | 760299 | "Dickkopf gene 3" | Hs.4909 | 0.39 + −0.01 |
| 178 | 24415 | "tumor protein p53 (Li-Fraumeni syndrome)" | Hs.1846 | 0.39 + −0.01 |
| 179 | 727251 | "CD9 antigen (p24)" | Hs.1244 | 0.39 + −0.01 |
| 180 | 770868 | "NGFI-A binding protein 2 (ERG1 binding protein 2)" | Hs.159223 | 0.39 + −0.01 |
| 181 | 364934 | "death-associated protein kinase 1" | Hs.153924 | 0.39 + −0.01 |
| 182 | 1E+06 | "creatine kinase, brain" | Hs.173724 | 0.39 + −0.01 |
| 183 | 769959 | "collagen, type IV, alpha 2" | Hs.75617 | 0.39 + −0.01 |
| 184 | 144797 | "a disintegrin-like and metalloprotease (reprolysin type) with thrombospondin type 1 motif, 1" | Hs.8230 | 0.39 + −0.01 |
| 185 | 108351 | "Homo sapiens cDNA FLJ11302 fis, clone PLACE1009971" | Hs.13781 | 0.38 + −0.01 |
| 186 | 51448 | "activating transcription factor 3" | Hs.460 | 0.38 + −0.01 |
| 187 | 301122 | "extracellular matrix protein 1" | Hs.81071 | 0.38 + −0.01 |
| 188 | 814798 | "aldehyde dehydrogenase 6" | Hs.75746 | 0.38 + −0.01 |
| 189 | 788695 | "troponin T3, skeletal, fast" | Hs.73454 | 0.38 + −0.01 |
| 190 | 769028 | "mesenchyme homeo box 1" | Hs.438 | 0.38 + −0.01 |

TABLE 5-continued

| Rank | Unique Image_Id | Name of Gene | Unigene number | Weight |
|---|---|---|---|---|
| 191 | 811028 | "cathepsin D (lysosomal aspartyl protease)" | Hs.79572 | 0.38 + −0.01 |
| 192 | 196992 | "aldo-keto reductase family 1, member C1 (dihydrodiol dehydrogenase 1; 20-alpha (3-alpha)-hydroxysteroid dehydrogenase)" | Hs.275374 | 0.38 + −0.01 |
| 193 | 586854 | "CGI-119 protein" | Hs.25615 | 0.38 + −0.01 |
| 194 | 1E+06 | "ATPase, Na+/K+ transporting, alpha 1 polypeptide" | Hs.190703 | 0.38 + −0.01 |
| 195 | 752652 | "transcription factor 7-like 2 (T-cell specific, HMG-box)" | Hs.154485 | 0.38 + −0.01 |
| 196 | 813168 | "ESTs" | Hs.59896 | 0.38 + −0.01 |
| 197 | 143306 | "lymphocyte-specific protein 1" | Hs.56729 | 0.38 + −0.01 |
| 198 | 810551 | "low density lipoprotein-related protein 1 (alpha-2-macroglobulin receptor)" | Hs.89137 | 0.37 + −0.01 |
| 199 | 882506 | "lysyl oxidase-like 2" | Hs.83354 | 0.37 + −0.01 |
| 200 | 141768 | "v-erb-b2 avian erythroblastic leukemia viral oncogene homolog 2 (neuro/glioblastoma derived oncogene homolog)" | Hs.173664 | 0.37 + −0.01 |

The ANN analysis utilized in this example has lead to the identification of genes specific for each of the four cancers (EWS, RMS, NB and BL), with implications for biology and therapy, a strength of this method is its lack of requirement for genes to be exclusively associated with a single cancer type. The top 96 discriminating genes included not only those that had high (61) or low levels (12 BLs and 1 EWS) of expression in one particular cancer, but also genes that were differentially expressed in two diagnostic categories as compared to the remaining two. The genes that are not exclusively expressed in two cancer types can be used for diagnosis (to separate these two from the other cancers) and are potential targets for these both these cancers.

Figure 8:
FIG. 8 represents a hierarchical clustering of the samples and genes, where each row represents one of the 96 cDNA clones, and each column represents a separate sample.

As expected, our method identified genes related to tumor histogenesis, but includes genes that may not normally be expressed in the corresponding mature tissue. Of the 16 genes highly expressed only in EWS, two (MIC2 (SEQ. ID. NO. 22) and GYG2 (SEQ. ID. NO. 21)) have been previously described. Of the 14 genes that have not previously been reported to be highly expressed in EWS, four (TUBB5 (SEQ. ID. NO. 1), ANXA1 (SEQ. ID. NO. 2), NOE1 (SEQ. ID. NO. 13) and GSTM5 (SEQ. ID. NO. 23)) were neural specific genes lending more credence to the proposed neural histogenesis of EWS. Twenty genes were highly expressed only in RMS, including 8 specific for muscle tissue and 5 (FGFR4 (SEQ. ID. NO. 71), IGF2 (SEQ. ID. NO. 72), MYL4 (SEQ. ID. NO. 75), ITGA7 (SEQ. ID. NO. 68), and IGFBP5 (SEQ. ID. NO. 64)) related to myogenesis. Among the latter, IGF2 (SEQ. ID. NO. 72), MYL4 (SEQ. ID. NO. 75) and IGFBP5 (SEQ. ID. NO. 64) expression has been reported in RMS, and only ITGA7 (SEQ. ID. NO. 68) and IGFBP5 (SEQ. ID. NO. 64) were found to be expressed in our two normal muscle samples, making the other genes good targets for therapy. Of the genes specifically expressed in a cancer type, 41 have not been previously reported, including 7 ESTs with no current known function (starred * in FIG. 8). All of these warrant further study and may provide new insights into the biology and importantly new targets for the treatment of these cancers. All or a combination of these genes can be used for designing drugs (small molecule screening), or be used in designing vaccines for cancer therapy.

An ANN method of the invention can also be used to rank genes that are important for each of the four SRBCTs: neuroblastoma (NB), rhabdomyosarcoma (RMS), Burkitt's (BL) and the Ewing family of tumors (EWS). Tables 6 through 9 show weighted gene lists (i.e the most important genes in order of importance) for NB, RMS, BL, and EWS respectively. The genes in each of these tables are more highly ranked and are highly expressed in each of the individual cancers.

TABLE 6

Ranked genes for Neuroblastoma (NB)

| Rank | Clone Id | GeneDescription | Unigene | Weight |
|---|---|---|---|---|
| 2 | 812105 | "ALL1-fused gene from chromosome 1q" | Hs.75823 | 0.96 + −0.03 |
| 6 | 325182 | "cadherin 2, N-cadherin (neuronal)" | Hs.161 | 0.84 + −0.03 |
| 8 | 629896 | "microtubule-associated protein 1B" | Hs.103042 | 0.82 + −0.03 |
| 10 | 878280 | "collapsin response mediator protein 1" | Hs.155392 | 0.80 + −0.03 |
| 11 | 308231 | "Homo sapiens cDNA FLJ20153 fis, clone COL08656, highly similar to AJ001381 Homo sapiens incomplete cDNA for a mutated allele" | Hs.109805 | 0.78 + −0.03 |
| 13 | 295985 | "Homo sapiens cDNA FLJ20653 fis, clone KAT01739" | Hs.180059 | 0.75 + −0.03 |
| 14 | 44563 | "growth associated protein 43" | Hs.79000 | 0.75 + −0.02 |
| 19 | 135688 | "GATA-binding protein 2" | Hs.760 | 0.68 + −0.02 |
| 21 | 383188 | "recoverin" | Hs.80539 | 0.64 + −0.02 |
| 23 | 395708 | "dihydropyrimidinase-like 4" | Hs.100058 | 0.63 + −0.02 |

TABLE 6-continued

Ranked genes for Neuroblastoma (NB)

| Rank | Clone Id | GeneDescription | Unigene | Weight |
|---|---|---|---|---|
| 25 | 82225 | "secreted frizzled-related protein 1" | Hs.7306 | 0.62 + −0.02 |
| 26 | 486787 | "calponin 3, acidic" | Hs.194662 | 0.62 + −0.02 |
| 28 | 377048 | "*Homo sapiens* cDNA FLJ20153 fis, clone COL08656, highly similar to AJ001381 *Homo sapiens* incomplete cDNA for a mutated allele" | Hs.109805 | 0.62 + −0.02 |
| 30 | 486110 | "profilin 2" | Hs.91747 | 0.59 + −0.02 |
| 32 | 768246 | "glucose-6-phosphate dehydrogenase" | Hs.80206 | 0.58 + −0.02 |
| 34 | 786084 | "chromobox homolog 1 (Drosophila HP1 beta)" | Hs.77254 | 0.57 + −0.02 |
| 36 | 211758 | "ribosomal protein S23" | Hs.3463 | 0.57 + −0.02 |
| 40 | 755228 | "dynamin 1" | Hs.166161 | 0.55 + −0.02 |
| 42 | 220096 | "—" | — | 0.55 + −0.02 |
| 43 | 823886 | "Smooth muscle myosin heavy chain isoform SMemb [human, umbilical cord, fetal aorta, mRNA Partial, 971 nt]" | Hs.2094 | 0.55 + −0.02 |
| 44 | 788472 | "nucleobindin 1" | Hs.172609 | 0.54 + −0.02 |
| 45 | 878652 | "procollagen C-endopeptidase enhancer" | Hs.202097 | 0.54 + −0.02 |
| 46 | 234237 | "Pirin" | Hs.279663 | 0.54 + −0.02 |
| 50 | 450152 | "Meis (mouse) homolog 3" | Hs.117313 | 0.51 + −0.02 |
| 51 | 743229 | "neurofilament 3 (150 kD medium)" | Hs.71346 | 0.51 + −0.02 |
| 56 | 134748 | "glycine cleavage system protein H (aminomethyl carrier)" | Hs.77631 | 0.49 + −0.02 |
| 60 | 486175 | "solute carrier family 16 (monocarboxylic acid transporters), member 1" | Hs.75231 | 0.48 + −0.02 |
| 61 | 376516 | "cell division cycle 4-like" | Hs.62354 | 0.48 + −0.02 |
| 63 | 292522 | "ESTs" | Hs.38022 | 0.48 + −0.02 |
| 66 | 843098 | "brain acid-soluble protein 1" | Hs.79516 | 0.48 + −0.02 |
| 68 | 448386 | "pre-B-cell leukemia transcription factor 3" | Hs.171680 | 0.47 + −0.02 |
| 70 | 756401 | "Ras homolog enriched in brain 2" | Hs.279903 | 0.47 + −0.02 |
| 74 | 842918 | "FERM, RhoGEF (ARHGEF) and pleckstrin domain protein 1 (chondrocyte-derived)" | Hs.183738 | 0.46 + −0.02 |
| 76 | 784593 | "ESTs" | Hs.6838 | 0.46 + −0.02 |
| 84 | 364510 | "special AT-rich sequence binding protein 1 (binds to nuclear matrix/scaffold-associating DNA's)" | Hs.74592 | 0.44 + −0.01 |
| 88 | 810864 | "CGI-48 protein" | Hs.6153 | 0.43 + −0.01 |
| 90 | 66977 | "androgen induced protein" | Hs.107528 | 0.43 + −0.01 |
| 92 | 151261 | "ESTs" | Hs.237971 | 0.43 + −0.01 |
| 95 | 289645 | "amyloid beta (A4) precursor-like protein 1" | Hs.74565 | 0.43 + −0.01 |
| 96 | 416959 | "nuclear factor I/B" | Hs.33287 | 0.43 + −0.01 |
| 98 | 47110 | "heterogeneous nuclear ribonucleoprotein D" | Hs.79625 | 0.43 + −0.01 |
| 101 | 244637 | "chromosome 15 open reading frame 3" | Hs.75847 | 0.42 + −0.01 |
| 102 | 949934 | "heterogeneous nuclear ribonucleoprotein A0" | Hs.77492 | 0.42 + −0.01 |
| 103 | 544664 | "matrin 3" | Hs.78825 | 0.42 + −0.01 |
| 108 | 782811 | "high-mobility group (nonhistone chromosomal) protein isoforms I and Y" | Hs.139800 | 0.42 + −0.01 |
| 109 | 812967 | "tetraspan 5" | Hs.20709 | 0.41 + −0.01 |
| 114 | 75254 | "cysteine and glycine-rich protein 2 (LIM domain only, smooth muscle)" | Hs.10526 | 0.41 + −0.01 |
| 115 | 235102 | "ESTs, Moderately similar to LAK-1 [*H. sapiens*]" | Hs.39488 | 0.41 + −0.01 |
| 118 | 81518 | "apelin; peptide ligand for APJ receptor" | Hs.181060 | 0.41 + −0.01 |
| 119 | 344243 | "uridine monophosphate kinase" | Hs.75939 | 0.41 + −0.01 |
| 120 | 789376 | "thioredoxin reductase 1" | Hs.13046 | 0.41 + −0.01 |
| 122 | 811956 | "RAN, member RAS oncogene family" | Hs.10842 | 0.40 + −0.01 |
| 124 | 811095 | "*Homo sapiens* mRNA for KIAA1291 protein, partial cds" | Hs.9805 | 0.40 + −0.01 |
| 125 | 823598 | "proteasome (prosome, macropain) 26S subunit, non-ATPase, 12" | Hs.4295 | 0.40 + −0.01 |
| 130 | 896949 | "3-hydroxy-3-methylglutaryl-Coenzyme A reductase" | Hs.11899 | 0.40 + −0.01 |
| 132 | 140806 | "peptidylglycine alpha-amidating monooxygenase" | Hs.83920 | 0.40 + −0.01 |
| 133 | 760299 | "Dickkopf gene 3" | Hs.4909 | 0.40 + −0.01 |
| 135 | 22260 | "cytochrome c-1" | Hs.697 | 0.40 + −0.01 |
| 137 | 294496 | "ESTs" | Hs.23037 | 0.39 + −0.01 |
| 138 | 813266 | "four and a half LIM domains 1" | Hs.239069 | 0.39 + −0.01 |
| 139 | 234150 | "myotubularin related protein 4" | Hs.141727 | 0.39 + −0.01 |
| 140 | 246194 | "ESTs" | Hs.125522 | 0.39 + −0.01 |
| 142 | 207358 | "solute carrier family 2 (facilitated glucose transporter), member 1" | Hs.169902 | 0.39 + −0.01 |
| 148 | 1456118 | "proteasome (prosome, macropain) subunit, beta type, 9 (large multifunctional protease 2)" | Hs.9280 | 0.38 + −0.01 |

TABLE 6-continued

Ranked genes for Neuroblastoma (NB)

| Rank | Clone Id | GeneDescription | Unigene | Weight |
|---|---|---|---|---|
| 149 | 753215 | "guanine nucleotide binding protein (G protein), alpha inhibiting activity polypeptide 1" | Hs.203862 | 0.38 + −0.01 |
| 151 | 51041 | "ESTs" | Hs.280770 | 0.38 + −0.01 |
| 153 | 813499 | "Sjogren's syndrome/scleroderma autoantigen 1" | Hs.25723 | 0.37 + −0.01 |
| 154 | 1142132 | "RaP2 interacting protein 8" | Hs.6755 | 0.37 + −0.01 |
| 155 | 789182 | "proliferating cell nuclear antigen" | Hs.78996 | 0.37 + −0.01 |
| 161 | 726236 | "paired mesoderm homeo box 1" | Hs.155606 | 0.37 + −0.01 |
| 164 | 866694 | "butyrate-induced transcript 1" | Hs.260622 | 0.37 + −0.01 |
| 165 | 853368 | "thymidylate synthetase" | Hs.82962 | 0.37 + −0.01 |
| 167 | 85259 | "heme oxygenase (decycling) 1" | Hs.202833 | 0.36 + −0.01 |
| 168 | 8327923 | "translocase of inner mitochondrial membrane (yeast) homolog" | Hs.11866 | 0.36 + −0.01 |
| 169 | 137535 | "transcriptional intermediary factor 1" | Hs.183858 | 0.36 + −0.01 |
| 170 | 770391 | "polymerase (RNA) II (DNA directed) polypeptide C (33 kD)" | Hs.79402 | 0.36 + −0.01 |
| 174 | 824591 | "heterogeneous nuclear ribonucleoprotein F" | Hs.808 | 0.36 + −0.01 |
| 177 | 783697 | "BCL2/adenovirus E1B 19 kD-interacting protein 3" | Hs.79428 | 0.36 + −0.01 |
| 178 | 144932 | "deleted in oral cancer (mouse, homolog) 1" | Hs.3436 | 0.36 + −0.01 |
| 179 | 795543 | "thioredoxin peroxidase (antioxidant enzyme)" | Hs.83383 | 0.36 + −0.01 |
| 181 | 292996 | "tyrosine 3-monooxygenase/tryptophan 5-monooxygenase activation protein, eta polypeptide" | Hs.75544 | 0.36 + −0.01 |
| 182 | 345833 | "heterogeneous nuclear ribonucleoprotein A/B" | Hs.81361 | 0.36 + −0.01 |
| 184 | 810510 | "ESTs" | Hs.14317 | 0.35 + −0.01 |
| 185 | 882510 | "karyopherin alpha 2 (RAG cohort 1, importin alpha 1)" | Hs.159557 | 0.35 + −0.01 |
| 186 | 144905 | "PRO1912 protein" | Hs.29494 | 0.35 + −0.01 |
| 188 | 878833 | "ubiquitin carboxyl-terminal esterase L1 (ubiquitin thiolesterase)" | Hs.76118 | 0.35 + −0.01 |
| 189 | 139835 | "UDP-glucose dehydrogenase" | Hs.28309 | 0.35 + −0.01 |
| 190 | 207082 | "glucosamine-6-phosphate deaminase" | Hs.278500 | 0.35 + −0.01 |
| 193 | 884718 | "Hairpin binding protein, histone" | Hs.75257 | 0.35 + −0.01 |
| 195 | 71672 | "electron-transfer-flavoprotein, alpha polypeptide (glutaric aciduria II)" | Hs.169919 | 0.34 + −0.01 |
| 197 | 789204 | "translocation protein 1" | Hs.8146 | 0.34 + −0.01 |
| 198 | 757404 | "von Hippel-Lindau binding protein 1" | Hs.198307 | 0.34 + −0.01 |
| 200 | 784257 | "kinesin family member 3C" | Hs.21611 | 0.34 + −0.01 |

TABLE 7

Ranked Genes for Rhabdomyosarcoma (RMS)

| Rank | Clone Id | GeneDescription | Unigene | Weight |
|---|---|---|---|---|
| 1 | 296448 | "insulin-like growth factor 2 (somatomedin A)" | Hs.251664 | 0.95 + −0.05 |
| 2 | 207274 | "insulin-like growth factor 2 (somatomedin A)" | Hs.251664 | 0.90 + −0.04 |
| 3 | 244618 | "ESTs" | Hs.15463 | 0.70 + −0.03 |
| 4 | 489631 | "chondroitin sulfate proteoglycan 2 (versican)" | Hs.81800 | 0.54 + −0.03 |
| 5 | 298062 | "troponin T2, cardiac" | Hs.89749 | 0.53 + −0.03 |
| 6 | 784224 | "fibroblast growth factor receptor 4" | Hs.165950 | 0.53 + −0.03 |
| 7 | 1409509 | "troponin T1, skeletal, slow" | Hs.73980 | 0.52 + −0.02 |
| 8 | 461425 | "myosin, light polypeptide 4, alkali; atrial, embryonic" | Hs.154156 | 0.50 + −0.02 |
| 9 | 245330 | "insulin-like growth factor 2 (somatomedin A)" | Hs.251664 | 0.47 + −0.02 |
| 10 | 796258 | "sarcoglycan, alpha (50 kD dystrophin-associated glycoprotein)" | Hs.99931 | 0.46 + −0.02 |
| 11 | 293500 | "ESTs" | Hs.49714 | 0.45 + −0.02 |
| 12 | 122159 | "collagen, type III, alpha 1 (Ehlers-Danlos syndrome type IV, autosomal dominant)" | Hs.119571 | 0.45 + −0.02 |
| 13 | 324494 | "heat shock 27 kD protein 2" | Hs.78846 | 0.44 + −0.02 |
| 14 | 898219 | "mesoderm specific transcript (mouse) homolog" | Hs.79284 | 0.44 + −0.02 |

TABLE 7-continued

Ranked Genes for Rhabdomyosarcoma (RMS)

| Rank | Clone Id | GeneDescription | Unigene | Weight |
|---|---|---|---|---|
| 15 | 714453 | "interleukin 4 receptor" | Hs.75545 | 0.44 + −0.02 |
| 16 | 42558 | "glycine amidinotransferase (L-arginine: glycine amidinotransferase)" | Hs.75335 | 0.44 + −0.02 |
| 17 | 377468 | "sprouty (Drosophila) homolog 1 (antagonist of FGF signaling)" | Hs.88044 | 0.43 + −0.02 |
| 18 | 769716 | "neurofibromin 2 (bilateral acoustic neuroma)" | Hs.902 | 0.42 + −0.02 |
| 19 | 809901 | "collagen, type XV, alpha 1" | Hs.83164 | 0.42 + −0.02 |
| 20 | 813841 | "plasminogen activator, tissue" | Hs.274404 | 0.41 + −0.02 |
| 21 | 795877 | "serum-inducible kinase" | Hs.3838 | 0.41 + −0.02 |
| 22 | 214572 | "ESTs" | Hs.280460 | 0.40 + −0.02 |
| 23 | 130057 | "ESTs" | Hs.23057 | 0.39 + −0.02 |
| 24 | 767495 | "GLI-Kruppel family member GLI3 (Greig cephalopolysyndactyly syndrome)" | Hs.72916 | 0.39 + −0.02 |
| 25 | 246035 | "ESTs" | Hs.78026 | 0.39 + −0.02 |
| 26 | 41591 | "meningioma (disrupted in balanced translocation) 1" | Hs.268515 | 0.38 + −0.02 |
| 27 | 714106 | "plasminogen activator, urokinase" | Hs.77274 | 0.38 + −0.02 |
| 28 | 770059 | "heparan sulfate proteoglycan 2 (perlecan)" | Hs.211573 | 0.38 + −0.02 |
| 29 | 814798 | "aldehyde dehydrogenase 6" | Hs.75746 | 0.37 + −0.02 |
| 30 | 365515 | "fibroblast growth factor 7 (keratinocyte growth factor)" | Hs.164568 | 0.37 + −0.02 |
| 31 | 788107 | "bridging integrator 1" | Hs.193163 | 0.36 + −0.02 |
| 32 | 250654 | "secreted protein, acidic, cysteine-rich (osteonectin)" | Hs.111779 | 0.36 + −0.02 |
| 33 | 295985 | "*Homo sapiens* cDNA FLJ20653 fis, clone KAT01739" | Hs.180059 | 0.36 + −0.02 |
| 34 | 789253 | "presenilin 2 (Alzheimer disease 4)" | Hs.25363 | 0.36 + −0.02 |
| 35 | 299737 | "*Homo sapiens* clone 24411 mRNA sequence" | Hs.20952 | 0.35 + −0.02 |
| 36 | 859359 | "quinone oxidoreductase homolog" | Hs.50649 | 0.35 + −0.02 |
| 37 | 66714 | "peanut (Drosophila)-like 2" | Hs.155524 | 0.34 + −0.02 |
| 39 | 755750 | "non-metastatic cells 2, protein (NM23B) expressed in" | Hs.275163 | 0.34 + −0.02 |
| 40 | 727251 | "CD9 antigen (p24)" | Hs.1244 | 0.33 + −0.02 |
| 41 | 25725 | "farnesyl-diphosphate farnesyltransferase 1" | Hs.48876 | 0.33 + −0.02 |
| 42 | 143306 | "lymphocyte-specific protein 1" | Hs.56729 | 0.33 + −0.02 |
| 45 | 491692 | "collagen, type IV, alpha 1" | Hs.119129 | 0.32 + −0.02 |
| 46 | 142134 | "hypothetical protein FLJ20185" | Hs.272972 | 0.32 + −0.02 |
| 47 | 813823 | "lumican" | Hs.79914 | 0.32 + −0.02 |
| 48 | 788695 | "troponin T3, skeletal, fast" | Hs.73454 | 0.32 + −0.02 |
| 49 | 308163 | "ESTs" | Hs.84520 | 0.32 + −0.02 |
| 50 | 377671 | "integrin, alpha 7" | Hs.74369 | 0.31 + −0.02 |
| 51 | 281901 | "ESTs" | Hs.74280 | 0.31 + −0.02 |
| 52 | 796904 | "pleomorphic adenoma gene-like 1" | Hs.75825 | 0.31 + −0.01 |
| 53 | 773215 | "runt-related transcription factor 1 (acute myeloid leukemia 1; aml1 oncogene)" | Hs.129914 | 0.30 + −0.01 |
| 55 | 486787 | "calponin 3, acidic" | Hs.194662 | 0.30 + −0.01 |
| 56 | 341588 | "CGI-119 protein" | Hs.25615 | 0.29 + −0.01 |
| 57 | 839552 | "nuclear receptor coactivator 1" | Hs.74002 | 0.29 + −0.01 |
| 58 | 365826 | "growth arrest-specific 1" | Hs.65029 | 0.29 + −0.01 |
| 59 | 111884 | "ESTs, Weakly similar to hTcf-4 [*H. sapiens*]" | Hs.102367 | 0.29 + −0.01 |
| 60 | 797048 | "bone morphogenetic protein 4" | Hs.68879 | 0.28 + −0.01 |
| 61 | 769959 | "collagen, type IV, alpha 2" | Hs.75617 | 0.28 + −0.01 |
| 62 | 204545 | "ESTs" | Hs.8966 | 0.28 + −0.01 |
| 63 | 771323 | "procollagen-lysine, 2-oxoglutarate 5-dioxygenase (lysine hydroxylase, Ehlers-Danlos syndrome type VI)" | Hs.75093 | 0.27 + −0.01 |
| 65 | 897865 | "midline 1 (Opitz/BBB syndrome)" | Hs.27695 | 0.27 + −0.01 |
| 66 | 298417 | "trefoil factor 3 (intestinal)" | Hs.82961 | 0.27 + −0.01 |
| 67 | 79022 | "FBJ murine osteosarcoma viral oncogene homolog B" | Hs.75678 | 0.27 + −0.01 |
| 68 | 290378 | "podocalyxin-like" | Hs.16426 | 0.27 + −0.01 |
| 69 | 784593 | "ESTs" | Hs.6838 | 0.27 + −0.01 |
| 70 | 32493 | "integrin, alpha 6" | Hs.227730 | 0.27 + −0.01 |
| 71 | 45542 | "Human insulin-like growth factor binding protein 5 (IGFBP5) mRNA" | Hs.103391 | 0.26 + −0.01 |
| 72 | 208001 | "CD59 antigen p18–20 (antigen identified by monoclonal antibodies 16.3A5, EJ16, EJ30, EL32 and G344)" | Hs.119663 | 0.26 + −0.01 |

TABLE 7-continued

Ranked Genes for Rhabdomyosarcoma (RMS)

| Rank | Clone Id | GeneDescription | Unigene | Weight |
|---|---|---|---|---|
| 73 | 413633 | "EST" | — | 0.26 + −0.01 |
| 74 | 284882 | "collagen, type II, alpha 1 (primary osteoarthritis, spondyloepiphyseal dysplasia, congenital)" | Hs.81343 | 0.26 + −0.01 |
| 75 | 273435 | "v-yes-1 Yamaguchi sarcoma viral oncogene homolog 1" | Hs.194148 | 0.26 + −0.01 |
| 76 | 839991 | "collagen, type I, alpha 2" | Hs.179573 | 0.26 + −0.01 |
| 78 | 323371 | "amyloid beta (A4) precursor protein (protease nexin-II, Alzheimer disease)" | Hs.177486 | 0.26 + −0.01 |
| 79 | 362483 | "spectrin, beta, non-erythrocytic 1" | Hs.107164 | 0.26 + −0.01 |
| 80 | 839736 | "crystallin, alpha B" | Hs.1940 | 0.25 + −0.01 |
| 81 | 380620 | "presenilin 2 (Alzheimer disease 4)" | Hs.25363 | 0.25 + −0.01 |
| 82 | 343867 | "allograft inflammatory factor 1" | Hs.76364 | 0.25 + −0.01 |
| 83 | 882506 | "lysyl oxidase-like 2" | Hs.83354 | 0.25 + −0.01 |
| 84 | 214990 | "gelsolin (amyloidosis, Finnish type)" | Hs.80562 | 0.25 + −0.01 |
| 85 | 878182 | "alpha-2-macroglobulin" | Hs.74561 | 0.25 + −0.01 |
| 86 | 301122 | "extracellular matrix protein 1" | Hs.81071 | 0.25 + −0.01 |
| 87 | 198982 | "DNA (cytosine-5-)-methyltransferase 2" | Hs.97681 | 0.25 + −0.01 |
| 88 | 138672 | "ESTs" | Hs.28412 | 0.25 + −0.01 |
| 89 | 246377 | "EST" | Hs.102670 | 0.24 + −0.01 |
| 90 | 50941 | "cadherin 13, H-cadherin (heart)" | Hs.63984 | 0.24 + −0.01 |
| 91 | 812196 | "UDP-glucose ceramide glucosyltransferase" | Hs.152601 | 0.24 + −0.01 |
| 92 | 120881 | "proteasome (prosome, macropain) subunit, alpha type, 4" | Hs.251531 | 0.24 + −0.01 |
| 93 | 813698 | "sprouty (Drosophila) homolog 2" | Hs.18676 | 0.24 + −0.01 |
| 94 | 810612 | "S100 calcium-binding protein A11 (calgizzarin)" | Hs.256290 | 0.24 + −0.01 |
| 97 | 767851 | "fibrillin 1 (Marfan syndrome)" | Hs.750 | 0.23 + −0.01 |
| 99 | 211758 | "ribosomal protein S23" | Hs.3463 | 0.23 + −0.01 |
| 100 | 506369 | "nidogen (enactin)" | Hs.62041 | 0.23 + −0.01 |
| 101 | 75254 | "cysteine and glycine-rich protein 2 (LIM domain only, smooth muscle)" | Hs.10526 | 0.23 + −0.01 |
| 103 | 823851 | "AE-binding protein 1" | Hs.118397 | 0.23 + −0.01 |
| 104 | 52096 | "platelet-derived growth factor receptor, alpha polypeptide" | Hs.74615 | 0.23 + −0.01 |
| 106 | 760224 | "X-ray repair complementing defective repair in Chinese hamster cells 1" | Hs.98493 | 0.23 + −0.01 |
| 107 | 725473 | "DNA segment on chromosome 12 (unique) 2489 expressed sequence" | Hs.74085 | 0.23 + −0.01 |
| 111 | 148028 | "epidermal growth factor receptor pathway substrate 8" | Hs.2132 | 0.23 + −0.01 |
| 113 | 769028 | "mesenchyme homeo box 1" | Hs.438 | 0.23 + −0.01 |
| 115 | 39093 | "methionine aminopeptidase; eIF-2-associated p67" | Hs.78935 | 0.22 + −0.01 |
| 116 | 854899 | "dual specificity phosphatase 6" | Hs.180383 | 0.22 + −0.01 |
| 118 | 547247 | "stanniocalcin" | Hs.25590 | 0.22 + −0.01 |
| 119 | 26418 | "endothelial differentiation, sphingolipid G-protein-coupled receptor, 1" | Hs.154210 | 0.22 + −0.01 |
| 120 | 811848 | "transforming growth factor beta 1 induced transcript 1" | Hs.25511 | 0.22 + −0.01 |
| 123 | 178463 | "transcription factor 8 (represses interleukin 2 expression)" | Hs.232068 | 0.22 + −0.01 |
| 124 | 810859 | "natural killer cell transcript 4" | Hs.943 | 0.22 + −0.01 |
| 125 | 40643 | "platelet-derived growth factor receptor, beta polypeptide" | Hs.76144 | 0.22 + −0.01 |
| 126 | 782193 | "thioredoxin" | Hs.76136 | 0.22 + −0.01 |
| 127 | 1412412 | "elastase 1, pancreatic" | Hs.21 | 0.22 + −0.01 |
| 128 | 470128 | "myosin IC" | Hs.82251 | 0.22 + −0.01 |
| 129 | 68950 | "cyclin E1" | Hs.9700 | 0.22 + −0.01 |
| 130 | 66552 | "ESTs" | Hs.119021 | 0.22 + −0.01 |
| 131 | 233721 | "insulin-like growth factor binding protein2 (36 kD)" | Hs.162 | 0.22 + −0.01 |
| 133 | 814444 | "cofactor required for Sp1 transcriptional activation, subunit 9 (33 kD)" | Hs.279902 | 0.21 + −0.01 |
| 134 | 160723 | "laminin, gamma 1 (formerly LAMB2)" | Hs.214982 | 0.21 + −0.01 |
| 135 | 752652 | "transcription factor 7-like 2 (T-cell specific, HMG-box)" | Hs.154485 | 0.21 + −0.01 |
| 136 | 180902 | "CGI-43 protein" | Hs.111515 | 0.21 + −0.01 |

TABLE 7-continued

Ranked Genes for Rhabdomyosarcoma (RMS)

| Rank | Clone Id | GeneDescription | Unigene | Weight |
|---|---|---|---|---|
| 137 | 154472 | "fibroblast growth factor receptor 1 (fms-related tyrosine kinase 2, Pfeiffer syndrome)" | Hs.748 | 0.21 + −0.01 |
| 139 | 82225 | "secreted frizzled-related protein 1" | Hs.7306 | 0.21 + −0.01 |
| 140 | 898092 | "connective tissue growth factor" | Hs.75511 | 0.21 + −0.01 |
| 141 | 0 | "—" | — | 0.21 + −0.01 |
| 142 | 773568 | "POU domain, class 4, transcription factor 1" | Hs.211588 | 0.21 + −0.01 |
| 143 | 144797 | "a disintegrin-like and metalloprotease (reprolysin type) with thrombospondin type 1 motif, 1" | Hs.8230 | 0.21 + −0.01 |
| 145 | 139818 | "KIAA0669 gene product" | Hs.52526 | 0.21 + −0.01 |
| 146 | 358433 | "retinoid X receptor, gamma" | Hs.26550 | 0.21 + −0.01 |
| 147 | 141192 | "Leman coiled-coil protein" | Hs.92186 | 0.21 + −0.01 |
| 148 | 813707 | "regulator of G-protein signalling 16" | Hs.183601 | 0.21 + −0.01 |
| 149 | 781014 | "suppression of tumorigenicity 5" | Hs.79265 | 0.21 + −0.01 |
| 150 | 857640 | "Human alpha-2 collagen type VI mRNA, 3' end" | Hs.281620 | 0.21 + −0.01 |
| 151 | 811028 | "cathepsin D (lysosomal aspartyl protease)" | Hs.79572 | 0.21 + −0.01 |
| 153 | 196992 | "aldo-keto reductase family 1, member C1 (dihydrodiol dehydrogenase 1; 20-alpha (3-alpha)-hydroxysteroid dehydrogenase)" | Hs.275374 | 0.20 + −0.01 |
| 154 | 781019 | "paraoxonase 2" | Hs.169857 | 0.20 + −0.01 |
| 155 | 491559 | "fatty acid binding protein 3, muscle and heart (mammary-derived growth inhibitor)" | Hs.49881 | 0.20 + −0.01 |
| 156 | 358531 | "v-jun avian sarcoma virus 17 oncogene homolog" | Hs.78465 | 0.20 + −0.01 |
| 157 | 127099 | "*Homo sapiens* cDNA FLJ20754 fis, clone HEP02246" | Hs.72249 | 0.20 + −0.01 |
| 158 | 263716 | "collagen, type VI, alpha 1" | Hs.108885 | 0.20 + −0.01 |
| 162 | 78761 | "dual-specificity tyrosine-(Y)-phosphorylation regulated kinase 2" | Hs.173135 | 0.20 + −0.01 |
| 163 | 246722 | "trinucleotide repeat containing 3" | Hs.21858 | 0.20 + −0.01 |
| 164 | 151449 | "protein tyrosine phosphatase, non-receptor type 21" | Hs.155693 | 0.20 + −0.01 |
| 165 | 81475 | "—" | — | 0.20 + −0.01 |
| 166 | 810512 | "thrombospondin 1" | Hs.87409 | 0.20 + −0.01 |
| 168 | 233071 | "transmembrane protein 2" | Hs. 160417 | 0.19 + −0.01 |
| 170 | 809910 | "interferon induced transmembrane protein 3 (1-8U)" | Hs.182241 | 0.19 + −0.01 |
| 171 | 233688 | "a disintegrin and metalloproteinase domain 12 (meltrin alpha)" | Hs.8850 | 0.19 + −0.01 |
| 172 | 128054 | "H2A histone family, member X" | Hs.147097 | 0.19 + −0.01 |
| 173 | 143523 | "collagen, type V, alpha 1" | Hs.146428 | 0.19 + −0.01 |
| 174 | 809719 | "protein tyrosine phosphatase, receptor type, c polypeptide" | Hs.170121 | 0.19 + −0.01 |
| 175 | 45291 | "dentatorubral-pallidoluysian atrophy (atrophin-1)" | Hs.169488 | 0.19 + −0.01 |
| 176 | 758266 | "thrombospondin 4" | Hs.75774 | 0.19 + −0.01 |
| 178 | 247818 | "ESTs" | Hs.239666 | 0.19 + −0.01 |
| 179 | 130824 | "S-phase kinase-associated protein 2 (p45)" | Hs.23348 | 0.19 + −0.01 |
| 180 | 341328 | "tropomyosin 1 (alpha)" | Hs.77899 | 0.19 + −0.01 |
| 181 | 123916 | "dystrophia myotonica-containing WD repeat motif" | Hs.275924 | 0.19 + −0.01 |
| 183 | 682555 | "insulin-like growth factor 1 receptor" | Hs.239176 | 0.19 + −0.01 |
| 184 | 868380 | "Fc fragment of IgG, low affinity IIa, receptor for (CD32)" | Hs.78864 | 0.19 + −0.01 |
| 187 | 869187 | "*Homo sapiens* clone 23698 mRNA sequence" | Hs.8136 | 0.19 + −0.01 |
| 190 | 207920 | "solute carrier family 17 (sodium phosphate), member 2" | Hs.19710 | 0.19 + −0.01 |
| 192 | 469345 | "kinase insert domain receptor (a type III receptor tyrosine kinase)" | Hs.12337 | 0.18 + −0.01 |
| 193 | 754406 | "integrin, alpha M (complement component receptor 3, alpha; also known as CD11b (p170), macrophage antigen alpha polypeptide)" | Hs.172631 | 0.18 + −0.01 |

TABLE 7-continued

Ranked Genes for Rhabdomyosarcoma (RMS)

| Rank | Clone Id | GeneDescription | Unigene | Weight |
|---|---|---|---|---|
| 196 | 43563 | "cytochrome P450, subfamily XXVIIA (steroid 27-hydroxylase, cerebrotendinous xanthomatosis), polypeptide 1" | Hs.82568 | 0.18 + −0.01 |
| 198 | 753775 | "guanosine monophosphate reductase" | Hs.1435 | 0.18 + −0.01 |

TABLE 8

Ranked genes for Burkitt's (BL)

| Rank | Clone Id | GeneDescription | Unigene | Weight |
|---|---|---|---|---|
| 2 | 80109 | "major histocompatibility complex, class II, DQ alpha 1" | Hs.198253 | 0.58 + −0.02 |
| 3 | 840942 | "major histocompatibility complex, class II, DP beta 1" | Hs.814 | 0.56 + −0.02 |
| 7 | 183337 | "major histocompatibility complex, class II, DM alpha" | Hs.77522 | 0.52 + −0.02 |
| 17 | 609663 | "protein kinase, cAMP-dependent, regulatory, type II, beta" | Hs.77439 | 0.45 + −0.02 |
| 23 | 767183 | "hematopoietic cell-specific Lyn substrate 1" | Hs.14601 | 0.43 + −0.02 |
| 27 | 297392 | "metallothionein 1L" | Hs.94360 | 0.42 + −0.02 |
| 30 | 200814 | "membrane metallo-endopeptidase (neutral endopeptidase, enkephalinase, CALLA, CD10)" | Hs.1298 | 0.41 + −0.02 |
| 33 | 241412 | "E74-like factor 1 (ets domain transcription factor)" | Hs.154365 | 0.41 + −0.02 |
| 35 | 1469292 | "pim-2 oncogene" | Hs.80205 | 0.39 + −0.02 |
| 45 | 417226 | "v-myc avian myelocytomatosis viral oncogene homolog" | Hs.79070 | 0.38 + −0.01 |
| 57 | 47475 | "p53 inducible protein" | Hs.258503 | 0.36 + −0.01 |
| 61 | 236282 | "Wiskott-Aldrich syndrome (ecezema-thrombocytopenia)" | Hs.2157 | 0.35 + −0.01 |
| 63 | 868304 | "actin, alpha 2, smooth muscle, aorta" | Hs.195851 | 0.34 + −0.01 |
| 65 | 740604 | "interferon stimulated gene (20 kD)" | Hs.183487 | 0.34 + −0.01 |
| 82 | 824602 | "interferon, gamma-inducible protein 16" | Hs.155530 | 0.31 + −0.01 |
| 83 | 624360 | "proteasome (prosome, macropain) subunit, beta type, 8 (large multifunctional protease 7)" | Hs.180062 | 0.31 + −0.01 |
| 84 | 344134 | "immunoglobulin lambda-like polypeptide 3" | Hs.170116 | 0.31 + −0.01 |
| 85 | 193913 | "v-yes-1 Yamaguchi sarcoma viral related oncogene homolog" | Hs.80887 | 0.31 + −0.01 |
| 88 | 814526 | "seb4D" | Hs.236361 | 0.31 + −0.01 |
| 101 | 236034 | "uncoupling protein 2 (mitochondrial, proton carrier)" | Hs.80658 | 0.30 + −0.01 |
| 106 | 745343 | "regenerating islet-derived 1 alpha (pancreatic stone protein, pancreatic thread protein)" | Hs.1032 | 0.30 + −0.01 |
| 114 | 788511 | "ribosomal protein S6 kinase, 90 kD, polypeptide 1" | Hs.149957 | 0.29 + −0.01 |
| 118 | 283315 | "phosphoglycerate mutase 2 (muscle)" | Hs.46039 | 0.29 + −0.01 |
| 135 | 502333 | "nuclear receptor coactivator 3" | Hs.225977 | 0.27 + −0.01 |
| 136 | 262920 | "endothelial differentiation-related factor 1" | Hs.174050 | 0.27 + −0.01 |
| 140 | 897177 | "phosphoglycerate mutase 1 (brain)" | Hs.181013 | 0.27 + −0.01 |
| 146 | 700792 | "cyclin-dependent kinase inhibitor 3 (CDK2-associated dual specificity phosphatase)" | Hs.84113 | 0.27 + −0.01 |
| 147 | 626502 | "actin related protein 2/3 complex, subunit 1B (41 kD)" | Hs.11538 | 0.27 + −0.01 |
| 149 | 769657 | "protein phosphatase 1, regulatory (inhibitor) subunit 2" | Hs.267819 | 0.27 + −0.01 |
| 152 | 435953 | "inositol 1,4,5-triphosphate receptor, type 3" | Hs.77515 | 0.26 + −0.01 |
| 155 | 812965 | "v-myc avian myelocytomatosis viral oncogene homolog" | Hs.79070 | 0.26 + −0.01 |
| 159 | 714453 | "interleukin 4 receptor" | Hs.75545 | 0.26 + −0.01 |

TABLE 8-continued

Ranked genes for Burkitt's (BL)

| Rank | Clone Id | GeneDescription | Unigene | Weight |
|---|---|---|---|---|
| 163 | 145112 | "intercellular adhesion molecule 1 (CD54), human rhinovirus receptor" | Hs.168383 | 0.25 + −0.01 |
| 164 | 80649 | "Rho-associated, coiled-coil containing protein kinase 1" | Hs.17820 | 0.25 + −0.01 |
| 172 | 240208 | "DKFZP434O125 protein" | Hs.102669 | 0.25 + −0.01 |
| 174 | 298155 | "acyl-Coenzyme A dehydrogenase, C-4 to C-12 straight chain" | Hs.79158 | 0.25 + −0.01 |
| 176 | 530185 | "CD83 antigen (activated B lymphocytes, immunoglobulin superfamily)" | Hs.79197 | 0.25 + −0.01 |
| 185 | 755145 | "villin 2 (ezrin)" | Hs.155191 | 0.24 + −0.01 |
| 192 | 68977 | "proteasome (prosome, macropain) subunit, beta type, 10" | Hs.9661 | 0.24 + −0.01 |

TABLE 9

Ranked genes for Ewing family of tumors (EWS)

| Rank | Clone Id | GeneDescription | Unigene | Weight |
|---|---|---|---|---|
| 2 | 866702 | "protein tyrosine phosphatase, non-receptor type 13 (APO-1/CD95 (Fas)-associated phosphatase)" | Hs.211595 | 0.47 + −0.03 |
| 3 | 770394 | "Fc fragment of IgG, receptor, transporter, alpha" | Hs.160741 | 0.47 + −0.03 |
| 5 | 377461 | "caveolin 1, caveolae protein, 22 kD" | Hs.281621 | 0.45 + −0.03 |
| 6 | 357031 | "tumor necrosis factor, alpha-induced protein 6" | Hs.29352 | 0.44 + −0.03 |
| 7 | 43733 | "glycogenin 2" | Hs.58589 | 0.42 + −0.03 |
| 9 | 52076 | "olfactomedin related ER localized protein" | Hs.74376 | 0.38 + −0.02 |
| 10 | 814260 | "follicular lymphoma variant translocation 1" | Hs.74050 | 0.36 + −0.02 |
| 11 | 755599 | "interferon induced transmembrane protein 1 (9–27)" | Hs.146360 | 0.35 + −0.02 |
| 13 | 377731 | "glutathione S-transferase M5" | Hs.75652 | 0.34 + −0.02 |
| 14 | 1473131 | "transducin-like enhancer of split 2, homolog of Drosophila E(sp1)" | Hs.173063 | 0.34 + −0.02 |
| 15 | 823928 | "glutathione S-transferase theta 2" | Hs.1581 | 0.32 + −0.02 |
| 16 | 1435862 | "antigen identified by monoclonal antibodies 12E7, F21 and O13" | Hs.177543 | 0.32 + −0.02 |
| 17 | 812965 | "v-myc avian myelocytomatosis viral oncogene homolog" | Hs.79070 | 0.32 + −0.02 |
| 18 | 841641 | "cyclin D1 (PRAD1: parathyroid adenomatosis 1)" | Hs.82932 | 0.31 + −0.02 |
| 19 | 208718 | "annexin A1" | Hs.78225 | 0.29 + −0.02 |
| 20 | 713922 | "glutathione S-transferase M1" | Hs.278633 | 0.29 + −0.02 |
| 21 | 291756 | "tubulin, beta, 5" | Hs.108014 | 0.29 + −0.02 |
| 23 | 1323448 | "cysteine-rich protein 1 (intestinal)" | Hs.17409 | 0.28 + −0.02 |
| 24 | 308497 | "KIAA0467 protein" | Hs.11147 | 0.28 + −0.02 |
| 25 | 789091 | "H2A histone family, member L" | Hs.28777 | 0.28 + −0.02 |
| 26 | 1471841 | "ATPase, Na + /K + transporting, alpha 1 polypeptide" | Hs.190703 | 0.27 + −0.02 |
| 27 | 178825 | "neurogranin (protein kinase C substrate, RC3)" | Hs.26944 | 0.26 + −0.02 |
| 28 | 810504 | "proteolipid protein 2 (colonic epithelium-enriched)" | Hs.77422 | 0.25 + −0.02 |
| 29 | 740554 | "*Homo sapiens* mRNA; cDNA DKFZp434I0812 (from clone DKFZp434I0812); partial cds" | Hs.263671 | 0.25 + −0.02 |
| 30 | 24415 | "tumor protein p53 (Li-Fraumeni syndrome)" | Hs.1846 | 0.25 + −0.02 |
| 31 | 811108 | "thyroid hormone receptor interactor 6" | Hs.119498 | 0.25 + −0.02 |
| 32 | 770868 | "NGFI-A binding protein 2 (ERG1 binding protein 2)" | Hs.159223 | 0.25 + −0.01 |
| 35 | 80338 | "selenium binding protein 1" | Hs.7833 | 0.24 + −0.01 |
| 38 | 212640 | "Rho GTPase activating protein 4" | Hs.3109 | 0.24 + −0.01 |
| 39 | 417226 | "v-myc avian myelocytomatosis viral oncogene homolog" | Hs.79070 | 0.24 + −0.01 |
| 40 | 742132 | "interferon-stimulated protein, 15 kDa" | Hs.833 | 0.23 + −0.01 |
| 41 | 365826 | "growth arrest-specific 1" | Hs.65029 | 0.23 + −0.01 |
| 42 | 161993 | "CCAAT/enhancer binding protein (C/EBP), beta" | Hs.99029 | 0.23 + −0.01 |
| 43 | 811000 | "lectin, galactoside-binding, soluble, 3 binding protein (galectin 6 binding protein)" | Hs.79339 | 0.23 + −0.01 |
| 44 | 768205 | "homeo box D9" | Hs.236646 | 0.22 + −0.01 |
| 48 | 345232 | "lymphotoxin alpha (TNF superfamily, member 1)" | Hs.36 | 0.22 + −0.01 |
| 49 | 586854 | "CGI-119 protein" | Hs.25615 | 0.22 + −0.01 |
| 52 | 744417 | "carnitine acetyltransferase" | Hs.12068 | 0.21 + −0.01 |
| 53 | 364934 | "death-associated protein kinase 1" | Hs.153924 | 0.21 + −0.01 |
| 54 | 809694 | "cellular retinoic acid-binding protein 1" | Hs.7678 | 0.21 + −0.01 |
| 55 | 491565 | "Cbp/p300-interacting transactivator, with Glu/Asp-rich carboxy-terminal domain, 2" | Hs.82071 | 0.21 + −0.01 |

TABLE 9-continued

Ranked genes for Ewing family of tumors (EWS)

| Rank | Clone Id | GeneDescription | Unigene | Weight |
|---|---|---|---|---|
| 56 | 1470048 | "lymphocyte antigen 6 complex, locus E" | Hs.77667 | 0.21 + −0.01 |
| 57 | 814266 | "protein kinase C, zeta" | Hs.78793 | 0.21 + −0.01 |
| 58 | 296030 | "ESTs" | Hs.10362 | 0.21 + −0.01 |
| 59 | 379708 | "chromodomain helicase DNA binding protein 3" | Hs.25601 | 0.21 + −0.01 |
| 60 | 755506 | "annexin A4" | Hs.77840 | 0.20 + −0.01 |
| 61 | 39796 | "3-hydroxymethyl-3-methylglutaryl-Coenzyme A lyase (hydroxymethylglutaricaciduria)" | Hs.831 | 0.20 + −0.01 |
| 62 | 741885 | "transcription factor binding to IGHM enhancer 3" | Hs.274184 | 0.20 + −0.01 |
| 63 | 271102 | "copper chaperone for superoxide dismutase" | Hs.5002 | 0.20 + −0.01 |
| 64 | 470261 | "SMA3" | Hs.251397 | 0.20 + −0.01 |
| 66 | 745343 | "regenerating islet-derived 1 alpha (pancreatic stone protein, pancreatic thread protein)" | Hs.1032 | 0.20 + −0.01 |
| 67 | 563673 | "antiquitin 1" | Hs.74294 | 0.20 + −0.01 |
| 68 | 39093 | "methionine aminopeptidase; eIF-2-associated p67" | Hs.78935 | 0.20 + −0.01 |
| 75 | 234376 | "*Homo sapiens* mRNA; cDNA DKFZp564F112 (from clone DKFZp564F112)" | Hs.166361 | 0.19 + −0.01 |
| 76 | 810133 | "ESTs" | Hs.10362 | 0.19 + −0.01 |
| 78 | 815239 | "Rho guanine nucleotide exchange factor (GEF) 1" | Hs.252280 | 0.19 + −0.01 |
| 80 | 172751 | "amyloid beta (A4) precursor protein-binding, family A, member 1 (X11)" | Hs.4880 | 0.18 + −0.01 |
| 81 | 289645 | "amyloid beta (A4) precursor-like protein 1" | Hs.74565 | 0.18 + −0.01 |
| 84 | 769579 | "mitogen-activated protein kinase kinase 2" | Hs.72241 | 0.18 + −0.01 |
| 85 | 1422723 | "interferon-induced protein 35" | Hs.50842 | 0.18 + −0.01 |
| 86 | 296880 | "membrane protein, palmitoylated 1 (55 kD)" | Hs.1861 | 0.18 + −0.01 |
| 87 | 744052 | "nuclear receptor subfamily 1, group H, member 2" | Hs.100221 | 0.18 + −0.01 |
| 88 | 782503 | "*Homo sapiens* clone 23716 mRNA sequence" | Hs.12214 | 0.18 + −0.01 |
| 89 | 1434905 | "homeo box B7" | Hs.819 | 0.18 + −0.01 |
| 90 | 212542 | "*Homo sapiens* mRNA; cDNA DKFZp586J2118 (from clone DKFZp586J2118)" | Hs.21851 | 0.18 + −0.01 |
| 91 | 506548 | "regulator of G-protein signalling 10" | Hs.82280 | 0.18 + −0.01 |
| 93 | 768443 | "microsomal glutathione S-transferase 1" | Hs.790 | 0.18 + −0.01 |
| 94 | 75923 | "Human zinc finger protein mRNA, complete cds" | Hs.78765 | 0.18 + −0.01 |
| 97 | 1475595 | "alkaline phosphatase, liver/bone/kidney" | Hs.250769 | 0.17 + −0.01 |
| 99 | 231355 | "vesicle-associated membrane protein 2 (synaptobrevin 2)" | Hs.194534 | 0.17 + −0.01 |
| 100 | 841620 | "dihydropyrimidinase-like 2" | Hs.173381 | 0.17 + −0.01 |
| 101 | 1456900 | "dipeptidase 1 (renal)" | Hs.109 | 0.17 + −0.01 |
| 103 | 773246 | "ring finger protein 1" | Hs.35384 | 0.17 + −0.01 |
| 104 | 191743 | "ESTs" | Hs.94814 | 0.17 + −0.01 |
| 105 | 265874 | "nuclear factor I/C (CCAAT-binding transcription factor)" | Hs.184771 | 0.17 + −0.01 |
| 106 | 767345 | "ESTs, Moderately similar to I59372 cadherin 12 — human [*H. sapiens*]" | Hs.44898 | 0.17 + −0.01 |
| 107 | 729964 | "sphingomyelin phosphodiesterase 1, acid lysosomal (acid sphingomyelinase)" | Hs.77813 | 0.17 + −0.01 |
| 108 | 768644 | "zona pellucida glycoprotein 3A (sperm receptor)" | Hs.250867 | 0.17 + −0.01 |
| 111 | 858469 | "thrombospondin 3" | Hs.169875 | 0.17 + −0.01 |
| 112 | 756556 | "complement component 1 inhibitor (angioedema, hereditary)" | Hs.151242 | 0.17 + −0.01 |
| 113 | 190887 | "myeloid differentiation primary response gene (88)" | Hs.82116 | 0.17 + −0.01 |
| 114 | 1475730 | "chaperonin containing TCP1, subunit 6A (zeta 1)" | Hs.82916 | 0.17 + −0.01 |
| 115 | 137158 | "chromogranin A (parathyroid secretory protein 1)" | Hs.172216 | 0.17 + −0.01 |
| 116 | 897774 | "adenine phosphoribosyltransferase" | Hs.28914 | 0.17 + −0.01 |
| 120 | 757248 | "calpain, large polypeptide L3" | Hs.40300 | 0.17 + −0.01 |
| 124 | 811920 | "interleukin 11 receptor, alpha" | Hs.64310 | 0.16 + −0.01 |
| 125 | 824602 | "interferon, gamma-inducible protein 16" | Hs.155530 | 0.16 + −0.01 |
| 126 | 150702 | "homeo box B5" | Hs.22554 | 0.16 + −0.01 |
| 127 | 37553 | "protein phosphatase 2A, regulatory subunit B' (PR 53)" | Hs.236963 | 0.16 + −0.01 |
| 128 | 139957 | "hypothetical protein FLJ11181" | Hs.28472 | 0.16 + −0.01 |
| 130 | 343646 | "v-ski avian sarcoma viral oncogene homolog" | Hs.2969 | 0.16 + −0.01 |
| 131 | 1031748 | "synovial sarcoma, X breakpoint 3" | Hs.178749 | 0.16 + −0.01 |
| 132 | 166236 | "glucose-6-phosphate dehydrogenase" | Hs.80206 | 0.16 + −0.01 |
| 133 | 740801 | "branched chain keto acid dehydrogenase E1, alpha polypeptide (maple syrup urine disease)" | Hs.78950 | 0.16 + −0.01 |
| 134 | 120468 | "excision repair cross-complementing rodent repair deficiency, complementation group 1 (includes overlapping antisense sequence)" | Hs.59544 | 0.16 + −0.01 |
| 137 | 785967 | "erythrocyte membrane protein band 4.1-like 2" | Hs.7857 | 0.16 + −0.01 |
| 139 | 361943 | "Meis1 (mouse) homolog" | Hs.170177 | 0.16 + −0.01 |
| 140 | 810551 | "low density lipoprotein-related protein 1 (alpha-2-macroglobulin receptor)" | Hs.89137 | 0.16 + −0.01 |

TABLE 9-continued

Ranked genes for Ewing family of tumors (EWS)

| Rank | Clone Id | GeneDescription | Unigene | Weight |
|---|---|---|---|---|
| 141 | 841698 | "exostoses (multiple) 1" | Hs.184161 | 0.16 + −0.01 |
| 142 | 753104 | "dopachrome tautomerase (dopachrome delta-isomerase, tyrosine-related protein 2)" | Hs.240217 | 0.16 + −0.01 |
| 143 | 878798 | "beta-2-microglobulin" | Hs.75415 | 0.16 + −0.01 |
| 145 | 811900 | "lymphotoxin beta receptor (TNFR superfamily, member 3)" | Hs.1116 | 0.16 + −0.01 |
| 146 | 741831 | "phospholipid transfer protein" | Hs.154854 | 0.15 + −0.01 |
| 147 | 549146 | "stimulated trans-acting factor (50 kDa)" | Hs.68054 | 0.15 + −0.01 |
| 149 | 841340 | "ATP-binding cassette, sub-family B (MDR/TAP), member 2" | Hs.158164 | 0.15 + −0.01 |
| 153 | 42576 | "ubiquitin-activating enzyme E1 (A1S9T and BN75 temperature sensitivity complementing)" | Hs.2055 | 0.15 + −0.01 |
| 154 | 53039 | "carbohydrate (keratan sulfate Gal-6) sulfotransferase 1" | Hs.104576 | 0.15 + −0.01 |
| 155 | 308163 | "ESTs" | Hs.84520 | 0.15 + −0.01 |
| 157 | 949938 | "cystatin C (amyloid angiopathy and cerebral hemorrhage)" | Hs.135084 | 0.15 + −0.01 |
| 158 | 166195 | "ribonuclease/angiogenin inhibitor" | Hs.75108 | 0.15 + −0.01 |
| 159 | 239611 | "hemoglobin, epsilon 1" | Hs.117848 | 0.15 + −0.01 |
| 160 | 36950 | "phosphofructokinase, liver" | Hs.155455 | 0.15 + −0.01 |
| 161 | 82903 | "TAP binding protein (tapasin)" | Hs.179600 | 0.15 + −0.01 |
| 162 | 183440 | "arylsulfatase A" | Hs.88251 | 0.15 + −0.01 |
| 163 | 787857 | "syntaxin 5A" | Hs.154546 | 0.15 + −0.01 |
| 164 | 840821 | "signal sequence receptor, delta (translocon-associated protein delta)" | Hs.102135 | 0.15 + −0.01 |
| 165 | 760148 | "uroporphyrinogen decarboxylase" | Hs.78601 | 0.15 + −0.01 |
| 166 | 1434948 | "HIV TAT specific factor 1" | Hs.171595 | 0.15 + −0.01 |
| 167 | 897788 | "protein tyrosine phosphatase, receptor type, F" | Hs.75216 | 0.15 + −0.01 |
| 168 | 810124 | "platelet-activating factor acetylhydrolase, isoform Ib, gamma subunit (29 kD)" | Hs.6793 | 0.15 + −0.01 |
| 169 | 50359 | "mannose phosphate isomerase" | Hs.75694 | 0.15 + −0.01 |
| 170 | 221826 | "guanine nucleotide binding protein (G protein), alpha 11 (Gq class)" | Hs.1686 | 0.15 + −0.01 |
| 171 | 753587 | "butyrophilin, subfamily 3, member A3" | Hs.167741 | 0.15 + −0.01 |
| 172 | 839980 | "glucose-6-phosphatase, transport (glucose-6-phosphate) protein 1" | Hs.26655 | 0.15 + −0.01 |
| 173 | 33327 | "*Homo sapiens* mRNA for KIAA1232 protein, partial cds" | Hs.11101 | 0.15 + −0.01 |
| 174 | 711961 | "general transcription factor IIF, polypeptide 1 (74 kD subunit)" | Hs.68257 | 0.15 + −0.01 |
| 175 | 809910 | "interferon induced transmembrane protein 3 (1-8U)" | Hs.182241 | 0.15 + −0.01 |
| 180 | 172783 | "hypothetical protein FLJ10390" | Hs.133475 | 0.15 + −0.01 |
| 182 | 1374571 | "paired basic amino acid cleaving enzyme (furin, membrane associated receptor protein)" | Hs.59242 | 0.14 + −0.01 |
| 183 | 138936 | "erythrocyte membrane protein band 7.2 (stomatin)" | Hs.160483 | 0.14 + −0.01 |
| 186 | 795321 | "mannosidase, alpha, class 2A, member 2" | Hs.182923 | 0.14 + −0.01 |
| 188 | 263727 | "DNA segment, single copy probe LNS-CAI/LNS-CAII (deleted in polyposis)" | Hs.178112 | 0.14 + −0.01 |
| 189 | 75009 | "EphB4" | Hs.155227 | 0.14 + −0.01 |
| 190 | 435953 | "inositol 1,4,5-triphosphate receptor, type 3" | Hs.77515 | 0.14 + −0.01 |
| 191 | 782335 | "ESTs" | Hs.38270 | 0.14 + −0.01 |
| 194 | 754600 | "nuclear factor I/X (CCAAT-binding transcription factor)" | Hs.35841 | 0.14 + −0.01 |
| 195 | 213890 | "2,4-dienoyl CoA reductase 1, mitochondrial" | Hs.81548 | 0.14 + −0.01 |
| 197 | 1472735 | "metallothionein 1E (functional)" | Hs.74170 | 0.14 + −0.01 |
| 199 | 781097 | "reticulon 3" | Hs.252831 | 0.14 + −0.01 |
| 200 | 810057 | "cold shock domain protein A" | Hs.1139 | 0.14 + −0.01 |

Alternatively, the genes expressed in the Tables 6 through 9 that are expressed in high levels in the specific cancers can be used as targets for designing vaccines for therapy and for making specific antibodies against and used to target these cancers. Also these genes or their protein products can be inhibited via a variety of methods including oligonucleotide DNA antisense, RNAi (making double stranded siRNA inhibitors, and drugs including small molecules and therefore be used for treatment of these cancers. Genes found in this manner, such as those shown in Tables 6 through 9 can be used in microarrays. For example, microarrays including any combination of at least one of the 200 genes from Table 5 can be fabricated.

Alternatively, Table 10 shows 19 genes that were found using a method of the invention and are involved with signal transduction. Signal transduction proteins can be important targets for therapy since they pass on signals from the outside of the cell to the nucleus to either survive or proliferate. Of this list of genes only the first (clone ID 200814 (SEQ. ID. NO. 94) has been previously used as a specific target for leukemia/lymphoma therapy. The remainder of the genes are novel targets. For example, FGFR4 (SEQ. ID. NO. 71), a tyrosine kinase receptor that is expressed during myogenesis and prevents terminal differentiation in myocytes, was found to be highly expressed only in RMS, and in particular not in normal muscle. The relatively strong differential expression of FGFR4 (SEQ. ID. NO. 71) in RMS was confirmed by immunostaining of tissue microarrays. The high expression of FGFR4 (SEQ. ID. NO. 71) in most cases of RMS suggests that it may be relevant to the biology of this tumor, it is also expressed in some other cancers. This suggests that, FGFR4 (SEQ. ID. NO. 71) expression in RMS is of biological and therapeutic interest.

TABLE 10

Genes involved with signal transduction

| name | CloneID | diagnosis | summaryfunction |
|---|---|---|---|
| membrane metallo-endopeptidase (neutral endopeptidase, enkephalinase, CALLA, CD10) | 200814 | BL | Enkephalinase; membrane zinc metalloendopeptidase, may inactivate peptide hormones\|Proteome |
| protein tyrosine phosphatase, receptor type, F | 897788 | NOTBL | Receptor-type protein tyrosine phosphatase F; interacts with the insulin receptor; has Ig-like and FN-III repeats in the extracellular domain\|Proteome |
| protein kinase, cAMP-dependent, regulatory, type II, beta | 609663 | BL* | Type II regulatory beta subunit of cAMP-dependent protein kinase (PKA)\|Proteome |
| annexin A1 | 208718 | EWS* | Annexin I (lipocortin 1); Ca2+-dependent phospholipid-binding protein, inhibits phospholipase A2 and has anti-inflammatory activity\|Proteome |
| interleukin 4 receptor | 714453 | RMS_BL | Subunit of the interleukin 4 receptor; member of the cytokine receptor family\|Proteome |
| recoverin | 383188 | NB* | Recoverin; calcium-binding protein that activates guanylate cyclase activity\|Proteome |
| fibroblast growth factor receptor 4 | 784224 | RMS* | Fibroblast growth factor receptor 4; receptor tyrosine kinase, preferentially binds acidic FGF; contains three extracellular immunoglobulin-like domains\|Proteome |
| transducin-like enhancer of split 2, homolog of Drosophila E(sp1) | 1473131 | EWS* | Enhancer of split groucho 2; possibly functions during epithelial differentiation; transducin-like, similar to Drosophila E(spI) m9/10, which is required for cell fate decisions\|Proteome |
| tumor necrosis factor, alpha-induced protein 6 | 357031 | EWS* | Similar to CD44; binds hyaluronate and may be involved in cell-cell communication during the immune response\|Proteome |
| ras homolog gene family, member B | 768370 | NOTBL | Ras-related GTP binding protein of the rho subfamily, member B; may regulate assembly of actin stress fibers and focal adhesions; very strongly similar to murine Arhb\|Proteome |
| insulin-like growth factor 2 (somatomedin A) | 245330 | RMS | Insulin-like growth factor II (somatomedin A); member of the insulin protein family\|Proteome |
| hematopoietic cell-specific Lyn substrate 1 | 767183 | BL | Contains a helix-turn-helix DNA binding domain and an SH3 domain\|Proteome |
| dihydropyrimidinase-like 2 | 841620 | EWS_NB | Member of the dihydropyrimidinase family\|Proteome |
| amyloid beta (A4) precursor protein (protease nexin-II, Alzheimer disease) | 323371 | NOTBL | Amyloid beta precursor protein (protease nexin-II); cell surface protease inhibitor; reduces Cu\|Proteome |
| interferon induced transmembrane protein 1 (9–27) | 755599 | EWS* | Interferon-inducible transmembrane protein 1; involved in relaying antiproliferative and homotypic adhesion signals\|Proteome |
| secreted frizzled-related protein 1 | 82225 | NB* | Secreted frizzled-related protein 1; may have an anti-apoptotic function and inhibit Wnt protein activity; strongly similar to murine Sfrp1\|Proteome |
| death-associated protein kinase 1 | 364934 | EWS* | Death associated protein kinase 1; serine/threonine kinase regulated by calmodulin, may mediate apoptosis induced by interferon-gamma; has ankyrin repeats\|Proteome |

TABLE 10-continued

Genes involved with signal transduction

| name | CloneID | diagnosis | summaryfunction |
|---|---|---|---|
| lectin, galactoside-binding, soluble, 3 binding protein | 811000 | EWS_NB | Mac-2-binding protein; potent immune stimulator; contains a macrophage scavenger receptor cysteine-rich domain\|Proteome |
| insulin-like growth factor binding protein 5 | 2907511 | RMS | Member of the insulin-like growth factor binding family of proteins; may bind to and modulate insulin-like growth factor activity\|Proteome |

Figure 6:
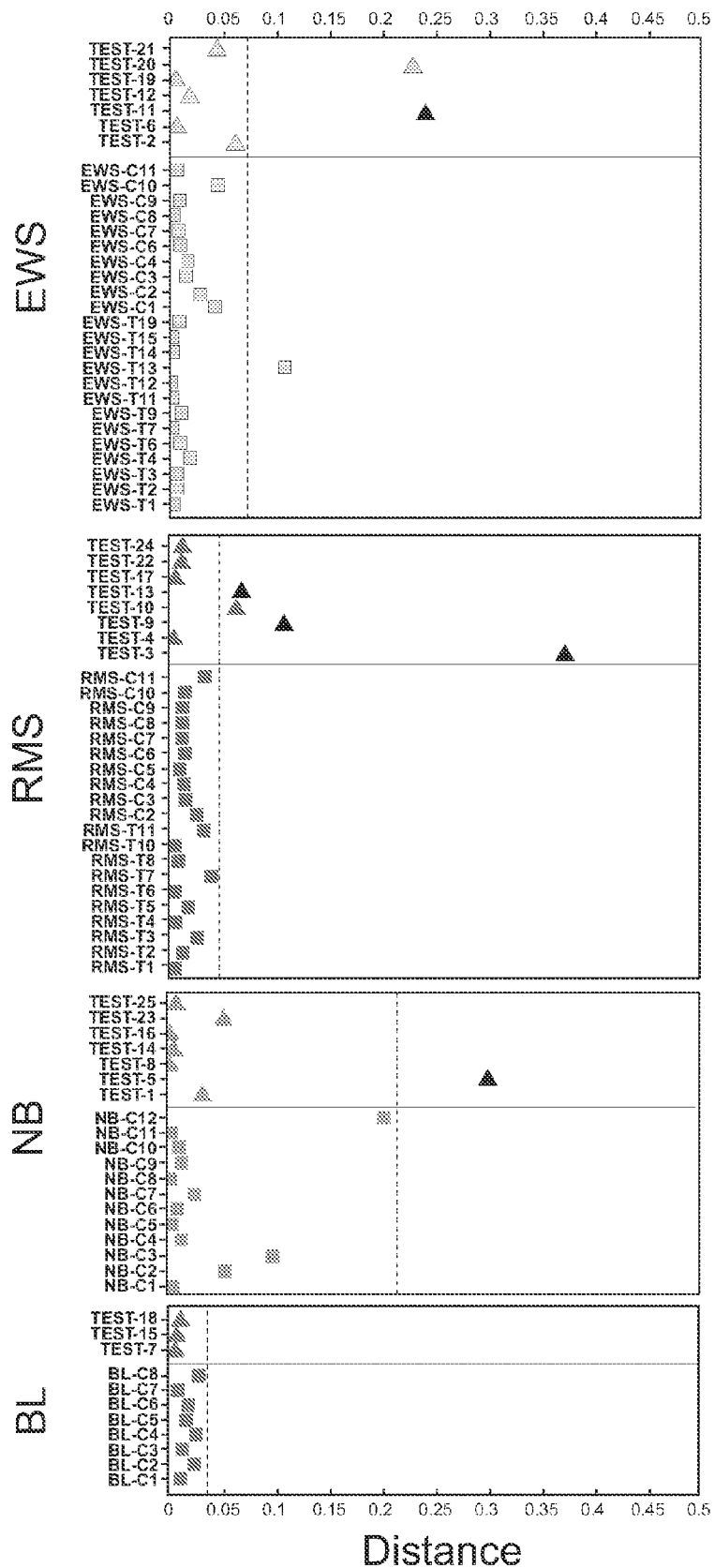
FIG. 6 represents a plot of the distance from the samples committee vote to the ideal vote for that diagnostic category.
Figure 7:
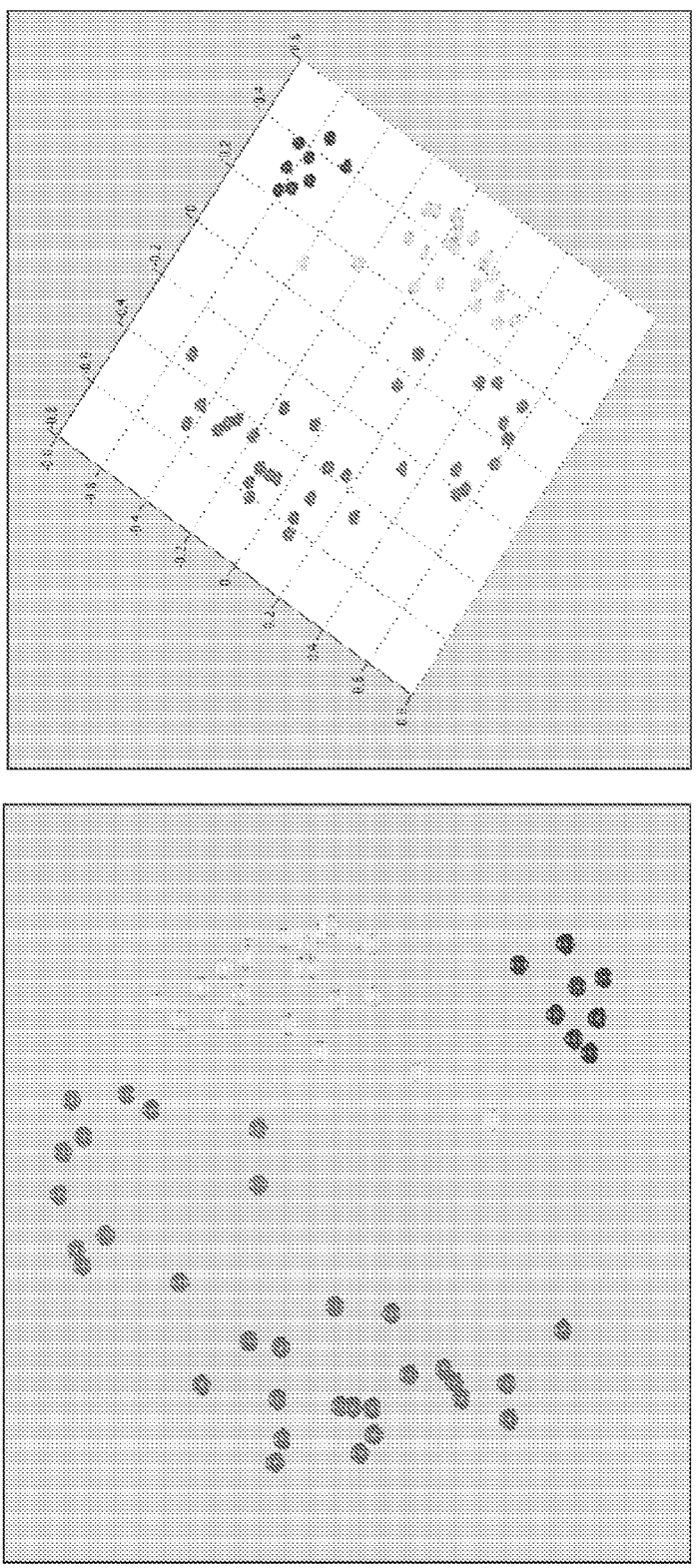
FIG. 7 represents two projections of the MDS plot of the training samples.

We then determined the classification error rate using increasing numbers of these ranked genes. The classification error rate minimized to 0% at 96 genes, see FIG. 5. The 10 dominant PCA components for these 96 genes contained 79% of the variance in the data matrix. Using only these 96 genes, we recalibrated the ANN models and again correctly classified all 63 samples, see FIG. 6. Moreover, multidimensional scaling (MDS) analysis using these 96 genes clearly separated the four cancer types, see FIG. 7. The top 96 discriminators represented 93 unique genes, see FIG. 8, as IGF2 was represented by three independent clones and MYC by two.

Of the 96 genes, 13 were anonymous expressed sequence tags (ESTs); 16 genes were specifically expressed in EWS, 20 in RMS, 15 in NB and 10 in BL. Twelve genes were good discriminators on the basis of lack of expression in BL and variable expression in the other three types. One gene (EST; Clone ID 295985 (SEQ. ID. NO. 26)) discriminated EWS from other cancer types by its lack of expression in this cancer. The remainder of the genes was expressed in two of the four cancer types. To our knowledge, of the 61 genes that were specifically expressed in cancer type, 41 have not been previously reported as associated with these diseases. These 41 genes can be seen in Table 2 given above.

Example 5

Diagnostic Classification and Hierarchical Clustering

The diagnostic classification capabilities of these ANN models were then tested on a set of 25 blinded test samples. Samples were classified to a diagnostic category if they received the highest vote for that category. As this classifier had only four possible outputs, all samples were classified to one of the four categories. We therefore established a diagnostic classification method based on a statistical cutoff to enable us to reject a diagnosis of a sample classified to a given category. If a sample falls outside the 95th percentile of the probability distribution of distances between samples and their ideal output (for example for EWS it is EWS=1, RMS=NB=BL=0), its diagnosis is rejected.

TABLE 11

| Sample label | ANN committee vote | | | | ANN classification | ANN diagnosis | Histological diagnosis | Source label | Source |
|---|---|---|---|---|---|---|---|---|---|
| | EWS | RMS | NB | BL | | | | | |
| Test 1 | 0.01 | 0.07 | 0.76 | 0.06 | NB | NB | NB-C | IMR32 | ATCC |
| Test 2 | 0.67 | 0.06 | 0.08 | 0.09 | EWS | EWS | EWS-C | CHOP1 | NCI |
| Test 3 | 0.11 | 0.17 | 0.16 | 0.11 | RMS | — | Osteosarcoma-C | OsA-Cl | ATCC |
| Test 4 | 0.00 | 0.95 | 0.06 | 0.03 | RMS | RMS | ARMS-T | ARMD1 | CHTN |
| Test 5 | 0.11 | 0.11 | 0.25 | 0.10 | NB | — | Sarcoma-C | A204 | ATCC |
| Test 6 | 0.98 | 0.04 | 0.10 | 0.03 | EWS | EWS | EWS-T | 9608P053 | CHTN |
| Test 7 | 0.05 | 0.02 | 0.05 | 0.93 | BL | BL | BL-C | EB1 | ATCC |
| Test 8 | 0.00 | 0.05 | 0.94 | 0.04 | NB | NB | NB-C | SMSSAN | NCI |
| Test 9 | 0.22 | 0.60 | 0.03 | 0.06 | RMS | — | Sk. Muscle | SkM1 | CHTN |
| Test 10 | 0.10 | 0.68 | 0.11 | 0.04 | RMS | — | ERMS-T | ERDM1 | CHTN |
| Test 11 | 0.39 | 0.04 | 0.28 | 0.15 | EWS | — | Prostate Ca.-C | PC3 | ATCC |
| Test 12 | 0.89 | 0.05 | 0.14 | 0.03 | EWS | EWS | EWS-T | SARC67 | CHTN |
| Test 13 | 0.20 | 0.7 | 0.03 | 0.05 | RMS | — | Sk. Muscle | SkM2 | CHTN |
| Test 14 | 0.03 | 0.02 | 0.90 | 0.07 | NB | NB | NB-T | N83 | DZNSG |
| Test 15 | 0.06 | 0.03 | 0.05 | 0.91 | BL | BL | BL-C | EB2 | ATCC |
| Test 16 | 0.03 | 0.02 | 0.93 | 0.05 | NB | NB | NB-T | NB1 | DZNSG |
| Test 17 | 0.01 | 0.90 | 0.05 | 0.03 | RMS | RMS | ARMS-T | ARMD2 | CHTN |
| Test 18 | 0.06 | 0.04 | 0.04 | 0.88 | BL | BL | BL-C | GA10 | ATCC |
| Test 19 | 0.99 | 0.02 | 0.04 | 0.05 | EWS | EWS | EWS-T | ET3 | CHTN |
| Test 20 | 0.40 | 0.30 | 0.10 | 0.06 | EWS | — | EWS-T | 9903P1339 | CHTN |
| Test 21 | 0.81 | 0.19 | 0.12 | 0.04 | EWS | EWS | EWS-T | ES23 | MSKCC |
| Test 22 | 0.01 | 0.88 | 0.09 | 0.04 | RMS | RMS | ERMS-T | ERMD2 | CHTN |
| Test 23 | 0.07 | 0.08 | 0.70 | 0.06 | NB | NB | NB-T | NB2 | DZNSG |

TABLE 11-continued

| Sample label | ANN committee vote | | | | ANN classification | ANN diagnosis | Histological diagnosis | Source label | Source |
|---|---|---|---|---|---|---|---|---|---|
| | EWS | RMS | NB | BL | | | | | |
| Test 24 | 0.05 | 0.87 | 0.06 | 0.03 | RMS | RMS | ERMS-T | RMS4 | MSKCC |
| Test 25 | 0.05 | 0.02 | 0.89 | 0.06 | NB | NB | NB-T | NB4 | DZNSG |

Source label refers to the original name of the sample as designated by the source. Histological diagnosis is defined as cancer type suffixed with -T for a tumor sample and -C for a cell line. Normal skeletal muscle (Sk. Muscle) is also included in the test set. The ANN classification as determined by the committee vote is bolded. NCI: National Cancer Institute, National Institutes of Health, ATCC: American Type Culture Collection, MSKCC: Memorial Sloan-Kettering Cancer Center, CHTN:Cooperative Human Tissue Network, DZNSG: German Cancer Research Center, Heidelberg.

The test samples contained both tumors (5 EWS, 5 RMS and 4 NB) and cell lines (1 EWS, 2 NB and 3 BL). The ability of these models to reject a diagnosis on 5 non-SRBCTs was also tested (consisting of 2 normal muscle tissues (Tests 9 and 13) and 3 cell lines including an undifferentiated sarcoma (Test 5), osteosarcoma (Test 3) and a prostate carcinoma (Test 11)). Using the 3750 ANN models calibrated with the 96 genes, we correctly classified 100% of the 20 SRBCT tests (FIG. 6 and Table 11) as well as all 63 training samples, see Table 4. Three of these samples, Test 10, Test 20 and EWS-T13 were correctly assigned to their categories (RMS, EWS and EWS respectively), having received the highest vote for their respective categories. However, their distance from a perfect vote was greater than the expected 95th percentile distance (FIG. 6); therefore, we could not confidently diagnose them by this criterion. All of the five non-SRBCT samples were excluded from any of the four diagnostic categories, since they fell outside the 95th percentiles. Using these criteria for all 88 samples, the sensitivity of the ANN models for diagnostic classification was 93% for EWS, 96% for RMS and 100% for both NB and BL. The specificity was 100% for all four diagnostic categories.

Figure 9:
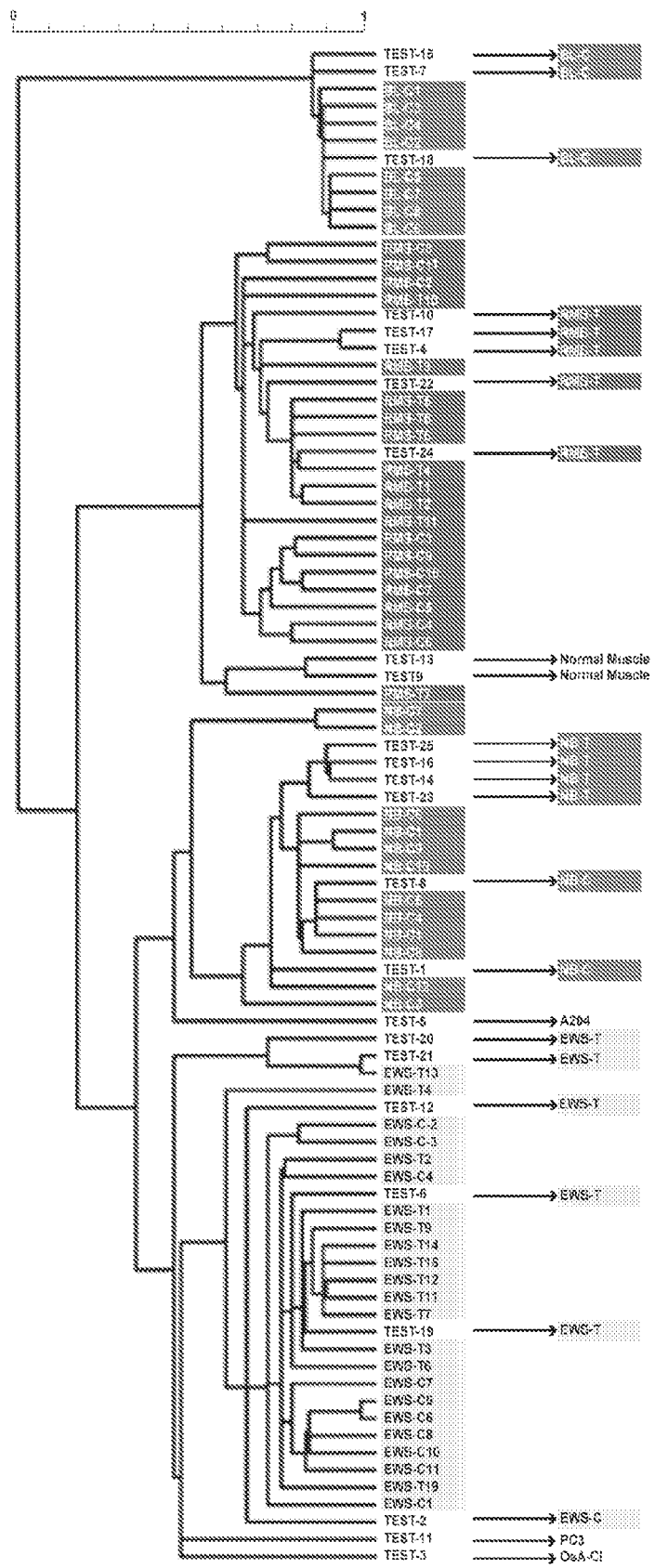
FIG. 9 represents a hierarchical clustering dendrogram of the samples in FIG. 8.

Also, hierarchical clustering using the 96 genes, identified from the ANN models, correctly clustered all 20 of the test samples (FIG. 9). Moreover, the two pairs of samples that were derived from two cell lines, BL-C2 and C4 (ST486) and NB-C2 and C7 (GICAN), were adjacent to one another in the same cluster.

Example 6

Expression of FGFR4 on SRBCT Tissue Array

To confirm the effectiveness of the ANN models to identify genes that show preferential high expression in specific cancer types at the protein level, we performed immunohistochemistry on SRBCT tissue arrays for the expression of fibroblast growth factor receptor 4 (FGFR4 (SEQ. ID. NO. 71)). This tyrosine kinase receptor is expressed during myogenesis but not in adult muscle, and is of interest because of its potential role in tumor growth and in prevention of terminal differentiation in muscle. Moderate to strong cytoplasmic immunostaining for FGFR4 (SEQ. ID. NO. 71) was seen in all 26 RMSs tested (17 alveolar, 9 embryonal). We also observed generally weaker staining in EWS and BL in agreement with the microarray results, except for one of anaplastic large cell lymphoma that was strongly positive (data not shown).

As such, the foregoing description of the exemplary embodiments of the invention has been presented for the purposes of illustration and description. They are not intended to be exhaustive or to limit the invention to the precise forms disclosed. Many modifications and variations are possible in light of the above teaching. It is intended that the scope of the invention be limited not with this detailed description, but rather by the claims appended hereto. The present invention is presently embodied as a method, apparatus, and a computer data product containing a computer program for classifying and diagnosing disease using artificial neural networks.

The above specification, examples and data provide a complete description of the manufacture and use of the composition of the invention. Since many embodiments of the invention can be made without departing from the spirit and scope of the invention, the invention resides in the claims hereinafter appended.

SEQUENCE LISTING

The patent contains a lengthy "Sequence Listing" section. A copy of the "Sequence Listing" is available in electronic form from the USPTO web site (http://seqdata.uspto.gov/?pageRequest=docDetail&DocID=US07655397B2). An electronic copy of the "Sequence Listing" will also be available from the USPTO upon request and payment of the fee set forth in 37 CFR 1.19(b)(3).

The claimed invention is:
1. A method for diagnosing a particular type of cancer selected from the group consisting of rhabdomyosarcoma, Ewing's sarcoma, neuroblastoma and Burkitt's lymphoma comprising:
   i) comparing a first expression profile of a set of genes from a human cell sample to the expression profiles of the set of genes from a cell of each of said types of cancer;
   wherein said set of genes comprises at least the human genes IGF2, CCND1, GAS1, CNN3, FCGRT, a gene that comprises SEQ ID NO: 457, IGFBP2, GYG2, and a gene that comprises SEQ ID NO:462,
   wherein the first expression profile is obtained by detecting expression
   of IGF2, wherein IGF2 comprises the nucleic acid sequence of SEQ ID NO:72 or SEQ ID NO:73,
   of CCND1, wherein CCND1 comprises the nucleic acid sequence of SEQ ID NO:5,
   of GAS1, wherein GAS1 comprises the nucleic acid sequence of SEQ ID NO:59,
   of CNN3, wherein CNN3 comprises the nucleic acid sequence of SEQ ID NO:43,
   of FCGRT, wherein FCGRT comprises the nucleic acid sequence of SEQ ID NO:20,
   of a gene that comprises SEQ ID NO:457, wherein the gene comprises the nucleic acid sequence of SEQ ID NO:77,
   of IGFBP2, wherein IGFBP2 comprises the nucleic acid sequence of SEQ ID NO:28,
   of GYG2, wherein GYG2 comprises the nucleic acid sequence of SEQ ID NO:21, and
   of a gene that comprises SEQ ID NO:462, wherein the gene comprises the nucleic acid sequence of SEQ ID NO:26; and
   ii) identifying the human cell sample as one of rhabdomyosarcoma, Ewing's sarcoma, neuroblastoma or Burkitt's lymphoma based on the comparison of the first expression profile of the human cell sample to each of the expression profiles of rhabdomyosarcoma, Ewing's sarcoma, neuroblastoma and Burkitt's lymphoma.

2. A method for distinguishing one type of human cancer cell from another type of human cancer cell, comprising:
   i) measuring the expression level of at least the human genes comprising IGF2, CCND1, GAS1, CNN3, FCGRT, a gene that comprises SEQ ID NO: 457, IGFBP2, GYG2, and a gene that comprises SEQ ID NO:462,
   wherein IGF2 comprises the nucleic acid sequence of SEQ ID NO:72 or SEQ ID NO:73
   wherein CCND1 comprises the nucleic acid sequence of SEQ ID NO:5,
   wherein GAS1 comprises the nucleic acid sequence of SEQ ID NO:59,
   wherein CNN3 comprises the nucleic acid sequence of SEQ ID NO:43,
   wherein FCGRT comprises the nucleic acid sequence of SEQ ID NO:20,
   wherein the gene that comprises SEQ ID NO:457 comprises the nucleic acid sequence of SEQ ID NO:77,
   wherein IGFBP2 comprises the nucleic acid sequence of SEQ ID NO:28,
   wherein GYG2 comprises the nucleic acid sequence of SEQ ID NO:21, and
   wherein the gene that comprises SEQ ID NO:462 comprises the nucleic acid sequence of SEQ ID NO:26; and
   ii) analyzing the expression level of the human genes in the human cancer cell using a pretrained supervised pattern recognition method to obtain an output; and
   iii) determining whether the human cancer cell is a neuroblastoma, rhabdomyosarcoma, Burkitt's lymphoma, or Ewing sarcoma cell by determining whether the output falls within the 95% of the output for the pretrained samples for that type of cancer cell.

3. A method according to claim 2, wherein a neuroblastoma cell is distinguished from a rhabdomyosarcoma cell, a Ewing's sarcoma cell, or a Burkitt's lymphoma cell or mixtures thereof.

4. A method according to claim 2, wherein a rhabdomyosarcoma cell is distinguished from a neuroblastoma cell, a Ewing's sarcoma cell, or a Burkitt's lymphoma cell or mixtures thereof.

5. A method according to claim 2, wherein a Ewing's sarcoma cell is distinguished from a rhabdomyosarcoma cell, a neuroblastoma cell, or a Burkitt's lymphoma cell or mixtures thereof.

6. A method according to claim 2, wherein a Burkitt's lymphoma cell is distinguished from a rhabdomyosarcoma cell, a Ewing's sarcoma cell, or a neuroblastoma cell or mixtures thereof.

7. The method of claim 1 wherein comparing the expression profile comprises obtaining cDNA from the cell, labeling the cDNA with a detectable label, and identifying the expression levels of the genes by hybridizing the labeled cDNA to cDNA known to code for the genes.

8. The method of claim 2, wherein the supervised pattern recognition method is an artificial neural network.

9. The method of claim 8, wherein artificial neural network comprises an algorithm architecture selected from the group consisting of hard competitive learning, soft competitive learning without a fixed network dimensionality, and soft competitive learning with a fixed network dimensionality.

10. The method of claim 2, wherein the supervised pattern recognition method is trained with the expression levels of at least the genes comprising IGF2, CCND1, GAS1, CNN3, FCGRT, a gene that comprises SEQ ID NO:457, IGFBP2, GYG2, and a gene that comprises SEQ ID NO:462, in each of known cancer cell samples selected from the group consisting of rhabdomyosarcoma, Ewing's tumor, neuroblastoma, and Burkitt's lymphoma.

* * * * *

UNITED STATES PATENT AND TRADEMARK OFFICE
CERTIFICATE OF CORRECTION

PATENT NO. : 7,655,397 B2
APPLICATION NO. : 10/159563
DATED : February 2, 2010
INVENTOR(S) : Khan et al.

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 341 days.

Signed and Sealed this

Twenty-third Day of November, 2010

David J. Kappos
*Director of the United States Patent and Trademark Office*

UNITED STATES PATENT AND TRADEMARK OFFICE
CERTIFICATE OF CORRECTION

| | | |
|---|---|---|
| PATENT NO. | : 7,655,397 B2 | Page 1 of 63 |
| APPLICATION NO. | : 10/159563 | |
| DATED | : February 2, 2010 | |
| INVENTOR(S) | : Khan et al. | |

It is certified that error appears in the above-identified patent and that said Letters Patent is hereby corrected as shown below:

Drawing Sheet 8 of 9: Delete sheet 8 of 9 and replace with the following sheet.

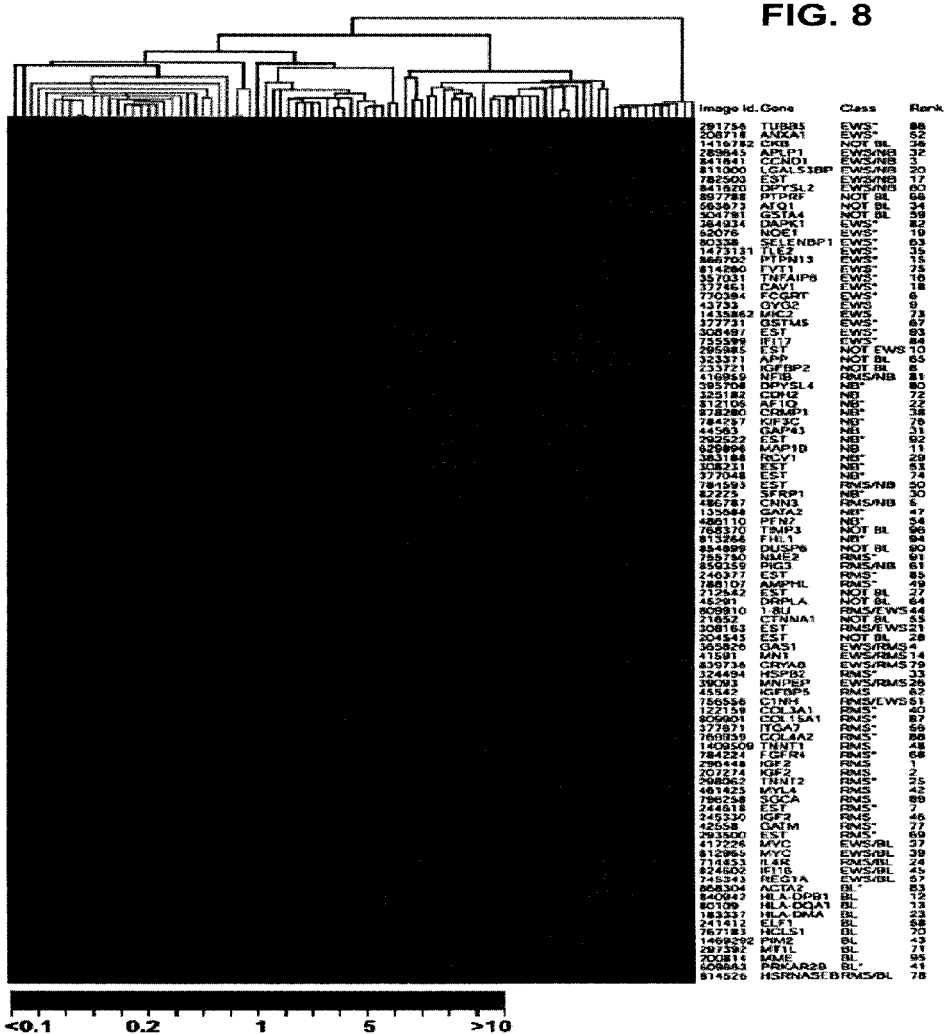

Signed and Sealed this

Seventh Day of February, 2012

David J. Kappos
*Director of the United States Patent and Trademark Office*

Col. 16, Table 2: Delete incorrect Table 2 and replace with correct Table 2:

TABLE 2

| Image Id. | Gene symbol | EWS Rank | EWS Sign | R MS Rank | R MS Sign | NB Rank | NB Sign | BL Rank | BL Sign | Cancer Type | SEQ. ID. NO. |
|---|---|---|---|---|---|---|---|---|---|---|---|
| 812105 | AF1Q | 670 | - | 934 | - | 2 | + | 51 | - | NB | SEQ. ID. NO. 32 |
| 383188 | RCV1 | 478 | - | 808 | + | 13 | + | 42 | - | NB | SEQ. ID. NO. 38 |
| 82225 | SFRP1 | 160 | - | 264 | + | 17 | + | 85 | - | NB | SEQ. ID. NO. 42 |
| 878280 | CRMP1 | 602 | - | 1255 | + | 12 | + | 45 | - | NB | SEQ. ID. NO.33 |
| 135688 | CATA2 | 354 | + | 155 | - | 37 | + | 88 | - | NB | SEQ. ID. NO. 44 |
| 308231 | EST | 524 | - | 1015 | + | 10 | + | 117 | - | NB | SEQ. ID. NO. 39 |
| 486110 | PFN2 | 1554 | + | 1500 | + | 31 | + | 31 | - | NB | SEQ. ID. NO. 45 |
| 377048 | EST | 733 | - | 560 | + | 23 | + | 102 | - | NB | SEQ. ID. NO. 40 |
| 784257 | KIF3C | 577 | + | 1099 | - | 64 | + | 44 | - | NB | SEQ. ID. NO. 34 |
| 395708 | DPYSL4 | 1269 | + | 591 | - | 28 | + | 91 | - | NB | SEQ. ID. NO. 30 |
| 292522 | EST | 221 | - | 667 | + | 32 | + | 189 | - | NB | SEQ. ID. NO. 36 |
| 813266 | FHL1 | 1045 | + | 1610 | - | 91 | + | 46 | - | NB | SEQ. ID. NO. 47 |
| 244618 | EST | 22 | - | 3 | + | 273 | - | 86 | - | RMS | SEQ. ID. NO. 77 |

| Image Id. | Gene symbol | EWS Rank | EWS Sign | R MS Rank | R MS Sign | NB Rank | NB Sign | BL Rank | BL Sign | Cancer Type | SEQ. ID. NO. |
|---|---|---|---|---|---|---|---|---|---|---|---|
| 298062 | TNNT2 | 43 | - | 4 | + | 95 | - | 475 | - | RMS | SEQ. ID. NO. 74 |
| 324494 | HSPB2 | 1605 | - | 13 | + | 7 | - | 420 | - | RMS | SEQ. ID. NO. 62 |
| 122159 | COL3A1 | 791 | + | 29 | + | 1062 | - | 16 | - | RMS | SEQ. ID. NO. 66 |
| 788107 | AMPHL | 74 | - | 14 | + | 817 | + | 108 | - | RMS | SEQ. ID. NO. 52 |
| 377671 | ITGA7 | 1044 | + | 24 | + | 66 | - | 135 | - | RMS | SEQ. ID. NO. 68 |
| 784224 | FGFR4 | 36 | - | 5 | + | 431 | - | 604 | + | RMS | SEQ. ID. NO. 71 |
| 293500 | EST | 262 | - | 9 | + | 1084 | - | 138 | - | RMS | SEQ. ID. NO. 80 |
| 42558 | GATM | 379 | - | 12 | + | 25 | - | 1020 | - | RMS | SEQ. ID. NO. 79 |
| 246377 | EST | 719 | - | 36 | + | 641 | + | 75` | - | RMS | SEQ. ID. NO. 51 |
| 809901 | COL15A1 | 1516 | - | 23 | + | 35 | - | 385 | - | RMS | SEQ. ID. NO. 67 |
| 769959 | COL4A2 | 1575 | + | 66 | + | 1786 | - | 26 | - | RMS | SEQ. ID. NO. 69 |
| 755750 | NME2 | 1840 | + | 26 | + | 591 | - | 82 | - | RMS | SEQ. ID. NO. 49 |
| 770394 | FCGRT | 3 | + | 186 | - | 79 | - | 18 | - | EWS | SEQ. ID. NO. 20 |
| 866702 | PTPN13 | 2 | + | 74 | - | 230 | - | 62 | - | EWS | SEQ. ID. NO. 16 |

| Image Id. | Gene symbol | EWS Rank | EWS Sign | R MS Rank | R MS Sign | NB Rank | NB Sign | BL Rank | BL Sign | Cancer Type | SEQ. ID. NO. |
|---|---|---|---|---|---|---|---|---|---|---|---|
| 357031 | TNFAIP6 | 5 | + | 119 | - | 103 | - | 60 | - | EWS | SEQ. ID. NO. 18 |
| 377461 | CAV1 | 6 | + | 91 | - | 90 | - | 101 | - | EWS | SEQ. ID. NO. 19 |
| 52076 | NOE1 | 7 | + | 33 | - | 1673 | + | 37 | - | EWS | SEQ. ID. NO. 13 |
| 1473131 | TLE2 | 10 | + | 1884 | - | 16 | - | 217 | - | EWS | SEQ. ID. NO. 15 |
| 208718 | ANXA1 | 12 | + | 827 | - | 1202 | - | 33 | - | EWS | SEQ. ID. NO. 2 |
| 80338 | SELENBP1 | 20 | + | 1316 | + | 42 | - | 151 | - | EWS | SEQ. ID. NO. 14 |
| 377731 | GSTM5 | 13 | + | 310 | - | 34 | - | 381 | - | EWS | SEQ. ID. NO. 23 |
| 814260 | FVT1 | 9 | + | 61 | - | 330 | - | 335 | - | EWS | SEQ. ID. NO. 17 |
| 364934 | DAPK1 | 42 | + | 1481 | + | 707 | - | 40 | - | EWS | SEQ. ID. NO. 12 |
| 755599 | IFI7 | 16 | + | 177 | - | 30 | - | 918 | - | EWS | SEQ. ID. NO. 25 |
| 291756 | TUBB5 | 17 | + | 31 | - | 1325 | + | 245 | - | EWS | SEQ. ID. NO. 1 |
| 308497 | EST | 27 | + | 1971 | - | 43 | - | 231 | - | EWS | SEQ. ID. NO. 24 |
| 609663 | PRKAR2B | 198 | - | 55 | - | 550 | + | 29 | + | BL | SEQ. ID. NO. 95 |
| 868304 | ACTA2 | 1286 | - | 151 | - | 122 | - | 71 | + | BL | SEQ. ID. NO. 86 |

Col. 16, Table 2b: Delete incorrect Table 2b and replace with correct Table 2b:

Table 2b

| Rank | Image Id. | Gene | EWS Rank | EWS Sign | RMS Rank | RMS Sign | NB Rank | NB Sign | BL Rank | BL Sign | Cancer Type | SEQ. ID. NO. |
|---|---|---|---|---|---|---|---|---|---|---|---|---|
| 1 | 296448 | IGF2 | 8 | - | 1 | + | 918 | - | 19 | - | RMS | SEQ ID NO 72 |
| 2 | 207274 | IGF2 | 19 | - | 2 | + | 1152 | - | 11 | - | RMS | SEQ ID NO 73 |
| 3 | 841641 | CCND1 | 11 | + | 38 | - | 118 | + | 6 | - | EWS/NB | SEQ ID NO 5 |
| 4 | 365826 | GAS1 | 25 | + | 69 | + | 22 | - | 9 | - | EWS/RMS | SEQ ID NO 59 |
| 5 | 486787 | CNN3 | 130 | - | 39 | + | 14 | + | 17 | - | RMS/NB | SEQ ID NO 43 |
| 6 | 770394 | FCGRT | 3 | + | 186 | - | 79 | - | 18 | - | EWS | SEQ ID NO 20 |
| 7 | 244618 | EST | 22 | - | 3 | + | 273 | - | 86 | - | RMS | SEQ ID NO 77 |
| 8 | 233721 | IGFBP2 | 148 | + | 43 | + | 598 | + | 1 | - | Not BL | SEQ ID NO 28 |
| 9 | 43733 | GYG2 | 4 | + | 261 | - | 99 | - | 21 | - | EWS | SEQ ID NO 21 |
| 10 | 295985 | EST | 1 | - | 51 | + | 9 | + | 522 | + | Not EWS | SEQ ID NO 26 |
| 11 | 629896 | MAP1B | 360 | - | 893 | + | 1 | + | 23 | - | NB | SEQ ID NO 37 |
| 12 | 840942 | HLA-DPB1 | 1161 | + | 383 | - | 6 | - | 12 | + | BL | SEQ ID NO 87 |
| 13 | 80109 | HLA-DQA1 | 226 | - | 1589 | - | 20 | - | 3 | + | BL | SEQ ID NO 88 |
| 14 | 41591 | MN1 | 257 | + | 18 | + | 4 | - | 169 | - | EWS/RMS | SEQ ID NO 60 |
| 15 | 866702 | PTPN13 | 2 | + | 74 | - | 230 | - | 62 | - | EWS | SEQ ID NO 16 |
| 16 | 357031 | TNFAIP6 | 5 | + | 119 | - | 103 | - | 60 | - | EWS | SEQ ID NO 18 |
| 17 | 782503 | EST | 26 | + | 219 | - | 104 | + | 14 | - | EWS/NB | SEQ ID NO 7 |
| 18 | 377461 | CAV1 | 6 | + | 91 | - | 90 | - | 101 | - | EWS | SEQ ID NO 19 |
| 19 | 52076 | NOE1 | 7 | + | 33 | - | 1673 | + | 37 | - | EWS | SEQ ID NO 13 |
| 20 | 811000 | LGALS3BP | 24 | + | 246 | - | 257 | + | 13 | - | EWS/NB | SEQ ID NO 6 |
| 21 | 308163 | EST | 49 | + | 88 | + | 191 | - | 22 | - | RMS/EWS | SEQ ID NO 57 |

| Rank | Image Id. | Gene | EWS Rank | EWS Sign | RMS Rank | RMS Sign | NB Rank | NB Sign | BL Rank | BL Sign | Cancer Type | SEQ. ID. NO. |
|---|---|---|---|---|---|---|---|---|---|---|---|---|
| 22 | 812105 | AF1Q | 670 | - | 934 | - | 2 | + | 51 | - | NB | SEQ ID NO 32 |
| 23 | 183337 | HLA/DMA | 317 | - | 1574 | - | 24 | - | 8 | + | BL | SEQ ID NO 89 |
| 24 | 714453 | IL4R | 208 | - | 20 | + | 8 | - | 238 | + | RMS/BL | SEQ ID NO 83 |
| 25 | 298062 | TNNT2 | 43 | - | 4 | + | 95 | - | 475 | - | RMS | SEQ ID NO 74 |
| 26 | 39093 | MNPEP | 46 | + | 224 | + | 21 | - | 103 | - | EWS/RMS | SEQ ID NO 63 |
| 27 | 212542 | EST | 62 | + | 993 | + | 1086 | + | 2 | - | Not BL | SEQ ID NO 53 |
| 28 | 204545 | EST | 471 | + | 49 | + | 1455 | + | 5 | - | Not BL | SEQ ID NO 58 |
| 29 | 383188 | RCV1 | 478 | - | 808 | + | 13 | + | 42 | - | NB | SEQ ID NO 38 |
| 30 | 82225 | SFRP1 | 160 | - | 264 | + | 17 | + | 85 | - | NB | SEQ ID NO 42 |
| 31 | 44563 | GAP43 | 693 | - | 191 | - | 3 | + | 166 | - | NB | SEQ ID NO 35 |
| 32 | 289645 | APLP1 | 41 | + | 102 | - | 107 | + | 61 | - | EWS/NB | SEQ ID NO 4 |
| 33 | 324494 | HSPB2 | 1605 | - | 13 | + | 7 | - | 420 | - | RMS | SEQ ID NO 62 |
| 34 | 563673 | ATQ1 | 35 | + | 1527 | - | 523 | + | 7 | - | Not BL | SEQ ID NO 10 |
| 35 | 1473131 | TLE2 | 10 | + | 1884 | - | 16 | - | 217 | - | EWS | SEQ ID NO 15 |
| 36 | 1416782 | CKB | 134 | + | 416 | + | 851 | + | 4 | - | Not BL | SEQ ID NO 3 |
| 37 | 417226 | MYC | 63 | + | 222 | - | 29 | - | 110 | + | EWS/BL | SEQ ID NO 81 |
| 38 | 878280 | CRMP1 | 602 | - | 1522 | + | 12 | + | 45 | - | NB | SEQ ID NO 33 |
| 39 | 812965 | MYC | 23 | + | 296 | - | 11 | - | 308 | + | EWS/BL | SEQ ID NO 82 |
| 40 | 122159 | COL3A1 | 791 | + | 29 | + | 1062 | - | 16 | - | RMS | SEQ ID NO 66 |
| 41 | 609663 | PRKAR2B | 198 | - | 55 | - | 550 | + | 29 | + | BL | SEQ ID NO 95 |
| 42 | 461425 | MYL4 | 98 | - | 7 | + | 80 | - | 419 | - | RMS | SEQ ID NO 75 |
| 43 | 1469292 | PIM2 | 1007 | + | 242 | - | 53 | - | 36 | + | BL | SEQ ID NO 92 |
| 44 | 809910 | 1-8U | 52 | + | 168 | + | 159 | - | 56 | - | RMS/EWS | SEQ ID NO 55 |
| 45 | 824602 | IFI16 | 336 | + | 149 | - | 33 | - | 89 | + | EWS/BL | SEQ ID NO 84 |
| 46 | 245330 | IGF2 | 65 | - | 6 | + | 147 | - | 434 | - | RMS | SEQ ID NO 78 |

CERTIFICATE OF CORRECTION (continued)
U.S. Pat. No. 7,655,397 B2

| Rank | Image Id. | Gene | EWS Rank | EWS Sign | RMS Rank | RMS Sign | NB Rank | NB Sign | BL Rank | BL Sign | Cancer Type | SEQ. ID. NO. |
|---|---|---|---|---|---|---|---|---|---|---|---|---|
| 47 | 135688 | GATA2 | 354 | + | 155 | - | 37 | + | 88 | - | NB | SEQ ID NO 44 |
| 48 | 1409509 | TNNT1 | 141 | - | 8 | + | 153 | - | 313 | - | RMS | SEQ ID NO 70 |
| 49 | 788107 | AMPHL | 74 | - | 14 | + | 817 | + | 108 | - | RMS | SEQ ID NO 52 |
| 50 | 784593 | EST | 224 | - | 299 | + | 39 | + | 68 | - | RMS/NB | SEQ ID NO 41 |
| 51 | 756556 | C1NH | 90 | + | 238 | + | 284 | - | 38 | - | RMS/EWS | SEQ ID NO 65 |
| 52 | 208718 | ANXA1 | 12 | + | 827 | - | 1202 | - | 33 | - | EWS | SEQ ID NO 2 |
| 53 | 308231 | EST | 524 | - | 1015 | + | 10 | + | 117 | - | NB | SEQ ID NO 39 |
| 54 | 486110 | PFN2 | 1554 | + | 1500 | + | 31 | + | 31 | - | NB | SEQ ID NO 45 |
| 55 | 21652 | CTNNA1 | 104 | + | 117 | + | 2245 | - | 15 | - | Not BL | SEQ ID NO 56 |
| 56 | 377671 | ITGA7 | 1044 | + | 24 | + | 66 | - | 135 | - | RMS | SEQ ID NO 68 |
| 57 | 745343 | REG1A | 166 | + | 93 | - | 40 | - | 153 | + | EWS/BL | SEQ ID NO 85 |
| 58 | 241412 | ELF1 | 882 | - | 1473 | - | 60 | - | 27 | + | BL | SEQ ID NO 90 |
| 59 | 504791 | GSTA4 | 276 | + | 2003 | + | 108 | + | 24 | - | Not BL | SEQ ID NO 11 |
| 60 | 841620 | DPYSL2 | 51 | + | 100 | - | 366 | + | 70 | - | EWS/NB | SEQ ID NO 8 |
| 61 | 859359 | PIG3 | 58 | - | 28 | + | 288 | + | 152 | - | RMS/NB | SEQ ID NO 50 |
| 62 | 45542 | IGFBP5 | 991 | + | 89 | + | 1661 | - | 10 | - | RMS | SEQ ID NO 64 |
| 63 | 80338 | SELENBP1 | 20 | + | 1316 | + | 42 | - | 151 | - | EWS | SEQ ID NO 14 |
| 64 | 45291 | DRPLA | 532 | + | 81 | + | 872 | - | 28 | - | Not BL | SEQ ID NO 54 |
| 65 | 323371 | APP | 1689 | - | 90 | + | 594 | + | 65 | - | Not BL | SEQ ID NO 27 |
| 66 | 897788 | PTPRF | 59 | + | 1358 | - | 734 | + | 20 | - | Not BL | SEQ ID NO 9 |
| 67 | 377731 | GSTM5 | 13 | + | 310 | - | 34 | - | 381 | - | EWS | SEQ ID NO 23 |
| 68 | 784224 | FGFR4 | 36 | - | 5 | + | 431 | - | 604 | - | RMS | SEQ ID NO 71 |
| 69 | 293500 | EST | 262 | - | 9 | + | 1084 | - | 138 | - | RMS | SEQ ID NO 80 |
| 70 | 767183 | HCLS1 | 1481 | - | 1424 | - | 50 | - | 32 | + | BL | SEQ ID NO 91 |
| 71 | 297392 | MT1L | 1361 | - | 483 | - | 113 | - | 30 | + | BL | SEQ ID NO 93 |

| Rank | Image Id. | Gene | EWS Rank | EWS Sign | RMS Rank | RMS Sign | NB Rank | NB Sign | BL Rank | BL Sign | Cancer Type | SEQ. ID. NO. |
|---|---|---|---|---|---|---|---|---|---|---|---|---|
| 72 | 325182 | CDH2 | 590 | - | 919 | - | 5 | + | 260 | - | NB | SEQ ID NO 31 |
| 73 | 1435862 | MIC2 | 14 | + | 518 | - | 371 | - | 97 | - | EWS | SEQ ID NO 22 |
| 74 | 377048 | EST | 733 | - | 560 | + | 23 | + | 102 | - | NB | SEQ ID NO 40 |
| 75 | 814260 | FVT1 | 9 | + | 61 | - | 330 | - | 335 | - | EWS | SEQ ID NO 17 |
| 76 | 784257 | KIF3C | 577 | + | 1099 | - | 64 | + | 44 | - | NB | SEQ ID NO 34 |
| 77 | 42558 | GATM | 379 | - | 12 | + | 25 | - | 1020 | - | RMS | SEQ ID NO 79 |
| 78 | 814526 | HSRNASEB | 164 | - | 198 | + | 98 | - | 105 | + | RMS/BL | SEQ ID NO 96 |
| 79 | 839736 | CRYAB | 516 | + | 67 | + | 51 | - | 183 | - | EWS/RMS | SEQ ID NO 61 |
| 80 | 395708 | DPYSL4 | 1269 | + | 591 | - | 28 | + | 91 | - | NB | SEQ ID NO 30 |
| 81 | 416959 | NFIB | 1420 | - | 86 | + | 160 | + | 72 | - | RMS/NB | SEQ ID NO 29 |
| 82 | 364934 | DAPK1 | 42 | + | 1481 | + | 707 | - | 40 | - | EWS | SEQ ID NO 12 |
| 83 | 868304 | ACTA2 | 1286 | - | 151 | - | 122 | - | 71 | + | BL | SEQ ID NO 86 |
| 84 | 755599 | IFI17 | 16 | + | 177 | - | 30 | - | 918 | - | EWS | SEQ ID NO 25 |
| 85 | 246377 | EST | 719 | - | 36 | + | 641 | + | 75 | - | RMS | SEQ ID NO 51 |
| 86 | 291756 | TUBB5 | 17 | + | 31 | - | 1325 | + | 245 | - | EWS | SEQ ID NO 1 |
| 87 | 809901 | COL15A1 | 1516 | - | 23 | + | 35 | - | 385 | - | RMS | SEQ ID NO 67 |
| 88 | 769959 | COL4A2 | 1575 | + | 66 | + | 1786 | - | 26 | - | RMS | SEQ ID NO 69 |
| 89 | 796258 | SGCA | 30 | - | 10 | + | 521 | - | 758 | - | RMS | SEQ ID NO 76 |
| 90 | 854899 | DUSP6 | 774 | + | 150 | + | 838 | + | 39 | - | Not BL | SEQ ID NO 48 |
| 91 | 755750 | NME2 | 1840 | + | 26 | + | 591 | - | 82 | - | RMS | SEQ ID NO 49 |
| 92 | 292522 | EST | 221 | - | 667 | + | 32 | + | 189 | - | NB | SEQ ID NO 36 |
| 93 | 308497 | EST | 27 | + | 1971 | - | 43 | - | 231 | - | EWS | SEQ ID NO 24 |
| 94 | 813266 | FHL1 | 1045 | + | 1610 | - | 91 | + | 46 | - | NB | SEQ ID NO 47 |
| 95 | 200814 | MME | 639 | - | 1081 | + | 78 | - | 66 | + | BL | SEQ ID NO 94 |
| 96 | 768370 | TIMP3 | 547 | + | 1132 | + | 606 | + | 25 | - | Not BL | SEQ ID NO 46 |

CERTIFICATE OF CORRECTION (continued)
U.S. Pat. No. 7,655,397 B2

Col. 37, table, line 35: The lines under the 50x Denhardt's row in the High Sample Blocking and High Array Blocking columns should be deleted Col. 39, line 4: "logarithm (In) of RRI" should read --logarithm (ln) of RRI--

Col. 39, line 12: "using centralized in" should read --using centralized ln--

Col. 43, Table 5: Delete incorrect Table 5 and replace with correct Table 5:

TABLE 5

| Rank | Unique Image_Id | Name of Gene | Unigene number | Weight | SEQ. ID. NO. |
|---|---|---|---|---|---|
| 1 | 296448 | "insulin-like growth factor 2 (somatomedin A)" | Hs.251664 | 1.00+-0.03 | SEQ. ID. NO. 72 |
| 2 | 207274 | "insulin-like growth factor 2 (somatomedin A)" | Hs.251664 | 0.97+-0.03 | SEQ. ID. NO. 73 |
| 3 | 295985 | "Homo sapiens cDNA FLJ20653 fis, clone KAT01739" | Hs.180059 | 0.87+-0.02 | SEQ. ID. NO. 26 |
| 4 | 41591 | "meningioma (disrupted in balanced translocation) 1" | Hs.268515 | 0.86+-0.02 | SEQ. ID. NO. 60 |
| 5 | 365826 | "growth arrest-specific 1" | Hs.65029 | 0.86+-0.02 | SEQ. ID. NO. 59 |
| 6 | 714453 | "interleukin 4 receptor" | Hs.75545 | 0.85+-0.02 | SEQ. ID. NO. 83 |
| 7 | 812965 | "v-myc avian myelocytomatosis viral oncogene homolog" | Hs.79070 | 0.81+-0.02 | SEQ. ID. NO. 82 |
| 8 | 486787 | "calponin 3, acidic" | Hs.194662 | 0.81+-0.02 | SEQ. ID. NO. 43 |
| 9 | 244618 | "ESTs" | Hs.15463 | 0.80+-0.02 | SEQ. ID. NO. 77 |
| 10 | 417226 | "v-myc avian myelocytomatosis viral oncogene homolog" | Hs.79070 | 0.80+-0.02 | SEQ. ID. NO. 81 |

| Rank | Unique Image_Id | Name of Gene | Unigene number | Weight | SEQ. ID. NO. |
|---|---|---|---|---|---|
| 11 | 840942 | "major histocompatibility complex, class II, DP beta 1" | Hs.814 | 0.79+-0.02 | SEQ. ID. NO. 87 |
| 12 | 770394 | "Fc fragment of IgG, receptor, transporter, alpha" | Hs.160741 | 0.78+-0.02 | SEQ. ID. NO. 20 |
| 13 | 812105 | "ALL1-fused gene from chromosome 1q" | Hs.75823 | 0.76+-0.02 | SEQ. ID. NO. 32 |
| 14 | 357031 | "tumor necrosis factor, alpha-induced protein 6" | Hs.29352 | 0.75+-0.02 | SEQ. ID. NO. 18 |
| 15 | 629896 | "microtubule-associated protein 1B" | Hs.103042 | 0.74+-0.02 | SEQ. ID. NO. 37 |
| 16 | 308163 | "ESTs" | Hs.84520 | 0.73+-0.02 | SEQ. ID. NO. 57 |
| 17 | 43733 | "glycogenin 2" | Hs.58589 | 0.72+-0.02 | SEQ. ID. NO. 21 |
| 18 | 489631 | "chondroitin sulfate proteoglycan 2 (versican)" | Hs.81800 | 0.71+-0.02 | SEQ. ID. NO. 100 |
| 19 | 866702 | "protein tyrosine phosphatase, non-receptor type 13 (APO-1/CD95 (Fas)-associated phosphatase)" | Hs.211595 | 0.71+-0.02 | SEQ. ID. NO. 16 |
| 20 | 377461 | "caveolin 1, caveolae protein, 22kD" | Hs.281621 | 0.70+-0.02 | SEQ. ID. NO. 19 |
| 21 | 324494 | "heat shock 27kD protein 2" | Hs.78846 | 0.69+-0.02 | SEQ. ID. NO. 62 |
| 22 | 80109 | "major histocompatibility complex, class II, DQ alpha 1" | Hs.198253 | 0.69+-0.02 | SEQ. ID. NO. 88 |

CERTIFICATE OF CORRECTION (continued)

U.S. Pat. No. 7,655,397 B2

| Rank | Unique Image_Id | Name of Gene | Unigene number | Weight | SEQ. ID. NO. |
|---|---|---|---|---|---|
| 23 | 39093 | "methionine aminopeptidase; eIF-2-associated p67" | Hs.78935 | 0.69+-0.01 | SEQ. ID. NO. 63 |
| 24 | 82225 | "secreted frizzled-related protein 1" | Hs.7306 | 0.67+-0.01 | SEQ. ID. NO. 42 |
| 25 | 308231 | "Homo sapiens cDNA FLJ20153 fis, clone COL08656, highly similar to AJ001381 Homo sapiens incomplete cDNA for a mutated allele" | Hs.109805 | 0.67+-0.02 | SEQ. ID. NO. 39 |
| 26 | 211758 | "ribosomal protein S23" | Hs.3463 | 0.67+-0.01 | SEQ. ID. NO. 101 |
| 27 | 1E+06 | "troponin T1, skeletal, slow" | Hs.73980 | 0.66+-0.02 | SEQ. ID. NO. 70 |
| 28 | 878280 | "collapsin response mediator protein 1" | Hs.155392 | 0.65+-0.02 | SEQ. ID. NO. 33 |
| 29 | 383188 | "recoverin" | Hs.80539 | 0.64+-0.01 | SEQ. ID. NO. 38 |
| 30 | 795877 | "serum-inducible kinase" | Hs.3838 | 0.64+-0.01 | SEQ. ID. NO. 102 |
| 31 | 784593 | "ESTs" | Hs.6838 | 0.63+-0.01 | SEQ. ID. NO. 41 |
| 32 | 135688 | "GATA-binding protein 2" | Hs.760 | 0.62+-0.01 | SEQ. ID. NO. 44 |
| 33 | 325182 | "cadherin 2, N-cadherin (neuronal)" | Hs.161 | 0.62+-0.01 | SEQ. ID. NO. 31 |
| 34 | 461425 | "myosin, light polypeptide 4, alkali; atrial, embryonic" | Hs.154156 | 0.61+-0.01 | SEQ. ID. NO. 75 |

| Rank | Unique Image_Id | Name of Gene | Unigene number | Weight | SEQ. ID. NO. |
|---|---|---|---|---|---|
| 35 | 1E+06 | "transducin-like enhancer of split 2, homolog of Drosophila E(sp1)" | Hs.173063 | 0.61+-0.02 | SEQ. ID. NO. 15 |
| 36 | 298062 | "troponin T2, cardiac" | Hs.89749 | 0.61+-0.02 | SEQ. ID. NO. 74 |
| 37 | 841641 | "cyclin D1 (PRAD1: parathyroid adenomatosis 1)" | Hs.82932 | 0.61+-0.01 | SEQ. ID. NO. 5 |
| 38 | 745343 | "regenerating islet-derived 1 alpha (pancreatic stone protein, pancreatic thread protein)" | Hs.1032 | 0.60+-0.01 | SEQ. ID. NO. 85 |
| 39 | 755599 | "interferon induced transmembrane protein 1 (9-27)" | Hs.146360 | 0.59+-0.02 | SEQ. ID. NO. 25 |
| 40 | 809901 | "collagen, type XV, alpha 1" | Hs.83164 | 0.59+-0.01 | SEQ. ID. NO. 67 |
| 41 | 859359 | "quinone oxidoreductase homolog" | Hs.50649 | 0.59+-0.01 | SEQ. ID. NO. 50 |
| 42 | 784224 | "fibroblast growth factor receptor 4" | Hs.165950 | 0.59+-0.02 | SEQ. ID. NO. 71 |
| 43 | 42558 | "glycine amidinotransferase (L-arginine:glycine amidinotransferase)" | Hs.75335 | 0.58+-0.01 | SEQ. ID. NO. 79 |
| 44 | 183337 | "major histocompatibility complex, class II, DM alpha" | Hs.77522 | 0.58+-0.01 | SEQ. ID. NO. 89 |
| 45 | 289645 | "amyloid beta (A4) precursor-like protein 1" | Hs.74565 | 0.58+-0.01 | SEQ. ID. NO. 4 |

CERTIFICATE OF CORRECTION (continued)
U.S. Pat. No. 7,655,397 B2

| Rank | Unique Image_Id | Name of Gene | Unigene number | Weight | SEQ. ID. NO. |
|---|---|---|---|---|---|
| 46 | 377048 | "Homo sapiens cDNA FLJ20153 fis, clone COL08656, highly similar to AJ001381 Homo sapiens incomplete cDNA for a mutated allele" | Hs.109805 | 0.57+-0.01 | SEQ. ID. NO. 40 |
| 47 | 122159 | "collagen, type III, alpha 1 (Ehlers-Danlos syndrome type IV, autosomal dominant)" | Hs.119571 | 0.57+-0.01 | SEQ. ID. NO. 66 |
| 48 | 245330 | "insulin-like growth factor 2 (somatomedin A)" | Hs.251664 | 0.57+-0.01 | SEQ. ID. NO. 78 |
| 49 | 814260 | "follicular lymphoma variant translocation 1" | Hs.74050 | 0.57+-0.01 | SEQ. ID. NO. 17 |
| 50 | 824602 | "interferon, gamma-inducible protein 16" | Hs.155530 | 0.57+-0.01 | SEQ. ID. NO. 84 |
| 51 | 44563 | "growth associated protein 43" | Hs.79000 | 0.56+-0.01 | SEQ. ID. NO. 35 |
| 52 | 767495 | "GLI-Kruppel family member GLI3 (Greig cephalopolysyndactyly syndrome)" | Hs.72916 | 0.56+-0.01 | SEQ. ID. NO. 103 |
| 53 | 769716 | "neurofibromin 2 (bilateral acoustic neuroma)" | Hs.902 | 0.55+-0.01 | SEQ. ID. NO. 104 |
| 54 | 486110 | "profilin 2" | Hs.91747 | 0.55+-0.01 | SEQ. ID. NO. 45 |
| 55 | 1E+06 | "pim-2 oncogene" | Hs.80205 | 0.55+-0.01 | SEQ. ID. NO. 92 |

| Rank | Unique Image_Id | Name of Gene | Unigene number | Weight | SEQ. ID. NO. |
|---|---|---|---|---|---|
| 56 | 756556 | "complement component 1 inhibitor (angioedema, hereditary)" | Hs.151242 | 0.54+-0.01 | SEQ. ID. NO. 65 |
| 57 | 377731 | "glutathione S-transferase M5" | Hs.75652 | 0.54+-0.01 | SEQ. ID. NO. 23 |
| 58 | 52076 | "olfactomedin related ER localized protein" | Hs.74376 | 0.54+-0.02 | SEQ. ID. NO. 13 |
| 59 | 810057 | "cold shock domain protein A" | Hs.1139 | 0.54+-0.01 | SEQ. ID. NO. 105 |
| 60 | 233721 | "insulin-like growth factor binding protein 2 (36kD)" | Hs.162 | 0.54+-0.01 | SEQ. ID. NO. 28 |
| 61 | 293500 | "ESTs" | Hs.49714 | 0.54+-0.01 | SEQ. ID. NO. 80 |
| 62 | 75254 | "cysteine and glycine-rich protein 2 (LIM domain only, smooth muscle)" | Hs.10526 | 0.54+-0.01 | SEQ. ID. NO. 106 |
| 63 | 377468 | "sprouty (Drosophila) homolog 1 (antagonist of FGF signaling)" | Hs.88044 | 0.53+-0.01 | SEQ. ID. NO. 107 |
| 64 | 809910 | "interferon induced transmembrane protein 3 (1-8U)" | Hs.182241 | 0.53+-0.01 | SEQ. ID. NO. 55 |
| 65 | 395708 | "dihydropyrimidinase-like 4" | Hs.100058 | 0.53+-0.01 | SEQ. ID. NO. 30 |
| 66 | 416959 | "nuclear factor I/B" | Hs.33287 | 0.53+-0.01 | SEQ. ID. NO. 29 |
| 67 | 1E+06 | "antigen identified by monoclonal antibodies 12E7, F21 and O13" | Hs.177543 | 0.52+-0.01 | SEQ. ID. NO. 22 |

| Rank | Unique Image_Id | Name of Gene | Unigene number | Weight | SEQ. ID. NO. |
|---|---|---|---|---|---|
| 68 | 609663 | "protein kinase, cAMP-dependent, regulatory, type II, beta" | Hs.77439 | 0.51+-0.01 | SEQ. ID. NO. 95 |
| 69 | 212640 | "Rho GTPase activating protein 4" | Hs.3109 | 0.51+-0.01 | SEQ. ID. NO. 108 |
| 70 | 130057 | "ESTs" | Hs.23057 | 0.51+-0.01 | SEQ. ID. NO. 109 |
| 71 | 563673 | "antiquitin 1" | Hs.74294 | 0.51+-0.01 | SEQ. ID. NO. 10 |
| 72 | 770059 | "heparan sulfate proteoglycan 2 (perlecan)" | Hs.211573 | 0.51+-0.01 | SEQ. ID. NO. 110 |
| 73 | 782503 | "Homo sapiens clone 23716 mRNA sequence" | Hs.12214 | 0.50+-0.01 | SEQ. ID. NO. 7 |
| 74 | 292522 | "ESTs" | Hs.38022 | 0.50+-0.01 | SEQ. ID. NO. 36 |
| 75 | 365515 | "fibroblast growth factor 7 (keratinocyte growth factor)" | Hs.164568 | 0.50+-0.01 | SEQ. ID. NO. 111 |
| 76 | 1E+06 | "cysteine-rich protein 1 (intestinal)" | Hs.17409 | 0.50+-0.01 | SEQ. ID. NO. 112 |
| 77 | 767183 | "hematopoietic cell-specific Lyn substrate 1" | Hs.14601 | 0.50+-0.01 | SEQ. ID. NO. 91 |
| 78 | 811000 | "lectin, galactoside-binding, soluble, 3 binding protein (galectin 6 binding protein)" | Hs.79339 | 0.50+-0.01 | SEQ. ID. NO. 6 |
| 79 | 308497 | "KIAA0467 protein" | Hs.11147 | 0.49+-0.01 | SEQ. ID. NO. 24 |

| Rank | Unique Image_Id | Name of Gene | Unigene number | Weight | SEQ. ID. NO. |
|---|---|---|---|---|---|
| 80 | 80338 | "selenium binding protein 1" | Hs.7833 | 0.49+-0.01 | SEQ. ID. NO. 14 |
| 81 | 200814 | "membrane metallo-endopeptidase (neutral endopeptidase, enkephalinase, CALLA, CD10)" | Hs.1298 | 0.49+-0.01 | SEQ. ID. NO. 94 |
| 82 | 898219 | "mesoderm specific transcript (mouse) homolog" | Hs.79284 | 0.49+-0.01 | SEQ. ID. NO. 113 |
| 83 | 796258 | "sarcoglycan, alpha (50kD dystrophin-associated glycoprotein)" | Hs.99931 | 0.49+-0.01 | SEQ. ID. NO. 76 |
| 84 | 377671 | "integrin, alpha 7" | Hs.74369 | 0.48+-0.01 | SEQ. ID. NO. 68 |
| 85 | 839736 | "crystallin, alpha B" | Hs.1940 | 0.48+-0.01 | SEQ. ID. NO. 61 |
| 86 | 208718 | "annexin A1" | Hs.78225 | 0.48+-0.01 | SEQ. ID. NO. 2 |
| 87 | 32299 | "inositol(myo)-1(or 4)-monophosphatase 2" | Hs.5753 | 0.48+-0.01 | SEQ. ID. NO. 114 |
| 88 | 246377 | "EST" | Hs.102670 | 0.48+-0.01 | SEQ. ID. NO. 51 |
| 89 | 413633 | "EST" | | 0.48+-0.01 | SEQ. ID. NO. 115 |
| 90 | 140806 | "peptidylglycine alpha-amidating monooxygenase" | Hs.83920 | 0.47+-0.01 | SEQ. ID. NO. 116 |
| 91 | 294496 | "ESTs" | Hs.23037 | 0.47+-0.01 | SEQ. ID. NO. 117 |

CERTIFICATE OF CORRECTION (continued)
U.S. Pat. No. 7,655,397 B2

| Rank | Unique Image_Id | Name of Gene | Unigene number | Weight | SEQ. ID. NO. |
|---|---|---|---|---|---|
| 92 | 755750 | "non-metastatic cells 2, protein (NM23B) expressed in" | Hs.275163 | 0.47+-0.01 | SEQ. ID. NO. 49 |
| 93 | 811108 | "thyroid hormone receptor interactor 6" | Hs.119498 | 0.47+-0.01 | SEQ. ID. NO. 118 |
| 94 | 246035 | "ESTs" | Hs.78026 | 0.47+-0.01 | SEQ. ID. NO. 119 |
| 95 | 796904 | "pleomorphic adenoma gene-like 1" | Hs.75825 | 0.47+-0.01 | SEQ. ID. NO. 120 |
| 96 | 788107 | "bridging integrator 1" | Hs.193163 | 0.47+-0.01 | SEQ. ID. NO. 52 |
| 97 | 714106 | "plasminogen activator, urokinase" | Hs.77274 | 0.47+-0.01 | SEQ. ID. NO. 121 |
| 98 | 842918 | "FERM, RhoGEF (ARHGEF) and pleckstrin domain protein 1 (chondrocyte-derived)" | Hs.183738 | 0.47+-0.01 | SEQ. ID. NO. 122 |
| 99 | 788472 | "nucleobindin 1" | Hs.172609 | 0.47+-0.01 | SEQ. ID. NO. 123 |
| 100 | 52096 | "platelet-derived growth factor receptor, alpha polypeptide" | Hs.74615 | 0.46+-0.01 | SEQ. ID. NO. 124 |
| 101 | 823886 | "Smooth muscle myosin heavy chain isoform SMemb [human, umbilical cord, fetal aorta, mRNA Partial, 971 nt]" | Hs.2094 | 0.46+-0.01 | SEQ. ID. NO. 125 |
| 102 | 782193 | "thioredoxin" | Hs.76136 | 0.46+-0.01 | SEQ. ID. NO. 126 |

| Rank | Unique Image_Id | Name of Gene | Unigene number | Weight | SEQ. ID. NO. |
|---|---|---|---|---|---|
| 103 | 214990 | "gelsolin (amyloidosis, Finnish type)" | Hs.80562 | 0.46+-0.01 | SEQ. ID. NO. 127 |
| 104 | 144932 | "deleted in oral cancer (mouse, homolog) 1" | Hs.3436 | 0.46+-0.01 | SEQ. ID. NO. 128 |
| 105 | 782811 | "high-mobility group (nonhistone chromosomal) protein isoforms I and Y" | Hs.139800 | 0.46+-0.01 | SEQ. ID. NO. 129 |
| 106 | 813698 | "sprouty (Drosophila) homolog 2" | Hs.18676 | 0.45+-0.01 | SEQ. ID. NO. 130 |
| 107 | 212542 | "Homo sapiens mRNA; cDNA DKFZp586J2118 (from clone DKFZp586J2118)" | Hs.21851 | 0.45+-0.01 | SEQ. ID. NO. 53 |
| 108 | 204545 | "ESTs" | Hs.8966 | 0.45+-0.01 | SEQ. ID. NO. 58 |
| 109 | 341588 | "CGI-119 protein" | Hs.25615 | 0.45+-0.01 | SEQ. ID. NO. 131 |
| 110 | 297392 | "metallothionein 1L" | Hs.94360 | 0.45+-0.01 | SEQ. ID. NO. 93 |
| 111 | 813841 | "plasminogen activator, tissue" | Hs.274404 | 0.45+-0.01 | SEQ. ID. NO. 132 |
| 112 | 491692 | "collagen, type IV, alpha 1" | Hs.119129 | 0.44+-0.01 | SEQ. ID. NO. 133 |
| 113 | 142134 | "hypothetical protein FLJ20185" | Hs.272972 | 0.44+-0.01 | SEQ. ID. NO. 134 |
| 114 | 214572 | "ESTs" | Hs.280460 | 0.44+-0.01 | SEQ. ID. NO. 135 |
| 115 | 878182 | "alpha-2-macroglobulin" | Hs.74561 | 0.44+-0.01 | SEQ. ID. NO. 136 |

| Rank | Unique Image_Id | Name of Gene | Unigene number | Weight | SEQ. ID. NO. |
|---|---|---|---|---|---|
| 116 | 360047 | "SWI/SNF related, matrix associated, actin dependent regulator of chromatin, subfamily d, member 3" | Hs.77069 | 0.44+-0.01 | SEQ. ID. NO. 137 |
| 117 | 878652 | "procollagen C-endopeptidase enhancer" | Hs.202097 | 0.44+-0.01 | SEQ. ID. NO. 138 |
| 118 | 450152 | "Meis (mouse) homolog 3" | Hs.117313 | 0.44+-0.01 | SEQ. ID. NO. 139 |
| 119 | 45542 | "Human insulin-like growth factor binding protein 5 (IGFBP5) mRNA" | Hs.103391 | 0.44+-0.01 | SEQ. ID. NO. 64 |
| 120 | 742132 | "interferon-stimulated protein, 15 kDa" | Hs.833 | 0.44+-0.01 | SEQ. ID. NO. 140 |
| 121 | 82903 | "TAP binding protein (tapasin)" | Hs.179600 | 0.44+-0.01 | SEQ. ID. NO. 141 |
| 122 | 773215 | "runt-related transcription factor 1 (acute myeloid leukemia 1; aml1 oncogene)" | Hs.129914 | 0.44+-0.01 | SEQ. ID. NO. 142 |
| 123 | 789253 | "presenilin 2 (Alzheimer disease 4)" | Hs.25363 | 0.44+-0.01 | SEQ. ID. NO. 143 |
| 124 | 814526 | "seb4D" | Hs.236361 | 0.44+-0.01 | SEQ. ID. NO. 96 |
| 125 | 435953 | "inositol 1,4,5-triphosphate receptor, type 3" | Hs.77515 | 0.44+-0.01 | SEQ. ID. NO. 144 |
| 126 | 245860 | "Homo sapiens mRNA; cDNA DKFZp564H1916 (from clone DKFZp564H1916)" | Hs.181104 | 0.44+-0.01 | SEQ. ID. NO. 145 |

| Rank | Unique Image_Id | Name of Gene | Unigene number | Weight | SEQ. ID. NO. |
|---|---|---|---|---|---|
| 127 | 159455 | "similar to vaccinia virus HindIII K4L ORF" | Hs.74573 | 0.44+-0.01 | SEQ. ID. NO. 146 |
| 128 | 220096 | "-" | - | 0.44+-0.01 | SEQ. ID. NO. 147 |
| 129 | 45291 | "dentatorubral-pallidoluysian atrophy (atrophin-1)" | Hs.169488 | 0.43+-0.01 | SEQ. ID. NO. 54 |
| 130 | 241412 | "E74-like factor 1 (ets domain transcription factor)" | Hs.154365 | 0.43+-0.01 | SEQ. ID. NO. 90 |
| 131 | 1E+06 | "matrix metalloproteinase 2 (gelatinase A, 72kD gelatinase, 72kD type IV collagenase)" | Hs.111301 | 0.43+-0.01 | SEQ. ID. NO. 148 |
| 132 | 250654 | "secreted protein, acidic, cysteine-rich (osteonectin)" | Hs.111779 | 0.43+-0.01 | SEQ. ID. NO. 149 |
| 133 | 343867 | "allograft inflammatory factor 1" | Hs.76364 | 0.43+-0.01 | SEQ. ID. NO. 150 |
| 134 | 234237 | "Pirin" | Hs.279663 | 0.42+-0.01 | SEQ. ID. NO. 151 |
| 135 | 713922 | "glutathione S-transferase M1" | Hs.278633 | 0.42+-0.01 | SEQ. ID. NO. 152 |
| 136 | 823928 | "glutathione S-transferase theta 2" | Hs.1581 | 0.42+-0.01 | SEQ. ID. NO. 153 |
| 137 | 810504 | "proteolipid protein 2 (colonic epithelium-enriched)" | Hs.77422 | 0.42+-0.01 | SEQ. ID. NO. 154 |
| 138 | 788511 | "ribosomal protein S6 kinase, 90kD, polypeptide 1" | Hs.149957 | 0.41+-0.01 | SEQ. ID. NO. 155 |

| Rank | Unique Image_Id | Name of Gene | Unigene number | Weight | SEQ. ID. NO. |
|---|---|---|---|---|---|
| 139 | 471266 | "DiGeorge syndrome critical region gene 6" | Hs.153910 | 0.41+-0.01 | SEQ. ID. NO. 156 |
| 140 | 299737 | "Homo sapiens clone 24411 mRNA sequence" | Hs.20952 | 0.41+-0.01 | SEQ. ID. NO. 157 |
| 141 | 740554 | "Homo sapiens mRNA; cDNA DKFZp434I0812 (from clone DKFZp434I0812); partial cds" | Hs.263671 | 0.41+-0.01 | SEQ. ID. NO. 158 |
| 142 | 754600 | "nuclear factor I/X (CCAAT-binding transcription factor)" | Hs.35841 | 0.41+-0.01 | SEQ. ID. NO. 159 |
| 143 | 151261 | "ESTs" | Hs.237971 | 0.41+-0.01 | SEQ. ID. NO. 160 |
| 144 | 815239 | "Rho guanine nucleotide exchange factor (GEF) 1" | Hs.252280 | 0.41+-0.01 | SEQ. ID. NO. 161 |
| 145 | 624360 | "proteasome (prosome, macropain) subunit, beta type, 8 (large multifunctional protease 7)" | Hs.180062 | 0.41+-0.01 | SEQ. ID. NO. 162 |
| 146 | 213136 | "BTG family, member 2" | Hs.75462 | 0.41+-0.01 | SEQ. ID. NO. 163 |
| 147 | 21652 | "catenin (cadherin-associated protein), alpha 1 (102kD)" | Hs.178452 | 0.41+-0.01 | SEQ. ID. NO. 56 |
| 148 | 813266 | "four and a half LIM domains 1" | Hs.239069 | 0.41+-0.01 | SEQ. ID. NO. 47 |
| 149 | 236282 | "Wiskott-Aldrich syndrome (ecezema-thrombocytopenia)" | Hs.2157 | 0.41+-0.01 | SEQ. ID. NO. 164 |

| Rank | Unique Image_Id | Name of Gene | Unigene number | Weight | SEQ. ID. NO. |
|---|---|---|---|---|---|
| 150 | 755228 | "dynamin 1" | Hs.166161 | 0.41+-0.01 | SEQ. ID. NO. 165 |
| 151 | 161993 | "CCAAT/enhancer binding protein (C/EBP), beta" | Hs.99029 | 0.41+-0.01 | SEQ. ID. NO. 166 |
| 152 | 358433 | "retinoid X receptor, gamma" | Hs.26550 | 0.41+-0.01 | SEQ. ID. NO. 167 |
| 153 | 841620 | "dihydropyrimidinase-like 2" | Hs.173381 | 0.41+-0.01 | SEQ. ID. NO. 8 |
| 154 | 293859 | "Putative prostate cancer tumor suppressor" | Hs.71119 | 0.41+-0.01 | SEQ. ID. NO. 168 |
| 155 | 190887 | "myeloid differentiation primary response gene (88)" | Hs.82116 | 0.41+-0.01 | SEQ. ID. NO. 169 |
| 156 | 362483 | "spectrin, beta, non-erythrocytic 1" | Hs.107164 | 0.41+-0.01 | SEQ. ID. NO. 170 |
| 157 | 139376 | "hypothetical protein" | Hs.91973 | 0.40+-0.01 | SEQ. ID. NO. 171 |
| 158 | 786084 | "chromobox homolog 1 (Drosophila HP1 beta)" | Hs.77254 | 0.40+-0.01 | SEQ. ID. NO. 172 |
| 159 | 193182 | "transforming, acidic coiled-coil containing protein 1" | Hs.173159 | 0.40+-0.01 | SEQ. ID. NO. 173 |
| 160 | 768246 | "glucose-6-phosphate dehydrogenase" | Hs.80206 | 0.40+-0.01 | SEQ. ID. NO. 174 |
| 161 | 774502 | "protein tyrosine phosphatase, non-receptor type 12" | Hs.62 | 0.40+-0.01 | SEQ. ID. NO. 175 |
| 162 | 868304 | "actin, alpha 2, smooth muscle, aorta" | Hs.195851 | 0.40+-0.01 | SEQ. ID. NO. 86 |

| Rank | Unique Image_Id | Name of Gene | Unigene number | Weight | SEQ. ID. NO. |
|---|---|---|---|---|---|
| 163 | 379708 | "chromodomain helicase DNA binding protein 3" | Hs.25601 | 0.40+-0.01 | SEQ. ID. NO. 176 |
| 164 | 504791 | "glutathione S-transferase A4" | Hs.169907 | 0.40+-0.01 | SEQ. ID. NO. 11 |
| 165 | 755506 | "annexin A4" | Hs.77840 | 0.40+-0.01 | SEQ. ID. NO. 177 |
| 166 | 1E+06 | "homeo box B7" | Hs.819 | 0.40+-0.01 | SEQ. ID. NO. 178 |
| 167 | 824704 | "mannose phosphate isomerase" | Hs.75694 | 0.40+-0.01 | SEQ. ID. NO. 179 |
| 168 | 770014 | "T cell receptor alpha locus" | Hs.74647 | 0.40+-0.01 | SEQ. ID. NO. 180 |
| 169 | 22040 | "matrix metalloproteinase 9 (gelatinase B, 92kD gelatinase, 92kD type IV collagenase)" | Hs.151738 | 0.40+-0.01 | SEQ. ID. NO. 181 |
| 170 | 66714 | "peanut (Drosophila)-like 2" | Hs.155524 | 0.40+-0.01 | SEQ. ID. NO. 182 |
| 171 | 172783 | "hypothetical protein FLJ10390" | Hs.133475 | 0.40+-0.01 | SEQ. ID. NO. 183 |
| 172 | 273435 | "v-yes-1 Yamaguchi sarcoma viral oncogene homolog 1" | Hs.194148 | 0.40+-0.01 | SEQ. ID. NO. 184 |
| 173 | 323371 | "amyloid beta (A4) precursor protein (protease nexin-II, Alzheimer disease)" | Hs.177486 | 0.39+-0.01 | SEQ. ID. NO. 27 |
| 174 | 344134 | "immunoglobulin lambda-like polypeptide 3" | Hs.170116 | 0.39+-0.01 | SEQ. ID. NO. 185 |
| 175 | 291756 | "tubulin, beta, 5" | Hs.108014 | 0.39+-0.01 | SEQ. ID. NO. 1 |

| Rank | Unique Image_Id | Name of Gene | Unigene number | Weight | SEQ. ID. NO. |
|---|---|---|---|---|---|
| 176 | 47475 | "p53 inducible protein" | Hs.258503 | 0.39+-0.01 | SEQ. ID. NO. 186 |
| 177 | 760299 | "Dickkopf gene 3" | Hs.4909 | 0.39+-0.01 | SEQ. ID. NO. 187 |
| 178 | 24415 | "tumor protein p53 (Li-Fraumeni syndrome)" | Hs.1846 | 0.39+-0.01 | SEQ. ID. NO. 188 |
| 179 | 727251 | "CD9 antigen (p24)" | Hs.1244 | 0.39+-0.01 | SEQ. ID. NO. 189 |
| 180 | 770868 | "NGFI-A binding protein 2 (ERG1 binding protein 2)" | Hs.159223 | 0.39+-0.01 | SEQ. ID. NO. 190 |
| 181 | 364934 | "death-associated protein kinase 1" | Hs.153924 | 0.39+-0.01 | SEQ. ID. NO. 12 |
| 182 | 1E+06 | "creatine kinase, brain" | Hs.173724 | 0.39+-0.01 | SEQ. ID. NO. 191 |
| 183 | 769959 | "collagen, type IV, alpha 2" | Hs.75617 | 0.39+-0.01 | SEQ. ID. NO. 69 |
| 184 | 144797 | "a disintegrin-like and metalloprotease (reprolysin type) with thrombospondin type 1 motif, 1" | Hs.8230 | 0.39+-0.01 | SEQ. ID. NO. 192 |
| 185 | 108351 | "Homo sapiens cDNA FLJ11302 fis, clone PLACE1009971" | Hs.13781 | 0.38+-0.01 | SEQ. ID. NO. 193 |
| 186 | 51448 | "activating transcription factor 3" | Hs.460 | 0.38+-0.01 | SEQ. ID. NO. 194 |
| 187 | 301122 | "extracellular matrix protein 1" | Hs.81071 | 0.38+-0.01 | SEQ. ID. NO. 195 |
| 188 | 814798 | "aldehyde dehydrogenase 6" | Hs.75746 | 0.38+-0.01 | SEQ. ID. NO. 196 |

| Rank | Unique Image Id | Name of Gene | Unigene number | Weight | SEQ. ID. NO. |
|---|---|---|---|---|---|
| 189 | 788695 | "troponin T3, skeletal, fast" | Hs.73454 | 0.38+-0.01 | SEQ. ID. NO. 197 |
| 190 | 769028 | "mesenchyme homeo box 1" | Hs.438 | 0.38+-0.01 | SEQ. ID. NO. 198 |
| 191 | 811028 | "cathepsin D (lysosomal aspartyl protease)" | Hs.79572 | 0.38+-0.01 | SEQ. ID. NO. 199 |
| 192 | 196992 | "aldo-keto reductase family 1, member C1 (dihydrodiol dehydrogenase 1; 20-alpha (3-alpha)-hydroxysteroid dehydrogenase)" | Hs.275374 | 0.38+-0.01 | SEQ. ID. NO. 200 |
| 193 | 586854 | "CGI-119 protein" | Hs.25615 | 0.38+-0.01 | SEQ. ID. NO. 201 |
| 194 | 1E+06 | "ATPase, Na+/K+ transporting, alpha 1 polypeptide" | Hs.190703 | 0.38+-0.01 | SEQ. ID. NO. 202 |
| 195 | 752652 | "transcription factor 7-like 2 (T-cell specific, HMG-box)" | Hs.154485 | 0.38+-0.01 | SEQ. ID. NO. 203 |
| 196 | 813168 | "ESTs" | Hs.59896 | 0.38+-0.01 | SEQ. ID. NO. 204 |
| 197 | 143306 | "lymphocyte-specific protein 1" | Hs.56729 | 0.38+-0.01 | SEQ. ID. NO. 205 |
| 198 | 810551 | "low density lipoprotein-related protein 1 (alpha-2-macroglobulin receptor)" | Hs.89137 | 0.37+-0.01 | SEQ. ID. NO. 206 |

| Rank | Unique Image_Id | Name of Gene | Unigene number | Weight | SEQ. ID. NO. |
|---|---|---|---|---|---|
| 199 | 882506 | "lysyl oxidase-like 2" | Hs.83354 | 0.37+-0.01 | SEQ. ID. NO. 207 |
| 200 | 141768 | "v-erb-b2 avian erythroblastic leukemia viral oncogene homolog 2 (neuro/glioblastoma derived oncogene homolog)" | Hs.173664 | 0.37+-0.01 | SEQ. ID. NO. 208 |

Col. 52, Table 6: Delete incorrect Table 6 and replace with correct Table 6:

TABLE 6 - Ranked genes for Neuroblastoma (NB)

| Rank | Clone Id | GeneDescription | Unigene | Weight | SEQ. ID. NO. |
|---|---|---|---|---|---|
| 2 | 812105 | "ALL1-fused gene from chromosome 1q" | Hs.75823 | 0.96+-0.03 | SEQ. ID. NO. 32 |
| 6 | 325182 | "cadherin 2, N-cadherin (neuronal)" | Hs.161 | 0.84+-0.03 | SEQ. ID. NO. 31 |
| 8 | 629896 | "microtubule-associated protein 1B" | Hs.103042 | 0.82+-0.03 | SEQ. ID. NO. 37 |
| 10 | 878280 | "collapsin response mediator protein 1" | Hs.155392 | 0.80+-0.03 | SEQ. ID. NO. 33 |
| 11 | 308231 | "Homo sapiens cDNA FLJ20153 fis, clone COL08656, highly similar to AJ001381 Homo sapiens incomplete cDNA for a mutated allele" | Hs.109805 | 0.78+-0.03 | SEQ. ID. NO. 39 |
| 13 | 295985 | "Homo sapiens cDNA FLJ20653 fis, clone KAT01739" | Hs.180059 | 0.75+-0.03 | SEQ. ID. NO. 26 |
| 14 | 44563 | "growth associated protein 43" | Hs.79000 | 0.75+-0.02 | SEQ. ID. NO. 35 |
| 19 | 135688 | "GATA-binding protein 2" | Hs.760 | 0.68+-0.02 | SEQ. ID. NO. 44 |
| 21 | 383188 | "recoverin" | Hs.80539 | 0.64+-0.02 | SEQ. ID. NO. 38 |
| 23 | 395708 | "dihydropyrimidinase-like 4" | Hs.100058 | 0.63+-0.02 | SEQ. ID. NO. 30 |
| 25 | 82225 | "secreted frizzled-related protein 1" | Hs.7306 | 0.62+-0.02 | SEQ. ID. NO. 42 |
| 26 | 486787 | "calponin 3, acidic" | Hs.194662 | 0.62+-0.02 | SEQ. ID. NO. 43 |

| Rank | Clone Id | GeneDescription | Unigene | Weight | SEQ. ID. NO. |
|---|---|---|---|---|---|
| 28 | 377048 | "Homo sapiens cDNA FLJ20153 fis, clone COL08656, highly similar to AJ001381 Homo sapiens incomplete cDNA for a mutated allele" | Hs.109805 | 0.62+-0.02 | SEQ. ID. NO. 40 |
| 30 | 486110 | "profilin 2" | Hs.91747 | 0.59+-0.02 | SEQ. ID. NO. 45 |
| 32 | 768246 | "glucose-6-phosphate dehydrogenase" | Hs.80206 | 0.58+-0.02 | SEQ. ID. NO. 174 |
| 34 | 786084 | "chromobox homolog 1 (Drosophila HP1 beta)" | Hs.77254 | 0.57+-0.02 | SEQ. ID. NO. 172 |
| 36 | 211758 | "ribosomal protein S23" | Hs.3463 | 0.57+-0.02 | SEQ. ID. NO. 101 |
| 40 | 755228 | "dynamin 1" | Hs.166161 | 0.55+-0.02 | SEQ. ID. NO. 165 |
| 42 | 220096 | "-" | - | 0.55+-0.02 | SEQ. ID. NO. 147 |
| 43 | 823886 | "Smooth muscle myosin heavy chain isoform SMemb [human, umbilical cord, fetal aorta, mRNA Partial, 971 nt]" | Hs.2094 | 0.55+-0.02 | SEQ. ID. NO. 125 |
| 44 | 788472 | "nucleobindin 1" | Hs.172609 | 0.54+-0.02 | SEQ. ID. NO. 123 |
| 45 | 878652 | "procollagen C-endopeptidase enhancer" | Hs.202097 | 0.54+-0.02 | SEQ. ID. NO. 138 |
| 46 | 234237 | "Pirin" | Hs.279663 | 0.54+-0.02 | SEQ. ID. NO. 151 |
| 50 | 450152 | "Meis (mouse) homolog 3" | Hs.117313 | 0.51+-0.02 | SEQ. ID. NO. 139 |
| 51 | 743229 | "neurofilament 3 (150kD medium)" | Hs.71346 | 0.51+-0.02 | SEQ. ID. NO. 209 |
| 56 | 134748 | "glycine cleavage system protein H (aminomethyl carrier)" | Hs.77631 | 0.49+-0.02 | SEQ. ID. NO. 210 |

| Rank | Clone Id | GeneDescription | Unigene | Weight | SEQ. ID. NO. |
|---|---|---|---|---|---|
| 60 | 486175 | "solute carrier family 16 (monocarboxylic acid transporters), member 1" | Hs.75231 | 0.48+-0.02 | SEQ. ID. NO. 211 |
| 61 | 376516 | "cell division cycle 4-like" | Hs.62354 | 0.48+-0.02 | SEQ. ID. NO. 212 |
| 63 | 292522 | "ESTs" | Hs.38022 | 0.48+-0.02 | SEQ. ID. NO. 36 |
| 66 | 843098 | "brain acid-soluble protein 1" | Hs.79516 | 0.48+-0.02 | SEQ. ID. NO. 213 |
| 68 | 448386 | "pre-B-cell leukemia transcription factor 3" | Hs.171680 | 0.47+-0.02 | SEQ. ID. NO. 214 |
| 70 | 756401 | "Ras homolog enriched in brain 2" | Hs.279903 | 0.47+-0.02 | SEQ. ID. NO. 215 |
| 74 | 842918 | "FERM, RhoGEF (ARHGEF) and pleckstrin domain protein 1 (chondrocyte-derived)" | Hs.183738 | 0.46+-0.02 | SEQ. ID. NO. 122 |
| 76 | 784593 | "ESTs" | Hs.6838 | 0.46+-0.02 | SEQ. ID. NO. 41 |
| 84 | 364510 | "special AT-rich sequence binding protein 1 (binds to nuclear matrix/scaffold-associating DNA's)" | Hs.74592 | 0.44+-0.01 | SEQ. ID. NO. 216 |
| 88 | 810864 | "CGI-48 protein" | Hs.6153 | 0.43+-0.01 | SEQ. ID. NO. 217 |
| 90 | 66977 | "androgen induced protein" | Hs.107528 | 0.43+-0.01 | SEQ. ID. NO. 218 |
| 92 | 151261 | "ESTs" | Hs.237971 | 0.43+-0.01 | SEQ. ID. NO. 160 |
| 95 | 289645 | "amyloid beta (A4) precursor-like protein 1" | Hs.74565 | 0.43+-0.01 | SEQ. ID. NO. 4 |
| 96 | 416959 | "nuclear factor I/B" | Hs.33287 | 0.43+-0.01 | SEQ. ID. NO. 29 |
| 98 | 47110 | "heterogeneous nuclear ribonucleoprotein D" | Hs.79625 | 0.43+-0.01 | SEQ. ID. NO. 219 |

CERTIFICATE OF CORRECTION (continued)
U.S. Pat. No. 7,655,397 B2

| | Clone Id | GeneDescription | Unigene | Weight | SEQ. ID. NO. |
|---|---|---|---|---|---|
| | 244637 | "chromosome 15 open reading frame 3" | Hs.75847 | 0.42+-0.01 | SEQ. ID. NO. 220 |
| 102 | 949934 | "heterogeneous nuclear ribonucleoprotein A0" | Hs.77492 | 0.42+-0.01 | SEQ. ID. NO. 221 |
| 103 | 544664 | "matrin 3" | Hs.78825 | 0.42+-0.01 | SEQ. ID. NO. 222 |
| 108 | 782811 | "high-mobility group (nonhistone chromosomal) protein isoforms I and Y" | Hs.139800 | 0.42+-0.01 | SEQ. ID. NO. 129 |
| 109 | 812967 | "tetraspan 5" | Hs.20709 | 0.41+-0.01 | SEQ. ID. NO. 223 |
| 114 | 75254 | "cysteine and glycine-rich protein 2 (LIM domain only, smooth muscle)" | Hs.10526 | 0.41+-0.01 | SEQ. ID. NO. 106 |
| 115 | 235102 | "ESTs, Moderately similar to LAK-1 [H.sapiens]" | Hs.39488 | 0.41+-0.01 | SEQ. ID. NO. 224 |
| 118 | 81518 | "apelin; peptide ligand for APJ receptor" | Hs.181060 | 0.41+-0.01 | SEQ. ID. NO. 225 |
| 119 | 344243 | "uridine monophosphate kinase" | Hs.75939 | 0.41+-0.01 | SEQ. ID. NO. 226 |
| 120 | 789376 | "thioredoxin reductase 1" | Hs.13046 | 0.41+-0.01 | SEQ. ID. NO. 227 |
| 122 | 811956 | "RAN, member RAS oncogene family" | Hs.10842 | 0.40+-0.01 | SEQ. ID. NO. 228 |
| 124 | 811095 | "Homo sapiens mRNA for KIAA1291 protein, partial cds" | Hs.9805 | 0.40+-0.01 | SEQ. ID. NO. 229 |
| 125 | 823598 | "proteasome (prosome, macropain) 26S subunit, non-ATPase, 12" | Hs.4295 | 0.40+-0.01 | SEQ. ID. NO. 230 |
| 130 | 896949 | "3-hydroxy-3-methylglutaryl-Coenzyme A reductase" | Hs.11899 | 0.40+-0.01 | SEQ. ID. NO. 231 |

| Rank | Clone Id | GeneDescription | Unigene | Weight | SEQ. ID. NO. |
|---|---|---|---|---|---|
| 132 | 140806 | "peptidylglycine alpha-amidating monooxygenase" | Hs.83920 | 0.40+-0.01 | SEQ. ID. NO. 116 |
| 133 | 760299 | "Dickkopf gene 3" | Hs.4909 | 0.40+-0.01 | SEQ. ID. NO. 187 |
| 135 | 22260 | "cytochrome c-1" | Hs.697 | 0.40+-0.01 | SEQ. ID. NO. 232 |
| 137 | 294496 | "ESTs" | Hs.23037 | 0.39+-0.01 | SEQ. ID. NO. 117 |
| 138 | 813266 | "four and a half LIM domains 1" | Hs.239069 | 0.39+-0.01 | SEQ. ID. NO. 47 |
| 139 | 234150 | "myotubularin related protein 4" | Hs.141727 | 0.39+-0.01 | SEQ. ID. NO. 233 |
| 140 | 246194 | "ESTs" | Hs.125522 | 0.39+-0.01 | SEQ. ID. NO. 234 |
| 142 | 207358 | "solute carrier family 2 (facilitated glucose transporter), member 1" | Hs.169902 | 0.39+-0.01 | SEQ. ID. NO. 235 |
| 148 | 1456118 | "proteasome (prosome, macropain) subunit, beta type, 9 (large multifunctional protease 2)" | Hs.9280 | 0.38+-0.01 | SEQ. ID. NO. 236 |
| 149 | 753215 | "guanine nucleotide binding protein (G protein), alpha inhibiting activity polypeptide 1" | Hs.203862 | 0.38+-0.01 | SEQ. ID. NO. 237 |
| 151 | 51041 | "ESTs" | Hs.280770 | 0.38+-0.01 | SEQ. ID. NO. 238 |
| 153 | 813499 | "Sjogren's syndrome/scleroderma autoantigen 1" | Hs.25723 | 0.37+-0.01 | SEQ. ID. NO. 239 |
| 154 | 1142132 | "RaP2 interacting protein 8" | Hs.6755 | 0.37+-0.01 | SEQ. ID. NO. 240 |
| 155 | 789182 | "proliferating cell nuclear antigen" | Hs.78996 | 0.37+-0.01 | SEQ. ID. NO. 241 |
| 161 | 726236 | "paired mesoderm homeo box 1" | Hs.155606 | 0.37+-0.01 | SEQ. ID. NO. 242 |

| Rank | Clone Id | GeneDescription | Unigene | Weight | SEQ. ID. NO. |
|---|---|---|---|---|---|
| 164 | 866694 | "butyrate-induced transcript 1" | Hs.260622 | 0.37+-0.01 | SEQ. ID. NO. 243 |
| 165 | 853368 | "thymidylate synthetase" | Hs.82962 | 0.37+-0.01 | SEQ. ID. NO. 244 |
| 167 | 85259 | "heme oxygenase (decycling) 1" | Hs.202833 | 0.36+-0.01 | SEQ. ID. NO. 245 |
| 168 | 83279 | "translocase of inner mitochondrial membrane 23 (yeast) homolog" | Hs.11866 | 0.36+-0.01 | SEQ. ID. NO. 246 |
| 169 | 137535 | "transcriptional intermediary factor 1" | Hs.183858 | 0.36+-0.01 | SEQ. ID. NO. 247 |
| 170 | 770391 | "polymerase (RNA) II (DNA directed) polypeptide C (33kD)" | Hs.79402 | 0.36+-0.01 | SEQ. ID. NO. 248 |
| 174 | 824591 | "heterogeneous nuclear ribonucleoprotein F" | Hs.808 | 0.36+-0.01 | SEQ. ID. NO. 249 |
| 177 | 783697 | "BCL2/adenovirus E1B 19kD-interacting protein 3" | Hs.79428 | 0.36+-0.01 | SEQ. ID. NO. 250 |
| 178 | 144932 | "deleted in oral cancer (mouse, homolog) 1" | Hs.3436 | 0.36+-0.01 | SEQ. ID. NO. 128 |
| 179 | 795543 | "thioredoxin peroxidase (antioxidant enzyme)" | Hs.83383 | 0.36+-0.01 | SEQ. ID. NO. 251 |
| 181 | 292996 | "tyrosine 3-monooxygenase/tryptophan 5-monooxygenase activation protein, eta polypeptide" | Hs.75544 | 0.36+-0.01 | SEQ. ID. NO. 252 |
| 182 | 345833 | "heterogeneous nuclear ribonucleoprotein A/B" | Hs.81361 | 0.36+-0.01 | SEQ. ID. NO. 253 |

| Rank | Clone Id | GeneDescription | Unigene | Weight | SEQ. ID. NO. |
|---|---|---|---|---|---|
| 184 | 810510 | "ESTs" | Hs.14317 | 0.35+-0.01 | SEQ. ID. NO. 254 |
| 185 | 882510 | "karyopherin alpha 2 (RAG cohort 1, importin alpha 1)" | Hs.159557 | 0.35+-0.01 | SEQ. ID. NO. 255 |
| 186 | 144905 | "PRO1912 protein" | Hs.29494 | 0.35+-0.01 | SEQ. ID. NO. 256 |
| 188 | 878833 | "ubiquitin carboxyl-terminal esterase L1 (ubiquitin thiolesterase)" | Hs.76118 | 0.35+-0.01 | SEQ. ID. NO. 257 |
| 189 | 139835 | "UDP-glucose dehydrogenase" | Hs.28309 | 0.35+-0.01 | SEQ. ID. NO. 258 |
| 190 | 207082 | "glucosamine-6-phosphate deaminase" | Hs.278500 | 0.35+-0.01 | SEQ. ID. NO. 259 |
| 193 | 884718 | "Hairpin binding protein, histone" | Hs.75257 | 0.35+-0.01 | SEQ. ID. NO. 260 |
| 195 | 71672 | "electron-transfer-flavoprotein, alpha polypeptide (glutaric aciduria II)" | Hs.169919 | 0.34+-0.01 | SEQ. ID. NO. 261 |
| 197 | 789204 | "translocation protein 1" | Hs.8146 | 0.34+-0.01 | SEQ. ID. NO. 262 |
| 198 | 757404 | "von Hippel-Lindau binding protein 1" | Hs.198307 | 0.34+-0.01 | SEQ. ID. NO. 263 |
| 200 | 784257 | "kinesin family member 3C" | Hs.21611 | 0.34+-0.01 | SEQ. ID. NO. 34 |

Col. 55, Table 7: Delete incorrect Table 7 and replace with correct Table 7:

TABLE 7 - Ranked Genes for Rhabdomyosarcoma (RMS)

| Rank | Clone Id | GeneDescription | Unigene | Weight | SEQ. ID. NO. |
|---|---|---|---|---|---|
| 1 | 296448 | "insulin-like growth factor 2 (somatomedin A)" | Hs.251664 | 0.95+-0.05 | SEQ. ID. NO. 72 |
| 2 | 207274 | "insulin-like growth factor 2 (somatomedin A)" | Hs.251664 | 0.90+-0.04 | SEQ. ID. NO. 73 |
| 3 | 244618 | "ESTs" | Hs.15463 | 0.70+-0.03 | SEQ. ID. NO. 77 |
| 4 | 489631 | "chondroitin sulfate proteoglycan 2 (versican)" | Hs.81800 | 0.54+-0.03 | SEQ. ID. NO. 99 |
| 5 | 298062 | "troponin T2, cardiac" | Hs.89749 | 0.53+-0.03 | SEQ. ID. NO. 74 |
| 6 | 784224 | "fibroblast growth factor receptor 4" | Hs.165950 | 0.53+-0.03 | SEQ. ID. NO. 71 |
| 7 | 1409509 | "troponin T1, skeletal, slow" | Hs.73980 | 0.52+-0.02 | SEQ. ID. NO. 70 |
| 8 | 461425 | "myosin, light polypeptide 4, alkali; atrial, embryonic" | Hs.154156 | 0.50+-0.02 | SEQ. ID. NO. 75 |
| 9 | 245330 | "insulin-like growth factor 2 (somatomedin A)" | Hs.251664 | 0.47+-0.02 | SEQ. ID. NO. 78 |
| 10 | 796258 | "sarcoglycan, alpha (50kD dystrophin-associated glycoprotein)" | Hs.99931 | 0.46+-0.02 | SEQ. ID. NO. 76 |
| 11 | 293500 | "ESTs" | Hs.49714 | 0.45+-0.02 | SEQ. ID. NO. 80 |

| Rank | Clone Id | GeneDescription | Unigene | Weight | SEQ. ID. NO. |
|---|---|---|---|---|---|
| 12 | 122159 | "collagen, type III, alpha 1 (Ehlers-Danlos syndrome type IV, autosomal dominant)" | Hs.119571 | 0.45+-0.02 | SEQ. ID. NO. 66 |
| 13 | 324494 | "heat shock 27kD protein 2" | Hs.78846 | 0.44+-0.02 | SEQ. ID. NO. 62 |
| 14 | 898219 | "mesoderm specific transcript (mouse) homolog" | Hs.79284 | 0.44+-0.02 | SEQ. ID. NO. 113 |
| 15 | 714453 | "interleukin 4 receptor" | Hs.75545 | 0.44+-0.02 | SEQ. ID. NO. 83 |
| 16 | 42558 | "glycine amidinotransferase (L-arginine:glycine amidinotransferase)" | Hs.75335 | 0.44+-0.02 | SEQ. ID. NO. 79 |
| 17 | 377468 | "sprouty (Drosophila) homolog 1 (antagonist of FGF signaling)" | Hs.88044 | 0.43+-0.02 | SEQ. ID. NO. 107 |
| 18 | 769716 | "neurofibromin 2 (bilateral acoustic neuroma)" | Hs.902 | 0.42+-0.02 | SEQ. ID. NO. 104 |
| 19 | 809901 | "collagen, type XV, alpha 1" | Hs.83164 | 0.42+-0.02 | SEQ. ID. NO. 67 |
| 20 | 813841 | "plasminogen activator, tissue" | Hs.274404 | 0.41+-0.02 | SEQ. ID. NO. 132 |
| 21 | 795877 | "serum-inducible kinase" | Hs.3838 | 0.41+-0.02 | SEQ. ID. NO. 102 |
| 22 | 214572 | "ESTs" | Hs.280460 | 0.40+-0.02 | SEQ. ID. NO. 135 |
| 23 | 130057 | "ESTs" | Hs.23057 | 0.39+-0.02 | SEQ. ID. NO. 109 |
| 24 | 767495 | "GLI-Kruppel family member GLI3 (Greig cephalopolysyndactyly syndrome)" | Hs.72916 | 0.39+-0.02 | SEQ. ID. NO. 103 |
| 25 | 246035 | "ESTs" | Hs.78026 | 0.39+-0.02 | SEQ. ID. NO. 119 |

| Rank | Clone Id | GeneDescription | Unigene | Weight | SEQ. ID. NO. |
|---|---|---|---|---|---|
| 26 | 41591 | "meningioma (disrupted in balanced translocation) 1" | Hs.268515 | 0.38+-0.02 | SEQ. ID. NO. 60 |
| 27 | 714106 | "plasminogen activator, urokinase" | Hs.77274 | 0.38+-0.02 | SEQ. ID. NO. 121 |
| 28 | 770059 | "heparan sulfate proteoglycan 2 (perlecan)" | Hs.211573 | 0.38+-0.02 | SEQ. ID. NO. 110 |
| 29 | 814798 | "aldehyde dehydrogenase 6" | Hs.75746 | 0.37+-0.02 | SEQ. ID. NO. 196 |
| 30 | 365515 | "fibroblast growth factor 7 (keratinocyte growth factor)" | Hs.164568 | 0.37+-0.02 | SEQ. ID. NO. 111 |
| 31 | 788107 | "bridging integrator 1" | Hs.193163 | 0.36+-0.02 | SEQ. ID. NO. 52 |
| 32 | 250654 | "secreted protein, acidic, cysteine-rich (osteonectin)" | Hs.111779 | 0.36+-0.02 | SEQ. ID. NO. 149 |
| 33 | 295985 | "Homo sapiens cDNA FLJ20653 fis, clone KAT01739" | Hs.180059 | 0.36+-0.02 | SEQ. ID. NO. 26 |
| 34 | 789253 | "presenilin 2 (Alzheimer disease 4)" | Hs.25363 | 0.36+-0.02 | SEQ. ID. NO. 143 |
| 35 | 299737 | "Homo sapiens clone 24411 mRNA sequence" | Hs.20952 | 0.35+-0.02 | SEQ. ID. NO. 157 |
| 36 | 859359 | "quinone oxidoreductase homolog" | Hs.50649 | 0.35+-0.02 | SEQ. ID. NO. 50 |
| 37 | 66714 | "peanut (Drosophila)-like 2" | Hs.155524 | 0.34+-0.02 | SEQ. ID. NO. 182 |
| 39 | 755750 | "non-metastatic cells 2, protein (NM23B) expressed in" | Hs.275163 | 0.34+-0.02 | SEQ. ID. NO. 49 |
| 40 | 727251 | "CD9 antigen (p24)" | Hs.1244 | 0.33+-0.02 | SEQ. ID. NO. 189 |

| Rank | Clone Id | GeneDescription | Unigene | Weight | SEQ. ID. NO. |
|---|---|---|---|---|---|
| 41 | 25725 | "farnesyl-diphosphate farnesyltransferase 1" | Hs.48876 | 0.33+-0.02 | SEQ. ID. NO. 264 |
| 42 | 143306 | "lymphocyte-specific protein 1" | Hs.56729 | 0.33+-0.02 | SEQ. ID. NO. 205 |
| 45 | 491692 | "collagen, type IV, alpha 1" | Hs.119129 | 0.32+-0.02 | SEQ. ID. NO. 133 |
| 46 | 142134 | "hypothetical protein FLJ20185" | Hs.272972 | 0.32+-0.02 | SEQ. ID. NO. 134 |
| 47 | 813823 | "lumican" | Hs.79914 | 0.32+-0.02 | SEQ. ID. NO. 265 |
| 48 | 788695 | "troponin T3, skeletal, fast" | Hs.73454 | 0.32+-0.02 | SEQ. ID. NO. 197 |
| 49 | 308163 | "ESTs" | Hs.84520 | 0.32+-0.02 | SEQ. ID. NO. 57 |
| 50 | 377671 | "integrin, alpha 7" | Hs.74369 | 0.31+-0.02 | SEQ. ID. NO. 68 |
| 51 | 281901 | "ESTs" | Hs.74280 | 0.31+-0.02 | SEQ. ID. NO. 266 |
| 52 | 796904 | "pleomorphic adenoma gene-like 1" | Hs.75825 | 0.31+-0.01 | SEQ. ID. NO. 120 |
| 53 | 773215 | "runt-related transcription factor 1 (acute myeloid leukemia 1; aml1 oncogene)" | Hs.129914 | 0.30+-0.01 | SEQ. ID. NO. 142 |
| 55 | 486787 | "calponin 3, acidic" | Hs.194662 | 0.30+-0.01 | SEQ. ID. NO. 43 |
| 56 | 341588 | "CGI-119 protein" | Hs.25615 | 0.29+-0.01 | SEQ. ID. NO. 131 |
| 57 | 839552 | "nuclear receptor coactivator 1" | Hs.74002 | 0.29+-0.01 | SEQ. ID. NO. 267 |
| 58 | 365826 | "growth arrest-specific 1" | Hs.65029 | 0.29+-0.01 | SEQ. ID. NO. 59 |
| 59 | 111884 | "ESTs, Weakly similar to hTcf-4 [H.sapiens]" | Hs.102367 | 0.29+-0.01 | SEQ. ID. NO. 268 |
| 60 | 797048 | "bone morphogenetic protein 4" | Hs.68879 | 0.28+-0.01 | SEQ. ID. NO. 269 |
| 61 | 769959 | "collagen, type IV, alpha 2" | Hs.75617 | 0.28+-0.01 | SEQ. ID. NO. 69 |

| Rank | Clone Id | GeneDescription | Unigene | Weight | SEQ. ID. NO. |
|---|---|---|---|---|---|
| 62 | 204545 | "ESTs" | Hs.8966 | 0.28+-0.01 | SEQ. ID. NO. 58 |
| 63 | 771323 | "procollagen-lysine, 2-oxoglutarate 5-dioxygenase (lysine hydroxylase, Ehlers-Danlos syndrome type VI)" | Hs.75093 | 0.27+-0.01 | SEQ. ID. NO. 270 |
| 65 | 897865 | "midline 1 (Opitz/BBB syndrome)" | Hs.27695 | 0.27+-0.01 | SEQ. ID. NO. 271 |
| 66 | 298417 | "trefoil factor 3 (intestinal)" | Hs.82961 | 0.27+-0.01 | SEQ. ID. NO. 272 |
| 67 | 79022 | "FBJ murine osteosarcoma viral oncogene homolog B" | Hs.75678 | 0.27+-0.01 | SEQ. ID. NO. 273 |
| 68 | 290378 | "podocalyxin-like" | Hs.16426 | 0.27+-0.01 | SEQ. ID. NO. 274 |
| 69 | 784593 | "ESTs" | Hs.6838 | 0.27+-0.01 | SEQ. ID. NO. 41 |
| 70 | 32493 | "integrin, alpha 6" | Hs.227730 | 0.27+-0.01 | SEQ. ID. NO. 275 |
| 71 | 45542 | "Human insulin-like growth factor binding protein 5 (IGFBP5) mRNA" | Hs.103391 | 0.26+-0.01 | SEQ. ID. NO. 64 |
| 72 | 208001 | "CD59 antigen p18-20 (antigen identified by monoclonal antibodies 16.3A5, EJ16, EJ30, EL32 and G344)" | Hs.119663 | 0.26+-0.01 | SEQ. ID. NO. 276 |
| 73 | 413633 | "EST" | - | 0.26+-0.01 | SEQ. ID. NO. 115 |
| 74 | 284882 | "collagen, type II, alpha 1 (primary osteoarthritis, spondyloepiphyseal dysplasia, congenital)" | Hs.81343 | 0.26+-0.01 | SEQ. ID. NO. 277 |

| Rank | Clone Id | GeneDescription | Unigene | Weight | SEQ. ID. NO. |
|---|---|---|---|---|---|
| 75 | 273435 | "v-yes-1 Yamaguchi sarcoma viral oncogene homolog 1" | Hs.194148 | 0.26+-0.01 | SEQ. ID. NO. 184 |
| 76 | 839991 | "collagen, type I, alpha 2" | Hs.179573 | 0.26+-0.01 | SEQ. ID. NO. 278 |
| 78 | 323371 | "amyloid beta (A4) precursor protein (protease nexin-II, Alzheimer disease)" | Hs.177486 | 0.26+-0.01 | SEQ. ID. NO. 27 |
| 79 | 362483 | "spectrin, beta, non-erythrocytic 1" | Hs.107164 | 0.26+-0.01 | SEQ. ID. NO. 170 |
| 80 | 839736 | "crystallin, alpha B" | Hs.1940 | 0.25+-0.01 | SEQ. ID. NO. 61 |
| 81 | 380620 | "presenilin 2 (Alzheimer disease 4)" | Hs.25363 | 0.25+-0.01 | SEQ. ID. NO. 279 |
| 82 | 343867 | "allograft inflammatory factor 1" | Hs.76364 | 0.25+-0.01 | SEQ. ID. NO. 150 |
| 83 | 882506 | "lysyl oxidase-like 2" | Hs.83354 | 0.25+-0.01 | SEQ. ID. NO. 207 |
| 84 | 214990 | "gelsolin (amyloidosis, Finnish type)" | Hs.80562 | 0.25+-0.01 | SEQ. ID. NO. 127 |
| 85 | 878182 | "alpha-2-macroglobulin" | Hs.74561 | 0.25+-0.01 | SEQ. ID. NO. 136 |
| 86 | 301122 | "extracellular matrix protein 1" | Hs.81071 | 0.25+-0.01 | SEQ. ID. NO. 195 |
| 87 | 198982 | "DNA (cytosine-5-)-methyltransferase 2" | Hs.97681 | 0.25+-0.01 | SEQ. ID. NO. 280 |
| 88 | 138672 | "ESTs" | Hs.28412 | 0.25+-0.01 | SEQ. ID. NO. 281 |
| 89 | 246377 | "EST" | Hs.102670 | 0.24+-0.01 | SEQ. ID. NO. 51 |
| 90 | 50941 | "cadherin 13, H-cadherin (heart)" | Hs.63984 | 0.24+-0.01 | SEQ. ID. NO. 282 |
| 91 | 812196 | "UDP-glucose ceramide glucosyltransferase" | Hs.152601 | 0.24+-0.01 | SEQ. ID. NO. 283 |

| Rank | Clone Id | GeneDescription | Unigene | Weight | SEQ. ID. NO. |
|---|---|---|---|---|---|
| 92 | 120881 | "proteasome (prosome, macropain) subunit, alpha type, 4" | Hs.251531 | 0.24+-0.01 | SEQ. ID. NO. 284 |
| 93 | 813698 | "sprouty (Drosophila) homolog 2" | Hs.18676 | 0.24+-0.01 | SEQ. ID. NO. 130 |
| 94 | 810612 | "S100 calcium-binding protein A11 (calgizzarin)" | Hs.256290 | 0.24+-0.01 | SEQ. ID. NO. 285 |
| 97 | 767851 | "fibrillin 1 (Marfan syndrome)" | Hs.750 | 0.23+-0.01 | SEQ. ID. NO. 286 |
| 99 | 211758 | "ribosomal protein S23" | Hs.3463 | 0.23+-0.01 | SEQ. ID. NO. 101 |
| 100 | 506369 | "nidogen (enactin)" | Hs.62041 | 0.23+-0.01 | SEQ. ID. NO. 287 |
| 101 | 75254 | "cysteine and glycine-rich protein 2 (LIM domain only, smooth muscle)" | Hs.10526 | 0.23+-0.01 | SEQ. ID. NO. 106 |
| 103 | 823851 | "AE-binding protein 1" | Hs.118397 | 0.23+-0.01 | SEQ. ID. NO. 288 |
| 104 | 52096 | "platelet-derived growth factor receptor, alpha polypeptide" | Hs.74615 | 0.23+-0.01 | SEQ. ID. NO. 124 |
| 106 | 760224 | "X-ray repair complementing defective repair in Chinese hamster cells 1" | Hs.98493 | 0.23+-0.01 | SEQ. ID. NO. 289 |
| 107 | 725473 | "DNA segment on chromosome 12 (unique) 2489 expressed sequence" | Hs.74085 | 0.23+-0.01 | SEQ. ID. NO. 290 |
| 111 | 148028 | "epidermal growth factor receptor pathway substrate 8" | Hs.2132 | 0.23+-0.01 | SEQ. ID. NO. 291 |
| 113 | 769028 | "mesenchyme homeo box 1" | Hs.438 | 0.23+-0.01 | SEQ. ID. NO. 198 |

| Rank | Clone Id | GeneDescription | Unigene | Weight | SEQ. ID. NO. |
|---|---|---|---|---|---|
| 115 | 39093 | "methionine aminopeptidase; eIF-2-associated p67" | Hs.78935 | 0.22+-0.01 | SEQ. ID. NO. 63 |
| 116 | 854899 | "dual specificity phosphatase 6" | Hs.180383 | 0.22+-0.01 | SEQ. ID. NO. 48 |
| 118 | 547247 | "stanniocalcin" | Hs.25590 | 0.22+-0.01 | SEQ. ID. NO. 292 |
| 119 | 26418 | "endothelial differentiation, sphingolipid G-protein-coupled receptor, 1" | Hs.154210 | 0.22+-0.01 | SEQ. ID. NO. 293 |
| 120 | 811848 | "transforming growth factor beta 1 induced transcript 1" | Hs.25511 | 0.22+-0.01 | SEQ. ID. NO. 294 |
| 123 | 178463 | "transcription factor 8 (represses interleukin 2 expression)" | Hs.232068 | 0.22+-0.01 | SEQ. ID. NO. 295 |
| 124 | 810859 | "natural killer cell transcript 4" | Hs.943 | 0.22+-0.01 | SEQ. ID. NO. 296 |
| 125 | 40643 | "platelet-derived growth factor receptor, beta polypeptide" | Hs.76144 | 0.22+-0.01 | SEQ. ID. NO. 297 |
| 126 | 782193 | "thioredoxin" | Hs.76136 | 0.22+-0.01 | SEQ. ID. NO. 126 |
| 127 | 1412412 | "elastase 1, pancreatic" | Hs.21 | 0.22+-0.01 | SEQ. ID. NO. 298 |
| 128 | 470128 | "myosin IC" | Hs.82251 | 0.22+-0.01 | SEQ. ID. NO. 299 |
| 129 | 68950 | "cyclin E1" | Hs.9700 | 0.22+-0.01 | SEQ. ID. NO. 300 |
| 130 | 66552 | "ESTs" | Hs.119021 | 0.22+-0.01 | SEQ. ID. NO. 301 |
| 131 | 233721 | "insulin-like growth factor binding protein 2 (36kD)" | Hs.162 | 0.22+-0.01 | SEQ. ID. NO. 28 |

| Rank | Clone Id | GeneDescription | Unigene | Weight | SEQ. ID. NO. |
|---|---|---|---|---|---|
| 133 | 814444 | "cofactor required for Sp1 transcriptional activation, subunit 9 (33kD)" | Hs.279902 | 0.21+-0.01 | SEQ. ID. NO. 302 |
| 134 | 160723 | "laminin, gamma 1 (formerly LAMB2)" | Hs.214982 | 0.21+-0.01 | SEQ. ID. NO. 303 |
| 135 | 752652 | "transcription factor 7-like 2 (T-cell specific, HMG-box)" | Hs.154485 | 0.21+-0.01 | SEQ. ID. NO. 203 |
| 136 | 180902 | "CGI-43 protein" | Hs.111515 | 0.21+-0.01 | SEQ. ID. NO. 304 |
| 137 | 154472 | "fibroblast growth factor receptor 1 (fms-related tyrosine kinase 2, Pfeiffer syndrome)" | Hs.748 | 0.21+-0.01 | SEQ. ID. NO. 305 |
| 139 | 82225 | "secreted frizzled-related protein 1" | Hs.7306 | 0.21+-0.01 | SEQ. ID. NO. 42 |
| 140 | 898092 | "connective tissue growth factor" | Hs.75511 | 0.21+-0.01 | SEQ. ID. NO. 306 |
| 142 | 773568 | "POU domain, class 4, transcription factor 1" | Hs.211588 | 0.21+-0.01 | SEQ. ID. NO. 307 |
| 143 | 144797 | "a disintegrin-like and metalloprotease (reprolysin type) with thrombospondin type 1 motif, 1" | Hs.8230 | 0.21+-0.01 | SEQ. ID. NO. 308 |
| 145 | 139818 | "KIAA0669 gene product" | Hs.52526 | 0.21+-0.01 | SEQ. ID. NO. 309 |
| 146 | 358433 | "retinoid X receptor, gamma" | Hs.26550 | 0.21+-0.01 | SEQ. ID. NO. 167 |
| 147 | 141192 | "Leman coiled-coil protein" | Hs.92186 | 0.21+-0.01 | SEQ. ID. NO. 310 |
| 148 | 813707 | "regulator of G-protein signalling 16" | Hs.183601 | 0.21+-0.01 | SEQ. ID. NO. 311 |
| 149 | 781014 | "suppression of tumorigenicity 5" | Hs.79265 | 0.21+-0.01 | SEQ. ID. NO. 312 |

| Rank | Clone Id | GeneDescription | Unigene | Weight | SEQ. ID. NO. |
|---|---|---|---|---|---|
| 150 | 857640 | "Human alpha-2 collagen type VI mRNA, 3' end" | Hs.281620 | 0.21+-0.01 | SEQ. ID. NO. 313 |
| 151 | 811028 | "cathepsin D (lysosomal aspartyl protease)" | Hs.79572 | 0.21+-0.01 | SEQ. ID. NO. 199 |
| 153 | 196992 | "aldo-keto reductase family 1, member C1 (dihydrodiol dehydrogenase 1; 20-alpha (3-alpha)-hydroxysteroid dehydrogenase)" | Hs.275374 | 0.20+-0.01 | SEQ. ID. NO. 200 |
| 154 | 781019 | "paraoxonase 2" | Hs.169857 | 0.20+-0.01 | SEQ. ID. NO. 314 |
| 155 | 491559 | "fatty acid binding protein 3, muscle and heart (mammary-derived growth inhibitor)" | Hs.49881 | 0.20+-0.01 | SEQ. ID. NO. 315 |
| 156 | 358531 | "v-jun avian sarcoma virus 17 oncogene homolog" | Hs.78465 | 0.20+-0.01 | SEQ. ID. NO. 316 |
| 157 | 127099 | "Homo sapiens cDNA FLJ20754 fis, clone HEP02246" | Hs.72249 | 0.20+-0.01 | SEQ. ID. NO. 317 |
| 158 | 263716 | "collagen, type VI, alpha 1" | Hs.108885 | 0.20+-0.01 | SEQ. ID. NO. 318 |
| 162 | 787861 | "dual-specificity tyrosine-(Y)-phosphorylation regulated kinase 2" | Hs.173135 | 0.20+-0.01 | SEQ. ID. NO. 319 |
| 163 | 246722 | "trinucleotide repeat containing 3" | Hs.21858 | 0.20+-0.01 | SEQ. ID. NO. 320 |

| Rank | Clone Id | GeneDescription | Unigene | Weight | SEQ. ID. NO. |
|---|---|---|---|---|---|
| 164 | 151449 | "protein tyrosine phosphatase, non-receptor type 21" | Hs.155693 | 0.20+-0.01 | SEQ. ID. NO. 321 |
| 165 | 81475 | "-" | - | 0.20+-0.01 | SEQ. ID. NO. 322 |
| 166 | 810512 | "thrombospondin 1" | Hs.87409 | 0.20+-0.01 | SEQ. ID. NO. 323 |
| 168 | 233071 | "transmembrane protein 2" | Hs.160417 | 0.19+-0.01 | SEQ. ID. NO. 324 |
| 170 | 809910 | "interferon induced transmembrane protein 3 (1-8U)" | Hs.182241 | 0.19+-0.01 | SEQ. ID. NO. 55 |
| 171 | 233688 | "a disintegrin and metalloproteinase domain 12 (meltrin alpha)" | Hs.8850 | 0.19+-0.01 | SEQ. ID. NO. 325 |
| 172 | 128054 | "H2A histone family, member X" | Hs.147097 | 0.19+-0.01 | SEQ. ID. NO. 326 |
| 173 | 143523 | "collagen, type V, alpha 1" | Hs.146428 | 0.19+-0.01 | SEQ. ID. NO. 327 |
| 174 | 809719 | "protein tyrosine phosphatase, receptor type, c polypeptide" | Hs.170121 | 0.19+-0.01 | SEQ. ID. NO. 328 |
| 175 | 45291 | "dentatorubral-pallidoluysian atrophy (atrophin-1)" | Hs.169488 | 0.19+-0.01 | SEQ. ID. NO. 54 |
| 176 | 758266 | "thrombospondin 4" | Hs.75774 | 0.19+-0.01 | SEQ. ID. NO. 329 |
| 178 | 247818 | "ESTs" | Hs.239666 | 0.19+-0.01 | SEQ. ID. NO. 330 |
| 179 | 130824 | "S-phase kinase-associated protein 2 (p45)" | Hs.23348 | 0.19+-0.01 | SEQ. ID. NO. 331 |
| 180 | 341328 | "tropomyosin 1 (alpha)" | Hs.77899 | 0.19+-0.01 | SEQ. ID. NO. 332 |
| 181 | 123916 | "dystrophia myotonica-containing WD repeat motif" | Hs.275924 | 0.19+-0.01 | SEQ. ID. NO. 333 |

| Rank | Clone Id | GeneDescription | Unigene | Weight | SEQ. ID. NO. |
|---|---|---|---|---|---|
| 183 | 682555 | "insulin-like growth factor 1 receptor" | Hs.239176 | 0.19+-0.01 | SEQ. ID. NO. 334 |
| 184 | 868380 | "Fc fragment of IgG, low affinity IIa, receptor for (CD32)" | Hs.78864 | 0.19+-0.01 | SEQ. ID. NO. 335 |
| 187 | 869187 | "Homo sapiens clone 23698 mRNA sequence" | Hs.8136 | 0.19+-0.01 | SEQ. ID. NO. 336 |
| 190 | 207920 | "solute carrier family 17 (sodium phosphate), member 2" | Hs.19710 | 0.19+-0.01 | SEQ. ID. NO. 337 |
| 192 | 469345 | "kinase insert domain receptor (a type III receptor tyrosine kinase)" | Hs.12337 | 0.18+-0.01 | SEQ. ID. NO. 338 |
| 193 | 754406 | "integrin, alpha M (complement component receptor 3, alpha; also known as CD11b (p170), macrophage antigen alpha polypeptide)" | Hs.172631 | 0.18+-0.01 | SEQ. ID. NO. 339 |
| 196 | 43563 | "cytochrome P450, subfamily XXVIIA (steroid 27-hydroxylase, cerebrotendinous xanthomatosis), polypeptide 1" | Hs.82568 | 0.18+-0.01 | SEQ. ID. NO. 340 |
| 198 | 753775 | "guanosine monophosphate reductase" | Hs.1435 | 0.18+-0.01 | SEQ. ID. NO. 341 |

CERTIFICATE OF CORRECTION (continued)
U.S. Pat. No. 7,655,397 B2

Col. 63, Table 8: Delete incorrect Table 8 and replace with correct Table 8:

TABLE 8 - Ranked genes for Burkitt's (BL)

| Rank | Clone Id | GeneDescription | Unigene | Weight | SEQ. ID. NO. |
|---|---|---|---|---|---|
| 2 | 80109 | "major histocompatibility complex, class II, DQ alpha 1" | Hs.198253 | 0.58+-0.02 | SEQ. ID. NO. 88 |
| 3 | 840942 | "major histocompatibility complex, class II, DP beta 1" | Hs.814 | 0.56+-0.02 | SEQ. ID. NO. 87 |
| 7 | 183337 | "major histocompatibility complex, class II, DM alpha" | Hs.77522 | 0.52+-0.02 | SEQ. ID. NO. 89 |
| 17 | 609663 | "protein kinase, cAMP-dependent, regulatory, type II, beta" | Hs.77439 | 0.45+-0.02 | SEQ. ID. NO. 95 |
| 23 | 767183 | "hematopoietic cell-specific Lyn substrate 1" | Hs.14601 | 0.43+-0.02 | SEQ. ID. NO. 91 |
| 27 | 297392 | "metallothionein 1L" | Hs.94360 | 0.42+-0.02 | SEQ. ID. NO. 93 |
| 30 | 200814 | "membrane metallo-endopeptidase (neutral endopeptidase, enkephalinase, CALLA, CD10)" | Hs.1298 | 0.41+-0.02 | SEQ. ID. NO. 94 |
| 33 | 241412 | "E74-like factor 1 (ets domain transcription factor)" | Hs.154365 | 0.41+-0.02 | SEQ. ID. NO. 90 |
| 35 | 1469292 | "pim-2 oncogene" | Hs.80205 | 0.39+-0.02 | SEQ. ID. NO. 92 |

| Rank | Clone Id | GeneDescription | Unigene | Weight | SEQ. ID. NO. |
|---|---|---|---|---|---|
| 45 | 417226 | "v-myc avian myelocytomatosis viral oncogene homolog" | Hs.79070 | 0.38+-0.01 | SEQ. ID. NO. 81 |
| 57 | 47475 | "p53 inducible protein" | Hs.258503 | 0.36+-0.01 | 186 |
| 61 | 236282 | "Wiskott-Aldrich syndrome (ecezema-thrombocytopenia)" | Hs.2157 | 0.35+-0.01 | SEQ. ID. NO. 164 |
| 63 | 868304 | "actin, alpha 2, smooth muscle, aorta" | Hs.195851 | 0.34+-0.01 | SEQ. ID. NO. 86 |
| 65 | 740604 | "interferon stimulated gene (20kD)" | Hs.183487 | 0.34+-0.01 | SEQ. ID. NO. 342 |
| 82 | 824602 | "interferon, gamma-inducible protein 16" | Hs.155530 | 0.31+-0.01 | SEQ. ID. NO. 84 |
| 83 | 624360 | "proteasome (prosome, macropain) subunit, beta type, 8 (large multifunctional protease 7)" | Hs.180062 | 0.31+-0.01 | SEQ. ID. NO. 162 |
| 84 | 344134 | "immunoglobulin lambda-like polypeptide 3" | Hs.170116 | 0.31+-0.01 | SEQ. ID. NO. 185 |
| 85 | 193913 | "v-yes-1 Yamaguchi sarcoma viral related oncogene homolog" | Hs.80887 | 0.31+-0.01 | SEQ. ID. NO. 343 |
| 88 | 814526 | "seb4D" | Hs.236361 | 0.31+-0.01 | SEQ. ID. NO. 96 |
| 101 | 236034 | "uncoupling protein 2 (mitochondrial, proton carrier)" | Hs.80658 | 0.30+-0.01 | SEQ. ID. NO. 344 |

| Rank | Clone Id | GeneDescription | Unigene | Weight | SEQ. ID. NO. |
|---|---|---|---|---|---|
| 106 | 745343 | "regenerating islet-derived 1 alpha (pancreatic stone protein, pancreatic thread protein)" | Hs.1032 | 0.30+-0.01 | SEQ. ID. NO. 85 |
| 114 | 788511 | "ribosomal protein S6 kinase, 90kD, polypeptide 1" | Hs.149957 | 0.29+-0.01 | SEQ. ID. NO. 155 |
| 118 | 283315 | "phosphoglycerate mutase 2 (muscle)" | Hs.46039 | 0.29+-0.01 | SEQ. ID. NO. 345 |
| 135 | 502333 | "nuclear receptor coactivator 3" | Hs.225977 | 0.27+-0.01 | SEQ. ID. NO. 316 |
| 136 | 262920 | "endothelial differentiation-related factor 1" | Hs.174050 | 0.27+-0.01 | SEQ. ID. NO. 347 |
| 140 | 897177 | "phosphoglycerate mutase 1 (brain)" | Hs.181013 | 0.27+-0.01 | SEQ. ID. NO. 348 |
| 146 | 700792 | "cyclin-dependent kinase inhibitor 3 (CDK2-associated dual specificity phosphatase)" | Hs.84113 | 0.27+-0.01 | SEQ. ID. NO. 349 |
| 147 | 626502 | "actin related protein 2/3 complex, subunit 1B (41 kD)" | Hs.11538 | 0.27+-0.01 | SEQ. ID. NO. 350 |
| 149 | 769657 | "protein phosphatase 1, regulatory (inhibitor) subunit 2" | Hs.267819 | 0.27+-0.01 | SEQ. ID. NO. 351 |
| 152 | 435953 | "inositol 1,4,5-triphosphate receptor, type 3" | Hs.77515 | 0.26+-0.01 | SEQ. ID. NO. 144 |
| 155 | 812965 | "v-myc avian myelocytomatosis viral oncogene homolog" | Hs.79070 | 0.26+-0.01 | SEQ. ID. NO. 82 |

CERTIFICATE OF CORRECTION (continued)
U.S. Pat. No. 7,655,397 B2

| Rank | Clone Id | GeneDescription | Unigene | Weight | SEQ. ID. NO. |
|------|----------|-----------------|---------|--------|--------------|
| 159 | 714453 | "interleukin 4 receptor" | Hs.75545 | 0.26+-0.01 | SEQ. ID. NO. 83 |
| 163 | 145112 | "intercellular adhesion molecule 1 (CD54), human rhinovirus receptor" | Hs.168383 | 0.25+-0.01 | SEQ. ID. NO. 352 |
| 164 | 80649 | "Rho-associated, coiled-coil containing protein kinase 1" | Hs.17820 | 0.25+-0.01 | SEQ. ID. NO. 353 |
| 172 | 240208 | "DKFZP434O125 protein" | Hs.102669 | 0.25+-0.01 | SEQ. ID. NO. 354 |
| 174 | 298155 | "acyl-Coenzyme A dehydrogenase, C-4 to C-12 straight chain" | Hs.79158 | 0.25+-0.01 | SEQ. ID. NO. 355 |
| 176 | 530185 | "CD83 antigen (activated B lymphocytes, immunoglobulin superfamily)" | Hs.79197 | 0.25+-0.01 | SEQ. ID. NO. 356 |
| 185 | 755145 | "villin 2 (ezrin)" | Hs.155191 | 0.24+-0.01 | SEQ. ID. NO. 357 |
| 192 | 68977 | "proteasome (prosome, macropain) subunit, beta type, 10" | Hs.9661 | 0.24+-0.01 | SEQ. ID. NO. 358 |

Col. 65, Table 9: Delete incorrect Table 9 and replace with correct Table 9:

TABLE 9 - Ranked genes for Ewing family of tumors (EWS)

| Rank | Clone Id | GeneDescription | Unigene | Weight | SEQ. ID. NO. |
|---|---|---|---|---|---|
| 2 | 866702 | "protein tyrosine phosphatase, non-receptor type 13 (APO-1/CD95 (Fas)-associated phosphatase)" | Hs.211595 | 0.47+-0.03 | SEQ. ID. NO. 16 |
| 3 | 770394 | "Fc fragment of IgG, receptor, transporter, alpha" | Hs.160741 | 0.47+-0.03 | SEQ. ID. NO. 20 |
| 5 | 377461 | "caveolin 1, caveolae protein, 22kD" | Hs.281621 | 0.45+-0.03 | SEQ. ID. NO. 19 |
| 6 | 357031 | "tumor necrosis factor, alpha-induced protein 6" | Hs.29352 | 0.44+-0.03 | SEQ. ID. NO. 18 |
| 7 | 43733 | "glycogenin 2" | Hs.58589 | 0.42+-0.03 | SEQ. ID. NO. 21 |
| 9 | 52076 | "olfactomedin related ER localized protein" | Hs.74376 | 0.38+-0.02 | SEQ. ID. NO. 13 |
| 10 | 814260 | "follicular lymphoma variant translocation 1" | Hs.74050 | 0.36+-0.02 | SEQ. ID. NO. 17 |
| 11 | 755599 | "interferon induced transmembrane protein 1 (9-27)" | Hs.146360 | 0.35+-0.02 | SEQ. ID. NO. 25 |
| 13 | 377731 | "glutathione S-transferase M5" | Hs.75652 | 0.34+-0.02 | SEQ. ID. NO. 23 |
| 14 | 1473131 | "transducin-like enhancer of split 2, homolog of Drosophila E(sp1)" | Hs.173063 | 0.34+-0.02 | SEQ. ID. NO. 15 |
| 15 | 823928 | "glutathione S-transferase theta 2" | Hs.1581 | 0.32+-0.02 | SEQ. ID. NO. 153 |
| 16 | 1435862 | "antigen identified by monoclonal antibodies 12E7, F21 and O13" | Hs.177543 | 0.32+-0.02 | SEQ. ID. NO. 22 |
| 17 | 812965 | "v-myc avian myelocytomatosis viral oncogene homolog" | Hs.79070 | 0.32+-0.02 | SEQ. ID. NO. 82 |

| Rank | Clone Id | GeneDescription | Unigene | Weight | SEQ. ID. NO. |
|---|---|---|---|---|---|
| 18 | 841641 | "cyclin D1 (PRAD1: parathyroid adenomatosis 1)" | Hs.82932 | 0.31+-0.02 | SEQ. ID. NO. 5 |
| 19 | 208718 | "annexin A1" | Hs.78225 | 0.29+-0.02 | SEQ. ID. NO. 2 |
| 20 | 713922 | "glutathione S-transferase M1" | Hs.278633 | 0.29+-0.02 | SEQ. ID. NO. 152 |
| 21 | 291756 | "tubulin, beta, 5" | Hs.108014 | 0.29+-0.02 | SEQ. ID. NO. 1 |
| 23 | 1323448 | "cysteine-rich protein 1 (intestinal)" | Hs.17409 | 0.28+-0.02 | SEQ. ID. NO. 112 |
| 24 | 308497 | "KIAA0467 protein" | Hs.11147 | 0.28+-0.02 | SEQ. ID. NO. 24 |
| 25 | 789091 | "H2A histone family, member L" | Hs.28777 | 0.28+-0.02 | SEQ. ID. NO. 359 |
| 26 | 1471841 | "ATPase, Na+/K+ transporting, alpha 1 polypeptide" | Hs.190703 | 0.27+-0.02 | SEQ. ID. NO. 202 |
| 27 | 178825 | "neurogranin (protein kinase C substrate, RC3)" | Hs.26944 | 0.26+-0.02 | SEQ. ID. NO. 360 |
| 28 | 810504 | "proteolipid protein 2 (colonic epithelium-enriched)" | Hs.77422 | 0.25+-0.02 | SEQ. ID. NO. 154 |
| 29 | 740554 | "Homo sapiens mRNA; cDNA DKFZp434I0812 (from clone DKFZp434I0812); partial cds" | Hs.263671 | 0.25+-0.02 | SEQ. ID. NO. 158 |
| 30 | 24415 | "tumor protein p53 (Li-Fraumeni syndrome)" | Hs.1846 | 0.25+-0.02 | SEQ. ID. NO. 188 |
| 31 | 811108 | "thyroid hormone receptor interactor 6" | Hs.119498 | 0.25+-0.02 | SEQ. ID. NO. 118 |
| 32 | 770868 | "NGFI-A binding protein 2 (ERG1 binding protein 2)" | Hs.159223 | 0.25+-0.01 | SEQ. ID. NO. 190 |
| 35 | 80338 | "selenium binding protein 1" | Hs.7833 | 0.24+-0.01 | SEQ. ID. NO. 14 |

| Rank | Clone Id | GeneDescription | Unigene | Weight | SEQ. ID. NO. |
|---|---|---|---|---|---|
| 38 | 212640 | "Rho GTPase activating protein 4" | Hs.3109 | 0.24+-0.01 | SEQ. ID. NO. 108 |
| 39 | 417226 | "v-myc avian myelocytomatosis viral oncogene homolog" | Hs.79070 | 0.24+-0.01 | SEQ. ID. NO. 81 |
| 40 | 742132 | "interferon-stimulated protein, 15 kDa" | Hs.833 | 0.23+-0.01 | SEQ. ID. NO. 140 |
| 41 | 365826 | "growth arrest-specific 1" | Hs.65029 | 0.23+-0.01 | SEQ. ID. NO. 59 |
| 42 | 161993 | "CCAAT/enhancer binding protein (C/EBP), beta" | Hs.99029 | 0.23+-0.01 | SEQ. ID. NO. 166 |
| 43 | 811000 | "lectin, galactoside-binding, soluble, 3 binding protein (galectin 6 binding protein)" | Hs.79339 | 0.23+-0.01 | SEQ. ID. NO. 6 |
| 44 | 768205 | "homeo box D9" | Hs.236646 | 0.22+-0.01 | SEQ. ID. NO. 361 |
| 48 | 345232 | "lymphotoxin alpha (TNF superfamily, member 1)" | Hs.36 | 0.22+-0.01 | SEQ. ID. NO. 362 |
| 49 | 586854 | "CGI-119 protein" | Hs.25615 | 0.22+-0.01 | SEQ. ID. NO. 201 |
| 52 | 744417 | "carnitine acetyltransferase" | Hs.12068 | 0.21+-0.01 | SEQ. ID. NO. 363 |
| 53 | 364934 | "death-associated protein kinase 1" | Hs.153924 | 0.21+-0.01 | SEQ. ID. NO. 12 |
| 54 | 809694 | "cellular retinoic acid-binding protein 1" | Hs.7678 | 0.21+-0.01 | SEQ. ID. NO. 364 |
| 55 | 491565 | "Cbp/p300-interacting transactivator, with Glu/Asp-rich carboxy-terminal domain, 2" | Hs.82071 | 0.21+-0.01 | SEQ. ID. NO. 365 |
| 56 | 1470048 | "lymphocyte antigen 6 complex, locus E" | Hs.77667 | 0.21+-0.01 | SEQ. ID. NO. 366 |
| 57 | 814266 | "protein kinase C, zeta" | Hs.78793 | 0.21+-0.01 | SEQ. ID. NO. 367 |
| 58 | 296030 | "ESTs" | Hs.10362 | 0.21+-0.01 | SEQ. ID. NO. 368 |
| 59 | 379708 | "chromodomain helicase DNA binding protein 3" | Hs.25601 | 0.21+-0.01 | SEQ. ID. NO. 176 |

| Rank | Clone Id | GeneDescription | Unigene | Weight | SEQ. ID. NO. |
|---|---|---|---|---|---|
| 60 | 755506 | "annexin A4" | Hs.77840 | 0.20+-0.01 | SEQ. ID. NO. 177 |
| 61 | 39796 | "3-hydroxymethyl-3-methylglutaryl-Coenzyme A lyase (hydroxymethylglutaricaciduria)" | Hs.831 | 0.20+-0.01 | SEQ. ID. NO. 369 |
| 62 | 741885 | "transcription factor binding to IGHM enhancer 3" | Hs.274184 | 0.20+-0.01 | SEQ. ID. NO. 370 |
| 63 | 271102 | "copper chaperone for superoxide dismutase" | Hs.5002 | 0.20+-0.01 | SEQ. ID. NO. 371 |
| 64 | 470261 | "SMA3" | Hs.251397 | 0.20+-0.01 | SEQ. ID. NO. 372 |
| 66 | 745343 | "regenerating islet-derived 1 alpha (pancreatic stone protein, pancreatic thread protein)" | Hs.1032 | 0.20+-0.01 | SEQ. ID. NO. 85 |
| 67 | 563673 | "antiquitin 1" | Hs.74294 | 0.20+-0.01 | SEQ. ID. NO. 10 |
| 68 | 39093 | "methionine aminopeptidase; eIF-2-associated p67" | Hs.78935 | 0.20+-0.01 | SEQ. ID. NO. 63 |
| 75 | 234376 | "Homo sapiens mRNA; cDNA DKFZp564F112 (from clone DKFZp564F112)" | Hs.166361 | 0.19+-0.01 | SEQ. ID. NO. 373 |
| 76 | 810133 | "ESTs" | Hs.10362 | 0.19+-0.01 | SEQ. ID. NO. 374 |
| 78 | 815239 | "Rho guanine nucleotide exchange factor (GEF) 1" | Hs.252280 | 0.19+-0.01 | SEQ. ID. NO. 161 |
| 80 | 172751 | "amyloid beta (A4) precursor protein-binding, family A, member 1 (X11)" | Hs.4880 | 0.18+-0.01 | SEQ. ID. NO. 375 |
| 81 | 289645 | "amyloid beta (A4) precursor-like protein 1" | Hs.74565 | 0.18+-0.01 | SEQ. ID. NO. 4 |
| 84 | 769579 | "mitogen-activated protein kinase kinase 2" | Hs.72241 | 0.18+-0.01 | SEQ. ID. NO. 376 |
| 85 | 1422723 | "interferon-induced protein 35" | Hs.50842 | 0.18+-0.01 | SEQ. ID. NO. 377 |

CERTIFICATE OF CORRECTION (continued)
U.S. Pat. No. 7,655,397 B2

| Rank | Clone Id | GeneDescription | Unigene | Weight | SEQ. ID. NO. |
|---|---|---|---|---|---|
| 86 | 296880 | "membrane protein, palmitoylated 1 (55kD)" | Hs.1861 | 0.18+-0.01 | SEQ. ID. NO. 378 |
| 87 | 744052 | "nuclear receptor subfamily 1, group H, member 2" | Hs.100221 | 0.18+-0.01 | SEQ. ID. NO. 379 |
| 88 | 782503 | "Homo sapiens clone 23716 mRNA sequence" | Hs.12214 | 0.18+-0.01 | SEQ. ID. NO. 7 |
| 89 | 1434905 | "homeo box B7" | Hs.819 | 0.18+-0.01 | SEQ. ID. NO. 178 |
| 90 | 212542 | "Homo sapiens mRNA; cDNA DKFZp586J2118 (from clone DKFZp586J2118)" | Hs.21851 | 0.18+-0.01 | SEQ. ID. NO. 53 |
| 91 | 506548 | "regulator of G-protein signalling 10" | Hs.82280 | 0.18+-0.01 | SEQ. ID. NO. 380 |
| 93 | 768443 | "microsomal glutathione S-transferase 1" | Hs.790 | 0.18+-0.01 | SEQ. ID. NO. 381 |
| 94 | 75923 | "Human zinc finger protein mRNA, complete cds" | Hs.78765 | 0.18+-0.01 | SEQ. ID. NO. 382 |
| 97 | 1475595 | "alkaline phosphatase, liver/bone/kidney" | Hs.250769 | 0.17+-0.01 | SEQ. ID. NO. 383 |
| 99 | 231355 | "vesicle-associated membrane protein 2 (synaptobrevin 2)" | Hs.194534 | 0.17+-0.01 | SEQ. ID. NO. 384 |
| 100 | 841620 | "dihydropyrimidinase-like 2" | Hs.173381 | 0.17+-0.01 | SEQ. ID. NO. 8 |
| 101 | 1456900 | "dipeptidase 1 (renal)" | Hs.109 | 0.17+-0.01 | SEQ. ID. NO. 385 |
| 103 | 773246 | "ring finger protein 1" | Hs.35384 | 0.17+-0.01 | SEQ. ID. NO. 386 |
| 104 | 191743 | "ESTs" | Hs.94814 | 0.17+-0.01 | SEQ. ID. NO. 387 |

| Rank | Clone Id | GeneDescription | Unigene | Weight | SEQ. ID. NO. |
|---|---|---|---|---|---|
| 105 | 265874 | "nuclear factor I/C (CCAAT-binding transcription factor)" | Hs.184771 | 0.17+-0.01 | SEQ. ID. NO. 388 |
| 106 | 767345 | "ESTs, Moderately similar to I59372 cadherin 12 - human [H.sapiens]" | Hs.44898 | 0.17+-0.01 | SEQ. ID. NO. 389 |
| 107 | 729964 | "sphingomyelin phosphodiesterase 1, acid lysosomal (acid sphingomyelinase)" | Hs.77813 | 0.17+-0.01 | SEQ. ID. NO. 390 |
| 108 | 768644 | "zona pellucida glycoprotein 3A (sperm receptor)" | Hs.250867 | 0.17+-0.01 | SEQ. ID. NO. 391 |
| 111 | 858469 | "thrombospondin 3" | Hs.169875 | 0.17+-0.01 | SEQ. ID. NO. 392 |
| 112 | 756556 | "complement component 1 inhibitor (angioedema, hereditary)" | Hs.151242 | 0.17+-0.01 | SEQ. ID. NO. 65 |
| 113 | 190887 | "myeloid differentiation primary response gene (88)" | Hs.82116 | 0.17+-0.01 | SEQ. ID. NO. 169 |
| 114 | 1475730 | "chaperonin containing TCP1, subunit 6A (zeta 1)" | Hs.82916 | 0.17+-0.01 | SEQ. ID. NO. 393 |
| 115 | 137158 | "chromogranin A (parathyroid secretory protein 1)" | Hs.172216 | 0.17+-0.01 | SEQ. ID. NO. 394 |
| 116 | 897774 | "adenine phosphoribosyltransferase" | Hs.28914 | 0.17+-0.01 | SEQ. ID. NO. 395 |
| 120 | 757248 | "calpain, large polypeptide L3" | Hs.40300 | 0.17+-0.01 | SEQ. ID. NO. 396 |
| 124 | 811920 | "interleukin 11 receptor, alpha" | Hs.64310 | 0.16+-0.01 | SEQ. ID. NO. 397 |
| 125 | 824602 | "interferon, gamma-inducible protein 16" | Hs.155530 | 0.16+-0.01 | SEQ. ID. NO. 84 |

| Rank | Clone Id | GeneDescription | Unigene | Weight | SEQ. ID. NO. |
|---|---|---|---|---|---|
| 126 | 150702 | "homeo box B5" | Hs.22554 | 0.16+-0.01 | SEQ. ID. NO. 398 |
| 127 | 37553 | "protein phosphatase 2A, regulatory subunit B' (PR 53)" | Hs.236963 | 0.16+-0.01 | SEQ. ID. NO. 399 |
| 128 | 139957 | "hypothetical protein FLJ11181" | Hs.28472 | 0.16+-0.01 | SEQ. ID. NO. 400 |
| 130 | 343646 | "v-ski avian sarcoma viral oncogene homolog" | Hs.2969 | 0.16+-0.01 | SEQ. ID. NO. 401 |
| 131 | 1031748 | "synovial sarcoma, X breakpoint 3" | Hs.178749 | 0.16+-0.01 | SEQ. ID. NO. 402 |
| 132 | 166236 | "glucose-6-phosphate dehydrogenase" | Hs.80206 | 0.16+-0.01 | SEQ. ID. NO. 403 |
| 133 | 740801 | "branched chain keto acid dehydrogenase E1, alpha polypeptide (maple syrup urine disease)" | Hs.78950 | 0.16+-0.01 | SEQ. ID. NO. 404 |
| 134 | 120468 | "excision repair cross-complementing rodent repair deficiency, complementation group 1 (includes overlapping antisense sequence)" | Hs.59544 | 0.16+-0.01 | SEQ. ID. NO. 405 |
| 137 | 785967 | "erythrocyte membrane protein band 4.1-like 2" | Hs.7857 | 0.16+-0.01 | SEQ. ID. NO. 406 |
| 139 | 361943 | "Meis1 (mouse) homolog" | Hs.170177 | 0.16+-0.01 | SEQ. ID. NO. 407 |
| 140 | 810551 | "low density lipoprotein-related protein 1 (alpha-2-macroglobulin receptor)" | Hs.89137 | 0.16+-0.01 | SEQ. ID. NO. 206 |
| 141 | 841698 | "exostoses (multiple) 1" | Hs.184161 | 0.16+-0.01 | SEQ. ID. NO. 408 |
| 142 | 753104 | "dopachrome tautomerase (dopachrome delta-isomerase, tyrosine-related protein 2)" | Hs.240217 | 0.16+-0.01 | SEQ. ID. NO. 409 |
| 143 | 878798 | "beta-2-microglobulin" | Hs.75415 | 0.16+-0.01 | SEQ. ID. NO. 410 |

| Rank | Clone Id | GeneDescription | Unigene | Weight | SEQ. ID. NO. |
|---|---|---|---|---|---|
| 145 | 811900 | "lymphotoxin beta receptor (TNFR superfamily, member 3" | Hs.1116 | 0.16+-0.01 | SEQ. ID. NO. 411 |
| 146 | 741831 | "phospholipid transfer protein" | Hs.154854 | 0.15+-0.01 | SEQ. ID. NO. 412 |
| 147 | 549146 | "stimulated trans-acting factor (50 kDa)" | Hs.68054 | 0.15+-0.01 | SEQ. ID. NO. 413 |
| 149 | 841340 | "ATP-binding cassette, sub-family B (MDR/TAP), member 2" | Hs.158164 | 0.15+-0.01 | SEQ. ID. NO. 414 |
| 153 | 42576 | "ubiquitin-activating enzyme E1 (A1S9T and BN75 temperature sensitivity complementing)" | Hs.2055 | 0.15+-0.01 | SEQ. ID. NO. 415 |
| 154 | 53039 | "carbohydrate (keratan sulfate Gal-6) sulfotransferase 1" | Hs.104576 | 0.15+-0.01 | SEQ. ID. NO. 416 |
| 155 | 308163 | "ESTs" | Hs.84520 | 0.15+-0.01 | SEQ. ID. NO. 57 |
| 157 | 949938 | "cystatin C (amyloid angiopathy and cerebral hemorrhage)" | Hs.135084 | 0.15+-0.01 | SEQ. ID. NO. 417 |
| 158 | 166195 | "ribonuclease/angiogenin inhibitor" | Hs.75108 | 0.15+-0.01 | SEQ. ID. NO. 418 |
| 159 | 239611 | "hemoglobin, epsilon 1" | Hs.117848 | 0.15+-0.01 | SEQ. ID. NO. 419 |
| 160 | 36950 | "phosphofructokinase, liver" | Hs.155455 | 0.15+-0.01 | SEQ. ID. NO. 420 |
| 161 | 82903 | "TAP binding protein (tapasin)" | Hs.179600 | 0.15+-0.01 | SEQ. ID. NO. 141 |
| 162 | 183440 | "arylsulfatase A" | Hs.88251 | 0.15+-0.01 | SEQ. ID. NO. 421 |
| 163 | 787857 | "syntaxin 5A" | Hs.154546 | 0.15+-0.01 | SEQ. ID. NO. 422 |
| 164 | 840821 | "signal sequence receptor, delta (translocon-associated protein delta)" | Hs.102135 | 0.15+-0.01 | SEQ. ID. NO. 423 |

| Rank | Clone Id | GeneDescription | Unigene | Weight | SEQ. ID. NO. |
|---|---|---|---|---|---|
| 165 | 760148 | "uroporphyrinogen decarboxylase" | Hs.78601 | 0.15+-0.01 | SEQ. ID. NO. 424 |
| 166 | 1434948 | "HIV TAT specific factor 1" | Hs.171595 | 0.15+-0.01 | SEQ. ID. NO. 425 |
| 167 | 897788 | "protein tyrosine phosphatase, receptor type, F" | Hs.75216 | 0.15+-0.01 | SEQ. ID. NO. 9 |
| 168 | 810124 | "platelet-activating factor acetylhydrolase, isoform Ib, gamma subunit (29kD)" | Hs.6793 | 0.15+-0.01 | SEQ. ID. NO. 426 |
| 169 | 50359 | "mannose phosphate isomerase" | Hs.75694 | 0.15+-0.01 | SEQ. ID. NO. 427 |
| 170 | 221826 | "guanine nucleotide binding protein (G protein), alpha 11 (Gq class)" | Hs.1686 | 0.15+-0.01 | SEQ. ID. NO. 428 |
| 171 | 753587 | "butyrophilin, subfamily 3, member A3" | Hs.167741 | 0.15+-0.01 | SEQ. ID. NO. 429 |
| 172 | 839980 | "glucose-6-phosphatase, transport (glucose-6-phosphate) protein 1" | Hs.26655 | 0.15+-0.01 | SEQ. ID. NO. 430 |
| 173 | 33327 | "Homo sapiens mRNA for KIAA1232 protein, partial cds" | Hs.11101 | 0.15+-0.01 | SEQ. ID. NO. 431 |
| 174 | 711961 | "general transcription factor IIF, polypeptide 1 (74kD subunit)" | Hs.68257 | 0.15+-0.01 | SEQ. ID. NO. 432 |
| 175 | 809910 | "interferon induced transmembrane protein 3 (1-8U)" | Hs.182241 | 0.15+-0.01 | SEQ. ID. NO. 55 |
| 180 | 172783 | "hypothetical protein FLJ10390" | Hs.133475 | 0.15+-0.01 | SEQ. ID. NO. 433 |
| 182 | 1374571 | "paired basic amino acid cleaving enzyme (furin, membrane associated receptor protein)" | Hs.59242 | 0.14+-0.01 | SEQ. ID. NO. 434 |

| Rank | Clone Id | GeneDescription | Unigene | Weight | SEQ. ID. NO. |
|---|---|---|---|---|---|
| 183 | 138936 | "erythrocyte membrane protein band 7.2 (stomatin)" | Hs.160483 | 0.14+-0.01 | SEQ. ID. NO. 435 |
| 186 | 795321 | "mannosidase, alpha, class 2A, member 2" | Hs.182923 | 0.14+-0.01 | SEQ. ID. NO. 436 |
| 188 | 263727 | "DNA segment, single copy probe LNS-CAI/LNS-CAII (deleted in polyposis" | Hs.178112 | 0.14+-0.01 | SEQ. ID. NO. 437 |
| 189 | 75009 | "EphB4" | Hs.155227 | 0.14+-0.01 | SEQ. ID. NO. 438 |
| 190 | 435953 | "inositol 1,4,5-triphosphate receptor, type 3" | Hs.77515 | 0.14+-0.01 | SEQ. ID. NO. 144 |
| 191 | 782335 | "ESTs" | Hs.38270 | 0.14+-0.01 | SEQ. ID. NO. 439 |
| 194 | 754600 | "nuclear factor I/X (CCAAT-binding transcription factor)" | Hs.35841 | 0.14+-0.01 | SEQ. ID. NO. 440 |
| 195 | 213890 | "2,4-dienoyl CoA reductase 1, mitochondrial" | Hs.81548 | 0.14+-0.01 | SEQ. ID. NO. 441 |
| 197 | 1472735 | "metallothionein 1E (functional)" | Hs.74170 | 0.14+-0.01 | SEQ. ID. NO. 442 |
| 199 | 781097 | "reticulon 3" | Hs.252831 | 0.14+-0.01 | SEQ. ID. NO. 443 |
| 200 | 810057 | "cold shock domain protein A" | Hs.1139 | 0.14+-0.01 | SEQ. ID. NO. 105 |

Col. 72, Table 10: Delete incorrect Table 10 and replace with correct Table 10:

TABLE 10 - Genes involved with signal transduction

| name | CloneID | diagnosis | summaryfunction | SEQ. ID. NO. |
|---|---|---|---|---|
| membrane metallo-endopeptidase (neutral endopeptidase, enkephalinase, CALLA, CD10) | 200814 | BL | Enkephalinase; membrane zinc metalloendopeptidase, may inactivate peptide hormones\|Proteome | SEQ. ID. NO. 94 |
| protein tyrosine phosphatase, receptor type, F | 897788 | NOTBL | Receptor-type protein tyrosine phosphatase F; interacts with the insulin receptor; has Ig-like and FN-III repeats in the extracellular domain\|Proteome | SEQ. ID. NO. 9 |
| protein kinase, cAMP-dependent, regulatory, type II, beta | 609663 | BL* | Type II regulatory beta subunit of cAMP-dependent protein kinase (PKA)\|Proteome | SEQ. ID. NO. 95 |
| annexin A1 | 208718 | EWS* | Annexin I (lipocortin 1); Ca2+-dependent phospholipid-binding protein, inhibits phospholipase A2 and has anti-inflammatory activity\|Proteome | SEQ. ID. NO. 2 |
| interleukin 4 receptor | 714453 | RMS_BL | Subunit of the interleukin 4 receptor; member of the cytokine receptor family\|Proteome | SEQ. ID. NO. 83 |

| name | CloneID | diagnosis | summaryfunction | SEQ. ID. NO. |
|---|---|---|---|---|
| recoverin | 383188 | NB* | Recoverin; calcium-binding protein that activates guanylate cyclase activity\|Proteome | SEQ. ID. NO. 38 |
| fibroblast growth factor receptor 4 | 784224 | RMS* | Fibroblast growth factor receptor 4; receptor tyrosine kinase, preferentially binds acidic FGF; contains three extracellular immunoglobulin-like domains\|Proteome | SEQ. ID. NO. 71 |
| transducin-like enhancer of split 2, homolog of Drosophila E(sp1) | 1473131 | EWS* | Enhancer of split groucho 2; possibly functions during epithelial differentiation; transducin-like, similar to Drosophila E(spI) m9/10, which is required for cell fate decisions\|Proteome | SEQ. ID. NO. 15 |
| tumor necrosis factor, alpha-induced protein 6 | 357031 | EWS* | Similar to CD44; binds hyaluronate and may be involved in cell-cell communication during the immune response\|Proteome | SEQ. ID. NO. 18 |
| ras homolog gene family, member B | 768370 | NOTBL | Ras-related GTP binding protein of the rho subfamily, member B; may regulate assembly of actin stress fibers and focal adhesions; very strongly similar to murine Arhb\|Proteome | SEQ. ID. NO. 46 |

| name | CloneID | diagnosis | summaryfunction | SEQ. ID. NO. |
|---|---|---|---|---|
| insulin-like growth factor 2 (somatomedin A) | 245330 | RMS | Insulin-like growth factor II (somatomedin A); member of the insulin protein family\|Proteome | SEQ. ID. NO. 78 |
| hematopoietic cell-specific Lyn substrate 1 | 767183 | BL | Contains a helix-turn-helix DNA binding domain and an SH3 domain\|Proteome | SEQ. ID. NO. 91 |
| dihydropyrimidinase-like 2 | 841620 | EWS_NB | Member of the dihydropyrimidinase family\|Proteome | SEQ. ID. NO. 8 |
| amyloid beta (A4) precursor protein (protease nexin-II, Alzheimer disease) | 323371 | NOTBL | Amyloid beta precursor protein (protease nexin-II); cell surface protease inhibitor; reduces Cu\|Proteome | SEQ. ID. NO. 27 |
| interferon induced transmembrane protein 1 (9-27) | 755599 | EWS* | Interferon-inducible transmembrane protein 1; involved in relaying antiproliferative and homotypic adhesion signals\|Proteome | SEQ. ID. NO. 25 |
| secreted frizzled-related protein 1 | 82225 | NB* | Secreted frizzled-related protein 1; may have an anti-apoptotic function and inhibit Wnt protein activity; strongly similar to murine Sfrp1\|Proteome | SEQ. ID. NO. 42 |

| name | CloneID | diagnosis | summaryfunction | SEQ. ID. NO. |
|---|---|---|---|---|
| death-associated protein kinase 1 | 364934 | EWS* | Death associated protein kinase 1; serine/threonine kinase regulated by calmodulin, may mediate apoptosis induced by interferon-gamma; has ankyrin repeats\|Proteome | SEQ. ID. NO. 12 |
| lectin, galactoside-binding, soluble, 3 binding protein | 811000 | EWS_NB | Mac-2-binding protein; potent immune stimulator; contains a macrophage scavenger receptor cysteine-rich domain\|Proteome | SEQ. ID. NO. 6 |
| insulin-like growth factor binding protein 5 | 2907511 | RMS | Member of the insulin-like growth factor binding family of proteins; may bind to and modulate insulin-like growth factor activity\|Proteome | SEQ. ID. NO. 444 |